US008980906B2

(12) United States Patent
Tafesse

(10) Patent No.: US 8,980,906 B2
(45) Date of Patent: Mar. 17, 2015

(54) PYRIDONEMORPHINAN ANALOGS AND BIOLOGICAL ACTIVITY ON OPIOID RECEPTORS

(71) Applicant: Purdue Pharma L.P., Stamford, CT (US)

(72) Inventor: Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/105,733

(22) Filed: Dec. 13, 2013

(65) Prior Publication Data
US 2014/0187549 A1 Jul. 3, 2014

Related U.S. Application Data

(60) Provisional application No. 61/789,147, filed on Mar. 15, 2013, provisional application No. 61/737,583, filed on Dec. 14, 2012.

(51) Int. Cl.
A61K 31/439 (2006.01)
C07D 471/22 (2006.01)
C07D 471/18 (2006.01)

(52) U.S. Cl.
CPC ............ C07D 471/22 (2013.01); C07D 471/18 (2013.01)
USPC ............................................. 514/281; 546/43

(58) Field of Classification Search
CPC ...................................................... C07D 471/22
USPC ............................................. 514/281; 546/43
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,698,155 | A | 12/1997 | Grosswald et al. |
| 5,733,566 | A | 3/1998 | Lewis |
| 5,952,495 | A | 9/1999 | Huang et al. |
| 7,655,671 | B2 | 2/2010 | Schmidhammer et al. |
| 8,067,596 | B2 | 11/2011 | Wang et al. |
| 2008/0312411 | A1 | 12/2008 | Wolf et al. |
| 2009/0156818 | A1 | 6/2009 | Wang et al. |
| 2009/0156820 | A1 | 6/2009 | Wang et al. |
| 2013/0231485 | A1 | 9/2013 | Tamura et al. |

FOREIGN PATENT DOCUMENTS

| EP | 0 829 481 A1 | 3/1998 |
| EP | 1 974 731 A1 | 10/2008 |
| GB | 1031364 | 6/1966 |
| JP | 2008-179554 | 8/2008 |
| WO | WO 91/05768 A1 | 5/1991 |
| WO | WO 98/02033 A1 | 1/1998 |
| WO | WO 01/12197 A1 | 2/2001 |
| WO | WO 2004/005294 A2 | 1/2004 |
| WO | WO 2006/035195 A1 | 4/2006 |
| WO | WO 2008/070462 A2 | 6/2008 |
| WO | WO 2009/067275 A1 | 5/2009 |

(Continued)

OTHER PUBLICATIONS

Bartho, L., et al., "Involvement of capsaicin-sensitive neurones in hyperalgesia and enhanced opiod antinociception in inflammation," Naunyn-Schmiedeberg's Arch. Pharmacol. 342:666-670, Springer Verlag, Germany (1990).

Bingham, A.L., et al., "Over one hundred solvates of sulfathiazole," Chem. Commun., 603-604, The Royal Society of Chemistry, England (2001).

Buchwald, H., et al., "Long-term, continuous intravenous heparin administration by an implantable infusion pump in ambulatory patients with recurrent venous thrombosis," Surgery 88:507-516, The C.V. Mosby Co., United States (1980).

Caira, M.R., et al., "Preparation and Crystal Characterization of Polymorph, a Monohydrate, and an Ethyl Acetate Solvate of the Antifungal Fluconazole," Journal of Pharmaceutical Sciences 93(3):601-611, Wiley-Liss, Inc., United States (2004).

D'Amour, F.E. and Smith, D.L., "A Method for Determining Loss of Pain Sensation," The Journal of Pharmacology and Experimental Therapeutics 72:74-79, The American Society for Pharmacology and Experimental Therapeutics Incorporated, United States (1941).

(Continued)

Primary Examiner — Taofiq A Solola
(74) Attorney, Agent, or Firm — Sterne, Kessler, Goldstein & Fox P.L.L.C.

(57) ABSTRACT

The application is directed to compounds of Formula I-A

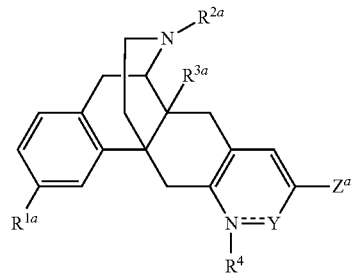

I-A and pharmaceutically acceptable salts and solvates thereof, wherein ---, $R^{1a}$—$R^{3a}$, $R^4$, Y and $Z^a$ are defined as set forth in the specification. The invention is also directed to use of compounds of Formula I-A to treat disorders responsive to the modulation of one or more opioid receptors, or as synthetic intermediates. Certain compounds of the present invention are especially useful for treating pain.

28 Claims, No Drawings

(56) References Cited

FOREIGN PATENT DOCUMENTS

| WO | WO 2012/063933 A1 | 5/2012 |
| WO | WO 2013/035833 A1 | 3/2013 |

OTHER PUBLICATIONS

During, M.J., et al., "Controlled Release of Dopamine from a Polymeric Brain Implant: In Vivo Characterization," *Annals of Neurology* 25(4): 351-356, Little, Brown and Company, United States (1989).

English machine translation of Japanese Patent Publication No. JP 2008-179554, date Aug. 7, 2008.

Grupp, I.L., et al., "Protection against Hypoxia-reoxygenation in the Absence of Poly(ADP-ribose) Synthetase in Isolated Working Hearts," *J. Mol. Cell. Cardiol.* 31:297-303, Academic Press, United States (1999).

Hargreaves, K., et al., "A new and sensitive method for measuring thermal nociception in cutaneous hyperalgesia," *Pain* 32(1):77-88, Elsevier, Netherlands (1988).

Howard III, M.A., et al., "Intracerebal drug delivery in rats with lesion-induced memory deficits," *J. Neurosurg.* 71(1):105-112, American Association of Neurological Surgeons, United States (1989).

Hupp, C.D. and Neumeyer, J.L., "Rapid access to morphinones: removal of 4,5-ether bridge with Pd-catalyzed triflate reduction," *Tetrahedron Letters* 51:2359-2361, Elsevier Ltd., England (2010).

Hopkins, G.C., et al., "Alkylations of Heterocyclic Ambident Anions. II. Alkylation Of 2-Pyridone Salts," *Journal of Organic Chemistry* 32: 4040-4044, American Chemical Society, United States (1967).

Ida, Y., et al., "Synthesis of quinolinomorphinan-4-ol derivatives as δ opioid receptor agonists," *Bioorganic & Medicinal Chemistry* 20:949-961, Elsevier Ltd., England (2012) (available online Dec. 2011).

Kim, S.H. and Chung, J.M., "An experimental model for peripheral neuropathy produced by segmental spinal nerve ligation in the rat," *Pain* 50:355-363, Elsevier Science Publishers B.V., Netherlands (1992).

Langer, R. and Peppas, N., "Chemical and Physical Structure of Polymers as Carriers for Controlled Release of Bioactive Agents: A Review," *JMS—Rev. Macromol. Chem. Phys. C*23(1):61-126, Marcel Dekker, Inc., United States (1983).

Langer, R. "New Methods of Drug Delivery," *Science* 249(4976):1527-1533, American Association for the Advancement of Science, United States (1990).

Levy, R.J., et al., "Inhibition of Calcification of Bioprosthetic Heart Valves by Local Controlled-Release Diphosphonate," *Science* 228(4696):190-192, American Association for the Advancement of Science, United States (1985).

Lopez-Berpstein, G., "Treatment of Systematic Fungal Infections with Liposomal-Amphotericin B," in *Liposomes in the Therapy of Infectious Diseases and Cancer*, 317-327, Alan R. Liss, Inc., United States (1989).

Nagase, H., et al., "Design and synthesis of KNT-127, a δ-opiod receptor agonist effective by systemic administration," *Bioorganic & Medicinal Chemistry Letters* 20:6302-6305, Elsevier Ltd., England (2010).

Negus, S.S., et al., "Effects of kappa opiods in an assay of pain-depressed intracranial self-stimulation in rats," *Pscyhopharmacology* 210:149-159, Springer-Verlag, Germany (2010).

Pande, A.C., et al., "Analgesic Efficacy of the κ-Receptor Agonist, Enadoline, in Dental Surgery Pain," *Clin. Neropharmacol.* 19(1):92-97, Lippincott-Raven Publishers, United States (1996).

Pande, A.C., et al., "Analgesic Efficacy of Enadoline Versus Placebo or Morphorine in Postsurgical Pain," *Clin. Neuropharmacol.* 19(5):451-456, Lippincott-Raven Publishers, United States (1996).

Polazzi, J.O., et al., "Analgesic Narcotic Antagonists. 2. 8-Alkymophinan-6-ones," *J. Med. Chem.* 23(2):174-179, American Chemical Society, United States (1980).

Saudek, C.D., et al., "A Preliminary Trial of the Programmable Implantable Medication System for Insulin Delivery," *The New England Journal of Medicine* 321(9):574-579, Massachusetts Medical Society, United States (1989).

Sefton, M.V., "Implantable Pumps," *Critical Reviews™ in Biomedical Engineering* 14(3):201-240, CRC Press, Inc., United States (1987).

Seltzer, Z., et al., "A novel behavioral model of neuropathic pain disorders produced in rats by partial sciatic nerve injury," *Pain* 43:205-218, Elsevier Science Publishers B.V., Netherlands (1990).

Shütz, J., et al., "Synthesis of 6-Amino Acid Substituted Derivatives of the Highly Potent Analgesic 14-*O*-Methyloxymorphone," *Helvetica Chimica Acta* 86: 2142-2148, Verlag Helvetica Chimica Acta AG, Switzerland (2003).

Stein, C., et al., "Unilateral Inflammation of the Hindpaw in Rats as the Model of Prolonged Noxious Stimulation: Alterations in Behavior and Nociceptive Thresholds," *Pharmacology Biochemistry & Behavior* 31:445-451, Pergamon Press PLC, United States (1988).

Torbati, D., et al., "Effect of hypothermia on ventilation in anesthetized, spontaneously breathing rats: theoretical implications for mechanical ventilation," *Intensive Care Med.* 26:585-591, Springer-Verlag, Germany (2000).

Treat, J., et al., "Liposome Encapsulated Doxorubicin Preliminary Results of Phase I and Phase II Trails," in *Liposomes in the Therapy of Infectious Diseases and Cancer*, 353-365, Alan R. Liss, Inc., United States (1989).

Van Tonder, E.C., et al., "Preperation and Physicochemical Characterization of 5 Niclosamide Solvates and 1 Hemisolvate," *AAPS PharmSciTech* 5(1):1-10, Article 12, Springer Science + Business Media LLC, United States (2004).

Vanderah, T.W., et al., "FE200041 (D-Phe-D-Ph-D-Nle-D-Arg-$NH_2$): A Peripheral Efficacious κ Opioid Agonist with Unprecedented Selectivity," *The Journal of Pharmacology and Experimental Therapeutics* 310(1):326-333, The American Society for Pharmacology and Experimental Therapeutics, United States (2004).

Wadenberg, M-L.G., "A Review of the Properties of Spiradoline: A Potent and Selective κ-Opioid Recepter Agonist," *CNS Durg Review* 9(2):187-198, Neva Press, United Sates (2003).

Woolfe, G. and MacDonald, A.D., "The Evaluation of the Analgesic Action of Pethidine Hydrocholoride (Demerol)," *The Journal of Pharmacology and Experimental Therapeutics* 80-81:300-307, The American Society for Pharmacology and Experimental Therapeutics Incorporated, United States (1944).

International Search Report and Written Opinion for International Patent Application No. PCT/IB2013/002772, mailed Mar. 12, 2014, European Patent Office, Rijswijk, Netherlands.

Taiwan IPO Search Report for Taiwanese Patent Application No. 102146080, Taiwan Patent Office, Taiwan, completed on Nov. 5, 2014, and became available in an Office Action dated Dec. 9, 2014.

PYRIDONEMORPHINAN ANALOGS AND BIOLOGICAL ACTIVITY ON OPIOID RECEPTORS

BACKGROUND OF THE INVENTION

1. Field of the Invention

This application is in the field of medicinal chemistry. The application relates to novel pyridonemorphinan analogs, and pharmaceutical compositions comprising one or more of these compounds. The application also relates to methods of making pyridonemorphinan analogs, and their use.

2. Description of the Related Art

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone, oxymorphone, or buprenorphine).

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This more recently discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Kappa ($\kappa$) opioid receptor agonists have been evaluated as alternatives to existing analgesics for the treatment of pain. Centrally penetrating $\kappa$ agonists produce antinociceptive effects in conventional preclinical assays of basal, inflammatory and neuropathic pain (Vanderah et al., *J. Pharmacol. Exp. Ther.* 310:326-233 (2004); Negus et al., *Psychopharmacology* (Berl) 210:149-159 (2010)). However, centrally penetrating K agonists can also produce undesirable side-effects, such as sedative and psychotomimetic effects (Pande et al., *Clin. Neuropharmacol.* 19:92-97 (1996); Pande et al., *Clin. Neuropharmacol.* 19:451-456 (1996); and Wadenberg, *CNS Drug Rev.* 9:187-198 (2003)).

Opioid receptor agonists that do not readily cross the blood-brain barrier are peripherically restricted and distribute poorly to the central nervous system after systemic administration. Such compounds would retain an ability to produce analgesia by acting on peripheral opioid receptors, such as peripheral $\kappa$-opioid receptors, but their potency to produce centrally mediated side-effects would be reduced.

There is a need for effective analgesics that work by acting on opioid receptors. There is also a need for analgesics that work by acting on peripheral opioid receptors. There is also a need for analgesics that work by acting on central opioid receptors. There is also a need for analgesics that work by acting on $\kappa$-opioid receptors. There is also a need for analgesics that work by acting on peripheral $\kappa$-opioid receptors.

BRIEF SUMMARY OF THE INVENTION

In one aspect, the present disclosure provides compounds represented by Formulae I-A to X-A and I-IX, below, and the pharmaceutically acceptable salts and solvates thereof, collectively referred to herein as "Compounds of the Invention" (each is individually referred to hereinafter as a "Compound of the Invention").

In another aspect, the present disclosure provides the use of Compounds of the Invention as synthesis intermediates.

In another aspect, the present disclosure provides the use of Compounds of the Invention as modulators of one or more opioid receptors. Specifically, the present disclosure provides the use of Compounds of the Invention as modulators of $\mu$, $\delta$, $\kappa$, and/or ORL-1 opioid receptors, and especially modulators of $\mu$ and/or $\kappa$ opioid receptors.

In another aspect, the present disclosure provides a method of treating or preventing a disorder responsive to the modulation of one or more opioid receptors in a patient, comprising administering to the patient an effective amount of a Compound of the Invention.

In another aspect, the present disclosure provides a use of a Compound of the Invention as an analgesic to treat or prevent pain; or as an agent to treat or prevent withdrawal from alcohol or drug addiction; or as an agent to treat of prevent addictive disorders; or as an agent to treat a pruritic condition; or as an agent to treat or prevent constipation; or as an agent to treat or prevent diarrhea (each of pain, alcohol withdrawal, drug withdrawal, addictive disorders, pruritis, constipation, and diarrhea being a "Condition").

The present invention further provides methods of treating or preventing a Condition, comprising administering to a patient in need thereof a therapeutically effective amount of a Compound of the Invention. In certain embodiments, the Condition is pain (including acute pain, chronic pain (which includes but is not limited to, neuropathic pain, postoperative pain, and inflammatory pain), and surgical pain). The Compounds of the Invention are particularly useful for treating or preventing chronic pain.

In another aspect, the present disclosure provides a pharmaceutical composition comprising a therapeutically effective amount of a Compound of the Invention and one or more pharmaceutically acceptable carriers. Such compositions are useful for treating or preventing a Condition in a patient.

In another aspect, the present disclosure provides Compounds of the Invention for use in treatment or prevention of a disorder responsive to the modulation of one or more opioid receptors. Preferably, the disorder is responsive to modulation of the $\mu$-opioid receptor or the $\kappa$-opioid receptor, or to modulation of a combination thereof.

In another aspect, the present disclosure provides a method of modulating one or more opioid receptors in a patient in need of said modulation, comprising administering to the patient an opioid receptor modulating amount of a Compound of the Invention.

In another aspect, the present disclosure provides Compounds of the Invention for use in treatment or prevention of one or more Conditions in a patient in need of said treatment or prevention.

In another aspect, the present disclosure provides Compounds of the Invention for use in treatment or prevention of pain in a patient, such as acute pain, chronic pain (which includes but is not limited to, neuropathic pain, postoperative pain, and inflammatory pain), or surgical pain.

In another aspect, the present disclosure provides Compounds of the Invention for use in modulation of one or more opioid receptors in a patient.

In another aspect, the present disclosure provides use of Compounds of the Invention in the manufacture of a medicament for treating or preventing a disorder responsive to the modulation of one or more opioid receptors.

In another aspect, the present disclosure provides use of Compounds of the Invention in the manufacture of a medicament for modulating of one or more opioid receptors in a patient. Preferably, the µ- or κ-opioid receptor is modulated, or both the µ- and κ-opioid receptors are modulated.

In another aspect, the present disclosure provides Compounds of the Invention for use as a medicament.

In another aspect, the present disclosure provides use of a Compound of the Invention in the manufacture of a medicament for treating or preventing a Condition in a patient.

In another aspect, the present disclosure provides use of a Compound of the Invention in the manufacture of a medicament for treating or preventing pain in a patient, such as acute pain, chronic pain, or surgical pain.

In another aspect, the present disclosure provides a pharmaceutical composition, comprising a Compound of the Invention for treating or preventing a disorder responsive to the modulation of one or more opioid receptors.

The present invention further provides methods for preparing a pharmaceutical composition, comprising admixing a Compound of the Invention and a pharmaceutically acceptable carrier to form the pharmaceutical composition.

In another aspect, the present invention provides radiolabeled Compounds of the Invention, especially $^1$H, $^{11}$C and $^{14}$C radiolabeled Compounds of the Invention, and the use of such compounds as radioligands to detect binding to an opioid receptor in screening assays.

In another aspect, the present invention provides a method for screening a candidate compound for the ability to bind to an opioid receptor, comprising a) introducing a fixed concentration of a radiolabeled Compound of the Invention to the receptor under conditions that permit binding of the radiolabeled compound to the receptor to form a complex; b) titrating the complex with a candidate compound; and c) determining the binding of the candidate compound to said receptor.

In a further aspect, the invention relates to a kit, comprising a sterile container containing an effective amount of a Compound of the Invention and instructions for therapeutic use.

In a further aspect, the present invention provides a method of making Compounds of the Invention.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Certain Compounds of the Invention are useful for modulating a pharmacodynamic response from one or more opioid receptors (µ, ε, κ, ORL-1) either centrally or peripherally, or both. The pharmacodynamic response may be attributed to the compound either stimulating (agonizing) or inhibiting (antagonizing) the one or more receptors. Certain Compounds of the Invention may antagonize one opioid receptor, while also agonizing one or more other receptors. Compounds of the Invention having agonist activity may be either full or partial agonists.

One aspect of the invention is based on the use of certain Compounds of the Invention as synthesis intermediates.

In one embodiment, Compounds of the Invention are compounds represented by Formula I-A:

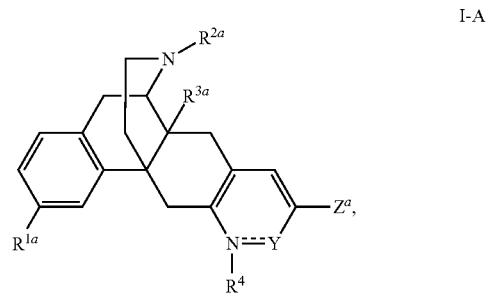

I-A and the pharmaceutically acceptable salts and solvates thereof, wherein:

$R^{1a}$ is hydrogen, hydroxy, halo, cyano, carboxy, or aminocarbonyl; or alkyl, alkenyl, alkynyl, alkoxy, alkenyloxy or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups; or —O-PG, wherein PG is a hydroxyl protecting group;

$R^{2a}$ is (a) hydrogen or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups;

$R^{3a}$ is hydrogen, hydroxy, or halo; or alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups;

is a single bond or a double bond;

R$^4$ is absent, hydrogen or alkyl;

Y is C(=O) or COR$^{4a}$; wherein

R$^{4a}$ is hydrogen or alkyl; provided that 1) when R$^4$ is hydrogen or alkyl, then is a single bond and Y is C(=P); and 2) when R$^4$ is absent, then is a double bond and Y is COR$^{4a}$;

Z$^a$ is —C(=O)R$^{5a}$, wherein

R$^{5a}$ is selected from the group consisting of (a) OH;

(b) optionally substituted alkoxy;

(c) —NR$^{6a}$R$^{7a}$;

(d) optionally substituted aryl;

(e) optionally substituted heteroaryl;

(f) optionally substituted cycloalkyl;

(g) optionally substituted cycloalkenyl (h) optionally substituted heterocyclo;

(i) optionally substituted arylalkyl;

(j) optionally substituted heteroarylalkyl;

(k) optionally substituted (cycloalkyl)alkyl;

(l) optionally substituted (cycloalkenyl)alkyl; and (m) optionally substituted (heterocyclo)alkyl; wherein two adjacent carbon atoms of said optionally substituted cycloalkyl and optionally substituted cycloalkenyl rings are optionally fused to a phenyl ring; and wherein R$^{6a}$ is hydrogen or alkyl;

R$^{7a}$ is selected from the group consisting of hydrogen, optionally substituted carboxyalkyl, optionally substituted (alkoxycarbonyl)alkyl, optionally substituted (carboxamido)alkyl, hydroxyalkyl, alkyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein two adjacent carbon atoms of said cycloalkyl and cycloalkenyl rings are optionally fused to a phenyl ring; and wherein said cycloalkyl, cycloalkenyl, heterocyclo, aryl and heteroaryl, and said cycloalkyl, cycloalkenyl, heterocyclo, aryl and heteroaryl portions are optionally substituted with 1, 2, or 3 independently selected R$^{8a}$ groups; or R$^{6a}$ and R$^{7a}$ together with the nitrogen atom to which they are attached form an optionally substituted heterocyclic ring; and each R$^{8a}$ is independently selected from the group consisting of hydroxy, halo, alkyl, haloalkyl, cyano, nitro, amino, alkylamino, dialkylamino, carboxy, alkoxy, and alkoxycarbonyl.

In another embodiment, Compounds of the Invention are compounds represented by Formula I-A, and the pharmaceutically acceptable salts and solvates thereof, wherein is a single bond, R$^4$ is hydrogen or alkyl, and Y is C(=O).

In another embodiment, Compounds of the Invention are compounds represented by Formula I-A, and the pharmaceutically acceptable salts and solvates thereof, wherein is a double bond, R$^4$ is absent, Y is COR$^{4a}$, and R$^{4a}$ is hydrogen or alkyl.

In another embodiment, Compounds of the Invention are compounds of Formula I-A, and the pharmaceutically acceptable salts and solvates thereof, wherein is a single bond;

R$^4$ is hydrogen or alkyl;

Y is C(=O);

R$^{5a}$ is selected from the group consisting of (a) OH;

(b) optionally substituted alkoxy; and (c) —NR$^{6a}$R$^{7a}$; wherein

R$^{6a}$ is hydrogen or alkyl;

R$^{7a}$ is selected from the group consisting of hydrogen, optionally substituted carboxyalkyl, optionally substituted (alkoxycarbonyl)alkyl, optionally substituted (carboxamido)alkyl, and hydroxyalkyl; and each R$^{8a}$ is independently selected from the group consisting of hydroxy, haloalkyl, amino, alkylamino, dialkylamino, carboxy, alkoxy, and alkoxycarbonyl; and R$^{1a}$—R$^{3a}$, and R$^4$ are as defined in connection with Formula I-A.

In another embodiment, Compounds of the Invention are compounds represented by Formula I:

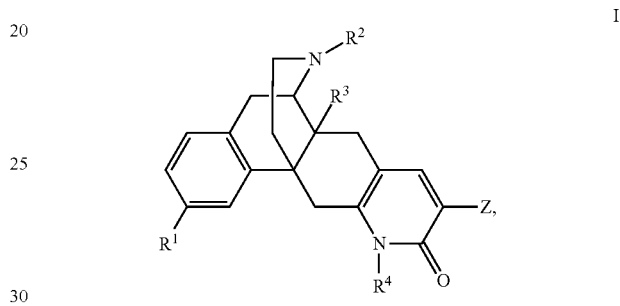

and the pharmaceutically acceptable salts and solvates thereof, wherein:

R$^1$ is hydrogen, OH, halo, cyano, carboxy, or aminocarbonyl; or alkyl, alkenyl, alkynyl, alkoxy, alkenyloxy or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected R$^8$ groups; or —O-PG, wherein PG is a hydroxyl protecting group;

R$^2$ is (a) hydrogen or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected R$^8$ groups;

R$^3$ is hydrogen, OH, or halo; or alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected R$^8$ groups;

$R^4$ is hydrogen or alkyl;
$Z$ is —C(=O)$R^5$, wherein
$R^5$ is selected from the group consisting of
(a) OH;
(b) optionally substituted alkoxy; and
(c) —N$R^6R^7$, wherein
$R^6$ is hydrogen or alkyl;
$R^7$ is hydrogen, optionally substituted carboxyalkyl, optionally substituted (alkoxycarbonyl)alkyl, optionally substituted (carboxamido)alkyl, or hydroxyalkyl; or
$R^6$ and $R^7$ together with the nitrogen atom to which they are attached form an optionally substituted heterocyclic ring; and
each $R^8$ is independently selected from the group consisting of hydroxy, alkyl, haloalkyl, amino, alkylamino, dialkylamino, carboxy, alkoxy, and alkoxycarbonyl.

In another embodiment, Compounds of the Invention are compounds represented by Formula II-A:

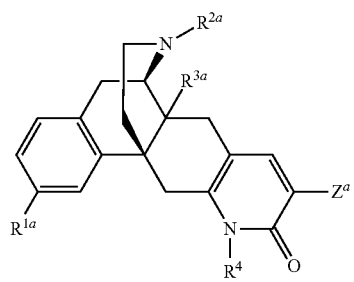

II-A and the pharmaceutically acceptable salts and solvates thereof, wherein $R^{1a}$—$R^{3a}$, $R^4$, and $Z^a$ are as defined for Formula I-A.

In another embodiment, Compounds of the Invention are compounds represented by Formula II:

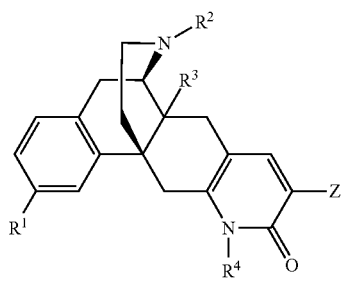

II and the pharmaceutically acceptable salts and solvates thereof, wherein $R^1$—$R^4$ and $Z$ are as defined for Formula I.

In another embodiment, Compounds of the Invention are compounds represented by Formula III-A:

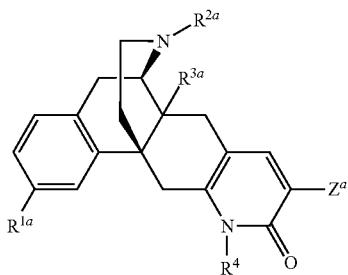

III-A and the pharmaceutically acceptable salts and solvates thereof, wherein $R^{1a}$—$R^{3a}$, $R^4$, and $Z^a$ are as defined for Formula I-A.

In another embodiment, Compounds of the Invention are compounds represented by Formula III:

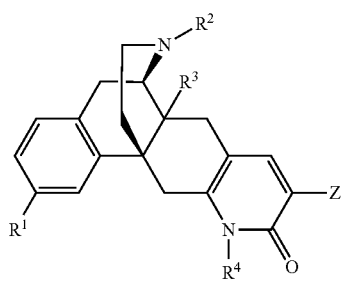

III and the pharmaceutically acceptable salts and solvates thereof, wherein $R^1$—$R^4$ and $Z$ are as defined for Formula I.

In another embodiment, Compounds of the Invention are compounds represented by Formula IV-A:

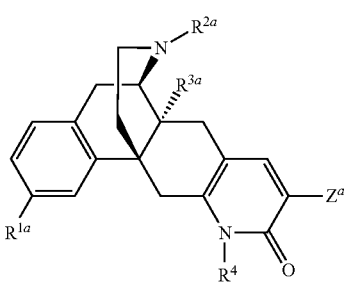

IV-A and the pharmaceutically acceptable salts and solvates thereof, wherein $R^{1a}$—$R^{3a}$, $R^4$, and $Z^a$ are as defined for Formula I-A.

In another embodiment, Compounds of the Invention are compounds represented by Formula IV:

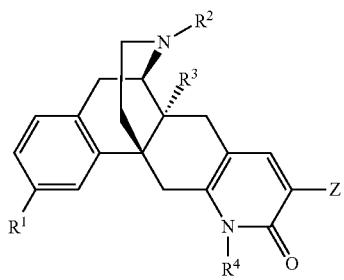

IV and the pharmaceutically acceptable salts and solvates thereof, wherein $R^1$—$R^4$ and $Z$ are as defined for Formula I.

In another embodiment, Compounds of the Invention are compounds represented by Formula V-A:

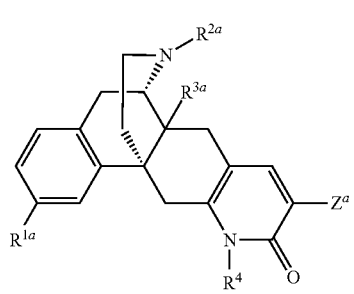

V-A and the pharmaceutically acceptable salts and solvates thereof, wherein $R^{1a}$—$R^{3a}$, $R^4$, and $Z^a$ are as defined for Formula I-A.

In another embodiment, Compounds of the Invention are compounds represented by Formula V:

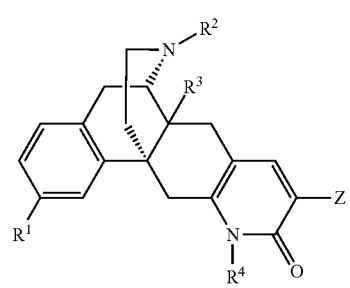

V and the pharmaceutically acceptable salts and solvates thereof, wherein $R^1$—$R^4$ and Z are as defined for Formula I.

In another embodiment, Compounds of the Invention are compounds represented by Formula VI-A:

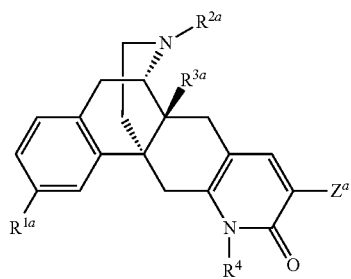

VI-A and the pharmaceutically acceptable salts and solvates thereof, wherein $R^{1a}$—$R^{3a}$, $R^4$, and $Z^a$ are as defined for Formula I-A.

In another embodiment, Compounds of the Invention are compounds represented by Formula VI:

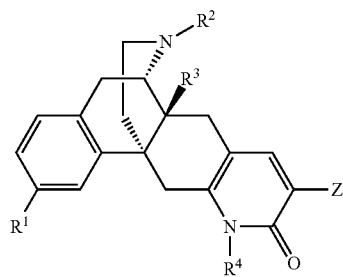

VI and the pharmaceutically acceptable salts and solvates thereof, wherein $R^1$—$R^4$ and Z are as defined for Formula I.

In another embodiment, Compounds of the Invention are compounds represented by Formula VII-A:

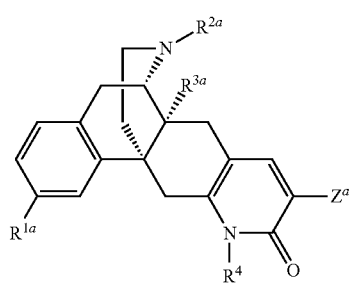

VII-A and the pharmaceutically acceptable salts and solvates thereof, wherein $R^{1a}$—$R^{3a}$, $R^4$, and $Z^a$ are as defined for Formula I-A.

In another embodiment, Compounds of the Invention are compounds represented by Formula VII:

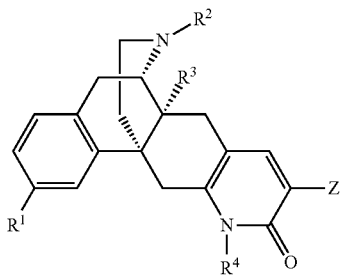

VII and the pharmaceutically acceptable salts and solvates thereof, wherein $R^1$—$R^4$ and Z are as defined for Formula I.

In another embodiment, Compounds of the Invention are compounds represented by Formula VIII-A:

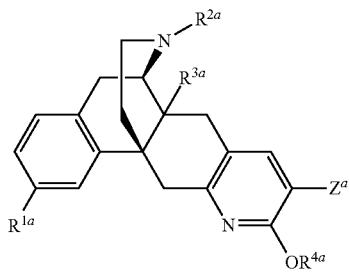

VIII-A and the pharmaceutically acceptable salts and solvates thereof, wherein $R^{1a}$—$R^{4a}$, and $Z^a$ are as defined for Formula I-A.

In another embodiment, Compounds of the Invention are compounds represented by any one of Formula I-A, II-A, III-A, IV-A, V-A, VI-A, VII-A, or VIII-A (referred to collectively as "Formulae I-A-VIII-A"), wherein $R^{1a}$ is H, hydroxy, halo, cyano, carboxy, or aminocarbonyl (i.e., —C(=O)NH$_2$). In another embodiment, $R^{1a}$ is hydroxy.

In another embodiment, Compounds of the Invention are compounds of any one of Formulae I-VII, wherein $R^1$ is H, OH, halo, cyano, carboxy, or aminocarbonyl (i.e., —C(=O)NH$_2$). In another embodiment, $R^1$ is OH.

In another embodiment, Compounds of the Invention are compounds of any one of Formulae I-A-VIII-A, wherein $R^{1a}$ is alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

In another embodiment, Compounds of the Invention are compounds of any one of Formulae I-A-VIII-A, wherein $R^{1a}$ is $C_{1-6}$ alkyl, $C_{2-6}$ alkenyl, $C_{2-6}$ alkynyl, $C_{1-6}$ alkoxy, $C_{2-6}$ alkenyloxy, or $C_{2-6}$ alkynyloxy, any of which is optionally substituted with 1, 2, or 3 substituents, each independently selected from the group consisting of hydroxy, halo, halo($C_{1-6}$)alkyl, amino, $C_{1-6}$ alkylamino, di($C_{1-6}$)alkylamino, carboxy, $C_{1-6}$ alkoxy, $C_{1-6}$ alkoxycarbonyl, $C_{6-10}$ aryl, 5- or 6-membered heteroaryl, 5- or 6-membered heterocyclo, $C_{3-7}$ cycloalkyl, and $C_{3-7}$ cycloalkenyl, wherein said aryl, heteroaryl, heterocyclo, cycloalkyl, and cycloalkenyl are optionally substituted with 1, 2, or 3 independently selected $R^{8a}$ groups. Useful $R^{8a}$ groups include hydroxy, halo, $C_{1-6}$ alkyl, halo($C_{1-6}$)alkyl, cyano, nitro, amino, $C_{1-6}$ alkylamino, di($C_{1-6}$)alkylamino, carboxy, $C_{1-6}$ alkoxy, and $C_{1-6}$ alkoxycarbonyl, and preferably hydroxy, halo, $C_{1-4}$ alkyl, halo($C_{1-4}$)alkyl, cyano, nitro, amino, $C_{1-4}$ alkylamino, di($C_{1-4}$)alkylamino, carboxy, $C_{1-4}$ alkoxy, and $C_{1-4}$ alkoxycarbonyl.

In another embodiment, Compounds of the Invention are compounds of any one of Formulae I-A-VIII-A, wherein $R^{1a}$ is $C_{1-6}$ alkoxy, $C_{2-6}$ alkenyloxy, or $C_{2-6}$ alkynyloxy, any of which are optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

In another embodiment, Compounds of the Invention are compounds of any one of Formulae I-A-VIII-A, wherein $R^{1a}$ is unsubstituted $C_{1-6}$ alkoxy, unsubstituted $C_{2-6}$ alkenyloxy, or unsubstituted $C_{2-6}$ alkynyloxy.

In another embodiment, Compounds of the Invention are compounds of any one of Formulae I-A-VIII-A, wherein $R^{1a}$ is unsubstituted methoxy, ethoxy, n-propoxy, iso-propoxy, n-butoxy, tert-butoxy, iso-butoxy, or sec-butoxy, and advantageously $R^{1a}$ is unsubstituted methoxy.

In another embodiment, Compounds of the Invention are compounds of any one of Formulae I-A-VIII-A, wherein $R^{1a}$ is unsubstituted ethenoxy, propenoxy, isopropenoxy, butenoxy, or sec-butenoxy. In another embodiment, $R^{1a}$ is unsubstituted ethynoxy, propynoxy, butynoxy, or 2-butynoxy.

In another embodiment, Compounds of the Invention are compounds of any one of Formulae I-VII, wherein $R^1$ is alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^8$ groups. In another embodiment, $R^1$ is $C_{1-6}$ alkyl, $C_{2-6}$ alkenyl, $C_{2-6}$ alkynyl, $C_{1-6}$ alkoxy, $C_{2-6}$ alkenyloxy, or $C_{2-6}$ alkynyloxy, any of which is optionally substituted with 1, 2, or 3 substituents, each independently selected from the group consisting of hydroxy, halo, halo($C_{1-6}$)alkyl, amino, $C_{1-6}$ alkylamino, di($C_{1-6}$)alkylamino, carboxy, $C_{1-6}$ alkoxy, $C_{1-6}$ alkoxycarbonyl, $C_{6-10}$ aryl, 5- or 6-membered heteroaryl, 5- or 6-membered heterocyclo, $C_{3-7}$ cycloalkyl, and $C_{3-7}$ cycloalkenyl, wherein said aryl, heteroaryl, heterocyclo, cycloalkyl, and cycloalkenyl are optionally substituted with 1, 2, or 3 independently selected $R^8$ groups. Useful $R^8$ groups include hydroxy, $C_{1-6}$ alkyl, halo($C_{1-6}$)alkyl, amino, $C_{1-6}$ alkylamino, di($C_{1-6}$)alkylamino, carboxy, $C_{1-6}$ alkoxy, and $C_{1-6}$ alkoxycarbonyl, and preferably hydroxy, $C_{1-4}$ alkyl, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In another embodiment, $R^1$ is $C_{1-6}$ alkoxy, $C_{2-6}$ alkenyloxy, or $C_{2-6}$ alkynyloxy, any of which are optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In another embodiment, $R^1$ is unsubstituted $C_{1-6}$ alkoxy, substituted $C_{2-6}$ alkenyloxy, or unsubstituted $C_{2-6}$ alkynyloxy. In another embodiment, $R^1$ is unsubstituted methoxy, ethoxy, n-propoxy, iso-propoxy, n-butoxy, tert-butoxy, iso-butoxy, or sec-butoxy, and advantageously $R^1$ is unsubstituted methoxy. In another embodiment, $R^1$ is unsubstituted ethenoxy, propenoxy, isopropenoxy, butenoxy, or sec-butenoxy. In another embodiment, $R^1$ is unsubstituted ethynoxy, propynoxy, butynoxy, or 2-butynoxy.

In another embodiment, Compounds of the Invention are compounds of any one of Formulae I-A-VIII-A, wherein $R^{1a}$ is unsubstituted $C_{1-6}$ alkoxy or hydroxy, and preferably unsubstituted $C_{1-4}$ alkoxy or hydroxy.

In another embodiment, Compounds of the Invention are compounds of any one of Formulae I-VII, wherein $R^1$ is unsubstituted $C_{1-6}$ alkoxy or OH, and preferably substituted $C_{1-4}$ alkoxy or OH.

In another embodiment, Compounds of the Invention are compounds of any one of Formulae I-A-VIII-A, wherein $R^{2a}$ is hydrogen or carboxamido. In this aspect of the invention, preferably $R^{2a}$ is hydrogen, —CONH$_2$, —CON(H)C$_{1-4}$ alkyl, —CON(C$_{1-4}$ alkyl)$_2$, or —CON(H)Ph, and more preferably $R^{2a}$ is hydrogen.

In another embodiment, Compounds of the Invention are compounds of any one of Formulae I-VII, wherein $R^2$ is hydrogen or carboxamido. In this aspect of the invention, preferably $R^2$ is hydrogen, —CONH$_2$, —CON(H)C$_{1-4}$ alkyl, —CON(C$_{1-4}$ alkyl)$_2$, or —CON(H)Ph, and more preferably $R^2$ is hydrogen.

In another embodiment, Compounds of the Invention are compounds of any one of Formulae I-A-VIII-A, wherein $R^{2a}$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl or (heteroarylalkoxy) carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

In another embodiment, Compounds of the Invention are compounds of any one of Formulae I-A-VIII-A, wherein $R^{2a}$ is C$_{1-6}$ alkyl, C$_{2-6}$ alkenyl, C$_{2-6}$ alkynyl, C$_{3-7}$ cycloalkyl, C$_{3-7}$ cycloalkenyl, 5- or 6-membered heterocyclo, C$_{6-10}$ aryl, 5- or 6-membered heteroaryl, C$_{3-7}$ cycloalkyl(C$_{1-4}$)alkyl, C$_{3-7}$ cycloalkenyl(C$_{1-4}$)alkyl, 5- or 6-membered heterocyclo(C$_{1-4}$)alkyl, C$_{6-10}$ aryl(C$_{1-4}$)alkyl, 5- or 6-membered heteroaryl(C$_{1-4}$)alkyl, C$_{1-6}$ alkylcarbonyl, C$_{1-6}$ alkoxycarbonyl, C$_{6-10}$ aryl(C$_{1-4}$)alkoxycarbonyl, or 5- or 6-membered heteroaryl(C$_{1-4}$)alkoxycarbonyl, any of which is optionally substituted with 1, 2, or 3 substituents, each independently selected from the group consisting of hydroxy, C$_{1-6}$ alkyl, halo, halo(C$_{1-6}$)alkyl, amino, C$_{1-6}$ alkylamino, di(C$_{1-6}$)alkylamino, carboxy, alkoxy, C$_{1-6}$ alkoxycarbonyl, C$_{6-10}$ aryl, 5- or 6-membered heteroaryl, 5- or 6-membered heterocyclo, C$_{3-7}$ cycloalkyl, and C$_{3-7}$ cycloalkenyl, wherein said aryl, heteroaryl, heterocyclo, cycloalkyl, and cycloalkenyl are optionally substituted with 1, 2, or 3 independently selected $R^{8a}$ groups. Useful $R^{8a}$ groups are those described above in connection with $R^{1a}$.

In another embodiment, Compounds of the Invention are compounds of any one of Formulae I-A-VIII-A, wherein $R^{2a}$ is C$_{1-6}$ alkyl, C$_{2-6}$ alkenyl, C$_{2-6}$ alkynyl, C$_{3-7}$ cycloalkyl, C$_{3-7}$ cycloalkenyl, 5- or 6-membered heterocyclo, C$_{6-10}$ aryl, 5- or 6-membered heteroaryl, C$_{3-7}$ (cycloalkyl)(C$_{1-4}$)alkyl, C$_{3-7}$ (cycloalkenyl)(C$_{1-4}$)alkyl, 5- or 6-membered heterocyclo(C$_{1-4}$)alkyl, C$_{6-10}$ aryl(C$_{1-4}$)alkyl, 5- or 6-membered heteroaryl(C$_{1-4}$)alkyl, C$_{1-4}$ alkylcarbonyl, C$_{1-4}$ alkoxycarbonyl, C$_{6-10}$ aryl(C$_{1-4}$)alkoxycarbonyl, or 5- or 6-membered heteroaryl(C$_{1-4}$)alkoxycarbonyl, any of which is optionally substituted with 1, 2, or 3 substituents, each independently selected from the group consisting of hydroxy, C$_{1-4}$ alkyl, halo, halo(C$_{1-4}$)alkyl, amino, C$_{1-4}$ alkylamino, di(C$_{1-4}$)alkylamino, carboxy, C$_{1-4}$ alkoxy, and C$_{1-4}$ alkoxycarbonyl, and preferably optionally substituted with 1 or 2 substituents, each independently selected from the group consisting of hydroxy, methyl, ethyl, halo, trifluoromethyl, amino, methylamino, ethylamino, dimethylamino, diethylamino, carboxy, methoxy, ethoxy, methoxycarbonyl, and ethoxycarbonyl. In another embodiment, $R^{2a}$ is alkyl, alkenyl, or alkynyl, any of which is optionally substituted with 1, 2, or 3 substituents, each independently selected from the group consisting of hydroxy, halo, haloalkyl, carboxy, alkoxy, alkoxycarbonyl, aryl, heteroaryl, heterocyclo, and cycloalkyl, wherein said aryl, heteroaryl, heterocyclo, and cycloalkyl, are optionally substituted with 1, 2, or 3 independently selected $R^{8a}$ groups. In another embodiment, $R^{2a}$ is selected from the group consisting of —CH$_3$, —CH$_2$CH$_3$, benzyl, —CH$_2$CH$_2$—C$_6$H$_5$, —(CH$_2$)$_4$—C$_6$H$_5$, —CH$_2$CH=CH—C$_6$H$_5$, —CH$_2$CF$_3$, —CH$_2$CH$_2$CF$_3$, —CH$_2$CH$_2$CH$_2$CF$_3$, —CH$_2$CHF$_2$, —CH$_2$C$_6$H$_{11}$, —CH$_2$—C$_3$H$_5$, —CH$_2$-tetrahydropyran, —CH$_2$CHC(CH$_3$)$_2$, and —CH$_2$CH$_2$C(=CH$_2$)(CH$_3$).

In another embodiment, Compounds of the Invention are compounds of any one of Formulae I-A-VIII-A, wherein $R^{2a}$ is unsubstituted C$_{1-6}$ alkyl, and preferably unsubstituted C$_{1-4}$ alkyl, such as methyl, ethyl, n-propyl, iso-propyl, n-butyl, or tert-butyl, and more preferably methyl or ethyl.

In another embodiment, Compounds of the Invention are compounds of any one of Formulae I-A-VIII-A, wherein $R^{2a}$ is C$_{3-7}$ (cycloalkyl)(C$_{1-4}$)alkyl or C$_{3-7}$ (cycloalkenyl)(C$_{1-4}$) alkyl, and especially C$_{3-7}$ (cycloalkyl)(C$_{1-4}$)alkyl, such as cyclopropyl(C$_{1-4}$)alkyl, cyclobutyl(C$_{1-4}$)alkyl, cyclopentyl (C$_{1-4}$)alkyl, or cyclohexyl(C$_{1-4}$)alkyl, optionally substituted with 1, 2, or 3 substituents, each independently selected from the group consisting of hydroxy, C$_{1-4}$ alkyl, halo, halo(C$_{1-4}$) alkyl, amino, C$_{1-4}$ alkylamino, di(C$_{1-4}$)alkylamino, carboxy, C$_{1-4}$ alkoxy, and C$_{1-4}$ alkoxycarbonyl, and preferably optionally substituted with 1 or 2 substituents, each independently selected from the group consisting of hydroxy, methyl, ethyl, halo, trifluoromethyl, amino, methylamino, ethylamino, dimethylamino, diethylamino, carboxy, methoxy, ethoxy, methoxycarbonyl, and ethoxycarbonyl. Preferably, $R^{2a}$ is unsubstituted cyclopropyl(C$_{1-4}$)alkyl. In another embodiment, $R^{2a}$ is unsubstituted cyclohexyl(C$_{1-4}$)alkyl, such as cyclohexylmethyl.

In another embodiment, Compounds of the Invention are compounds of any one of Formulae I-A-VIII-A, wherein $R^{2a}$ is unsubstituted (cyclopropyl)methyl, 2-(cyclopropyl)ethyl or 3-(cyclopropyl)propyl.

In another embodiment, Compounds of the Invention are compounds of any one of Formulae I-A-VIII-A, wherein $R^{2a}$ is C$_{1-6}$ alkyl, and preferably C$_{1-4}$ alkyl, substituted with 1, 2, or 3 substituents selected from the group consisting of halo (such as fluoro), halo(C$_{1-4}$)alkyl (such as, for example, trifluoro(C$_{1-2}$)alkyl), phenyl, and heterocyclo (such as tetrahydropyranyl). In one embodiment of this aspect of the invention, $R^{2a}$ is benzyl, phenethyl, 3-phenylpropyl, tetrahydropyran-4-ylmethyl, 2,2,2-trifluoroethyl, 2-fluoroethyl, 3,3,3-trifluoropropyl, 4,4,4-trifluorobutyl, or 2,2-difluoroethyl.

In another embodiment, Compounds of the Invention are compounds of any one of Formulae I-A-VIII-A, wherein $R^{2a}$ is C$_{2-6}$ alkenyl, and preferably C$_{2-4}$ alkenyl, which is unsubstituted or substituted with 1, 2, or 3 substituents selected from the group consisting of C$_{1-4}$ alkyl (such as methyl), halo (such as fluoro), halo(C$_{1-4}$)alkyl (such as, for example, trifluoro(C$_{1-2}$)alkyl), phenyl, and heterocyclo (such as tetrahydropyranyl). In one embodiment of this aspect of the invention, $R^{2a}$ is 3-methyl-but-2-enyl, 3-methylbut-3-enyl, or 4-phenylbut-2-enyl.

In another embodiment, Compounds of the Invention are compounds of any one of Formulae I-VII, wherein $R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^8$ groups. In one embodiment, $R^2$ is $C_{1-6}$ alkyl, $C_{2-6}$ alkenyl, $C_{2-6}$ alkynyl, $C_{3-7}$ cycloalkyl, $C_{3-7}$ cycloalkenyl, 5- or 6-membered heterocyclo, $C_{6-10}$ aryl, 5- or 6-membered heteroaryl, $C_{3-7}$ cycloalkyl($C_{1-4}$)alkyl, $C_{3-7}$ cycloalkenyl($C_{1-4}$)alkyl, 5- or 6-membered heterocyclo($C_{1-4}$)alkyl, aryl($C_{1-4}$)alkyl, 5- or 6-membered heteroaryl($C_{1-4}$)alkyl, $C_{1-6}$ alkylcarbonyl, $C_{1-6}$ alkoxycarbonyl, $C_{6-10}$ aryl($C_{1-4}$)alkoxycarbonyl, or 5- or 6-membered heteroaryl($C_{1-4}$)alkoxycarbonyl, any of which is optionally substituted with 1, 2, or 3 substituents, each independently selected from the group consisting of hydroxy, $C_{1-6}$ alkyl, talo, halo($C_{1-6}$)alkyl, amino, $C_{1-6}$ alkylamino, di($C_{1-6}$)alkylamino, carboxy, $C_{1-6}$ alkoxy, $C_{1-6}$ alkoxycarbonyl, $C_{6-10}$ aryl, 5- or 6-membered heteroaryl, 5- or 6-membered heterocyclo, $C_{3-7}$ cycloalkyl, and $C_{3-7}$ cycloalkenyl, wherein said aryl, heteroaryl, heterocyclo, cycloalkyl, and cycloalkenyl are optionally substituted with 1, 2, or 3 independently selected $R^8$ groups. Useful $R^8$ groups are those described above in connection with $R^1$. In another embodiment, $R^2$ is $C_{1-6}$ alkyl, $C_{2-6}$ alkenyl, $C_{2-6}$ alkynyl, $C_{3-7}$ cycloalkyl, $C_{3-7}$ cycloalkenyl, 5- or 6-membered heterocyclo, $C_{6-10}$ aryl, 5- or 6-membered heteroaryl, $C_{3-7}$ (cycloalkyl)($C_{1-4}$)alkyl, $C_{3-7}$ (cycloalkenyl)($C_{1-4}$)alkyl, 5- or 6-membered heterocyclo($C_{1-4}$)alkyl, $C_{6-10}$ aryl($C_{1-4}$)alkyl, 5- or 6-membered heteroaryl($C_{1-4}$)alkyl, $C_{1-4}$ alkylcarbonyl, $C_{1-4}$ alkoxycarbonyl, $C_{6-10}$ aryl($C_{1-4}$)alkoxycarbonyl, or 5- or 6-membered heteroaryl($C_{1-4}$)alkoxycarbonyl, any of which is optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of hydroxy, methyl, ethyl, halo, trifluoromethyl, amino, methylamino, ethylamino, dimethylamino, diethylamino, carboxy, methoxy, ethoxy, methoxycarbonyl, and ethoxycarbonyl.

In another embodiment, $R^2$ is $C_{3-7}$ (cycloalkyl)($C_{1-4}$)alkyl or $C_{3-7}$ (cycloalkenyl)($C_{1-4}$)alkyl, and especially $C_{3-7}$ (cycloalkyl)($C_{1-4}$)alkyl, such as cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of hydroxy, methyl, ethyl, halo, trifluoromethyl, amino, methylamino, ethylamino, dimethylamino, diethylamino, carboxy, methoxy, ethoxy, methoxycarbonyl, and ethoxycarbonyl. Preferably, $R^2$ is unsubstituted cyclopropyl($C_{1-4}$)alkyl. In another embodiment, $R^2$ is unsubstituted (cyclopropyl)methyl, 2-(cyclopropyl)ethyl or 3-(cyclopropyl)propyl.

In another embodiment, $R^2$ is unsubstituted $C_{1-6}$ alkyl, and preferably unsubstituted $C_{1-4}$ alkyl, such as methyl, ethyl, n-propyl, iso-propyl, n-butyl, or tert-butyl, and more preferably methyl or ethyl.

In another embodiment, Compounds of the Invention are compounds of any one of Formulae I-A-VIII-A, wherein $R^{3a}$ is hydrogen.

In another embodiment, Compounds of the Invention are compounds of any one of Formulae I-VII, wherein $R^3$ is hydrogen.

In another embodiment. Compounds of the Invention are compounds of any one of Formulae I-A-VIII-A, wherein $R^{3a}$ is hydroxy or halo. In another embodiment, $R^3$ is hydroxy.

In another embodiment, Compounds of the Invention are compounds of any one of Formulae I-VII, wherein $R^3$ is OH or halo. In another embodiment, $R^3$ is OH.

In another embodiment, Compounds of the Invention are compounds of any one of Formulae I-A-VIII-A, wherein $R^{3a}$ is alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

In another embodiment, Compounds of the Invention are compounds of any one of Formulae I-A-VIII-A, wherein $R^{3a}$ is $C_{1-6}$ alkoxy, $C_{1-6}$ alkylamino, or di($C_{1-6}$)alkylamino, any of which is optionally substituted with 1, 2, or 3 substituents, each independently selected from the group consisting of hydroxy, halo, halo($C_{1-6}$)alkyl, amino, $C_{1-6}$ alkylamino, di($C_{1-6}$)alkylamino, carboxy. $C_{1-4}$ alkoxy, $C_{1-6}$ alkoxycarbonyl, $C_{6-10}$ aryl, 5- or 6-membered heteroaryl, 5- or 6-membered heterocyclo, $C_{3-7}$ cycloalkyl, and $C_{3-7}$ cycloalkenyl, wherein said aryl, heteroaryl, heterocyclo, cycloalkyl, and cycloalkenyl are optionally substituted with 1, 2, or 3 independently selected $R^{8a}$ groups. Useful $R^{8a}$ groups are those described above in connection with $R^{1a}$.

In another embodiment, Compounds of the Invention are compounds of any one of Formulae I-A-VIII-A, wherein $R^{1a}$ is unsubstituted $C_{1-6}$ alkoxy or $C_{1-6}$ alkoxy substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

In another embodiment, Compounds of the Invention are compounds of any one of Formulae I-VII, wherein $R^3$ is alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy; alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^8$ groups. In another embodiment, $R^3$ is $C_{1-6}$ alkoxy. $C_{1-6}$ alkylamino, or di($C_{1-6}$)alkylamino, any of which is optionally substituted with 1, 2, or 3 substituents, each independently selected from the group consisting of hydroxy, halo, halo($C_{1-6}$)alkyl, amino, $C_{1-6}$ alkylamino, carboxy, $C_{1-6}$ alkoxy, $C_{1-6}$ alkoxycarbonyl, $C_{6-10}$ aryl, 5- or 6-membered heteroaryl, 5- or 6-membered heterocyclo, $C_{3-7}$ cycloalkyl, and $C_{3-7}$ cycloalkenyl, wherein said aryl, heteroaryl heterocyclo, cycloalkyl, and cycloalkenyl are optionally substituted with 1, 2, or 3 independently selected $R^8$ groups. Useful $R^8$ groups are those described above in connection with $R^1$. In another embodiment, $R^3$ is substituted $C_{1-6}$ alkoxy or $C_{1-6}$ alkoxy substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

In another embodiment, Compounds of the Invention are compounds of any one of Formulae I-A-VII-A and I-VII, wherein $R^4$ hydrogen.

In another embodiment, Compounds of the Invention are compounds of any one of Formulae I-A-VII-A and I-VII, $R^4$ is alkyl, preferably $C_{1-6}$ alkyl, and more preferably $C_{1-4}$ alkyl, such as methyl, ethyl, n-propyl, isopropyl, n-butyl, or tert-butyl, In another embodiment, Compounds of the Invention are compounds of Formula I-A, wherein $R^4$ is absent and $R^{4a}$ is hydrogen or alkyl.

In another embodiment, Compounds of the Invention are compounds of any one of Formulae I-A-VIII-A, wherein $R^{5a}$ is OH.

In another embodiment, Compounds of the Invention are compounds of any one of Formulae I-VII, wherein $R^5$ is OH.

In another embodiment, Compounds of the Invention are compounds of any one of Formulae I-A-VIII-A, wherein $R^{5a}$ is optionally substituted alkoxy. In this aspect of the invention, Compounds of the invention are compounds of any one of Formulae I-A-VIII-A, wherein $R^{5a}$ is unsubstituted $C_{1-6}$ alkoxy or $C_{1-6}$ alkoxy substituted with 1, 2, or 3 substituents, each independently selected from the group consisting of hydroxy, halo, haloalkyl, cyano, nitro, amino, alkylamino, dialkylamino, carboxy, alkoxy, and alkoxycarbonyl. In another embodiment, $R^{5a}$ is unsubstituted $C_{1-4}$ alkoxy, such as methoxy, ethoxy, n-propoxy, iso-propoxy, n-butoxy, or tert-butoxy, or $C_{1-4}$ alkoxy substituted with 1, 2, or 3 substituents, each independently selected from the group consisting of hydroxy, halo, halo($C_{1-4}$)alkyl, cyano, nitro, amino, $C_{1-4}$ alkylamino, di($C_{1-4}$)alkylamino, carboxy, $C_{1-4}$ alkoxy, and $C_{1-4}$ alkoxycarbonyl. In one embodiment, $R^{5a}$ is methoxy, ethoxy, n-propoxy, iso-propoxy, n-butoxy, or tert-butoxy.

In another embodiment, Compounds of the Invention are compounds of any one of Formulae I-VII, wherein $R^5$ is optionally substituted alkoxy. In this aspect of the invention, Compounds of the Invention are compounds of any one of Formulae I-VII, wherein $R^5$ is unsubstituted $C_{1-6}$ alkoxy or $C_{1-6}$ alkoxy substituted with 1, 2, or 3 substituents, each independently selected from the group consisting of hydroxy, halo, haloalkyl, amino, alkylamino, dialkylamino, carboxy, alkoxy, and alkoxycarbonyl. In another embodiment, $R^5$ is unsubstituted $C_{1-4}$ alkoxy, such as methoxy, ethoxy, n-propoxy, iso-propoxy, n-butoxy, or tert-butoxy, or $C_{1-4}$ alkoxy substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In one embodiment, $R^3$ is methoxy, ethoxy, n-propoxy, iso-propoxy, n-butoxy, or tert-butoxy.

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl; and $R^{7a}$ is selected from the group consisting of hydrogen, optionally substituted carboxyalkyl, optionally substituted (alkoxycarbonyl)alkyl, optionally substituted (carboxamido)alkyl, hydroxyalkyl, alkyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein said cycloalkyl, cycloalkenyl, heterocyclo, aryl and heteroaryl, and said cycloalkyl, cycloalkenyl, heterocyclo, aryl and heteroaryl portions are optionally substituted with 1, 2, or 3 independently selected $R^{8a}$ groups.

In another embodiment, Compounds of the Invention are compounds of any one of Formulae I-A-VIII-A, wherein $R^{5a}$ is —$NR^{6a}R^{7a}$, wherein $R^{6a}$ is hydrogen and $R^{7a}$ is as defined in connection with Formula I-A.

In another embodiment, Compounds of the Invention are compounds of any one of Formulae I-A-VIII-A, wherein $R^{5a}$ is —$NR^{6a}R^{7a}$, wherein $R^{6a}$ is alkyl, and preferably $C_{1-6}$ alkyl (such as, for example, methyl, ethyl, propyl, butyl, or 3-methylbutyl) and $R^{7a}$ is as defined in connection with Formula I-A.

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl, and preferably $C_{1-6}$ alkyl, and $R^{7a}$ is hydrogen.

In another embodiment, Compounds of the Invention are compounds of any one of Formulae I-A-VIII-A, wherein —$R^{5a}$ is —$NR^{6a}R^{7a}$, wherein $R^{6a}$ and $R^{7a}$ are both hydrogen.

In another embodiment, Compounds of the Invention are compounds of any one of Formulae I-A-VIII-A, wherein $R^{5a}$ is —$NR^{6a}R^{7a}$, wherein $R^{6a}$ and $R^{7a}$ are each independently alkyl, such as $C_{1-6}$ alkyl (such as, for example, methyl or ethyl).

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl and $R^{7a}$ is selected from the group consisting of optionally substituted carboxyalkyl, optionally substituted (alkoxycarbonyl)alkyl, optionally substituted (carboxamido)alkyl, and hydroxyalkyl. The optional substituents in the carboxyalkyl, (alkoxycarbonyl)alkyl, and (carboxamido)alkyl groups, typically 1, 2, or 3 independently selected substituents, are attached to the alkyl portions of the $R^{7a}$ group. Useful optional substituents in this aspect of the invention are selected from the group consisting of hydroxy, carboxy, amino, aminocarbonyl, alkylaminocarbonyl, dialkylaminocarbonyl, SH, alkylthio, guanidine, aryl, cycloalkyl, cycloalkenyl, heterocyclo and heteroaryl, wherein said aryl, cycloalkyl, cycloalkenyl, heterocyclo, and heteroaryl is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl. In one embodiment, the optional substituents are selected from the group consisting of hydroxy, carboxy, amino, aminocarbonyl, $C_{1-6}$ alkylaminocarbonyl, di($C_{1-6}$)alkylaminocarbonyl, SH, $C_{1-6}$ alkylthio, guanidine, $C_{6-12}$ aryl, $C_{3-7}$ cycloalkyl, $C_{3-7}$ cycloalkenyl, 5- to 10-membered heterocyclo, and 5- to 10-membered heteroaryl, wherein the aryl, cycloalkyl, cycloalkenyl, heterocyclo, and heteroaryl portions are optionally substituted with 1, 2, or 3 substituents, each independently selected from the group consisting of $C_{1-6}$ alkyl, hydroxy, halo, halo($C_{1-6}$)alkyl, amino, $C_{1-6}$ alkylamino, di($C_{1-6}$)alkylamino, carboxy, alkoxy, and $C_{1-6}$ alkoxycarbonyl.

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl, and $R^{7a}$ is selected from the group consisting of unsubstituted carboxyalkyl, unsubstituted (alkoxycarbonyl)alkyl, unsubstituted (carboxamido)alkyl, and hydroxyalkyl.

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl, and $R^{7a}$ is selected from the group consisting of carboxyalkyl, (alkoxycarbonyl)alkyl, and (carboxamido)alkyl, any of which is substituted at the alkyl portion with 1 or 2 substituents independently selected from the group consisting of hydroxy, carboxy, amino, aminocarbonyl, $C_{1-4}$ alkylaminocarbonyl, di($C_{1-4}$)alkylaminocarbonyl, SH, $C_{1-4}$ alkylthio, guanidine, $C_{6-10}$ aryl, $C_{3-6}$ cycloalkyl, $C_{3-6}$ cycloalkenyl, 5- or 6-membered heterocyclo, and 5- or 6-membered heteroaryl, wherein the aryl, cycloalkyl, cycloalkenyl, heterocyclo, and heteroaryl portions are optionally substituted with 1 or 2 substituents, each independently selected from the group consisting of $C_{1-4}$ alkyl, hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl, and $R^{7a}$ is selected from the group consisting of cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein two adjacent carbon atoms of said cycloalkyl and cycloalkenyl rings are optionally fused to a phenyl ring; and wherein said cycloalkyl, cycloalkenyl, heterocyclo, aryl and heteroaryl portions are optionally substituted with 1, 2, or 3 independently selected $R^{8a}$ groups. In one embodiment, $R^{7a}$ is selected from the group consisting of $C_{3-7}$ cycloalkyl, $C_{3-7}$ cycloalkenyl, 3- to 7-membered heterocyclo, $C_{6-14}$ aryl, 5- to 10-membered heteroaryl, ($C_{3-7}$ cycloalkyl)($C_{1-6}$)alkyl, ($C_{3-7}$ cycloalkenyl)($C_{1-6}$)alkyl, (3- to 7-membered heterocyclo)($C_{1-6}$)alkyl, $C_{6-14}$ aryl($C_{1-6}$)alkyl, and (5- to 10-membered heteroaryl)($C_{1-6}$)alkyl, wherein two adjacent carbon atoms of said cycloalkyl and cycloalkenyl rings are optionally fused to a phenyl ring; and wherein said cycloalkyl, cycloalkenyl, heterocyclo, aryl, and heteroaryl portions are optionally substituted with 1, 2, or 3 independently selected $R^{8a}$ groups. In another embodiment, $R^{7a}$ is selected from the group consisting of $C_{3-6}$ cycloalkyl, $C_{3-6}$ cycloalkenyl, 5- or 6-membered heterocyclo, $C_{6-10}$ aryl, 5- or 6-membered heteroaryl, ($C_{3-6}$ cycloalkyl)($C_{1-4}$)alkyl, ($C_{3-6}$ cycloalkenyl)($C_{1-4}$)alkyl, (5- or 6-membered heterocyclo)($C_{1-4}$)alkyl, $C_{6-10}$ aryl($C_{1-4}$)alkyl, and (5- or 6-membered heteroaryl)($C_{1-4}$)alkyl, wherein two adjacent carbon atoms of said cycloalkyl and cycloalkenyl rings are optionally fused to a phenyl ring; and wherein said cycloalkyl, cycloalkenyl, heterocyclo, aryl and heteroaryl portions are optionally substituted with 1, 2, or 3 independently selected $R^{8a}$ groups. In another embodiment, $R^{7a}$ is selected from the group consisting of $C_{3-6}$ cycloalkyl and $C_{3-6}$ cycloalkenyl fused to a phenyl ring, such as 2,3-dihydro-1H-inden-1-yl. Suitable $R^{8a}$ groups are those described in connection with $R^{1a}$.

In another embodiment, Compounds of the Invention are compounds of any one of Formulae I-A-VIII-A, wherein $R^{5a}$ is —$NR^{6a}R^{7a}$, wherein $R^{6a}$ is hydrogen or alkyl, and $R^{7a}$ is selected from the group consisting of cyclohexyl, cyclohexylmethyl, cyclohexylethyl, phenyl, benzyl, phenethyl, and 2,3-dihydro-1H-inden-1-yl, any of which is optionally substituted with 1, 2, or 3 independently selected $R^{8a}$ groups.

In another embodiment, Compounds of the Invention are compounds of any one of Formulae I-VII, wherein $R^5$ is —$NR^6R^7$, wherein $R^6$ is hydrogen or alkyl; and $R^7$ is hydrogen, optionally substituted carboxyalkyl, optionally substituted (alkoxycarbonyl)alkyl, optionally substituted (carboxamido)alkyl, or hydroxyalkyl. The optional substituents, typically 1, 2, or 3 substituents, are attached to the alkyl portions of the $R^7$ group. Useful optional substituents in this aspect of the invention are selected from the group consisting of hydroxy, carboxy, amino, aminocarbonyl, alkylaminocarbonyl, dialkylaminocarbonyl, SH, alkylthio, guanidine, aryl, cycloalkyl, cycloalkenyl, heterocyclo and heteroaryl, wherein the aryl, cycloalkyl, cycloalkenyl, heterocyclo, and heteroaryl portions are optionally substituted with 1, 2, or 3 substituents, each independently selected from the group consisting of hydroxy, halo, haloalkyl, amino, alkylamino, dialkylamino, carboxy, alkoxy, and alkoxycarbonyl. Preferably, the optional substituents are selected from the group consisting of hydroxy, carboxy, amino, aminocarbonyl, $C_{1-6}$ alkylaminocarbonyl, di($C_{1-6}$)alkylaminocarbonyl, SH, $C_{1-6}$ alkylthio, guanidine, $C_{6-12}$ aryl, $C_{3-7}$ cycloalkyl, $C_{3-7}$ cycloalkenyl, 5- to 10-membered heterocyclo, and 5- to 10-membered heteroaryl, wherein the aryl, cycloalkyl, cycloalkenyl, heterocyclo, and heteroaryl portions are optionally substituted with 1, 2, or 3 substituents, each independently selected from the group consisting of hydroxy, halo, halo($C_{1-6}$)alkyl, amino, $C_{1-6}$ alkylamino, di($C_{1-6}$)alkylamino, carboxy, $C_{1-6}$ alkoxy, and $C_{1-6}$ alkoxycarbonyl. More preferably, the alkyl portion of $R^7$ is substituted with 1 or 2 optional substituents selected from the group consisting of hydroxy, carboxy, amino, aminocarbonyl, $C_{1-4}$ alkylaminocarbonyl, di($C_{1-4}$)alkylaminocarbonyl, SH, $C_{1-4}$ alkylthio, guanidine, $C_{6-10}$ aryl, $C_{3-6}$ cycloalkyl, $C_{3-6}$ cycloalkenyl, 5- or 6-membered heterocyclo, and 5- or 6-membered heteroaryl, wherein the aryl, cycloalkyl, cycloalkenyl, heterocyclo, and heteroaryl portions are optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

In one embodiment of this aspect of the invention, $R^6$ is hydrogen or $C_{1-6}$ alkyl and $R^7$ is hydrogen. In another embodiment, $R^6$ and $R^7$ are both hydrogen.

In another embodiment, $Z^a$ is selected from the group consisting of

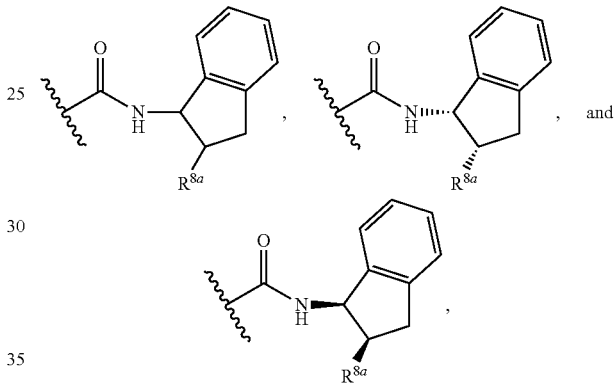

wherein $R^{8a}$ is as defined above in connection with Formula I-A.

In another embodiment, Compounds of the Invention are compounds of any one of Formulae I-A-VIII-A, wherein $Z^a$ is selected from the group consisting of

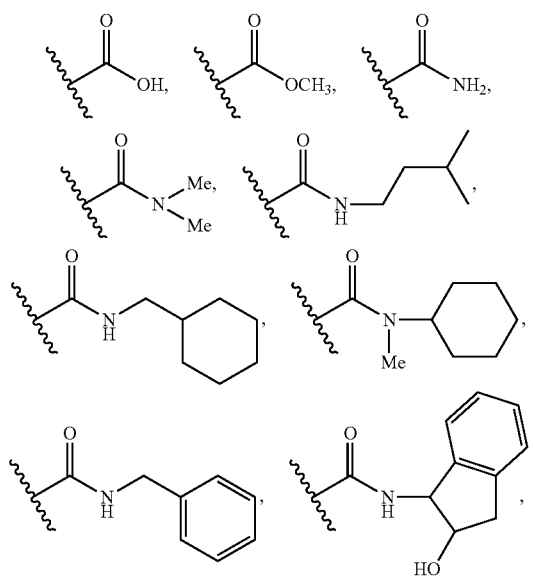

-continued

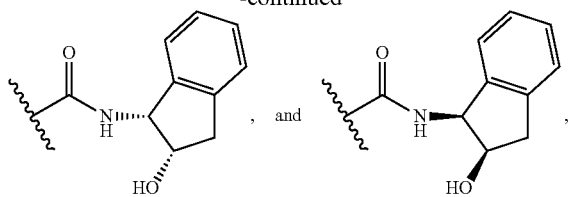

In another embodiment, Compounds of the Invention are compounds of any one of Formulae I-VII, wherein Z is selected from the group consisting of

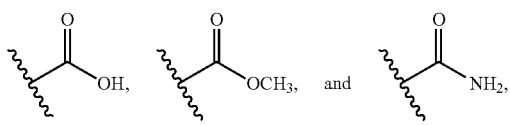

In another embodiment, Compounds of the Invention are compounds of any one of Formulae I-A-VIII-A, wherein $R^{5a}$ is $-NR^{6a}R^{7a}$, $R^{6a}$ is hydrogen or $C_{1-6}$ alkyl, and $R^{7a}$ is optionally substituted carboxy($C_{1-6}$)alkyl, optionally substituted ($C_{1-6}$ alkoxycarbonyl)($C_{1-6}$)alkyl, or optionally substituted (carboxamido)($C_{1-6}$)alkyl, and preferably $R^{7a}$ is optionally substituted carboxy($C_{1-6}$)alkyl, optionally substituted ($C_{1-4}$ alkoxycarbonyl)($C_{1-6}$)alkyl, or optionally substituted (carboxamido)($C_{1-6}$)alkyl. In this aspect of the invention, preferably $R^{7a}$ is $-CHR^{9a}-C(=O)-Z^{1a}$, wherein $R^{9a}$ is selected from the group consisting of hydrogen, alkyl, hydroxyalkyl, carboxyalkyl, aminoalkyl, (aminocarbonyl)alkyl, (alkylaminocarbonyl)alkyl, (dialkylaminocarbonyl)alkyl, mercaptoalkyl, (alkylthio)alkyl, guanidinoalkyl, arylalkyl, (cycloalkyl)alkyl, (cycloalkenyl)alkyl, (heterocyclo)alkyl, and (heteroaryl)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, alkyl, haloalkyl, cyano, nitro, amino, alkylamino, dialkylamino, carboxy, alkoxy, and alkoxycarbonyl; and $Z^{1a}$ is $OR^{10a}$ or $NR^{11a}R^{12a}$, wherein $R^{10a}$ is hydrogen or alkyl; and $R^{11a}$ and $R^{12a}$ are each independently selected from the group consisting of hydrogen and alkyl.

Typically, $R^{9a}$ is selected from the group consisting of hydrogen, $C_{1-6}$ alkyl, monohydroxy($C_{1-6}$)alkyl, carboxy($C_{1-6}$)alkyl, amino($C_{1-6}$)alkyl, (aminocarbonyl)($C_{1-6}$)alkyl, ($C_{1-4}$ alkylaminocarbonyl)($C_{1-6}$)alkyl, (di($C_{1-4}$)alkylaminocarbonyl)($C_{1-6}$)alkyl, mercapto($C_{1-6}$)alkyl, ($C_{1-4}$ alkylthio)($C_{1-6}$)alkyl, guanidino($C_{1-6}$)alkyl, $C_{6-12}$ aryl($C_{1-6}$)alkyl, ($C_{3-7}$ cycloalkyl)($C_{1-6}$)alkyl, ($C_{3-7}$ cycloalkenyl)($C_{1-6}$)alkyl, (5- or 6-membered heterocyclo)($C_{1-6}$)alkyl, and (5- or 6-membered heteroaryl)($C_{1-6}$)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, $C_{1-4}$ alkyl, halo($C_{1-4}$)alkyl, cyano, nitro, amino, $C_{1-4}$ alkylamino, di($C_{1-4}$)alkylamino, carboxy, $C_{1-4}$ alkoxy, and $C_{1-4}$ alkoxycarbonyl. In another embodiment, $R^{9a}$ is selected from the group consisting of $C_{1-4}$ alkyl, monohydroxy($C_{1-4}$)alkyl, carboxy($C_{1-4}$)alkyl, amino($C_{1-4}$)alkyl, (aminocarbonyl)($C_{1-4}$)alkyl, alkylaminocarbonyl)($C_{1-4}$) alkyl, (di($C_{1-2}$)alkylaminocarbonyl)($C_{1-4}$)alkyl, mercapto ($C_{1-4}$)alkyl, ($C_{1-2}$ alkylthio)($C_{1-4}$)alkyl, guanidino($C_{1-4}$) alkyl, $C_{6-10}$ aryl($C_{1-4}$)alkyl, ($C_{3-6}$ cycloalkyl)($C_{1-4}$)alkyl, ($C_{3-6}$ cycloalkenyl)($C_{1-4}$)alkyl, (5- or 6-membered heterocyclo)($C_{1-4}$)alkyl, and (5- or 6-membered heteroaryl)($C_{1-4}$) alkyl, wherein the aryl, cycloalkyl, cycloalkenyl, heterocyclo, and heteroaryl portions are optionally substituted with 1, 2, or 3 substituents, each independently selected from the group consisting of hydroxy, halo, $C_{1-2}$ alkyl, halo($C_{1-2}$)alkyl, cyano, nitro, amino, $C_{1-2}$ alkylamino, di($C_{1-2}$)alkylamino, carboxy, $C_{1-2}$ alkoxy, and $C_{1-2}$ alkoxycarbonyl. In another embodiment, $R^{9a}$ is selected from the group consisting of $C_{1-4}$ alkyl, carboxy($C_{1-4}$)alkyl, (aminocarbonyl)($C_{1-4}$)alkyl, ($C_{1-2}$ alkylaminocarbonyl)($C_{1-4}$)alkyl, (di($C_{1-2}$)alkylaminocarbonyl)($C_{1-4}$)alkyl, phenyl($C_{1-4}$)alkyl, ($C_{3-6}$ cycloalkyl)($C_{1-4}$) alkyl, ($C_{3-6}$ cycloalkenyl)($C_{1-4}$)alkyl, (5- or 6-membered heterocyclo)($C_{1-4}$)alkyl (such as morpholin-4-yl($C_{1-4}$)alkyl), and (5- or 6-membered heteroaryl)($C_{1-4}$)alkyl (such as tetrazolyl($C_{1-4}$)alkyl (1H-tetrazol-1-yl or 1H-tetrazol-5-yl) and pyridinyl($C_{1-4}$)alkyl (pyridin-2-yl($C_{1-4}$)alkyl, pyridin-3-yl ($C_{1-4}$)alkyl or pyridin-4-yl($C_{1-4}$)alkyl), wherein the phenyl, cycloalkyl, cycloalkenyl, heterocyclo, and heteroaryl portions are optionally substituted with 1, 2, or 3 substituents, each independently selected from the group consisting of hydroxy, halo, $C_{1-2}$ alkyl, halo($C_{1-2}$)alkyl, cyano, nitro, amino, $C_{1-2}$ alkylamino, di($C_{1-2}$)alkylamino, carboxy, $C_{1-2}$ alkoxy, and $C_{1-2}$ alkoxycarbonyl. In another embodiment, $R^{9a}$ is selected from the group consisting of $C_{1-4}$ alkyl, (aminocarbonyl)($C_{1-2}$)alkyl, and phenyl($C_{1-2}$)alkyl, such as methyl, ethyl, propyl, butyl, tert-butyl, aminocarbonylmethyl, and benzyl.

In one embodiment, $Z^{1a}$ is $OR^{10a}$, wherein $R^{10a}$ is hydrogen or alkyl, preferably hydrogen or $C_{1-6}$ alkyl, and more preferably $R^{10a}$ is hydrogen or $C_{1-4}$ alkyl. In another embodiment, $Z^{1a}$ is OH. In another embodiment, $Z^{1a}$ is $OCH_3$ or $OC_2H_5$.

In another embodiment, $Z^{1a}$ is $NR^{11a}R^{12a}$, wherein $R^{11a}$ and $R^{12a}$ are each independently selected from the group consisting of hydrogen and alkyl, and preferably each independently selected from the group consisting of hydrogen and $C_{1-6}$ alkyl, and more preferably each independently selected from the group consisting of hydrogen and $C_{1-4}$ alkyl. In another embodiment, $Z^{1a}$ is $NH_2$. In another embodiment, $Z^{1a}$ is $N(H)CH_3$, $N(H)C_2H_5$, or $N(CH_3)_2$.

In another embodiment, Compounds of the Invention are compounds of any one of Formulae I-VII, wherein $R^5$ is $-NR^6R^7$, $R^6$ is hydrogen or $C_{1-6}$ alkyl, and $R^7$ is optionally substituted carboxy($C_{1-6}$)alkyl, optionally substituted ($C_{1-6}$ alkoxycarbonyl)($C_{1-6}$)alkyl, or optionally substituted (carboxamido)($C_{1-6}$)alkyl, and preferably $R^7$ is optionally substituted carboxy($C_{1-6}$)alkyl, optionally substituted ($C_{1-4}$ alkoxycarbonyl)($C_{1-6}$)alkyl, or optionally substituted (carboxamido)($C_{1-6}$)alkyl. In this aspect of the invention, preferably $R^7$ is $-CHR^9-C(=O)-Z^1$, wherein $R^9$ is selected from the group consisting of hydrogen, alkyl, hydroxyalkyl, carboxyalkyl, aminoalkyl, (aminocarbonyl)alkyl, (alkylaminocarbonyl)alkyl, (dialkylaminocarbonyl) alkyl, mercaptoalkyl, (alkylthio)alkyl, guanidinoalkyl, arylalkyl, (cycloalkyl)alkyl, (cycloalkenyl)alkyl, (heterocyclo) alkyl, and (heteroaryl)alkyl, wherein the aryl, cycloalkyl, cycloalkenyl, heterocyclo, and heteroaryl, portions are optionally substituted with 1, 2, or 3 substituents, each independently selected from the group consisting of hydroxy, halo, haloalkyl, alkylamino, dialkylamino, carboxy, alkoxy, and alkoxycarbonyl; and $Z^1$ is $OR^{10}$ or $NR^{11}R^{12}$, wherein $R^{10}$ is hydrogen or alkyl; and $R^{11}$ and $R^{12}$ are each independently selected from the group consisting of hydrogen and alkyl.

Typically, $R^9$ is selected from the group consisting of hydrogen, $C_{1-6}$ alkyl, monohydroxy($C_{1-6}$)alkyl, carboxy($C_{1-6}$)alkyl, amino($C_{1-6}$)alkyl, (aminocarbonyl)($C_{1-6}$)alkyl, ($C_{1-4}$ alkylaminocarbonyl)($C_{1-6}$)alkyl, (di($C_{1-4}$)alkylaminocarbonyl)($C_{1-6}$)alkyl, mercapto($C_{1-6}$)alkyl, ($C_{1-4}$ alkylthio)($C_{1-6}$)alkyl, guanidino($C_{1-6}$)alkyl, $C_{6-12}$ aryl($C_{1-6}$)alkyl, ($C_{3-7}$ cycloalkyl)($C_{1-6}$)alkyl, ($C_{3-7}$ cycloalkenyl)($C_{1-6}$)alkyl, (5- or 6-membered heterocyclo)($C_{1-6}$)alkyl, and (5- or 6-membered heteroaryl)($C_{1-6}$)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In another embodiment, $R^9$ is selected from the group consisting of $C_{1-4}$ alkyl, monohydroxy($C_{1-4}$)alkyl, carboxy($C_{1-4}$)alkyl, amino($C_{1-4}$)alkyl, (aminocarbonyl)($C_{1-4}$)alkyl, ($C_{1-2}$ alkylaminocarbonyl)($C_{1-4}$)alkyl, (di($C_{1-2}$)alkylaminocarbonyl)($C_{1-4}$)alkyl, mercapto($C_{1-4}$)alkyl, ($C_{1-2}$ alkylthio)($C_{1-4}$)alkyl, guanidino($C_{1-4}$)alkyl, $C_{6-10}$ aryl($C_{1-4}$)alkyl, ($C_{3-6}$ cycloalkyl)($C_{1-4}$)alkyl, ($C_{3-6}$ cycloalkenyl)($C_{1-4}$)alkyl, (5- or 6-membered heterocyclo)($C_{1-4}$)alkyl, and (5- or 6-membered heteroaryl)($C_{1-4}$)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, halo($C_{1-2}$)alkyl, amino, $C_{1-2}$ alkylamino, di($C_{1-2}$)alkylamino, carboxy, $C_{1-2}$ alkoxy, and $C_{1-2}$ alkoxycarbonyl. In another embodiment, $R^9$ is selected from the group consisting of $C_{1-4}$ alkyl, carboxy($C_{1-4}$)alkyl, (aminocarbonyl)($C_{1-4}$)alkyl, ($C_{1-2}$ alkylaminocarbonyl)($C_{1-4}$)alkyl, (di($C_{1-2}$)alkylaminocarbonyl)($C_{1-4}$)alkyl, phenyl($C_{1-4}$)alkyl, ($C_{3-6}$ cycloalkyl)($C_{1-4}$)alkyl, ($C_{3-6}$ cycloalkenyl)($C_{1-4}$)alkyl, (5- or 6-membered heterocyclo)($C_{1-4}$)alkyl (such as morpholin-4-yl($C_{1-4}$)alkyl), and (5- or 6-membered heteroaryl)($C_{1-4}$)alkyl (such as tetrazolyl($C_{1-4}$)alkyl (1H-tetrazol-1-yl or 1H-tetrazol-5-yl) and pyridinyl($C_{1-4}$)alkyl (pyridin-2-yl($C_{1-4}$)alkyl, pyridin-3-yl($C_{1-4}$)alkyl or pyridin-4-yl($C_{1-4}$)alkyl), wherein the phenyl, cycloalkyl, cycloalkenyl, heterocyclo, and heteroaryl portions are optionally substituted with 1, 2, or 3 substituents, each independently selected from the group consisting of hydroxy, halo, halo($C_{1-2}$)alkyl, amino, $C_{1-2}$ alkylamino, di($C_{1-2}$)alkylamino, carboxy, $C_{1-2}$ alkoxy, and $C_{1-2}$ alkoxycarbonyl. In another embodiment, $R^9$ is selected from the group consisting of $C_{1-4}$ alkyl, (aminocarbonyl)($C_{1-2}$)alkyl, and phenyl($C_{1-2}$)alkyl, such as methyl, ethyl, propyl, butyl, tert-butyl, aminocarbonylmethyl, and benzyl.

In one embodiment, $Z^1$ is $OR^{10}$, wherein $R^{10}$ is hydrogen or alkyl, preferably hydrogen or $C_{1-6}$ alkyl, and more preferably $R^{10}$ is hydrogen or $C_{1-4}$ alkyl. In another embodiment, $Z^1$ is OH. In another embodiment, $Z^1$ is $OCH_3$ or $OC_2H_5$.

In another embodiment, $Z^1$ is $NR^{11}R^{12}$, wherein $R^{11}$ and $R^{12}$ are each independently selected from the group consisting of hydrogen and alkyl, and preferably each independently selected from the group consisting of hydrogen and $C_{1-6}$ alkyl, and more preferably each independently selected from the group consisting of hydrogen and $C_{1-4}$ alkyl. In another embodiment, $Z^1$ is $NH_2$. In another embodiment, $Z^1$ is $N(H)CH_3$, $N(H)C_2H_5$, or $N(CH_3)_2$.

In another embodiment, Compounds of the Invention are compounds of any one of Formulae IA-VIII-A, wherein $Z^a$ is selected from the group consisting of

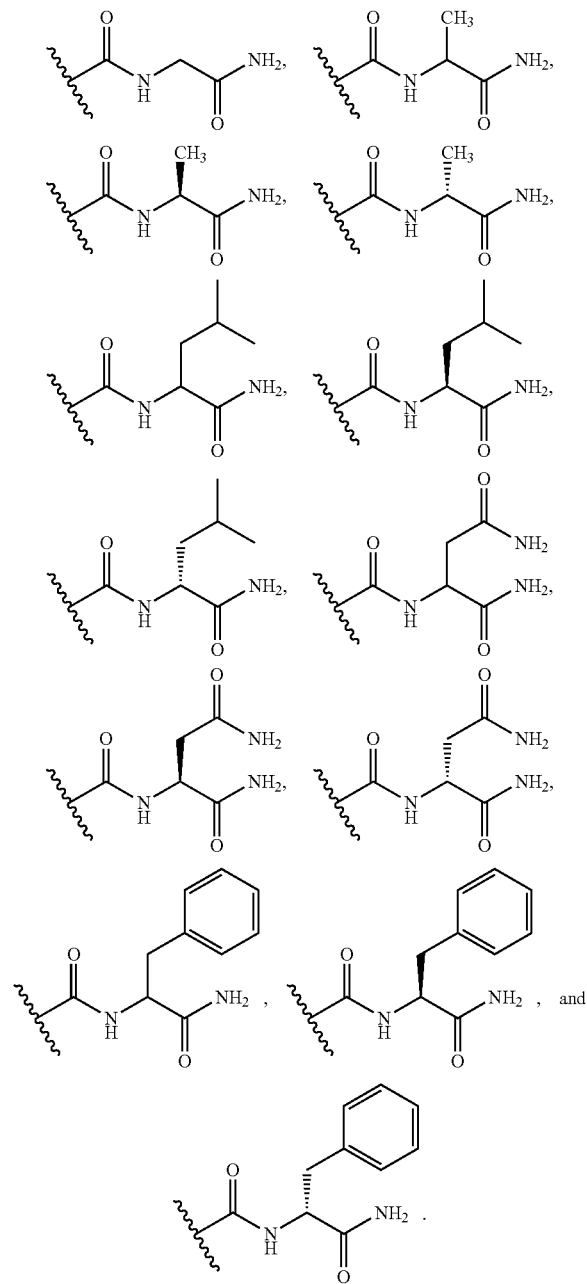

In another embodiment, Compounds of the Invention are compounds of any one of Formulae I-VII, wherein Z is selected from the group consisting of

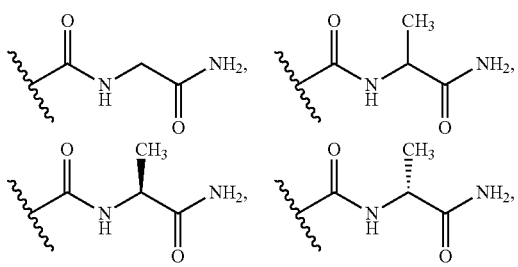

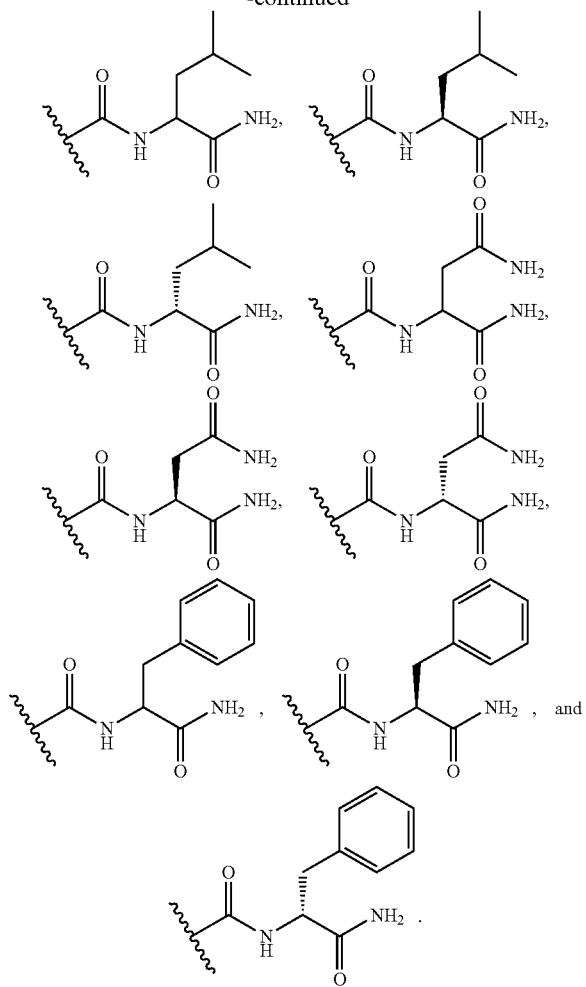

In another embodiment, Compounds of the Invention are compounds of any one of Formulae I-A-VIII-A, wherein $R^{5a}$ is —$NR^{6a}R^{7a}$, $R^{6a}$ is hydrogen or $C_{1-6}$ alkyl, and $R^{7a}$ is hydroxyalkyl. In this embodiment, $R^{7a}$ is preferably monohydroxy($C_{1-4}$)alkyl or dihydroxy($C_{1-4}$)alkyl. Advantageously, $R^{7a}$ is 1,2-dihydroxyethyl.

In another embodiment, Compounds of the Invention are compounds of any one of Formulae I-VII, wherein $R^5$ is —$NR^6R^7$, $R^6$ is hydrogen or $C_{1-6}$ alkyl, and $R^7$ is hydroxyalkyl. In this embodiment, $R^7$ is preferably monohydroxy($C_{1-4}$)alkyl or dihydroxy($C_{1-4}$)alkyl. Advantageously, $R^7$ is 1,2-dihydroxyethyl.

In another embodiment, Compounds of the Invention are compounds of any one of Formulae I-A-VIII-A, wherein $R^{5a}$ is —$NR^{6a}R^{7a}$ and $R^{6a}$ and $R^{7a}$ together with the nitrogen atom to which they are attached form an optionally substituted heterocyclic ring. In another embodiment, the optionally substituted heterocyclic ring is an optionally substituted 5- or 6-membered heterocyclic ring. In this aspect of the invention, useful heterocyclic rings include unsubstituted or substituted 5- or 6-membered heterocyclic rings containing 1-2 nitrogen atoms and optionally 1 or 2 other heteroatoms. In one embodiment, the heterocyclic ring is a substituted or unsubstituted 5-membered heterocyclic ring containing 1 nitrogen atom, such as substituted or unsubstituted pyrrolidin-1-yl. In another embodiment, the heterocyclic ring is a substituted or unsubstituted 6-membered heterocyclic ring containing 1 nitrogen atom and 1 heteroatom selected from the group consisting of oxygen or sulphur, such as, for example, a substituted or unsubstituted morpholinyl, thiomorpholinyl, and dioxidothiomorpholinyl. In another embodiment, the optionally substituted heterocyclic ring is an optionally substituted bicyclic ring system. In this aspect, suitable heterocyclic rings include unsubstituted or substituted 7-10 membered bicyclic ring systems containing 1-2 nitrogen atoms and optionally 1 or 2 other heteroatoms, such as, for example, isoindolin-2-yl and azabicyclo[3.2.1]octan-8-yl. Suitable optional substituents include hydroxy, halo, $C_{1-4}$ alkyl, halo($C_{1-4}$)alkyl, cyano, nitro, amino, aminocarbonyl, ($C_{1-4}$ alkylamino)carbonyl, $C_{1-4}$ alkylamino, di($C_{1-4}$) alkylamino, carboxy, $C_{1-4}$ alkoxy, and $C_{1-4}$ alkoxycarbonyl.

In another embodiment, $R^{6a}$ and $R^{7a}$ together with the nitrogen atom to which they are attached form

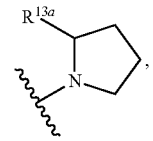

wherein $R^{13a}$ is hydrogen, aminocarbonyl or ($C_{1-4}$ alkylamino)carbonyl; and preferably $R^{13a}$ is hydrogen, aminocarbonyl, (methylamino)carbonyl or (ethylamino)carbonyl.

In another embodiment, $R^{6a}$ and $R^{7a}$ together with the nitrogen atom to which they are attached form

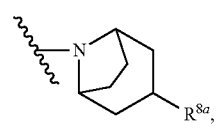

wherein $R^{8a}$ is as defined above in connection with Formula I-A.

In another embodiment, Compounds of the Invention are compounds of any one of Formulae I-A-VIII-A, wherein $Z^a$ is selected from the group consisting of

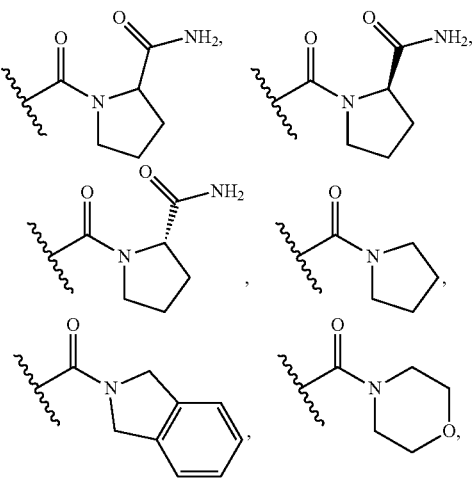

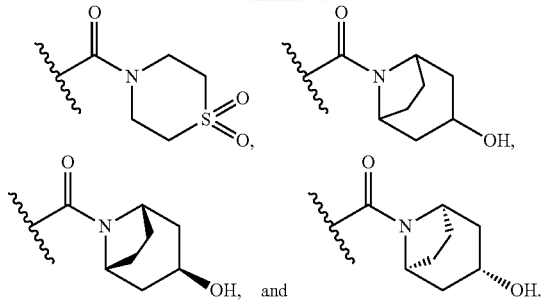

In another embodiment, Compounds of the Invention are compounds of any one of Formulae I-VII, wherein $R^5$ is $-NR^6R^7$ and $R^6$ and $R^7$ together with the nitrogen atom to which they are attached form an optionally substituted heterocyclic ring, and preferably an optionally substituted 5- or 6-membered heterocyclic ring. Useful heterocyclic rings include unsubstituted or substituted 5- or 6-membered heterocyclic rings containing 1-2 nitrogen atoms, and preferably a substituted 5-membered heterocyclic ring containing 1 nitrogen atom. Suitable optional substituents include hydroxy, halo, halo($C_{1-4}$)alkyl, amino, aminocarbonyl, ($C_{1-4}$ alkylamino)carbonyl, $C_{1-4}$ alkylamino, di($C_{1-4}$)alkylamino, carboxy, $C_{1-4}$ alkoxy, and $C_{1-4}$ alkoxycarbonyl. In one embodiment, $R^6$ and $R^7$ together with the nitrogen atom to which they are attached form

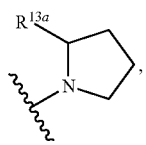

wherein
$R^{13}$ is aminocarbonyl or ($C_{1-4}$ alkylamino)carbonyl; and preferably $R^{13}$ is aminocarbonyl, (methylamino)carbonyl or (ethylamino)carbonyl.

In another embodiment, Compounds of the Invention are compounds of any one of Formulae I-VII, wherein Z is selected from the group consisting of

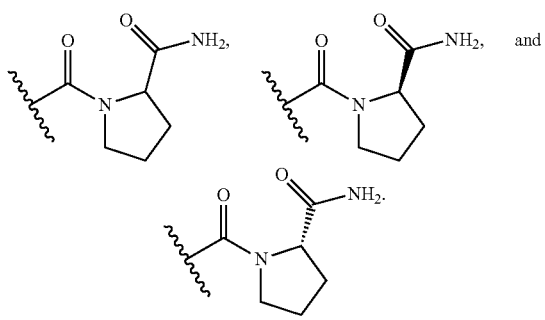

In another embodiment, Compounds of the Invention are compounds of any one of Formulae I-A-VIII-A, wherein $R^{5a}$ is selected from the group consisting of aryl, heteroaryl, cycloalkyl, cycloalkenyl, heterocyclo, arylalkyl, heteroarylalkyl, (cycloalkyl)alkyl, (cycloalkenyl)alkyl, and (heterocyclo)alkyl, any of which is optionally substituted; and wherein two adjacent carbon atoms of said cycloalkyl or cycloalkenyl rings are optionally fused to a phenyl ring. In one embodiment, $R^{5a}$ is selected from the group consisting of $C_{6-14}$ aryl, 5- to 10-membered heteroaryl, $C_{3-7}$ cycloalkyl, $C_{3-7}$ cycloalkenyl, 3- to 7-membered heterocyclo, $C_{6-14}$ aryl($C_{1-6}$)alkyl, and (5- to 10-membered heteroaryl)($C_{1-6}$)alkyl, ($C_{3-7}$ cycloalkyl)($C_{1-6}$)alkyl, ($C_{3-7}$ cycloalkenyl)($C_{1-6}$)alkyl, (3- to 7-membered heterocyclo)($C_{1-6}$)alkyl, wherein two adjacent carbon atoms of said cycloalkyl and cycloalkenyl rings are optionally fused to a phenyl ring; and wherein said aryl, heteroaryl, cycloalkyl, cycloalkenyl, and heterocyclo portions are optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups. In another embodiment, $R^{5a}$ is selected from the group consisting of $C_{6-10}$ aryl, 5- or 6-membered heteroaryl, $C_{3-6}$ cycloalkyl, $C_{3-6}$ cycloalkenyl, 5- or 6-membered heterocyclo, $C_{6-10}$ aryl($C_{1-4}$)alkyl, and (5- or 6-membered heteroaryl)($C_{1-4}$)alkyl, ($C_{3-6}$ cycloalkyl)($C_{1-4}$)alkyl, ($C_{3-6}$ cycloalkenyl)($C_{1-4}$)alkyl, and (5- or 6-membered heterocyclo)($C_{1-4}$)alkyl, wherein two adjacent carbon atoms of said cycloalkyl and cycloalkenyl rings are optionally fused to a phenyl ring; and wherein said aryl, heteroaryl, cycloalkyl, cycloalkenyl, and heterocyclo portions are optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 2 independently selected $R^{8a}$ groups. Suitable $R^{8a}$ groups are those described in connection with $R^{1a}$.

In another embodiment, Compounds of the Invention are compounds of any one of Formulae I-A-VIII-A, wherein re is unsubstituted phenyl or phenyl substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

In another embodiment, Compounds of the Invention are compounds of any one of Formulae I-A-VIII-A, wherein $Z^a$ is

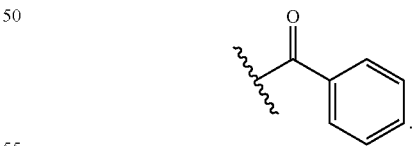

In another embodiment, Compounds of the Invention are compounds of any one of Formulae I-A-VIII-A, wherein
$R^{1a}$ is hydroxy or unsubstituted $C_{1-6}$ alkoxy;
$R^{2a}$ is cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;
$R^{3a}$ is hydrogen; and
$R^4$ is hydrogen or methyl.

In another embodiment, Compounds of the Invention are compounds of any one of Formulae I-VII, wherein $R^1$ is OH or unsubstituted $C_{1-6}$ alkoxy;

$R^2$ is cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;

$R^3$ is hydrogen; and $R^4$ is hydrogen.

Compounds of the Invention are compounds of any one of Formulae I-A-VIII-A, wherein $R^{2a}$ is unsubstituted cyclopropyl($C_{1-4}$)alkyl.

In another embodiment, Compounds of the Invention are compounds of any one of Formulae I-A-VII-A, and especially Formula III-A, wherein $R^{1a}$ is hydroxy or unsubstituted $C_{1-6}$ alkoxy; $R^{2a}$ is unsubstituted $C_{1-4}$ alkyl, or cyclopropyl ($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; $R^{3a}$ is hydrogen or OH; and $R^4$ is hydrogen. In this embodiment, $R^{2a}$ is preferably unsubstituted cyclopropyl($C_{1-4}$)alkyl.

In another embodiment, Compounds of the Invention are compounds of any one of Formulae I-A-VII-A, wherein $R^{1a}$ is hydroxy or unsubstituted $C_{1-6}$ alkoxy; $R^{2a}$ is $C_{1-6}$ alkyl (preferably $C_{1-4}$ alkyl) substituted with 1, 2, or 3 substituents independently selected from the group consisting of halo (such as fluoro), halo($C_{1-4}$)alkyl (such as, for example, trifluoro($C_{1-2}$)alkyl), phenyl, and heterocyclo (such as tetrahydropyranyl); unsubstituted $C_{2-6}$ alkenyl (preferably $C_{2-4}$ alkenyl) substituted with 1, 2, or 3 substituents each independently selected from the group consisting of $C_{1-4}$ alkyl (such as methyl), halo (such as fluoro), halo($C_{1-4}$)alkyl (such as, for example, trifluoro($C_{1-2}$)alkyl), phenyl, and heterocyclo (such as tetrahydropyranyl); $R^{3a}$ is hydrogen or hydroxyl; and $R^4$ is hydrogen.

Compounds of the Invention are compounds of any one of Formulae I-VII, wherein $R^2$ is unsubstituted cyclopropyl($C_{1-4}$)alkyl.

In another embodiment, Compounds of the Invention are compounds of any one of Formulae I-VII, and especially Formula III, wherein $R^1$ is OH or unsubstituted $C_{1-6}$ alkoxy; $R^2$ is unsubstituted $C_{1-4}$ alkyl, or cyclopropyl($C_{1-4}$)alkyl, cyclobutyl($C_{1-4}$)alkyl, cyclopentyl($C_{1-4}$)alkyl, or cyclohexyl ($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; $R^3$ is hydrogen or OH; and $R^4$ is hydrogen. In this embodiment, $R^2$ is preferably unsubstituted cyclopropyl ($C_{1-4}$)alkyl.

In another embodiment, Compounds of the Invention are compounds of Formula I-A, wherein $R^{2a}$ is (cyclopropyl)methyl and $R^4$ is hydrogen, represented by Formula X-A:

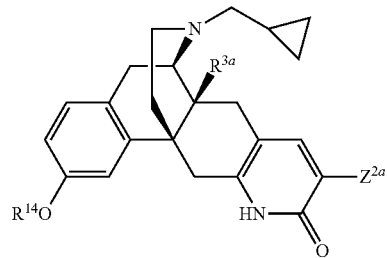

X-A and the pharmaceutically acceptable salts and solvates thereof, wherein $R^{14}$ is H or $C_{1-6}$ alkyl optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and $R^{3a}$ is hydrogen or OH, and $Z^{2a}$ is selected from the group consisting of

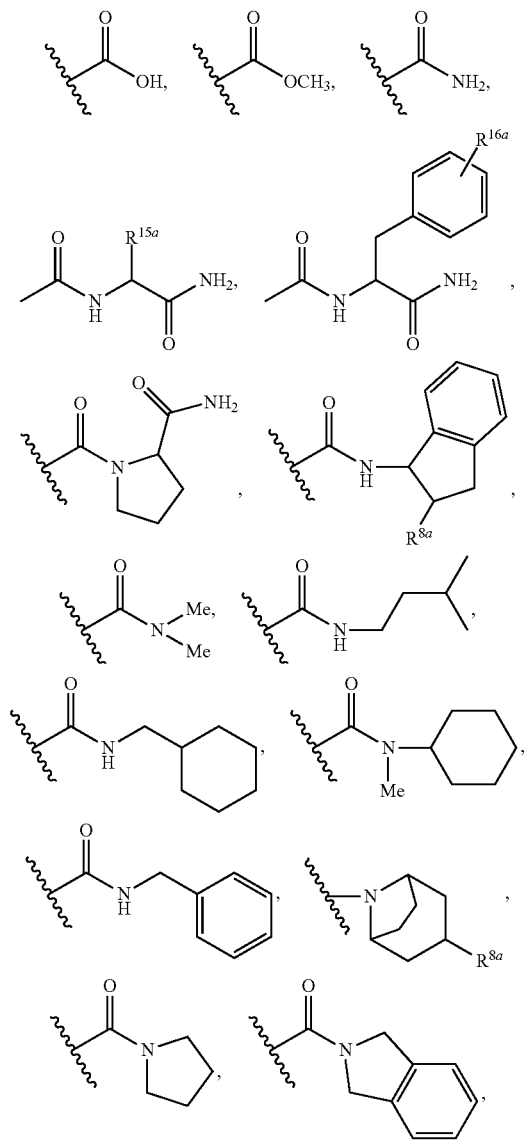

-continued

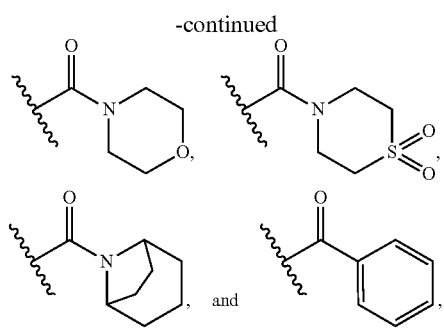
and wherein $R^{15a}$ is hydrogen, $C_{1-4}$ alkyl or —$(C_{1-4})$alkyl-C(=O) NH$_2$, $R^{16a}$ is selected from the group consisting of hydrogen, $C_{1-4}$ alkyl, hydroxy, halo, halo($C_{1-2}$)alkyl, $C_{1-2}$ alkoxy, $C_{1-2}$ alkoxycarbonyl, and aminocarbonyl, and $R^{8a}$ is as defined for Formula I-A.

In another embodiment, Compounds of the Invention are compounds of Formula I, wherein $R^2$ is (cyclopropyl)methyl and $R^4$ is hydrogen, represented by Formula VIII:

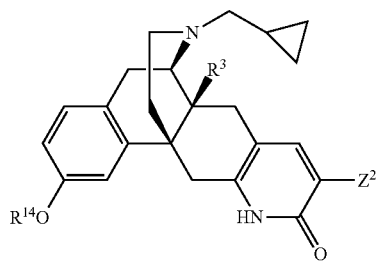

VIII and the pharmaceutically acceptable salts and solvates thereof, wherein $R^{14}$ is H or $C_{1-6}$ alkyl optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and $R^3$ is hydrogen or OH, and $Z^2$ is selected from the group consisting of

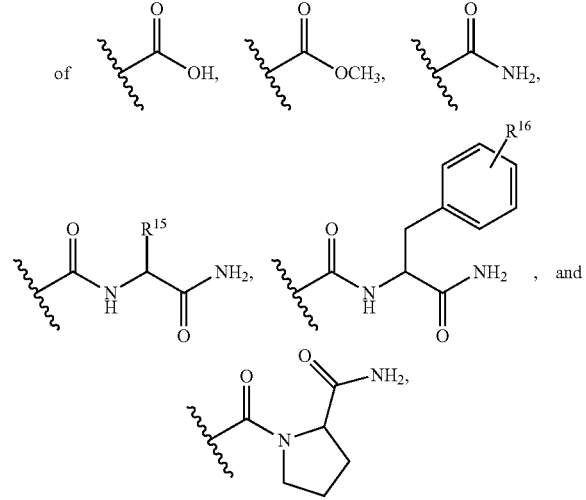

wherein $R^{15}$ is $C_{1-4}$ alkyl or —$(C_{1-4})$alkyl-C(=O)NH$_2$, and $R^{16}$ is selected from the group consisting of $C_{1-4}$ alkyl, hydroxy, halo, halo($C_{1-2}$)alkyl, $C_{1-2}$ alkoxy, $C_{1-2}$ alkoxycarbonyl, and aminocarbonyl.

In another embodiment, Compounds of the Invention include:

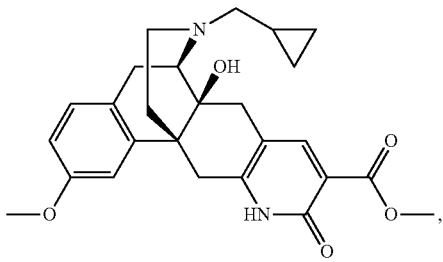

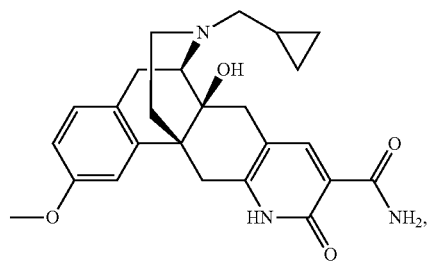

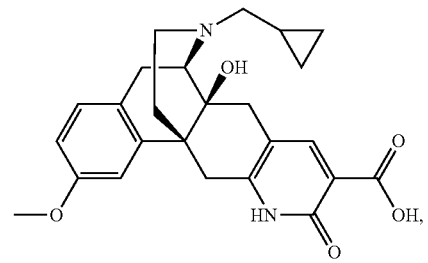

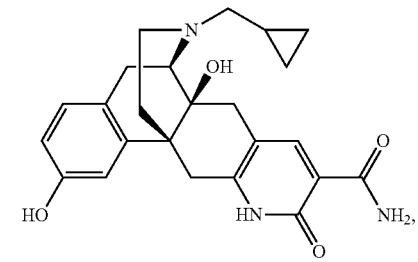

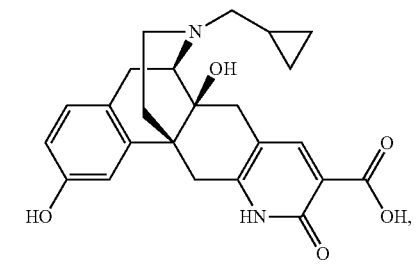

33
-continued
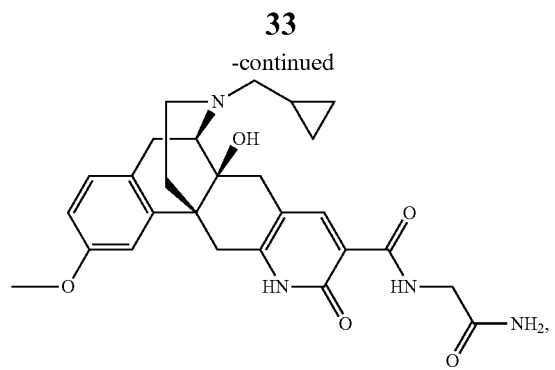
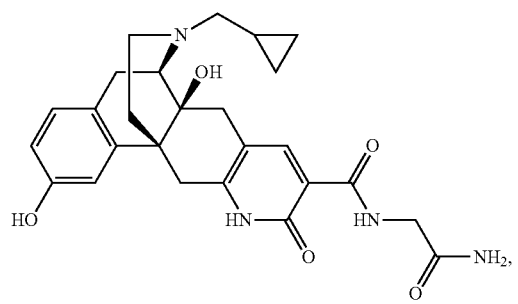
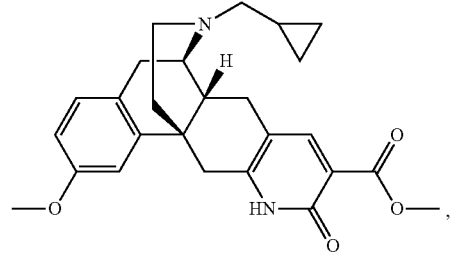
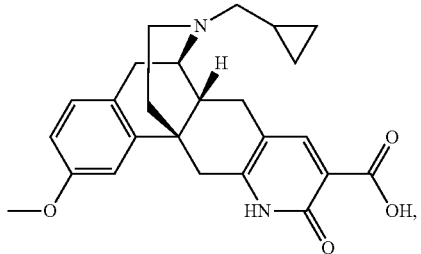
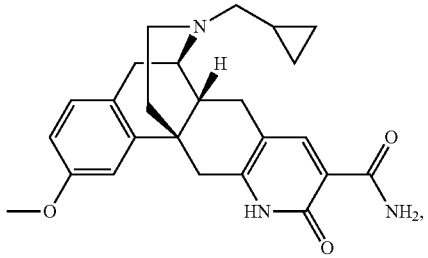
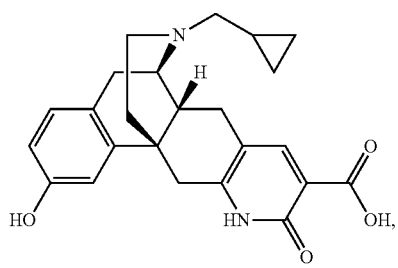
34
-continued
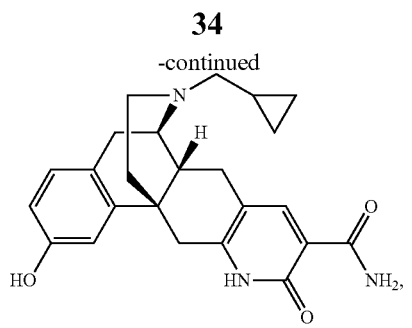
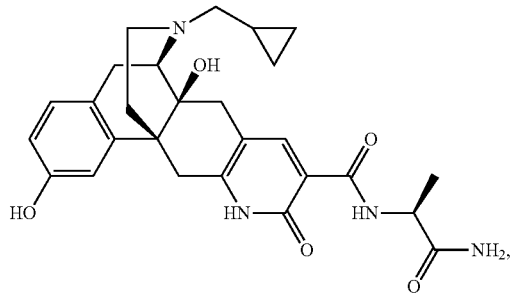
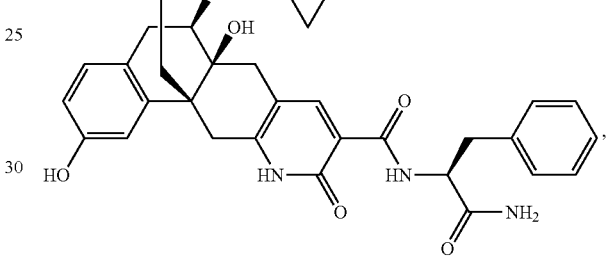
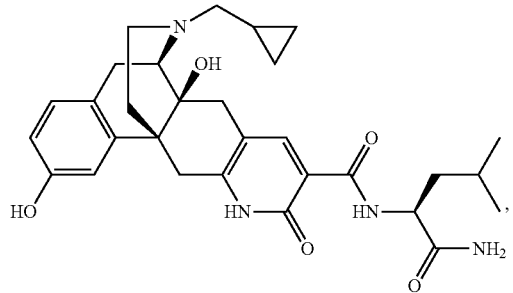
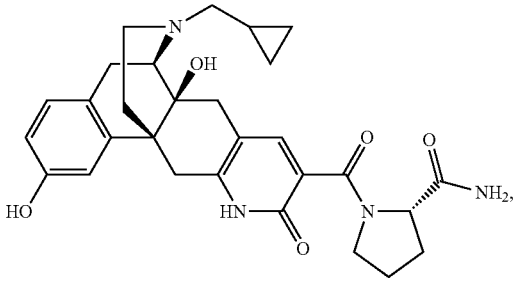
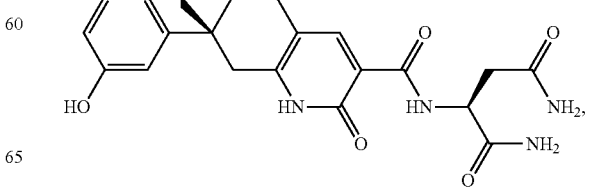

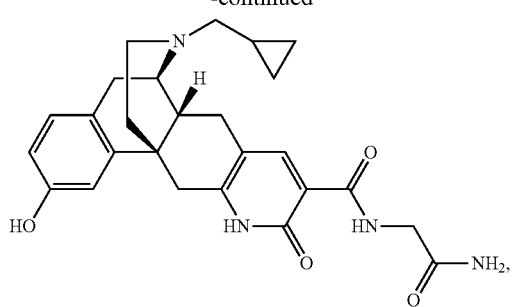
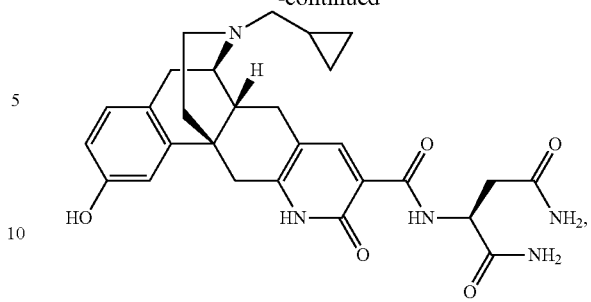
and the pharmaceutically acceptable salts and solvates thereof.
In another embodiment, Compounds of the Invention include:
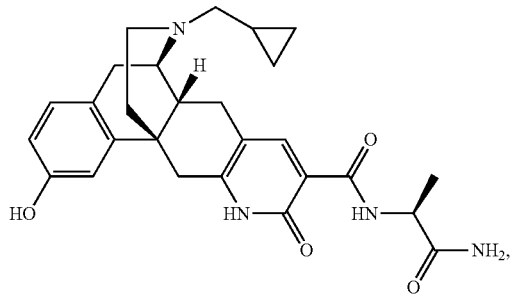
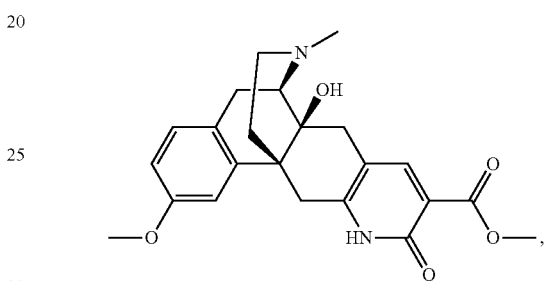
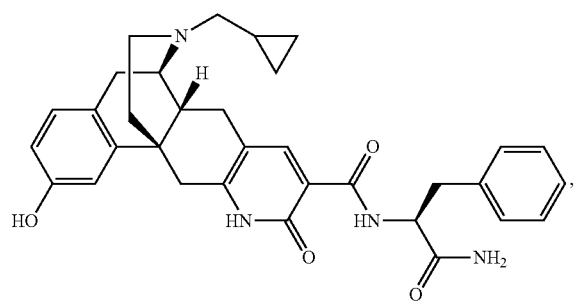
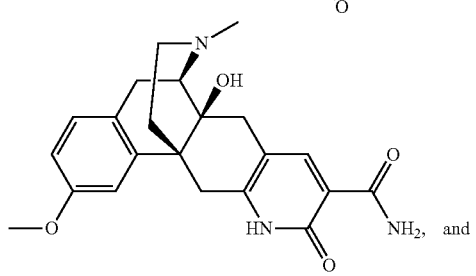
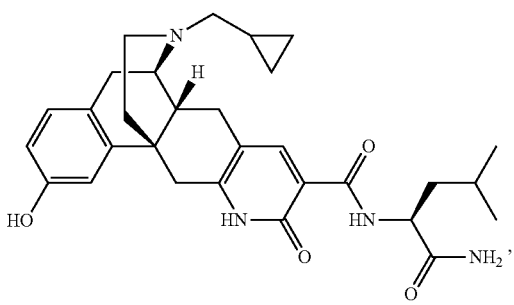
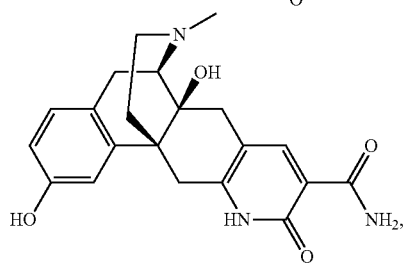
and the pharmaceutically acceptable salts and solvates thereof.
In another embodiment, Compounds of the Invention include:
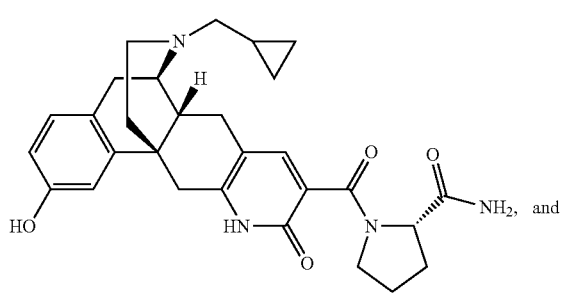
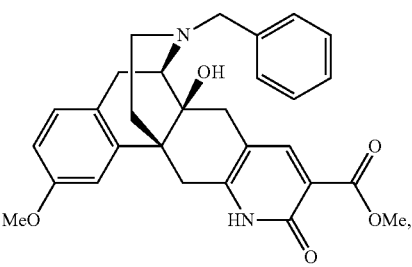

37
-continued
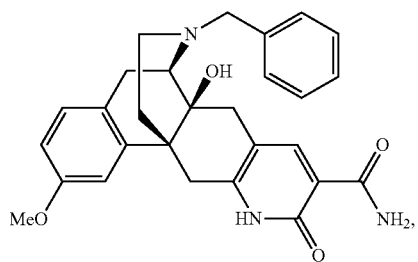
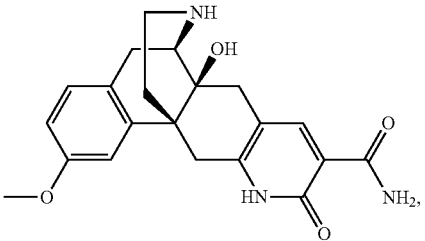
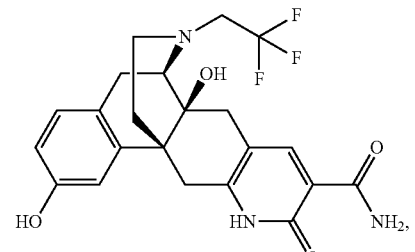
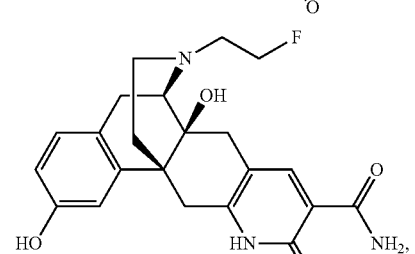
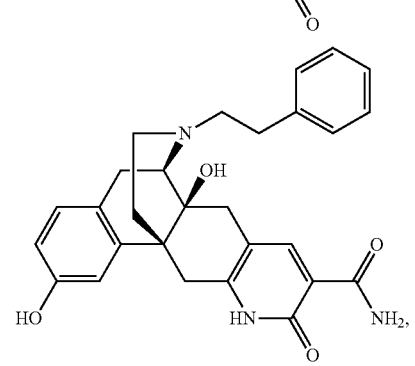
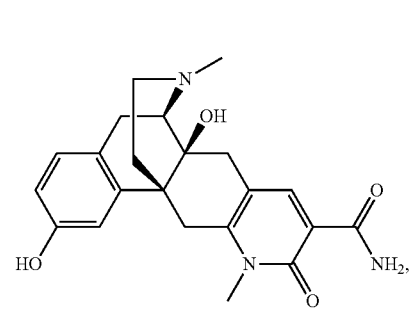
38
-continued
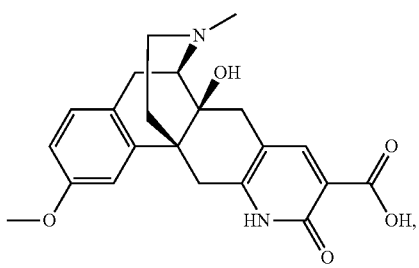
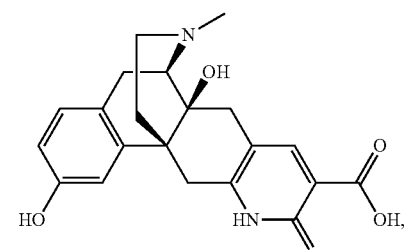
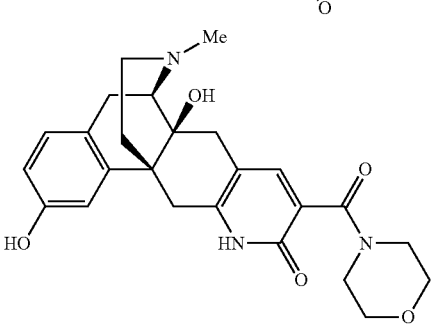
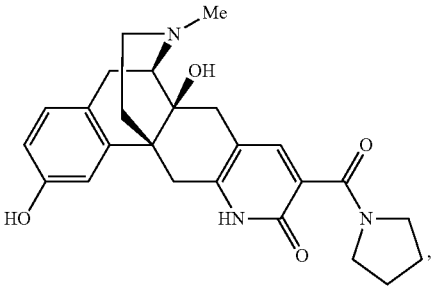
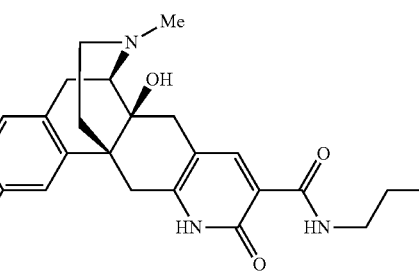
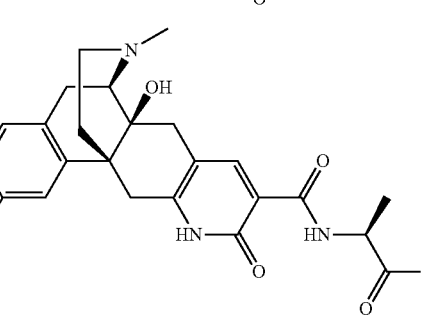

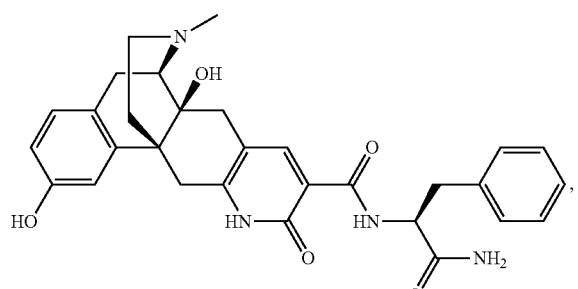
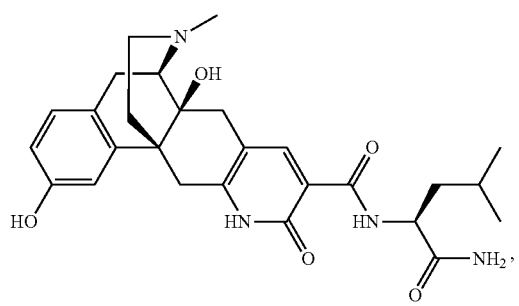
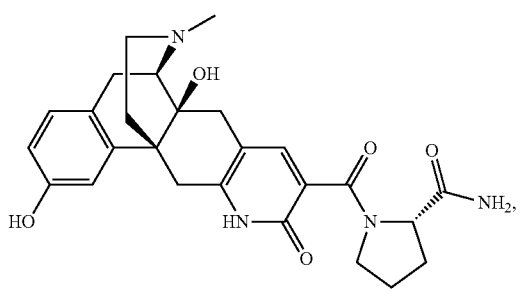
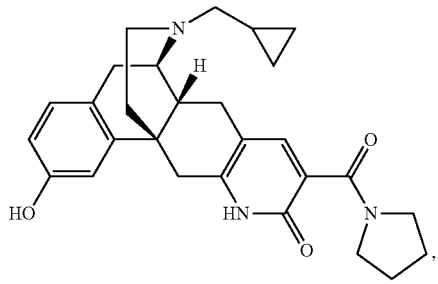
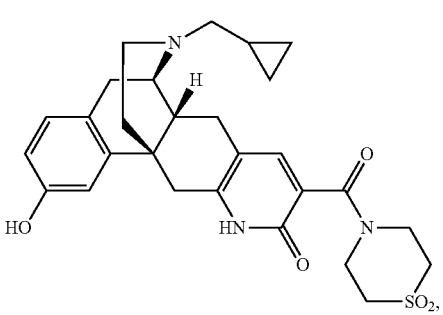
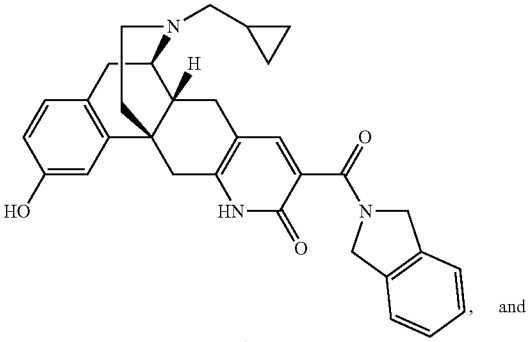
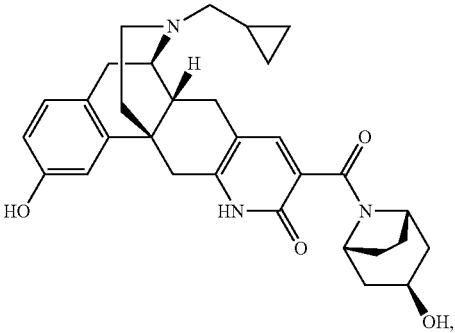
and the pharmaceutically acceptable salts and solvates thereof.
In another embodiment, Compounds of the Invention include:
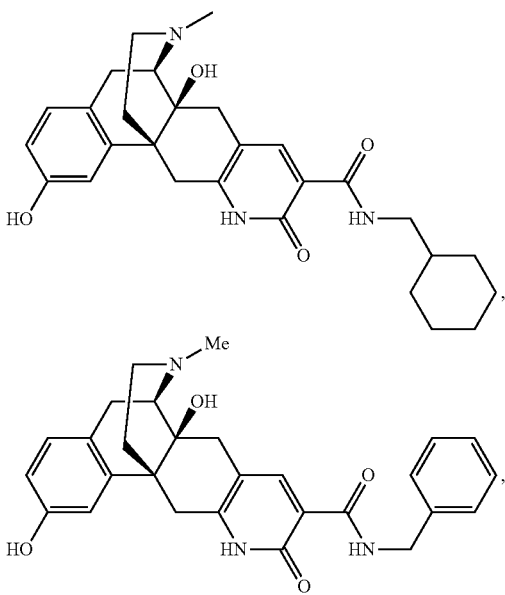
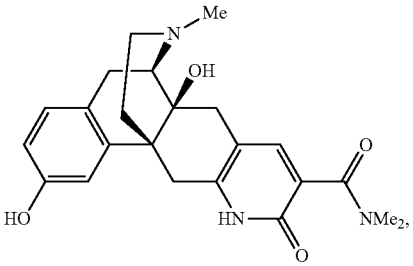

-continued

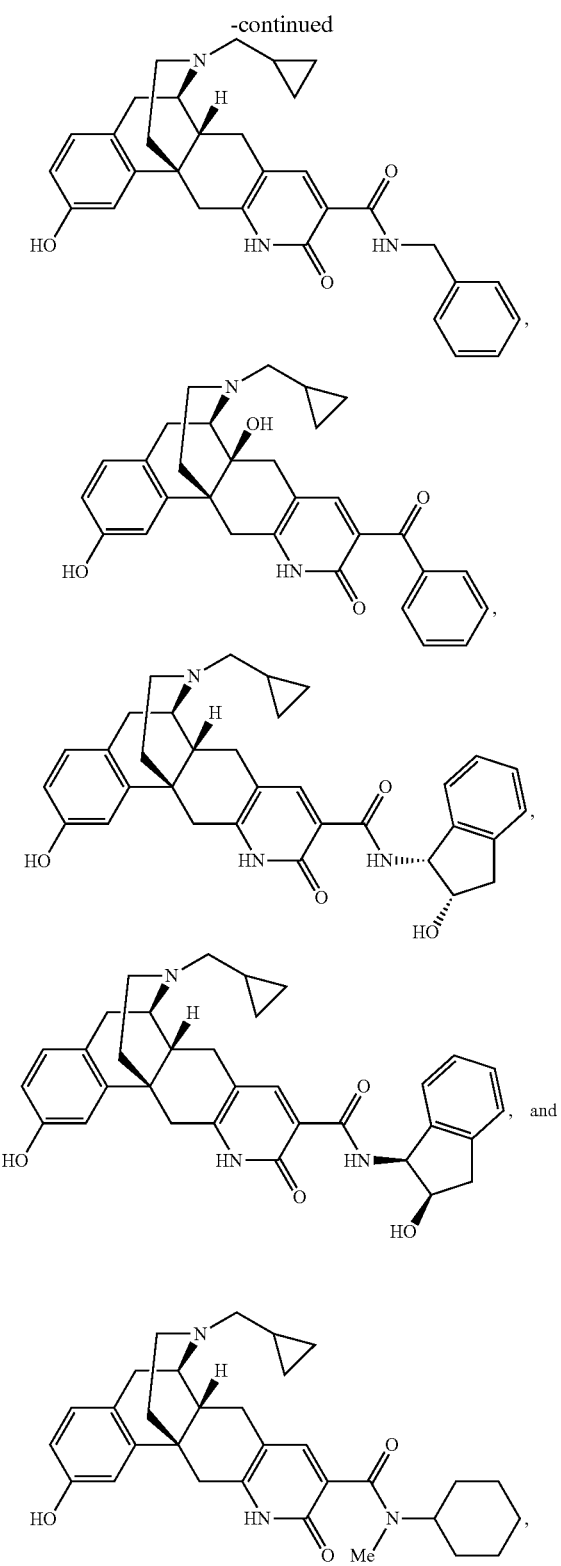

and the pharmaceutically acceptable salts and solvates thereof.

In another embodiment, Compounds of the Invention are compounds of any one of Formulae I-A-VIII-A and X-A, wherein $R^{1a}$ is —O-PG, wherein PG is a hydroxyl protecting group.

In another embodiment, Compounds of the Invention are compounds of Formula I-A, represented by Formula IX-A:

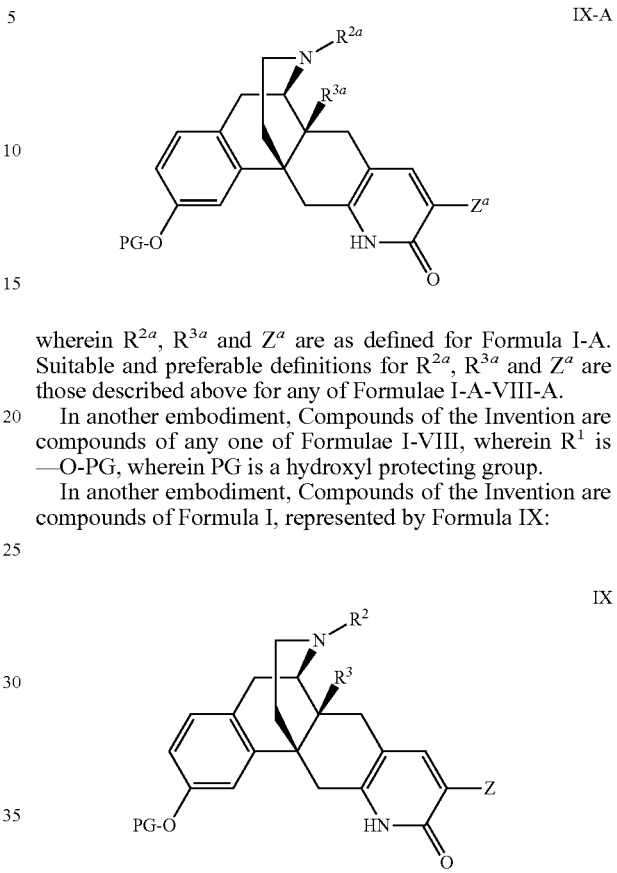

wherein $R^{2a}$, $R^{3a}$ and $Z^a$ are as defined for Formula I-A. Suitable and preferable definitions for $R^{2a}$, $R^{3a}$ and $Z^a$ are those described above for any of Formulae I-A-VIII-A.

In another embodiment, Compounds of the Invention are compounds of any one of Formulae I-VIII, wherein $R^1$ is —O-PG, wherein PG is a hydroxyl protecting group.

In another embodiment, Compounds of the Invention are compounds of Formula I, represented by Formula IX:

wherein $R^2$, $R^3$ and Z are as defined for Formula I. Suitable and preferable definitions for $R^2$, $R^3$ and Z are those described above for any of Formulae I-VII.

Suitable hydroxyl protecting groups for PG are well known and include, for example, any suitable hydroxyl protecting group disclosed in Wuts, P. G. M. & Greene, T. W., *Greene's Protective Groups in Organic Synthesis*, 4rd Ed., pp. 16-430 (J. Wiley & Sons, 2007), herein incorporated by reference in its entirety. The term "hydroxyl protecting group" as used herein refers to a group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular synthetic scheme planned. Suitable hydroxy protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Greene, T. W. and Wuts, above. Additional hydroxyl protecting groups can be found, for example, in U.S. Pat. No. 5,952,495, U.S. Patent Appl. Pub. No. 2008/0312411, WO 2006/035195, and WO 98/02033, which are herein incorporated in their entireties. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

It will be apparent to a person of ordinary skill in the art in view of this disclosure that certain groups included in the definitions of —O-PG overlap with the other definitions for $R^1$, such as methoxy, tert-butoxy, etc., and, thus, certain Compounds of the Invention having $R^1$ groups that include groups acting as hydroxyl protecting groups can be pharmaceutically active as described herein.

In one embodiment, the hydroxyl protecting group PG is selected from the group consisting of alkyl, arylalkyl, heterocyclo, (heterocyclo)alkyl, acyl, silyl, and carbonate, any of which are optionally substituted.

In another embodiment, the hydroxyl protecting group PG is an alkyl group, typically an optionally substituted $C_{1-6}$ alkyl group, and suitably unsubstituted methyl or tert-butyl.

In another embodiment, the hydroxyl protecting group PG is an arylalkyl group. Suitable arylalkyl groups include, for example, an unsubstituted benzyl group, substituted benzyl groups, such as p-methoxybenzyl, and naphthylmethyl.

In another embodiment, the hydroxyl protecting group PG is a heterocyclo group, such as unsubstituted tetrahydropyranyl or optionally substituted tetrahydropyranyl.

In another embodiment, the hydroxyl protecting group PG is a (heterocyclo)alkyl group. Suitable (heterocyclo)alkyl groups include, for example, 4-morpholinyl($C_{1-4}$)alkyl groups, such as, 2-(4-morpholinyl)ethyl.

In another embodiment, the hydroxyl protecting group PG is a silyl group. The term "silyl" as employed herein refers to the group having the following structure:

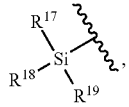

wherein $R^{17}$, $R^{18}$, and $R^{19}$ are each independently selected from the group consisting of alkyl, cycloalkyl, aryl, (cycloalkyl)alkyl, or arylalkyl, any of which is optionally substituted. In one embodiment, the silyl group is trimethyl silyl, tert-butyldimethyl silyl, tert-butyldiphenyl silyl, or tri-isopropyl silyl.

In another embodiment, the hydroxyl protecting group PG is an acyl group. The term "acyl" as employed herein refers to the following structure:

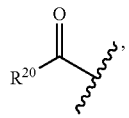

wherein $R^{20}$ is alkyl, cycloalkyl, aryl, (cycloalkyl)alkyl, or arylalkyl, any of which is optionally substituted. The acyl group can be, for example, $C_{1-4}$ alkylcarbonyl (such as, for example, acetyl), arylcarbonyl (such as, for example, benzoyl), levulinoyl, or pivaloyl. In another embodiment, the acyl group is benzoyl.

In another embodiment, the hydroxyl protecting group is a carbonate group. The term "carbonate" as employed herein refers to the following structure:

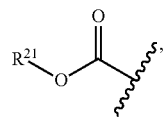

wherein $R^{21}$ is alkyl, alkenyl, cycloalkyl, aryl, (cycloalkyl)alkyl, or arylalkyl, any of which is optionally substituted. Typically, $R^{21}$ is $C_{1-10}$ alkyl (e.g., 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl. In one embodiment, the carbonate is (benzyloxy)carbonyl.

The present invention also pertains to the preparation of Compounds of the Invention. Accordingly, the present invention is directed to a process for preparing compounds of any one of Formulae I-A-VII-A and X-A, comprising reacting a suitable morphinan ketone, such as a compound of Formula XI-A

XI-A

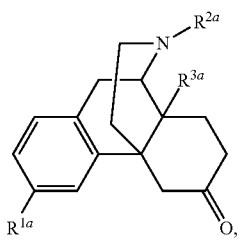

and preferably a compound of Formula XII-A

XII-A

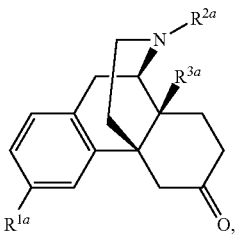

wherein $R^{1a}$—$R^{3a}$ are as defined above,
with N,N-dimethylformamideacetal to form an intermediate, and
reacting the intermediate with

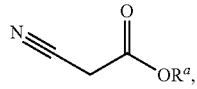

wherein $R^a$ is an optionally substituted alkyl, to obtain a compound of Formula I-A, wherein $R^4$ is hydrogen and $Z^a$ is

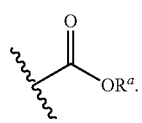

In one embodiment, $R^a$ is a $C_{1-4}$ alkyl optionally substituted with 1, 2, or 3 substituents, each independently selected from the group consisting of hydroxy, halo, haloalkyl, cyano, nitro, amino, alkylamino, dialkylamino, carboxy, alkoxy, and alkoxycarbonyl. In another embodiment, $R^a$ is an unsubstituted $C_{1-4}$ alkoxy, such as methoxy, ethoxy, n-propoxy, iso-propoxy, n-butoxy, or tert-butoxy, or $C_{1-4}$ alkoxy substituted with 1, 2, or 3 substituents, each independently selected from the group consisting of hydroxy, halo, halo($C_{1-4}$)alkyl, cyano, nitro, amino, $C_{1-4}$ alkylamino, di($C_{1-4}$)alkylamino, carboxy, $C_{1-4}$ alkoxy, and $C_{1-4}$ alkoxycarbonyl. In one embodiment, R is methoxy, ethoxy, n-propoxy, iso-propoxy, n-butoxy, or tert-butoxy.

The reaction with N,N-dimethylformamideacetal (DMF-dimethylacetal) is typically conducted at an elevated temperature (e.g., at a reflux temperature). The reaction with the optionally substituted alkyl cyanoacetate is conducted in a presence of a solvent (preferably an alcohol, such as MeOH) at an elevated temperature, and preferably at a reflux temperature.

In one embodiment, $R^{2a}$ is cyclopropyl($C_{1-4}$)alkyl, cyclobutyl($C_{1-4}$)alkyl, cyclopentyl($C_{1-4}$)alkyl, or cyclohexyl ($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In another embodiment, $R^{2a}$ is unsubstituted $C_{1-4}$ alkyl. In another embodiment, $R^{1a}$ is OH or $C_{1-4}$ alkoxy. In another embodiment, $R^{3a}$ is H or OH.

The present invention also pertains to the preparation of Compounds of the Invention. Accordingly, the present invention is directed to a process for preparing compounds of any one of Formulae I-VIII, comprising reacting a suitable morphinan ketone, such as a compound of Formula X

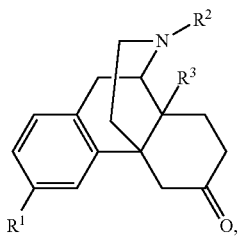

and preferably a compound of Formula XI

XI

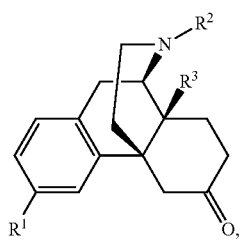

wherein $R^1$—$R^3$ are as defined above,
with N,N-dimethylformamideacetal to form an intermediate, and
reacting the intermediate with

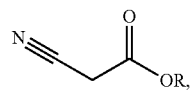

wherein R is an optionally substituted alkyl, to obtain a compound of Formula I, wherein $R^4$ is hydrogen and Z is

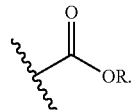

In one embodiment, R is a $C_{1-4}$ alkyl optionally substituted with 1, 2, or 3 substituents, each independently selected from the group consisting of hydroxy, halo, haloalkyl, amino, alkylamino, dialkylamino, carboxy, alkoxy, and alkoxycarbonyl. In another embodiment, R is an unsubstituted $C_{1-4}$ alkoxy, such as methoxy, ethoxy, n-propoxy, iso-propoxy, n-butoxy, or tert-butoxy, or $C_{1-4}$ alkoxy substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In one embodiment, R is methoxy, ethoxy, n-propoxy, iso-propoxy, n-butoxy, or tert-butoxy.

The reaction with N,N-dimethylformamideacetal (DMF-dimethylacetal) is typically conducted at an elevated temperature (e.g., at a reflux temperature). The reaction the optionally substituted alkyl cyanoacetate is conducted in a presence of a solvent (preferably an alcohol, such as MeOH) at an elevated temperature, and preferably at a reflux temperature.

In one embodiment, $R^2$ is cyclopropyl($C_{1-4}$)alkyl, cyclobutyl($C_{1-4}$)alkyl, cyclopentyl($C_{1-4}$)alkyl, or cyclohexyl($C_{1-4}$) alkyl, optionally substituted with 1, 2, or 3 substituents, each independently selected, from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl. In another embodiment, $R^2$ is unsubstituted $C_{1-4}$ alkyl. In another embodiment, $R^1$ is OH or $C_{1-4}$ alkoxy. In another embodiment, $R^3$ is H or OH.

In one aspect, the present disclosure is drawn to the following particular embodiments:

Embodiment I: A compound of Formula

I-A

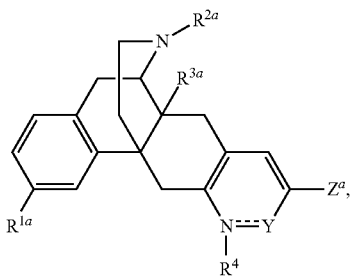

or a pharmaceutically acceptable salt or solvate thereof, wherein:

$R^{1a}$ is hydrogen, hydroxy, halo, cyano, carboxy, or aminocarbonyl; or alkyl, alkenyl, alkynyl, alkoxy, alkenyloxy or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups; or —O—PG, wherein PG is a hydroxyl protecting group;

$R^{2a}$ is (a) hydrogen or carboxamido; or (b) alkyl, alkenyl, alkynyl, cycloalkyl, cycloalkenyl, heterocyclo, aryl, heteroaryl, (cycloalkyl)alkyl, (cycloakenyl)alkyl, (heterocyclo)alkyl, arylalkyl, heteroarylalkyl, alkyl carbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups;

$R^{3a}$ is hydrogen, hydroxy, or halo; or alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups;

═══ is a single bond or a double bond;

$R^4$ is absent, hydrogen or alkyl;

Y is C(═O) or $COR^{4a}$; wherein $R^{4a}$ is hydrogen or alkyl; provided that 1) when $R^4$ is hydrogen or alkyl, then ═══ is a single bond and Y is C(═O); and 2) when $R^4$ is absent, then ═══ is a double bond and Y is $COR^{4a}$;

$Z^a$ is —C(═O)$R^{5a}$, wherein $R^{5a}$ is selected from the group consisting of (a) OH;

(b) optionally substituted alkoxy;

(c) —$NR^{6a}R^{7a}$;

(d) optionally substituted aryl;

(e) optionally substituted heteroaryl;

(f) optionally substituted cycloalkyl;

(g) optionally substituted cycloalkenyl;

(h) optionally substituted heterocyclo;

(i) optionally substituted arylalkyl;

(j) optionally substituted heteroarylalkyl;

(k) optionally substituted (cycloalkyl)alkyl;

(l) optionally substituted (cycloalkenyl)alkyl; and (m) optionally substituted (heterocyclo)alkyl; wherein two adjacent carbon atoms of said optionally substituted cycloalkyl and optionally substituted cycloalkenyl rings are optionally fused to a phenyl ring; and wherein $R^{6a}$ is hydrogen or alkyl;

$R^{7a}$ is selected from the group consisting of hydrogen, optionally substituted carboxyalkyl, optionally substituted (alkoxycarbonyl)alkyl, optionally substituted (carboxamido)alkyl, hydroxyalkyl, alkyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein two adjacent carbon atoms of said cycloalkyl and cycloalkenyl rings are optionally fused to a phenyl ring; and wherein said cycloalkyl, cycloalkenyl, heterocyclo, aryl and heteroaryl, and said cycloalkyl, cycloalkenyl, heterocyclo, aryl and heteroaryl portions are optionally substituted with 1, 2, or 3 independently selected $R^{8a}$ groups; or $R^{6a}$ and $R^{7a}$ together with the nitrogen atom to which they are attached form an optionally substituted heterocyclic ring; and each $R^{8a}$ is independently selected from the group consisting of hydroxy, halo, alkyl, haloalkyl, cyano, nitro, amino, alkylamino, dialkylamino, carboxy, alkoxy, and alkoxycarbonyl.

Embodiment II: The compound of Embodiment I, or a pharmaceutically acceptable salt or solvate thereof, wherein ═══ is a single bond, $R^4$ is hydrogen or alkyl, and Y is C(═O).

Embodiment III: The compound of Embodiment II, or a pharmaceutically acceptable salt or solvate thereof, wherein $R^{1a}$ is hydrogen, hydroxy, halo, cyano, carboxy, or aminocarbonyl; or alkyl, alkenyl, alkynyl, alkoxy, alkenyloxy or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups; or —O-PG, wherein PG is a hydroxyl protecting group;

$R^{2a}$ is (a) hydrogen or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups;

$R^{3a}$ is hydrogen, hydroxy, or halo; or alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups;

$R^{5a}$ is selected from the group consisting of (a) OH;

(b) optionally substituted alkoxy; and (c) —$NR^{6a}R^{7a}$; wherein $R^{6a}$ is hydrogen or alkyl;

$R^{7a}$ is selected from the group consisting of hydrogen, optionally substituted carboxyalkyl, optionally substituted (alkoxycarbonyl)alkyl, optionally substituted (carboxamido)alkyl, and hydroxyalkyl; and each $R^{8a}$ is independently selected from the group consisting of hydroxy, alkyl, haloalkyl, amino, alkylamino, dialkylamino, carboxy, alkoxy, and alkoxycarbonyl.

Embodiment IV: The compound of any one of Embodiments I-III, having the Formula II-A:

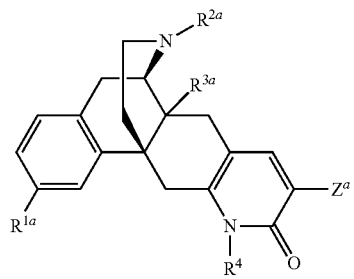

II-A or a pharmaceutically acceptable salt or solvate thereof.

Embodiment V: The compound of any one of Embodiments having the Formula III-A:

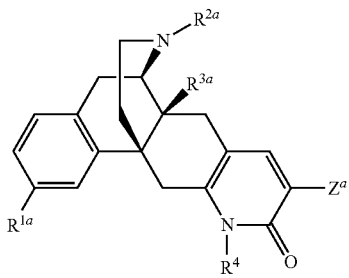

III-A or a pharmaceutically acceptable salt or solvate thereof.

Embodiment VI: The compound of any one of Embodiments I-IV, having the Formula IV-A:

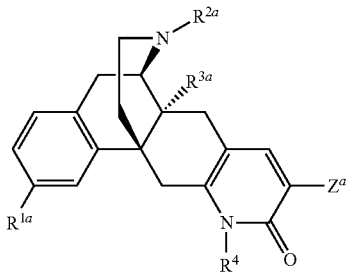

IV-A or a pharmaceutically acceptable salt or solvate thereof.

Embodiment VII: The compound of any one of Embodiments I-III, having the Formula V-A:

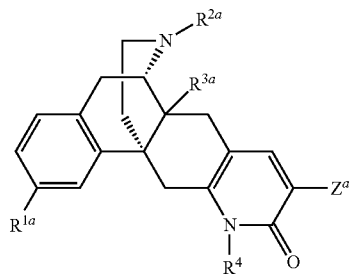

V-A or a pharmaceutically acceptable salt or solvate thereof.

Embodiment VIII: The compound of any one of Embodiments I-III and VII, having the Formula VI-A:

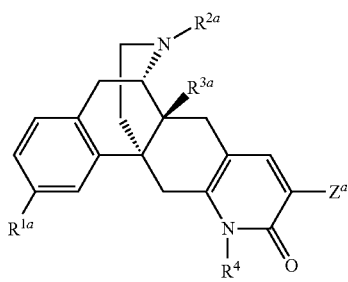

VI-A or a pharmaceutically acceptable salt or solvate thereof.

Embodiment IX: The compound of any one of Embodiments I-III and VII, having the Formula VII-A:

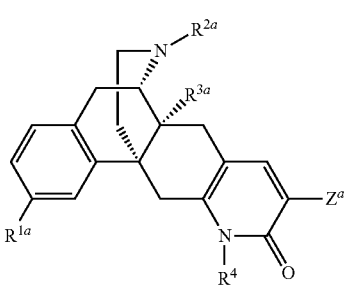

VII-A or a pharmaceutically acceptable salt or solvate thereof.

Embodiment X: The compound of Embodiment I, or a pharmaceutically acceptable salt or solvate thereof, wherein $\equiv$ is a double bond, $R^4$ is absent, Y is $COR^{4a}$, and $R^{4a}$ is hydrogen or alkyl.

Embodiment XI: The compound of Embodiment I or X, having the Formula VIII-A:

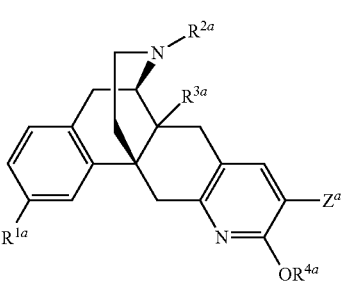

VIII-A or a pharmaceutically acceptable salt or solvate thereof.

Embodiment XII: The compound of any one of Embodiments I-XI, or a pharmaceutically acceptable salt or solvate thereof, wherein $R^{1a}$ is hydrogen, hydroxy, halo, cyano, carboxy, or aminocarbonyl; or alkyl, alkenyl, alkynyl, alkoxy, alkenyloxy or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

Embodiment XIII: The compound of any one of Embodiments I-XII, or a pharmaceutically acceptable salt or solvate thereof, wherein $R^{1a}$ is hydroxy or unsubstituted $C_{1-6}$ alkoxy.

Embodiment XIV: The compound of any one of Embodiments I-XI, or a pharmaceutically acceptable salt or solvate thereof, wherein $R^{1a}$ is —O-PG.

Embodiment XV: The compound of Embodiment XIV, or a pharmaceutically acceptable salt or solvate thereof, wherein PG is selected from the group consisting of alkyl, arylalkyl, heterocyclo, (heterocyclo)alkyl, acyl, silyl, and carbonate, any of which is optionally substituted.

Embodiment XVI: The compound of Embodiment XV, or a pharmaceutically acceptable salt or solvate thereof, wherein PG is selected from the group consisting of alkyl, arylalkyl, heterocyclo, (heterocyclo)alkyl, benzoyl, (benzyloxy)carbonyl, alkoxycarbonyl, alkylcarbonyl, and silyl, any of which is optionally substituted.

Embodiment XVII: The compound of Embodiment XVI, or a pharmaceutically acceptable salt or solvate thereof, wherein PG is selected from the group consisting of methyl, tert-butyl, optionally substituted benzyl, optionally substituted benzoyl, acetyl, trimethyl silyl, tert-butyldimethyl silyl, tert-butyldiphenyl silyl, and tri-isopropyl silyl.

Embodiment XVIII: The compound of any one of Embodiments I-XVII, or a pharmaceutically acceptable salt or solvate thereof, wherein $R^{2a}$ is hydrogen or carboxamido.

Embodiment XIX: The compound of any one of Embodiments I-XVII, or a pharmaceutically acceptable salt or solvate thereof, wherein $R^{2a}$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

Embodiment XX: The compound of Embodiment XIX, or a pharmaceutically acceptable salt or solvate thereof, wherein $R^{2a}$ is $C_{3-7}$ (cycloalkyl)($C_{1-4}$)alkyl or $C_{3-7}$ (cycloalkenyl)($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

Embodiment XXI: The compound of Embodiment XIX, or a pharmaceutically acceptable salt or solvate thereof, wherein $R^{2a}$ is unsubstituted $C_{1-4}$ alkyl, or cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

Embodiment XXII: The compound of any one of Embodiments I-XXI, or a pharmaceutically acceptable salt or solvate thereof, wherein $R^{3a}$ is hydrogen.

Embodiment XXIII: The compound of any one of Embodiments I-XXI, or a pharmaceutically acceptable salt or solvate thereof, wherein $R^{3a}$ is hydroxy.

Embodiment XXIV: The compound of any one of Embodiments I-XXI, or a pharmaceutically acceptable salt or solvate thereof, wherein $R^{3a}$ is unsubstituted $C_{1-6}$ alkoxy or $C_{1-6}$ alkoxy substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

Embodiment XXV: The compound of any one of Embodiments I-IX and XII-XXIV, or a pharmaceutically acceptable salt or solvate thereof, wherein $R^4$ is hydrogen.

Embodiment XXVI: The compound of any one of Embodiments I-IX and XII-XXIV, or a pharmaceutically acceptable salt or solvate thereof, wherein $R^4$ is $C_{1-4}$ alkyl.

Embodiment XXVII: The compound of any one of Embodiments I and X-XXIV, or a pharmaceutically acceptable salt or solvate thereof, wherein $R^4$ is absent and $R^{4a}$ is hydrogen or alkyl.

Embodiment XXVIII: The compound of any one of Embodiments I-XXVII, or a pharmaceutically acceptable salt or solvate thereof, wherein $R^{5a}$ is OH.

Embodiment XXIX: The compound of any one of Embodiments I-XXVII, or a pharmaceutically acceptable salt or solvate thereof, wherein $R^{5a}$ is optionally substituted alkoxy.

Embodiment XXX: The compound of Embodiment XXIX, or a pharmaceutically acceptable salt or solvate thereof, wherein $R^{5a}$ is unsubstituted $C_{1-6}$ alkoxy or $C_{1-6}$ alkoxy substituted with 1, 2, or 3 substituents independently selected from the group consisting of hydroxy, halo, haloalkyl, cyano, nitro, amino, alkylamino, dialkylamino, carboxy, alkoxy, and alkoxycarbonyl.

Embodiment XXXI: The compound of any one of Embodiments I-XXVII, or a pharmaceutically acceptable salt or solvate thereof, wherein $R^{5a}$ is —$NR^{6a}R^{7a}$, wherein $R^{6a}$ is hydrogen or alkyl; and $R^{7a}$ is selected from the group consisting of hydrogen, optionally substituted carboxyalkyl, optionally substituted (alkoxycarbonyl)alkyl, optionally substituted (carboxamido)alkyl, hydroxyalkyl, alkyl, cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein said cycloalkyl, cycloalkenyl, heterocyclo, aryl and heteroaryl, and said cycloalkyl, cycloalkenyl, heterocyclo, aryl and heteroaryl portions are optionally substituted with 1, 2, or 3 independently selected $R^{8a}$ groups.

Embodiment XXXII: The compound of any one of Embodiments I-XXVII and XXXI, or a pharmaceutically acceptable salt or solvate thereof, wherein $R^{5a}$ is —$NR^{6a}R^{7a}$, wherein $R^{6a}$ is hydrogen or $C_{1-6}$ alkyl, and $R^{7a}$ is hydrogen.

Embodiment XXXIII: The compound of Embodiment I-XXVII and XXXI, or a pharmaceutically acceptable salt or solvate thereof, wherein $R^{5a}$ is —$NR^{6a}R^{7a}$, wherein $R^{6a}$ and $R^{7a}$ are each independently alkyl.

Embodiment XXXIV: The compound of any one of Embodiments I-XXVII and XXXI, or a pharmaceutically acceptable salt or solvate thereof, wherein $R^{5a}$ is —$NR^{6a}R^{7a}$, wherein $R^{6a}$ is hydrogen or alkyl and $R^{7a}$ is selected from the group consisting of optionally substituted carboxyalkyl, optionally substituted (alkoxycarbonyl)alkyl, optionally substituted (carboxamido)alkyl, and hydroxyalkyl.

Embodiment XXXV: The compound of any one of Embodiments I-XXVII and XXXI, or a pharmaceutically acceptable salt or solvate thereof, wherein $R^{5a}$ is —$NR^{6a}R^{7a}$, wherein $R^{6a}$ is hydrogen or alkyl, and $R^{7a}$ is selected from the group consisting of cycloalkyl, cycloalkenyl, heterocyclo, aryl, heteroaryl, (cycloalkyl)alkyl, (cycloalkenyl)alkyl, (heterocyclo)alkyl, arylalkyl, and heteroarylalkyl, wherein two adjacent carbon atoms of said cycloalkyl and cycloalkenyl rings are optionally fused to a phenyl ring; and wherein said cycloalkyl, cycloalkenyl, heterocyclo, aryl and heteroaryl portions are optionally substituted with 1, 2, or 3 independently selected $R^{8a}$ groups.

Embodiment XXXVI: The compound of any one of Embodiments I-XXVII, XXXI, and XXXIV, or a pharmaceutically acceptable salt or solvate thereof, wherein $R^{5a}$ is —$NR^{6a}R^{7a}$, $R^{6a}$ is hydrogen or $C_{1-6}$ alkyl, and $R^{7a}$ is optionally substituted carboxy($C_{1-6}$)alkyl, optionally substituted ($C_{1-6}$ alkoxycarbonyl)($C_{1-6}$)alkyl, or optionally substituted (carboxamido)($C_{1-6}$)alkyl.

Embodiment XXXVII: The compound of Embodiment XXXVI, or a pharmaceutically acceptable salt or solvate thereof, wherein $R^{7a}$ is —$CHR^{9a}$—$C(=O)$—$Z^{1a}$, wherein $R^{9a}$ is selected from the group consisting of hydrogen, alkyl, hydroxyalkyl, carboxyalkyl, aminoalkyl, (aminocarbonyl)alkyl, (alkylaminocarbonyl)alkyl, (dialkylaminocarbonyl)alkyl, mercaptoalkyl, (alkylthio)alkyl, guanidinoalkyl, arylalkyl, (cycloalkyl)alkyl, (cycloalkenyl)alkyl, (heterocyclo)alkyl, and (heteroaryl)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, alkyl, haloalkyl, cyano, nitro, amino, alkylamino, dialkylamino, carboxy, alkoxy, and alkoxycarbonyl; and $Z^{1a}$ is $OR^{10a}$ or $NR^{11a}R^{12a}$, wherein $R^{10a}$ is hydrogen or alkyl; and $R^{11a}$ and $R^{12a}$ are each independently selected from the group consisting of hydrogen and alkyl.

Embodiment XXXVIII: The compound of Embodiment XXXVII, or a pharmaceutically acceptable salt or solvate thereof, wherein $R^{9a}$ is selected from the group consisting of hydrogen, $C_{1-6}$ alkyl, monohydroxy($C_{1-6}$)alkyl, carboxy ($C_{1-6}$)alkyl, amino($C_{1-6}$)alkyl, (aminocarbonyl)($C_{1-6}$)alkyl, ($C_{1-4}$ alkylaminocarbonyl)($C_{1-6}$)alkyl, (di($C_{1-4}$)alkylaminocarbonyl)($C_{1-6}$)alkyl, mercapto($C_{1-6}$)alkyl, ($C_{1-4}$ alkylthio)($C_{1-6}$)alkyl, guanidino ($C_{1-6}$)alkyl, $C_{6-12}$ aryl($C_{1-6}$)alkyl, ($C_{3-7}$ cycloalkyl)($C_{1-6}$)alkyl, ($C_{3-7}$ cycloalkenyl)($C_{1-6}$)alkyl, (5- or 6-membered heterocyclo)($C_{1-6}$)alkyl, and (5- or 6-membered heteroaryl)($C_{1-6}$)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, $C_{1-4}$ alkyl, halo($C_{1-4}$)alkyl, cyano, nitro, amino, $C_{1-4}$ alkylamino, di($C_{1-4}$)alkylamino, carboxy, $C_{1-4}$ alkoxy, and $C_{1-4}$ alkoxycarbonyl.

Embodiment XXXIX: The compound of Embodiment XXXVII or XXXVIII, or a pharmaceutically acceptable salt or solvate thereof, wherein $Z^{1a}$ is $OR^{10a}$, wherein $R^{10a}$ is hydrogen or $C_{1-4}$ alkyl.

Embodiment XL: The compound of Embodiments XXXVII or XXXVIII, or a pharmaceutically acceptable salt or solvate thereof, wherein $Z^{1a}$ is $NR^{11a}R^{12a}$, wherein $R^{11a}$ and $R^{12a}$ are each independently selected from the group consisting of hydrogen and $C_{1-4}$ alkyl.

Embodiment XLI: The compound of any one of Embodiments I-XXVII and XXXI, or a pharmaceutically acceptable salt or solvate thereof, wherein $R^{5a}$ is —$NR^{6a}R^{7a}$, $R^{6a}$ is hydrogen or $C_{1-6}$ alkyl, and $R^{7a}$ is hydroxyalkyl.

Embodiment XLII: The compound of Embodiment XLI, or a pharmaceutically acceptable salt or solvate thereof, wherein $R^{7a}$ is 1,2-dihydroxyethyl.

Embodiment XLIII: The compound of any one of Embodiments I-XXVII and XXXI, or a pharmaceutically acceptable salt or solvate thereof, wherein $R^{5a}$ is —$NR^{6a}R^{7a}$ and $R^{6a}$ and $R^{7a}$ together with the nitrogen atom form an optionally substituted heterocyclic ring.

Embodiment XLIV: The compound of Embodiment XLIII, or a pharmaceutically acceptable salt or solvate thereof, wherein $R^{6a}$ and $R^{7a}$ together with the nitrogen atom to which they are attached form an optionally substituted 5- or 6-membered heterocyclic ring.

Embodiment XLV: The compound of Embodiment XLIII, or a pharmaceutically acceptable salt or solvate thereof, wherein $R^{6a}$ and $R^{7a}$ together with the nitrogen atom form an optionally substituted 7-10 membered bicyclic ring system.

Embodiment XLVI: The compound of any one of Embodiments I-XXVII, or a pharmaceutically acceptable salt or solvate thereof, wherein $R^{5a}$ is selected from the group consisting of optionally substituted aryl, optionally substituted heteroaryl, optionally substituted cycloalkyl, optionally substituted cycloalkenyl, optionally substituted heterocyclo, optionally substituted arylalkyl, optionally substituted heteroarylalkyl, optionally substituted (cycloalkyl)alkyl, optionally substituted (cycloalkenyl)alkyl, and optionally substituted (heterocyclo)alkyl, wherein two adjacent carbon atoms of said cycloalkyl or cycloalkenyl rings are optionally fused to a phenyl ring.

Embodiment XLVII: The compound of Embodiment XLVI, or a pharmaceutically acceptable salt or solvate thereof, wherein $R^{5a}$ is unsubstituted phenyl or phenyl substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^{8a}$ groups.

Embodiment XLVIII: The compound of any one of Embodiments I-XXVII, or a pharmaceutically acceptable salt or solvate thereof, wherein $Z^a$ is selected from the group consisting of

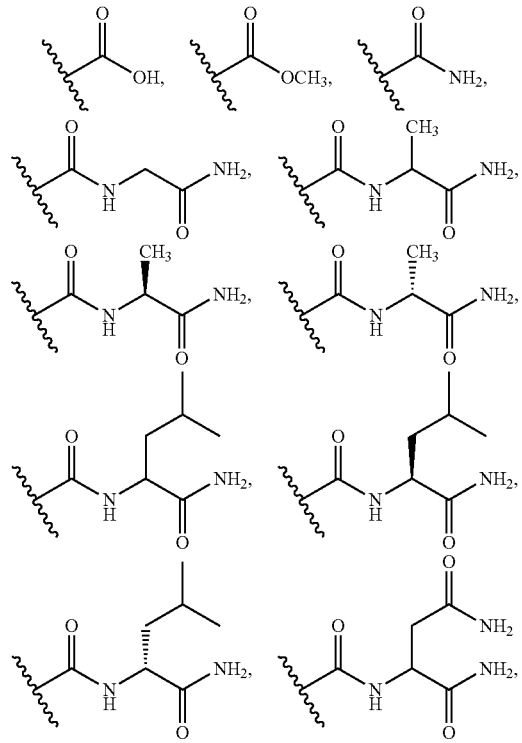

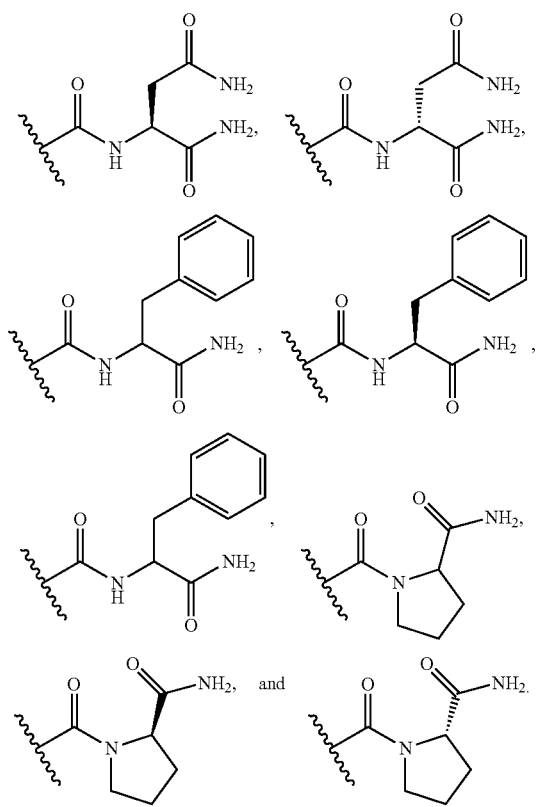

Embodiment XLIX: The compound of any one of Embodiments I-XXVII, or a pharmaceutically acceptable salt or solvate thereof, wherein $Z^a$ is selected from the group consisting of

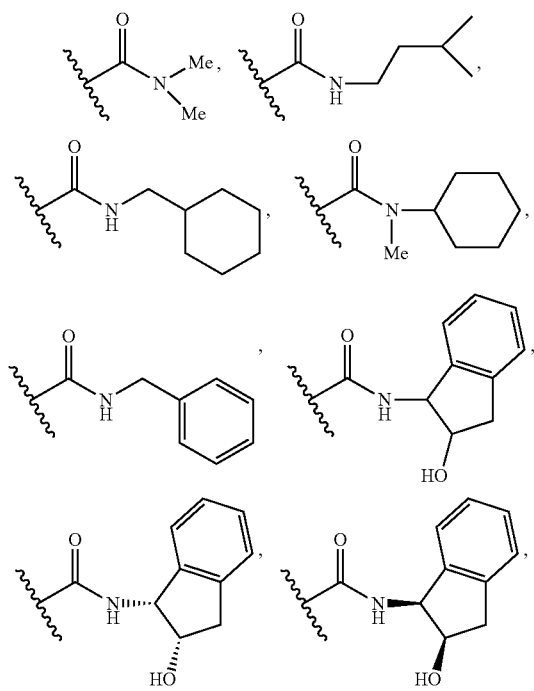

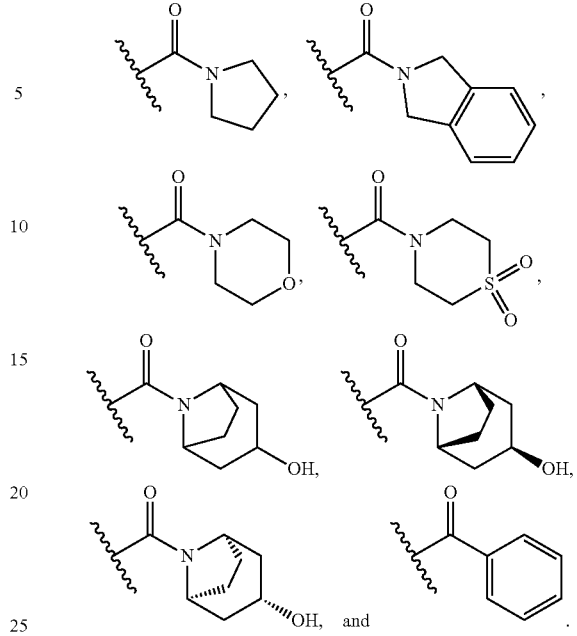

Embodiment L: The compound of Embodiment XLIX, or a pharmaceutically acceptable salt or solvate thereof, wherein
$R^{1a}$ is hydroxy or unsubstituted $C_{1-6}$ alkoxy;
$R^{2a}$ is cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;
$R^{3a}$ is hydrogen; and
$R^4$ is hydrogen or methyl.

Embodiment LI: The compound of any one of Embodiments I-L, or a pharmaceutically acceptable salt or solvate thereof, wherein $R^{2a}$ is unsubstituted cyclopropyl($C_{1-4}$)alkyl.

Embodiment LII: The compound of any one of Embodiments I-IX, or a pharmaceutically acceptable salt or solvate thereof, wherein
$R^{1a}$ is hydroxy or unsubstituted alkoxy;
$R^{2a}$ is unsubstituted $C_{1-4}$ alkyl, or cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, cyano, nitro, amino, $C_{1-4}$ alkylamino, di($C_{1-4}$)alkylamino, carboxy, $C_{1-4}$ alkoxy, and $C_{1-4}$ alkoxycarbonyl;
$R^{3a}$ is hydrogen or OH; and
$R^4$ is hydrogen.

Embodiment LIII: The compound of any one of Embodiments I-IX, or a pharmaceutically acceptable salt or solvate thereof, wherein
$R^{1a}$ is hydroxy or unsubstituted $C_{1-6}$ alkoxy;
$R^{2a}$ is
$C_{1-6}$ alkyl substituted with 1, 2, or 3 substituents independently selected from the group consisting of halo, halo($C_{1-4}$)alkyl, phenyl, and heterocyclo;
unsubstituted $C_{2-6}$ alkenyl; or
$C_{2-6}$ alkenyl substituted with 1, 2, or 3 substituents independently selected from the group consisting of $C_{1-4}$ alkyl, halo, halo($C_{1-4}$)alkyl, phenyl, and heterocyclo;
$R^{1a}$ is hydrogen or hydroxy; and
$R^4$ is hydrogen.

Embodiment LIV: The compound of any one of Embodiments I-IX, having the Formula X-A:

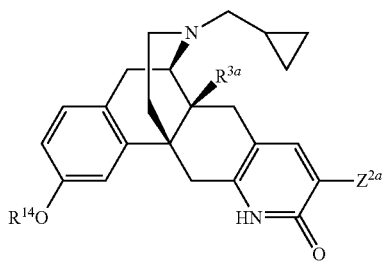

or a pharmaceutically acceptable salt or solvate thereof, wherein $R^{14}$ is H or $C_{1-6}$ alkyl optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and $R^{3a}$ is hydrogen or OH, and $Z^{2a}$ is selected from the group consisting of

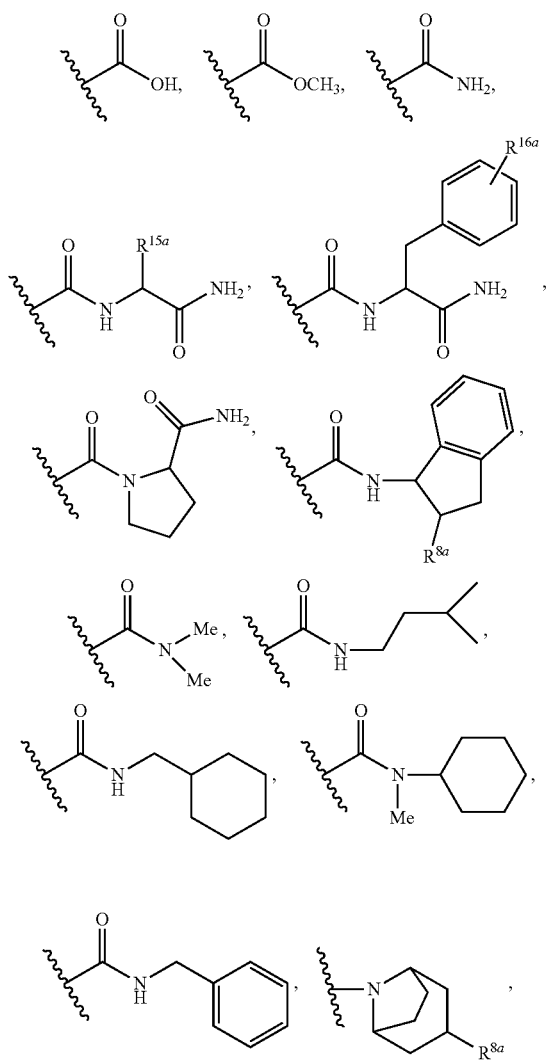

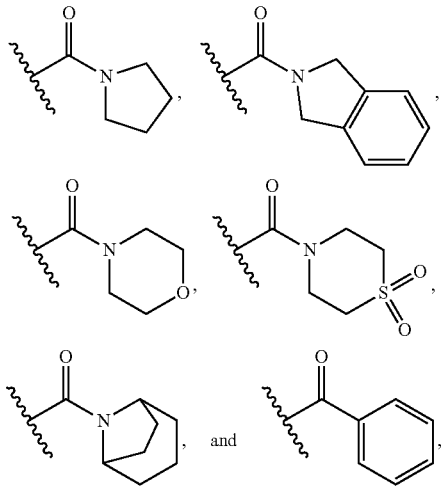

wherein $R^{15a}$ is hydrogen, $C_{1-4}$ alkyl or —($C_{1-4}$)alkyl-C(=O)$NH_2$, $R^{16a}$ is selected from the group consisting of hydrogen, $C_{1-4}$ alkyl, hydroxy, halo, halo($C_{1-2}$)alkyl, $C_{1-2}$ alkoxy, $C_{1-2}$ alkoxycarbonyl, and aminocarbonyl.

Embodiment LV: The compound of Embodiment I or II, selected from the group consisting of

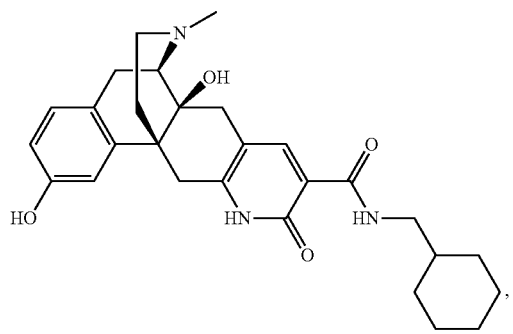

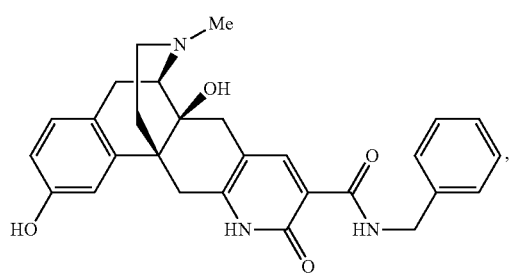

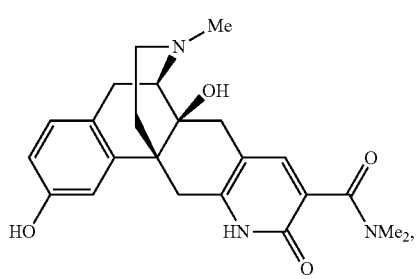

-continued
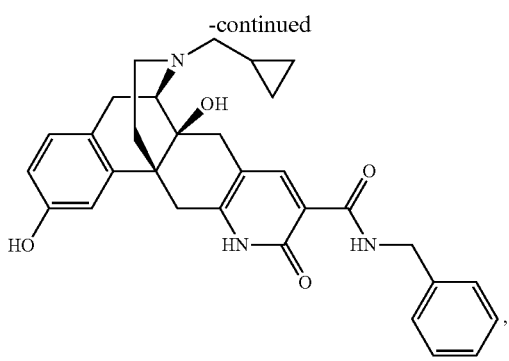
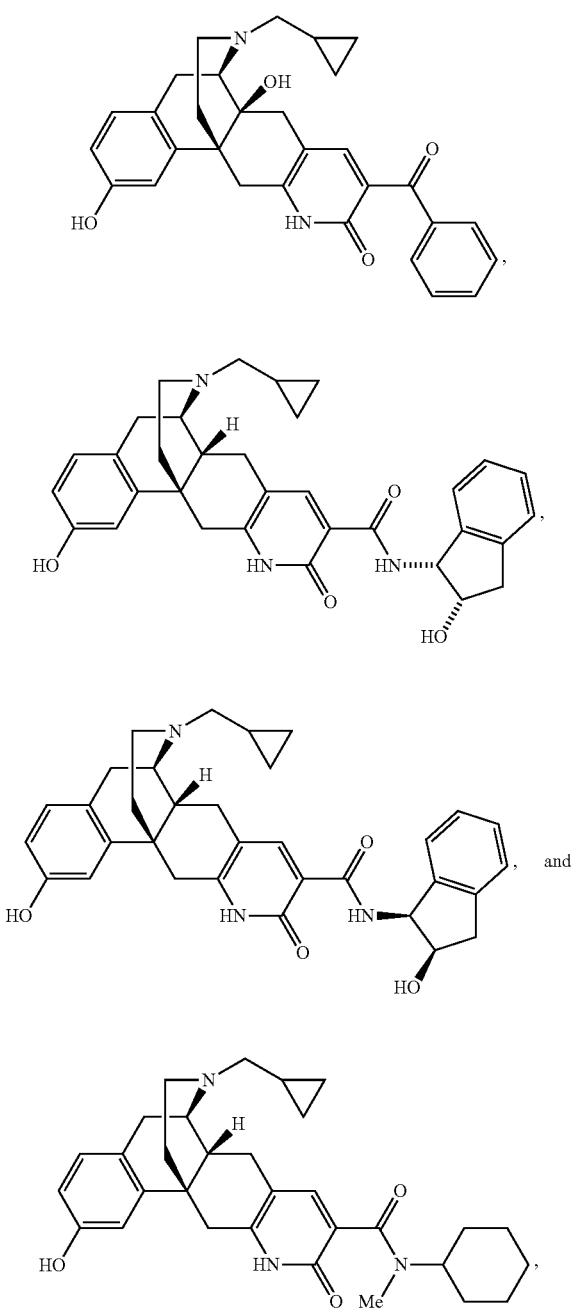
or a pharmaceutically acceptable salt or solvate thereof.
Embodiment LVI: The compound of Embodiment III, selected from the group consisting of 61
-continued
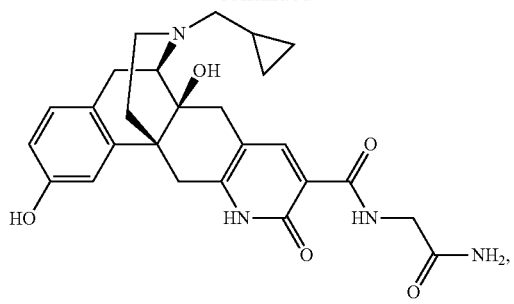
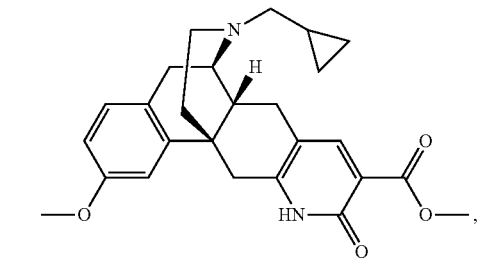
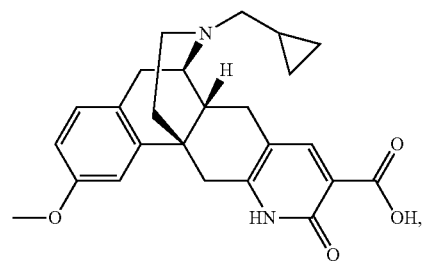
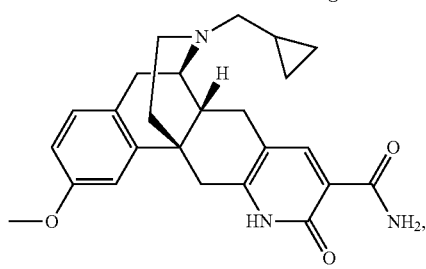
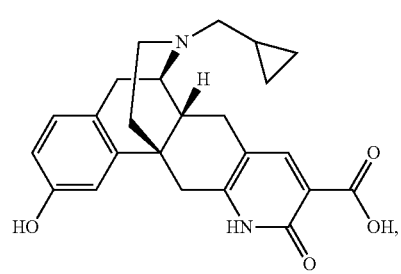
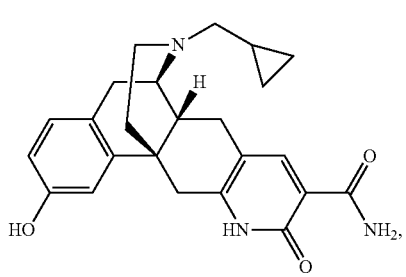
62
-continued
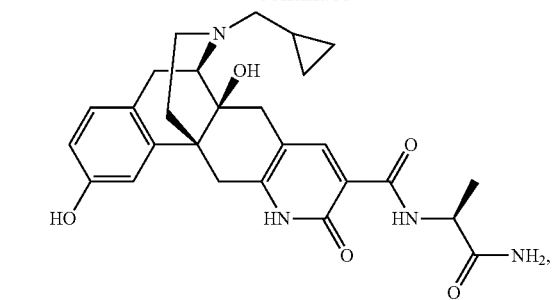
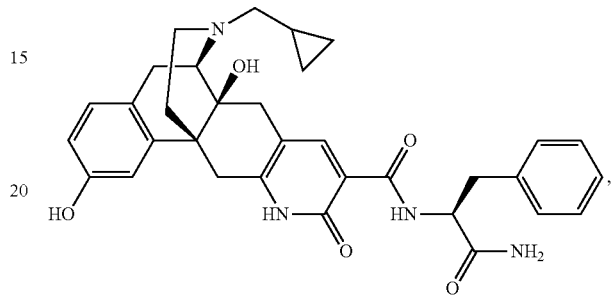
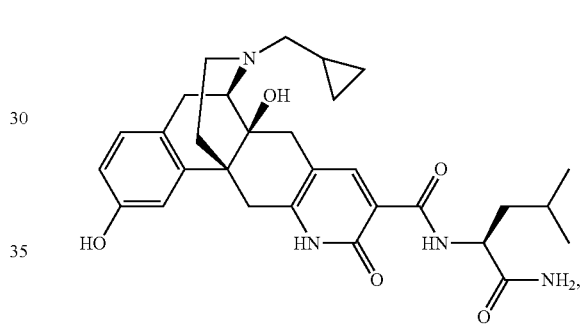
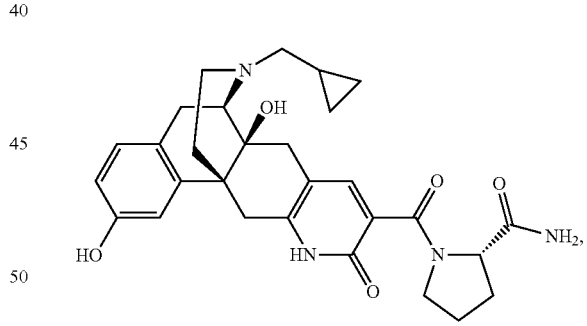
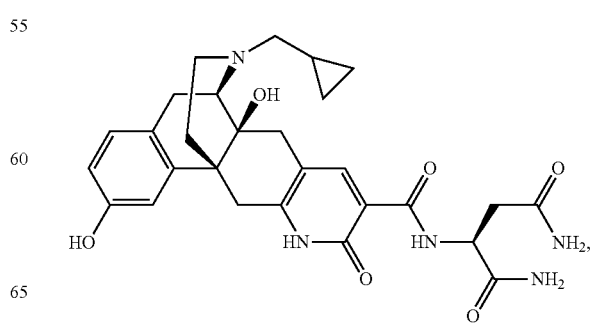

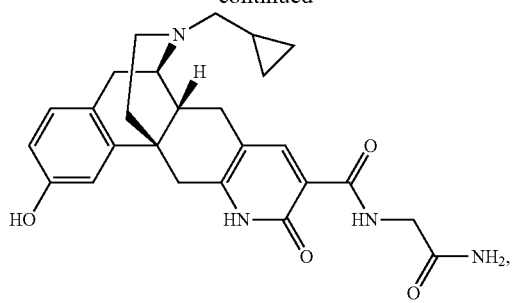
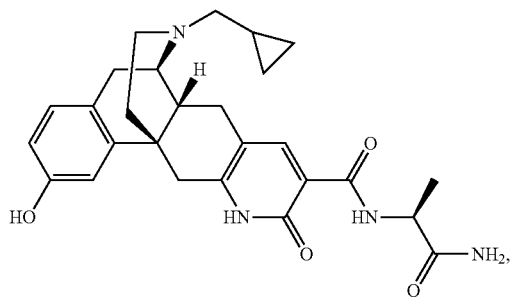
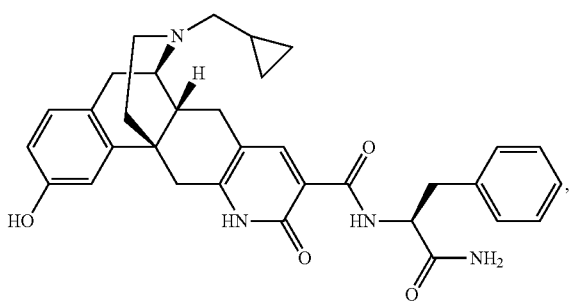
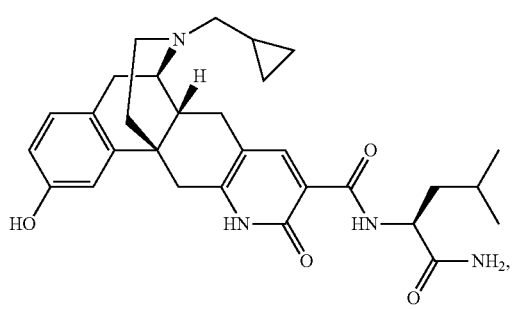
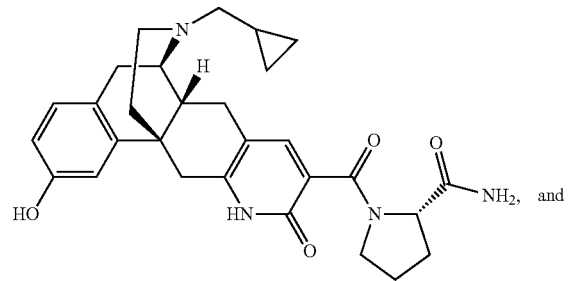
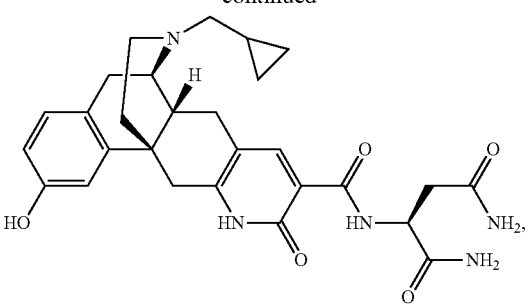
or a pharmaceutically acceptable salt or solvate thereof,
Embodiment LVII: The compound of Embodiment III, selected from the group consisting of
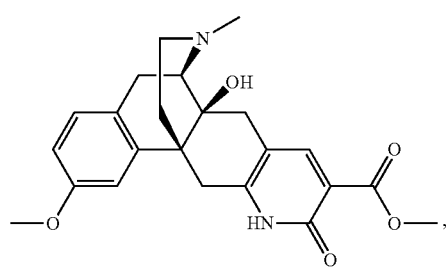
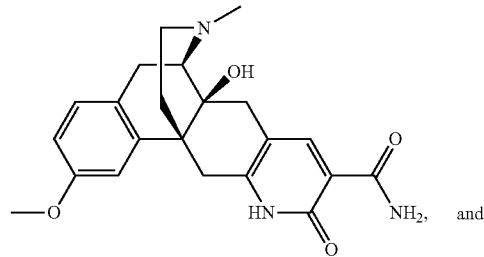 and
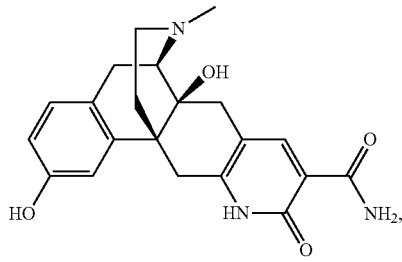
or a pharmaceutically acceptable salt or solvate thereof.
Embodiment LVIII: The compound of Embodiment III, selected from the group consisting of
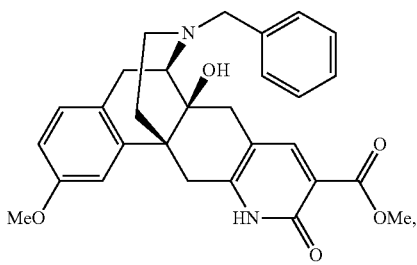

-continued
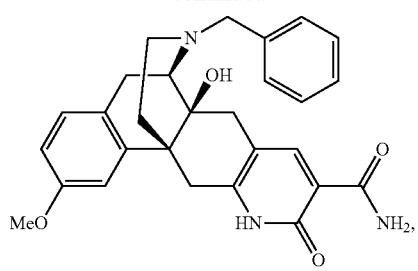
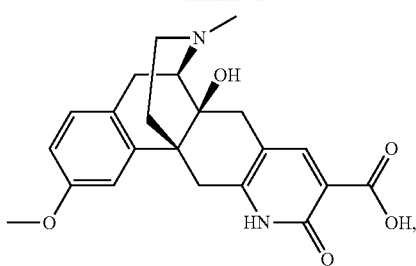
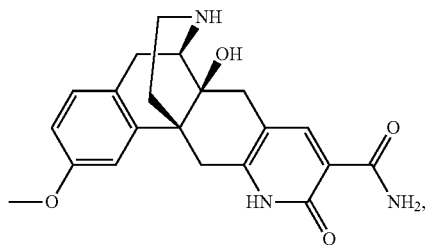
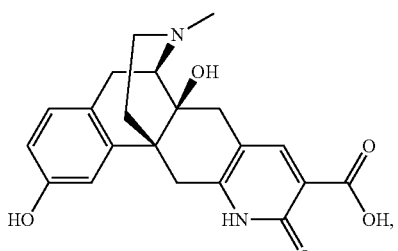
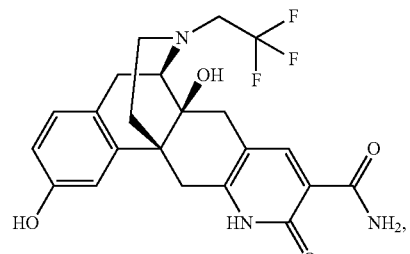
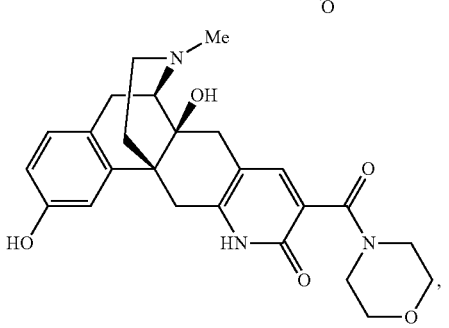
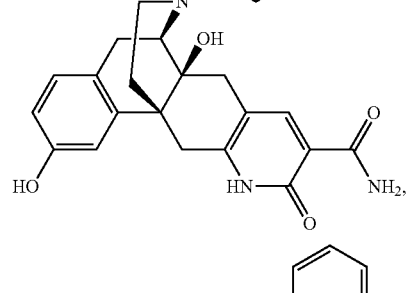
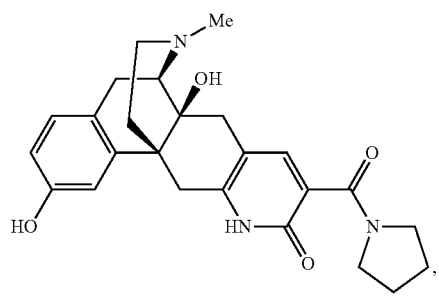
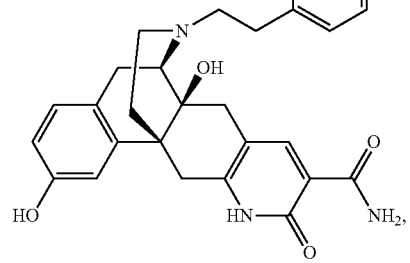
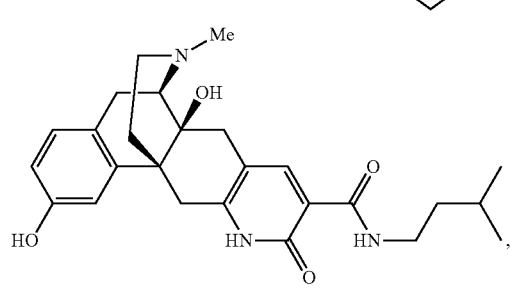
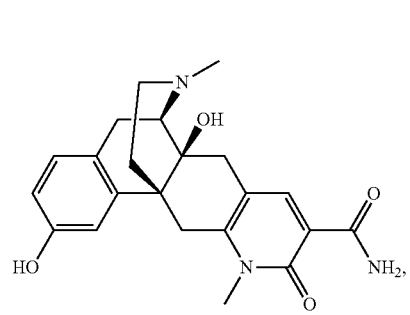
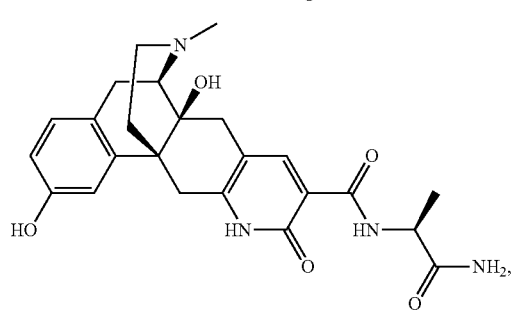

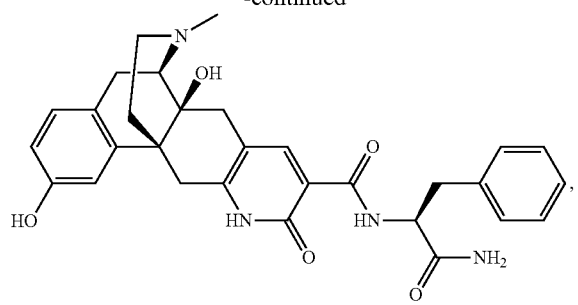

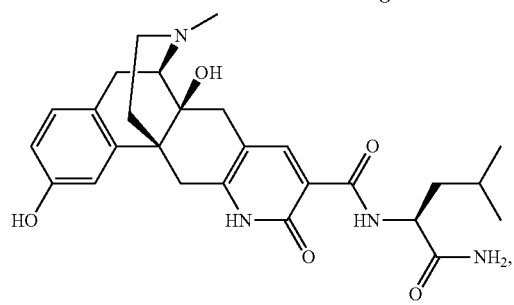

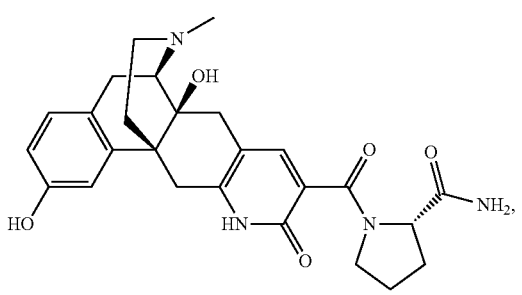

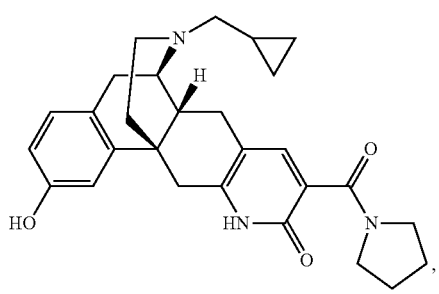

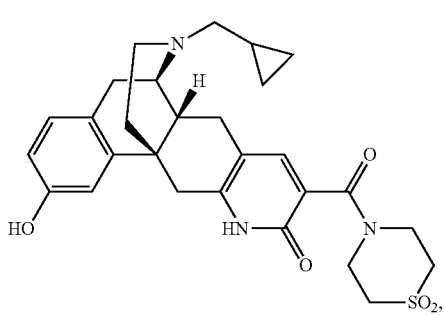

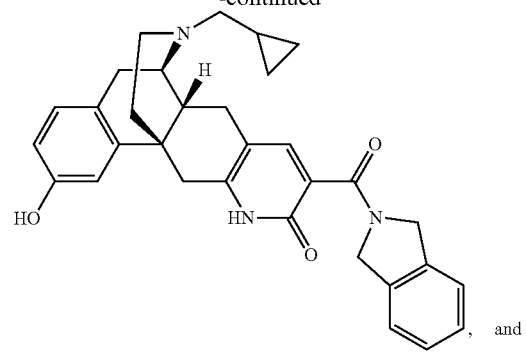

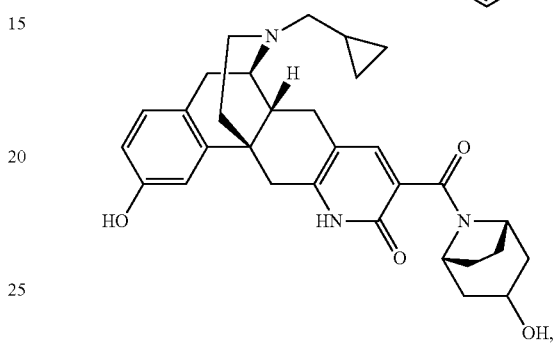

or a pharmaceutically acceptable salt or solvate thereof.

Embodiment LIX: A pharmaceutical composition, comprising a therapeutically effective amount of a compound of any one of Embodiments I-LIX, or a pharmaceutically acceptable salt or solvate thereof, and one or more pharmaceutically acceptable carriers.

Embodiment LX: A method of treating or preventing a disorder responsive to the modulation of one or more opioid receptors in a patient, comprising administering to a patient in need of such treatment or prevention an effective amount of a compound of any one of Embodiments I-LIX, or a pharmaceutically acceptable salt or solvate thereof.

Embodiment LXI: The method of Embodiment LX, wherein the disorder is responsive to modulation of the μ-opioid receptor or the κ-opioid receptor, or to modulation of a combination thereof.

Embodiment LXII: The method of Embodiment LXI, wherein the disorder is responsive to modulation of the κ-opioid receptor.

Embodiment LXIII: The method of Embodiment LXI, wherein the disorder is pain.

Embodiment LXIV: A method of treating or preventing pain, constipation, diarrhea, pruritis, an addictive disorder, withdrawal from alcohol addiction or withdrawal from drug addiction in a patient, comprising administering an effective amount of a compound of any one of Embodiments I-LIX, or a pharmaceutically acceptable salt or solvate thereof, to the patient in need of such treatment or prevention.

Embodiment LXV: The method of Embodiment LXIV, wherein the method is for treating pain.

Embodiment LXVI: The method of Embodiment LXV, wherein said pain is acute pain, chronic pain or surgical pain.

Embodiment LXVII: The method of Embodiment LXVI, wherein said pain is chronic pain.

Embodiment LXVIII: The method of Embodiment LXVII, wherein said chronic pain is neuropathic pain, postoperative pain, or inflammatory pain.

Embodiment LXIX: A method of modulating one or more opioid receptors in a patient, comprising administering to the patient an effective amount of a compound of any one of Embodiments I-LIX, or a pharmaceutically acceptable salt or solvate thereof.

Embodiment LXX: The method of Embodiment LXIX, wherein the μ- or κ-opioid receptor is modulated, or both the μ- and κ-opioid receptors are modulated.

Embodiment LXXI: A compound of any one of Embodiments I-LIX, or a pharmaceutically acceptable salt or solvate thereof, for use in treatment or prevention of a disorder responsive to the modulation of one or more opioid receptors in a patient.

Embodiment LXXII: The compound of Embodiment LXXI, wherein the disorder is responsive to modulation of the μ-opioid receptor or the κ-opioid receptor, or to modulation of a combination thereof.

Embodiment LXXIII: The compound of Embodiment LXXI or LXXII, wherein the disorder is responsive to the modulation of the κ-opioid receptor.

Embodiment LXXIV: The compound of any one of Embodiments LXXI-LXXIII, wherein the disorder is pain.

Embodiment LXXV: A compound of any one of Embodiments I-LIX, or a pharmaceutically acceptable salt or solvate thereof, for use in treatment or prevention of pain, constipation, diarrhea, pruritus, an addictive disorder, withdrawal from alcohol addiction or withdrawal from drug addiction in a patient.

Embodiment LXXVI: The compound of Embodiment LXXV, wherein said use is for the treatment or prevention of pain.

Embodiment LXXVII: The compound of Embodiment LXXVI, wherein said pain is acute pain, chronic pain or surgical pain.

Embodiment LXXVIII: The compound of Embodiment LXXVII, wherein said chronic pain is neuropathic pain, postoperative pain, or inflammatory pain.

Embodiment LXXIX: A compound of any one of Embodiments I-LIX, or a pharmaceutically acceptable salt or solvate thereof, for use in modulating of one or more opioid receptors in a patient.

Embodiment LXXX: The compound of Embodiment LXXIX, wherein the μ- or κ-opioid receptor is modulated, or both the μ- and κ-receptors are modulated.

Embodiment LXXXI: Use of a compound of any one of Embodiments I-LIX, or a pharmaceutically acceptable salt or solvate thereof, in the manufacture of a medicament for treating or preventing a disorder responsive to the modulation of one or more opioid receptors.

Embodiment LXXXII: The use of Embodiment LXXXI, wherein the disorder is responsive to modulation of the μ-opioid receptor or the κ-opioid receptor, or both the μ-opioid and the κ-opioid receptors.

Embodiment LXXXIII: The use of Embodiment LXXXII, wherein the disorder is responsive to modulation of the κ-opioid receptor.

Embodiment LXXXIV: The use of any one of Embodiments LXXXI-LXXXIII, wherein the disorder is pain.

Embodiment LXXXV: Use of a compound of any one of Embodiments I-LIX, or a pharmaceutically acceptable salt or solvate thereof, in the manufacture of a medicament for treating or preventing pain, constipation, diarrhea, pruritus, an addictive disorder, withdrawal from alcohol addiction or withdrawal from drug addiction in a patient.

Embodiment LXXXVI: The use of Embodiment LXXXV, wherein said use is for treating or preventing pain.

Embodiment LXXXVII: The use of Embodiment LXXXVI, wherein said pain is acute pain, chronic pain or surgical pain.

Embodiment LXXXVIII: The use of Embodiment LXXXVII, wherein said chronic pain is neuropathic pain, postoperative pain, or inflammatory pain.

Embodiment LXXXIX: Use of a compound of any one of Embodiments I-LIX, or a pharmaceutically acceptable salt or solvate thereof, in the manufacture of a medicament for modulating of one or more opioid receptors.

Embodiment XC: The use of Embodiment LXXXIX, wherein the μ- or κ-opioid receptor is modulated, or both the μ- and κ-opioid receptors are modulated.

Embodiment XCI: A compound of any one of Embodiments I-LIX, or a pharmaceutically acceptable salt or solvate thereof, for use as a medicament.

Embodiment XCII: A pharmaceutical composition, comprising a compound of any one of Embodiments I-LIX, or a pharmaceutically acceptable salt or solvate thereof, and a pharmaceutically acceptable carrier.

Embodiment XCIII: A compound of any one of Embodiments or a pharmaceutically acceptable salt or solvate thereof, wherein the compound is $^3$H, $^{11}$C, or $^{14}$C radiolabeled.

Embodiment XCIV: A method of screening a candidate compound for the ability to bind to an opioid receptor using a radiolabeled compound of Embodiment XCIII, comprising a) introducing a fixed concentration of the radiolabeled compound to the receptor to form a complex; b) titrating the complex with a candidate compound; and c) determining the binding of the candidate compound to said receptor.

Embodiment XCV: A method of preparing a pharmaceutical composition, comprising admixing a therapeutically effective amount of a compound of any one of Embodiments I-LIX, or a pharmaceutically acceptable salt or solvate thereof, with a pharmaceutically acceptable carrier.

Embodiment XCVI: A kit, comprising a sterile container containing an effective amount of the compound of any one of Embodiments I-LIX, or a pharmaceutically acceptable salt or solvate thereof, and instructions for therapeutic use.

Embodiment XCVII: A process for preparing a compound of Embodiment I, wherein --- is a single bond, $R^4$ is hydrogen or alkyl, and Y is C(=O), comprising reacting a compound of Formula XI-A

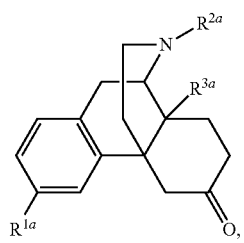

XI-A wherein $R^{1a}$—$R^{3a}$ are as defined in Embodiment I,
with N,N-dimethylformamideacetal to form an intermediate, and
reacting the intermediate with

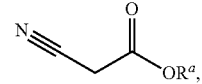

wherein $R^a$ is an optionally substituted alkyl, to obtain a compound of Formula I-A, wherein $R^4$ is hydrogen, ⁼ is a single bond, Y is C(=O), and $Z^a$ is

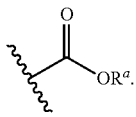

Embodiment XCVIII: The process of Embodiment XCVII, wherein $R^a$ is a $C_{1-4}$ alkyl optionally substituted with 1, 2, or 3 substituents, each independently selected from the group consisting of hydroxy, halo, haloalkyl, cyano, nitro, amino, alkylamino, dialkylamino, carboxy, alkoxy, and alkoxycarbonyl.

Embodiment XCIX: The process of Embodiment XCVII or XCVIII, wherein $R^{2a}$ is unsubstituted $C_{1-4}$ alkyl, or cyclopropyl($C_{1-4}$)alkyl, cyclobutyl($C_{1-4}$)alkyl, cyclopentyl($C_{1-4}$) alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

Embodiment C: The process of any one of Embodiments XCVII-XCIX, wherein $R^{1a}$ is OH or $C_{1-4}$ alkoxy.

Embodiment CI: The process of any one of Embodiments XCVII-C, wherein $R^{1a}$ is H or OH.

Optional substituents attached to aryl, phenyl and heteroaryl rings each take the place of a hydrogen atom that would otherwise be present in any position on the aryl, phenyl or heteroaryl rings.

Useful halo or halogen groups include fluorine, chlorine, bromine and iodine.

Useful alkyl groups are selected from straight-chain and branched-chain $C_{1-10}$ alkyl groups. Typical $C_{1-10}$ alkyl groups include methyl, ethyl, n-propyl, n-butyl, n-pentyl, n-hexyl, n-heptyl, n-octyl, n-nonyl, and n-decyl, isopropyl, sec-butyl, tert-butyl, iso-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-n ethylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl, among others. In one embodiment, useful alkyl groups are selected from straight chain $C_{1-6}$ alkyl groups and branched chain $C_{3-6}$ alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain $C_{2-6}$ alkyl groups and branched chain $C_{3-6}$ alkyl groups. Typical $C_{2-6}$ alkyl groups include ethyl, propyl, isopropyl, butyl, sec-butyl, tert-butyl, iso-butyl, pentyl, 3-pentyl, hexyl among others. In one embodiment, useful alkyl groups are selected from straight chain $C_{1-4}$ alkyl groups and branched chain $C_{3-4}$ alkyl groups. Typical $C_{1-4}$ alkyl groups include methyl, ethyl, propyl, isopropyl, butyl, sec-butyl, tert-butyl, and iso-butyl.

Useful alkenyl groups are selected from straight-chain and branched-chain $C_{2-6}$ alkenyl groups, preferably $C_{2-4}$ alkenyl. Typical $C_{2-6}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl.

Useful alkynyl groups are selected from straight-chain and branched-chain $C_{2-6}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups.

Useful haloalkyl groups include any of the above-mentioned $C_{1-10}$ alkyl groups, and preferably $C_{1-6}$ alkyl groups, and preferably any of the above-mentioned $C_{1-4}$ alkyl groups, substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful hydroxyalkyl groups include any of the above-mentioned $C_{1-10}$ alkyl groups, preferably any of the above-mentioned $C_{1-6}$ alkyl groups, and more preferably any of the above-mentioned $C_{1-4}$ alkyl groups, substituted by one or more hydroxy groups, such as monohydroxyalkyl and dihydroxyalkyl groups (e.g., hydroxymethyl, hydroxyethyl, hydroxypropyl, hydroxybutyl, hydroxypentyl, and hydroxyhexyl groups, and especially hydroxymethyl, 1-hydroxyethyl, 2-hydroxyethyl, 1,2-dihydroxyethyl, 2-hydroxypropyl, 2-hydroxyprop-2-yl, 3-hydroxypropyl, 2,3-dihydroxypropyl, 3-hydroxybutyl, 4-hydroxybutyl, 2-hydroxy-1-methylpropyl, and 1,3-dihydroxyprop-2-yl). In one embodiment, the monohydroxyalkyl is monohydroxy($C_{1-4}$)alkyl. In one embodiment, the dihydroxyalkyl is dihydroxy($C_{1-4}$)alkyl.

Useful cycloalkyl groups are selected from saturated cyclic hydrocarbon groups containing 1, 2, or 3 rings having 3, 4, 5, 6, 7, 8, 9, 10, 11, or 12 carbon atoms (i.e., $C_3$-$C_{12}$ cycloalkyl) or the number of carbons designated. In one embodiment, the cycloalkyl has one or two rings. In another embodiment, the cycloalkyl is a $C_3$-$C_8$ cycloalkyl. In another embodiment, the cycloalkyl is a $C_{3-7}$ cycloalkyl. In another embodiment, the cycloalkyl is a $C_{3-6}$ cycloalkyl. Exemplary cycloalkyl groups include cyclopropyl cyclobutyl, cyclopentyl, cyclohexyl, cycloheptyl, cyclooctyl, norbornyl, decalin, and adamantyl.

Useful cycloalkenyl groups are selected from partially unsaturated (i.e., containing one or two double bonds) cyclic hydrocarbon groups containing 1, 2, or 3 rings having 4, 5, 6, 7, 8, 9, 10, 11, or 12 carbon atoms (i.e., $C_4$-$C_{12}$ cycloalkenyl) or the number of carbons designated. In one embodiment; the cycloalkenyl has one or two rings. In another embodiment, the cycloalkenyl is a $C_3$-$C_8$ cycloalkenyl. In another embodiment, the cycloalkenyl is a $C_3$-$C_7$ cycloalkenyl. In another embodiment, the cycloalkenyl is a $C_3$-$C_6$ cycloalkenyl. In one embodiment, the cycloalkenyl group contains one double bond. Exemplary cycloalkenyl groups containing one double bond include cyclobutenyl, cyclopentenyl, cyclohexenyl, cycloheptenyl, cyclooctenyl, cyclononenyl, and cyclodecenyl. In another embodiment, the cycloalkenyl group contains two double bonds. Preferably, the cycloalkenyl groups containing two double bonds have 5, 6, 7, 8, 9, 10, 11, or 12 carbon atoms (i.e., $C_5$-$C_{12}$ cycloalkadienyl). Exemplary cycloalkenyl groups having two double bonds include cyclopentadienyl, cyclohexadienyl, cycloheptadienyl, cyclooctadienyl, cyclononadienyl, and cyclodecadienyl.

Useful alkoxy groups include oxygen substituted by one of the $C_{1-10}$ alkyl groups mentioned above (e.g., methoxy, ethoxy, propoxy, iso-propoxy, butoxy, tert-butoxy, butoxy, sec-butoxy, pentyloxy, hexyloxy, heptyloxy, octyloxy, nonyloxy and decyloxy), preferably by one of the $C_{1-6}$ alkyl groups, and more preferably one of the $C_{1-4}$ alkyl groups.

Useful alkenyloxy groups include oxygen substituted by one of the $C_{2-6}$ alkenyl groups, and preferably the $C_{2-4}$ alkenyl groups, mentioned above (e.g., ethenyloxy, propenyloxy, isopropenyloxy, butenyloxy, sec-butenyloxy, pentenyloxy, and hexenyloxy).

Useful alkynyloxy groups include oxygen substituted by one of the $C_{2-6}$ alkynyl groups, preferably the $C_{2-4}$ alkynyl groups, mentioned above (e.g., ethynyloxy, propynyloxy, butynyloxy, 2-butynyloxy, pentynyloxy, and hexynyloxy).

Useful alkoxyalkyl groups include any of the above-mentioned $C_{1-10}$ alkyl groups, and preferably any of the above-mentioned $C_{1-6}$ alkyl groups, substituted with any of the above-mentioned alkoxy groups (e.g., methoxymethyl, methoxyethyl, methoxypropyl, methoxybutyl, ethoxymethyl, 2-ethoxyethyl, 3-ethoxypropyl, 4-ethoxybutyl, propoxymethyl, iso-propoxymethyl, 2-propoxyethyl, 3-propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups, and preferably one of the $C_{1-6}$ haloalkyl groups, mentioned above (e.g., fluoromethoxy, difluoromethoxy, trifluoromethoxy, and 2,2,2-trifluoroethoxy).

Useful (cycloalkyl)alkyl groups include any of the above-mentioned $C_{1-10}$ alkyl groups, and preferably any of the above-mentioned $C_{1-6}$ alkyl groups, substituted with any of the above-mentioned cycloalkyl groups (e.g., (cyclopropyl)methyl, 2-(cyclopropyl)ethyl, (cyclopropyl)propyl, (cyclobutyl)methyl, (cyclopentyl)methyl, and (cyclohexyl)methyl).

Useful (cycloalkenyl)alkyl groups include any of the above-mentioned $C_{1-10}$ alkyl groups, and preferably any of the above-mentioned $C_{1-6}$ alkyl groups, substituted with any of the above-mentioned cycloalkenyl groups (e.g., (cyclobutenyl)methyl, 2-(cyclobutenyl)ethyl, (cyclobutenyl)propyl, (cyclopentenyl)methyl, (cyclohexenyl)methyl, and (cyclopentadienyl)methyl).

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenyl enyl, and fluorenyl groups, more preferably phenyl, naphthyl, and biphenyl groups.

Useful aryloxy groups include oxygen substituted by one of the aryl groups mentioned above (e.g., phenoxy).

Useful arylalkyl groups include any of the above-mentioned $C_{1-10}$ alkyl groups, and preferably any of the above-mentioned $C_{1-6}$ alkyl groups, substituted by any of the above-mentioned aryl groups (e.g., benzyl and phenethyl).

Useful arylalkenyl groups include any of the above-mentioned $C_{2-6}$ alkenyl groups substituted by any of the above-mentioned aryl groups (e.g., phenylethenyl).

Useful arylalkynyl groups include any of the above-mentioned $C_{2-6}$ alkynyl groups substituted by any of the above-mentioned aryl groups (e.g., phenylethynyl).

Useful aralkyloxy or arylalkoxy groups include oxygen substituted by one of the above-mentioned arylalkyl groups (e.g., benzyloxy).

Useful (arylalkoxy)carbonyl groups include a carbonyl group substituted by any of the above-mentioned arylalkoxy groups (e.g., (benzyloxy)carbonyl).

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. In one embodiment, the heteroaryl group is a 5- to 10-membered heteroaryl group. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., pyrrol-1-yl, 1H-pyrrol-2-yl and 1H-pyrrol-3-yl), imidazolyl (e.g., imidazol-1-yl, 1H-imidazol-2-yl and 1H-imidazol-4-yl), tetrazolyl (e.g., tetrazol-1-yl and tetrazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). A 5-membered heteroaryl can contain up to 4 heteroatoms. A 6-membered heteroaryl can contain up to 3 heteroatoms. Each heteroatom is independently selected from nitrogen, oxygen and sulfur.

Useful heteroarylalkyl groups include any of the above-mentioned $C_{1-10}$ alkyl groups substituted by any of the above-mentioned heteroaryl groups (e.g., (thien-2-yl)methyl, 2-furylmethyl, (pyrrol-1-yl)methyl, and 2-(1H-pyrrol-2-yl)ethyl).

Useful heteroarylalkoxy groups include oxygen substituted by one of the above-mentioned heteroaryl groups.

Useful (heteroarylalkoxy)carbonyl groups include a carbonyl group substituted by any of the above-mentioned heteroarylalkoxy groups.

The terms "heterocyclic" and "heterocyclo" are used herein to mean saturated or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. In one embodiment, the 3- to 7-membered monocyclic heterocyclic ring is either a saturated, or unsaturated non-aromatic ring. A 3-membered heterocyclo can contain up to 1 heteroatom, a 4-membered heterocyclo can contain up to 2 heteroatoms, a 5-membered heterocyclo can contain up to 4 heteroatoms, a 6-membered heterocyclo can contain up to 4 heteroatoms, and a 7-membered heterocyclo can contain up to 5 heteroatoms. Each heteroatom is independently selected from nitrogen, which can be quaternized; oxygen; and sulfur, including sulfoxide and sulfone. The 3- to 7-membered heterocyclo can be attached via a nitrogen or carbon atom. A 7- to 10-membered bicyclic heterocyclo contains from 1 to 4 heteroatoms independently selected from nitrogen, which can be quaternized; oxygen; and sulfur, including sulfoxide and sulfone. The 7- to 10-membered bicyclic heterocyclo can be attached via a nitrogen or carbon atom. Examples of the heterocyclic rings include, but are not limited to, pyrrolidinyl, piperidinyl, piperazinyl, morpholinyl, imidazolinyl, pyrazolidinyl, tetrahydrofuranyl, oxazolidinyl, 2-oxooxazolidinyl, tetrahydrothienyl, imidazolidinyl, hexahydropyrimidinyl, and benzodiazepines.

Useful (heterocyclo)alkyl groups include any of the above-mentioned $C_{1-10}$ alkyl groups, and preferably any of the above-mentioned $C_{1-6}$ alkyl groups, substituted by any of the above-mentioned heterocyclic groups (e.g., (pyrrolidin-2-yl)methyl, (pyrrolidin-1-yl)methyl, (piperidin-1-yl)methyl, (morpholin-4-yl)methyl, (2-oxooxazolidin-4-yl)methyl, 2-(2-oxooxazolidin-4-yl)ethyl, (2-oxo-imidazolidin-1-yl)methyl, (2-oxo-imidazolidin-1-yl)ethyl, and (2-oxo-imidazolidin-1-yl)propyl).

As used herein, the term "amino" or "amino group" refers to —$NH_2$.

Useful aminoalkyl groups include any of the above-mentioned $C_{1-10}$ alkyl groups, and preferably any of the above-mentioned $C_{1-6}$ alkyl groups, substituted with one or more amino group.

Useful alkylamino and dialkylamino groups are —$NHR^{22}$ and —$NR^{22}R^{23}$, respectively, wherein $R^{22}$ and $R^{23}$ are each independently selected from a $C_{1-10}$ alkyl group.

As used herein, the term "aminocarbonyl" refers to —$C(=O)NH_2$.

Useful (aminocarbonyl)alkyl groups include any of the above-mentioned $C_{1-10}$ alkyl groups, and preferably any of the above-mentioned $C_{1-6}$ alkyl groups, substituted with one or more aminocarbonyl groups.

Useful alkylcarbonyl groups include a carbonyl group, i.e., —$C(=O)$—, substituted by any of the above-mentioned $C_{1-10}$ alkyl groups.

Useful alkoxycarbonyl groups include a carbonyl group substituted by any of the above-mentioned alkoxy groups (e.g., methoxycarbonyl, ethoxycarbonyl, propoxycarbonyl, iso-propoxycarbonyl, butoxycarbonyl, tert-butoxycarbonyl, iso-butoxycarbonyl, sec-butoxycarbonyl, and pentyloxycarbonyl).

Useful (alkoxycarbonyl)alkyl groups include any of the above-mentioned $C_{1-10}$ alkyl groups, and preferably any of the above-mentioned $C_{1-6}$ alkyl groups, substituted by any of the above-mentioned alkoxycarbonyl groups.

Useful arylcarbonyl groups include a carbonyl group substituted by any of the above-mentioned aryl groups (e.g., benzoyl).

Useful alkylcarbonyloxy or acyloxy groups include oxygen substituted by one of the above-mentioned alkylcarbonyl groups.

Useful alkylcarbonylamino or acylamino groups include any of the above-mentioned alkylcarbonyl groups attached to an amino nitrogen, such as methylcarbonylamino.

As used herein, the term "carboxamido" refers to a radical of formula —$C(=O)NR^{24}R^{25}$, wherein $R^{24}$ and $R^{25}$ are each independently hydrogen, optionally substituted $C_{1-10}$ alkyl, or optionally substituted aryl. Exemplary carboxamido groups include —$CONH_2$, —$CON(H)CH_3$, —$CON(CH_3)_2$, and —$CON(H)Ph$.

Useful (carboxamido)alkyl groups are any of the above-mentioned $C_{1-10}$ groups, and preferably any of the above-mentioned $C_{1-6}$ alkyl groups, substituted with any of the above-mentioned carboxamido groups.

Useful alkylaminocarbonyl and dialkylaminocarbonyl groups are any of the above-mentioned carboxamido groups, where $R^{24}$ is H and $R^{25}$ is $C_{1-10}$ alkyl or where $R^{24}$ and $R^{25}$ are each independently selected from a $C_{1-10}$ alkyl group, respectively.

Useful (alkylaminocarbonyl)alkyl groups include any of the of the above-mentioned $C_{1-10}$ alkyl groups, and preferably any of the above-mentioned $C_{1-6}$ alkyl groups, substituted with any of the above-mentioned alkylaminocarbonyl groups.

Useful (dialkylaminocarbonyl)alkyl groups include any of the of the above-mentioned $C_{1-10}$ alkyl groups, and preferably any of the above-mentioned $C_{1-6}$ alkyl groups, substituted with any of the above-mentioned dialkylaminocarbonyl groups.

As used herein, the term "sulfonamido" refers to a radical of formula —$SO_2NR^{26}R^{27}$, wherein $R^{26}$ and $R^{27}$ are each independently hydrogen, optionally substituted $C_{1-10}$ alkyl, or optionally substituted aryl. Exemplary sulfonamido groups include —$SO_2NH_2$, —$SO_2N(H)CH_3$, and —$SO_2N(H)Ph$.

As used herein, the term "thiol" refers to —SH.

Useful mercaptoalkyl groups include any of the above-mentioned $C_{1-10}$ alkyl groups, and preferably any of the above-mentioned $C_{1-6}$ alkyl groups, substituted by a —SH group.

Useful alkylthio groups include sulphur substituted by one of the $C_{1-10}$ alkyl groups mentioned above (e.g., methylthio, ethylthio, propylthio, iso-propylthio, butylthio, tert-butylthio, iso-butylthio, sec-butylthio, pentylthio, hexylthio, heptylthio, octylthio, nonylthio and decylthio), and preferably by one of the $C_{1-6}$ alkyl groups.

Useful (alkylthio)alkyl groups include any of the above-mentioned $C_{1-10}$ alkyl groups, and preferably any of the above-mentioned $C_{1-6}$ alkyl groups, substituted with one more of the above-mentioned alkylthio groups (e.g., methylthiomethyl, methylthioethyl, methylthiopropyl, methylthiobutyl, ethylthiomethyl, 2-ethylthioethyl, 3-ethylthiopropyl, 4-ethylthiobutyl, propylthiomethyl, iso-propylthiomethyl, 2-propylthioethyl, 3-propylthiopropyl, butylthiomethyl, tert-butylthiomethyl, isobutylthiomethyl, sec-butylthiomethyl, and pentylthiomethyl).

As used herein, the term "carboxy" refers to —COOH.

Useful carboxyalkyl groups include any of the above-mentioned $C_{1-10}$ alkyl groups, and preferably any of the above-mentioned $C_{1-6}$ alkyl groups, substituted by —COOH.

As used herein, the terms "hydroxyl" or "hydroxy" refer to —OH.

As used herein, the term "cyano" refers to —CN.

As used herein, the term "nitro" refers to —$NO_2$.

As used herein, the term "ureido" refers to —NH—C(=O)—$NH_2$.

As used herein, the term "azido" refers to —$N_3$.

The term "guanidino" refers to —$NH(NH=)CNH_2$.

Useful guanidinoalkyl groups include any of the above-mentioned $C_{1-10}$ alkyl groups, preferably any of the above-mentioned $C_{1-6}$ alkyl groups, substituted by —$NH(NH=)CNH_2$.

The term "ambient temperature" as used herein means the temperature of the surroundings. The ambient temperature indoors is the same as room temperature, which is from about 20° C. to about 25° C.

The term "about," as used herein in connection with a measured quantity, refers to the normal variations in that measured quantity, as expected by the skilled artisan making the measurement and exercising a level of care commensurate with the objective of measurement and the precision of the measuring equipment. Typically, the term "about" includes the recited number ±10%. Thus, "about 10" means 9 to 11.

As used herein, the term "optionally substituted" refers to a group that may be unsubstituted or substituted.

As used herein, the term "optionally fused to a phenyl ring" refers to a group that may have a fused phenyl ring or may not have a fused phenyl ring.

As used herein, the phrase "two adjacent carbon atoms of said cycloalkyl or cycloalkenyl rings are fused to a phenyl ring" refers to a group where any of the above-mentioned cycloalkyl and cycloalkenyl groups that have a fused phenyl ring. Such groups include, for example,

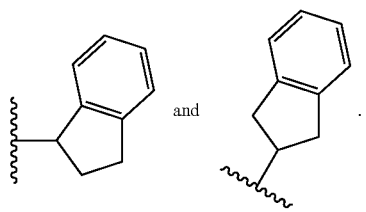 [SMILES: *C1CCc2ccccc21 ; *C1Cc2ccccc2C1]

Optional substituents on optionally substituted groups, when not otherwise indicated, include one or more groups, typically 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$) alkyl, aryl($C_{2-6}$)alkenyl, aryl($C_{2-6}$)alkynyl, cycloalkyl($C_{1-6}$) alkyl, heterocyclo($C_{1-6}$)alkyl, hydroxy($C_{1-6}$)alkyl, amino ($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, aryloxy, ar($C_{1-6}$)alkyloxy, carboxamido, sulfonamido, azido, $C_{1-6}$ alkoxy, halo($C_{1-6}$)alkoxy, carboxy, aminocarbonyl, (=O), and mercapto($C_{1-6}$)alkyl groups mentioned above. Preferred optional substituents include halo, halo($C_{1-6}$)alkyl, hydroxy($C_{1-6}$)alkyl, amino($C_{1-6}$)alkyl, hydroxy, nitro, $C_{1-6}$ alkyl, $C_{1-6}$ alkoxy, halo($C_{1-6}$)alkoxy, and amino.

Compounds of the Invention encompass all the salts of the disclosed compounds of Formulae I-A to X-A and I-IX. The present invention preferably includes all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparaginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

Compounds of the Invention also encompass solvates of any of the disclosed compounds of Formulae I-A to X-A and I-IX. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Invention may be present as solvated forms with a pharmaceutically acceptable solvent, such as water, methanol, ethanol, and the like, and it is intended that the invention includes both solvated and unsolvated forms of compounds of any of Formulae I-A to X-A and I-IX. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.*: 603-604 (2001). A typical, non-limiting, process of preparing a solvate would involve dissolving a compound of any of Formulae I-A to X-A and I-IX in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$, respectively, and preferably $^3H$, $^{11}C$, and $^{14}C$. Isotopically-labeled Compounds of the invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Isotopically labeled Compounds of the Invention, as well as the pharmaceutically acceptable salts and solvates thereof, can be used as radioligands to test for the binding of compounds to an opioid receptor. For example, a radio-labeled Compound of the Invention can be used to characterize specific binding of a test or candidate compound to the receptor. Binding assays utilizing such radio-labeled compounds can provide an in vitro alternative to animal testing for the evaluation of chemical structure-activity relationships. For example, the receptor assay may be performed at a fixed concentration of a radiolabeled Compound of the Invention and at increasing concentrations of a test compound in a competition assay. In a non-limiting embodiment, the present invention provides a method for screening a candidate compound for the ability to bind to an opioid receptor, comprising a) introducing a fixed concentration of a radio-labeled Compound of the Invention to the receptor under conditions that permit binding of the radio-labeled compound to the receptor to form a complex; b) titrating the complex with a candidate compound; and c) determining the binding of the candidate compound to said receptor.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centres present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

Open terms such as "include," "including," "contain," "containing" and the like mean "comprising."

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001)).

In certain embodiments, the Compound of the Invention is an agonist at one or more of the μ, δ and/or κ opioid receptors. In certain non-limiting embodiments, the Compound of the Invention produces fewer side effects and/or less severe side effects than currently available analgesic opioid compounds when administered at doses producing equivalent levels of analgesia and/or anti-hyperalgesia. In certain embodiments, the Compound of the Invention is an agonist at ORL-1 opioid receptor.

In certain embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, antidepressant, a $Ca^{2+}$-channel blocker, an anticancer agent, or a mixture thereof.

Compounds of the Invention potently bind to the μ and/or κ and/or δ and/or ORL-1 opioid receptors. Compounds of the Invention can be modulators at the μ and/or κ and/or δ and/or ORL-1 opioid receptors, and therefore Compounds of the Invention can be used/administered to treat, ameliorate, or prevent pain.

In some embodiments, Compounds of the Invention are antagonists of one or more opioid receptors. In another embodiment, Compounds of the Invention are antagonists of the μ and/or κ opioid receptors.

In some embodiments, Compounds of the Invention are partial agonists of one or more opioid receptors. In another embodiment, Compounds of the Invention are partial agonists of the μ and/or κ opioid receptors.

In another embodiments, Compounds of the Invention are agonists of one or more opioid receptors. In another embodiment, Compounds of the Invention are agonists of the μ and/or κ opioid receptors.

In some embodiments, Compounds of the Invention have both: (i) antagonist activity at the ORL-1 receptor; and (ii) agonist activity at one or more of the μ, δ and/or κ receptors. In another embodiments, Compounds of the Invention have both: (i) antagonist activity at the ORL-1 receptor; and (ii) agonist activity at the μ receptor. In another embodiments, Compounds of the Invention have both: (i) antagonist activity at the μ receptor; and (ii) agonist activity at the κ receptor. In another embodiments, Compounds of the Invention have: (i) antagonist activity at the ORL-1 receptor; (ii) antagonist activity at the μ receptor; and (iii) agonist activity at the κ receptor. In another embodiments, Compounds of the Invention have: (i) antagonist activity at the μ receptor; (ii) agonist activity at the κ receptor; and (iii) antagonist activity at the δ receptor.

Compounds of the Invention that are antagonists of the μ-opioid receptor or agonists of κ-opioid receptor, or both, can be used/administered to treat or ameliorate constipation. Compounds of the Invention that are agonists of μ-opioid receptor can be used/administered to treat or ameliorate diarrhea.

Compounds of the Invention can be used to treat or prevent acute, chronic pain (which includes but is not limited to, neuropathic pain, postoperative pain, and inflammatory pain), or surgical pain. Examples of pain that can be treated or prevented using a Compound of the Invention include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Compounds of the Invention can be used to treat or prevent pain associated with inflammation or with an inflammatory disease in a patient. Such pain can arise where there is an inflammation of the body tissue which can be a local inflammatory response or a systemic inflammation. For example, a Compound of the Invention can be used to treat or prevent pain associated with inflammatory diseases including, but not limited to, organ transplant rejection; reoxygenation injury resulting from organ transplantation (see Grupp et al., *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. Compounds of the Invention can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Compounds of the Invention can be used to treat or prevent pain associated with nerve injury (i.e., neuropathic pain). Chronic neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Chronic neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the Invention can be used to treat or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

Compounds of the Invention can also be used as an agent to treat withdrawal from alcohol addiction or drug addiction; as an agent to treat or prevent addictive disorders; an agent to treat a pruritic condition; and in treating or ameliorating constipation and diarrhea.

The present invention is also directed to the use of a compound represented by any of defined Formulae I-A to VIII-A, X-A, and I-VIII, or a pharmaceutically acceptable salt or solvate thereof, in the manufacture of a medicament for treating a disorder responsive to the modulation of one or more opioids receptors (e.g., any of the disorders listed above) in a patient suffering from said disorder.

Furthermore, the present invention is directed to a method of modulating, in particular activating, one or more opioid receptors in a patient in need thereof, said method comprising administering to the patient at least one compound represented by any of defined Formulae I-A to VIII-A, X-A, and I-VIII, or a pharmaceutically acceptable salt or solvate thereof.

The present invention is also directed to the use of a compound represented by any of defined Formulae I-A to VIII-A, X-A, and I-VIII, or a pharmaceutically acceptable salt or solvate thereof, in the manufacture of a medicament, in particular a medicament for modulating, in particular activating, one or more opioid receptors, in a patient in need thereof.

Synthesis of Compounds

Compounds of the Invention can be prepared using methods known to those skilled in the art in view of this disclosure, or by the illustrative methods shown in the schemes below. Additional methods of synthesis are described and illustrated in the working examples set forth below.

Scheme 1
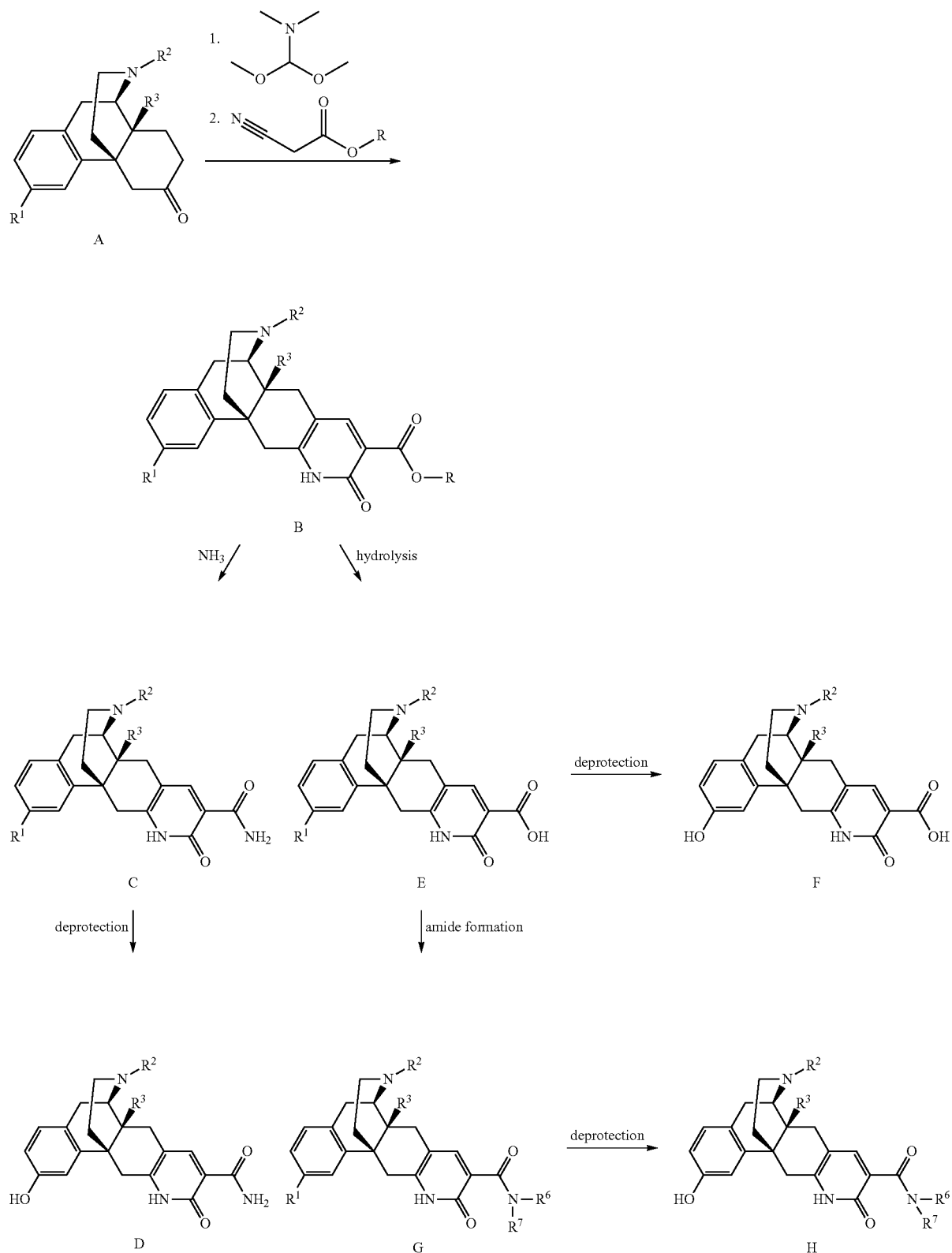

In Scheme 1, $R^1$—$R^3$, $R^6$, and $R^7$ are as defined for Formula I. R is an optionally substituted alkyl as defined above. The deprotection can be performed when $R^1$ is —O-PG using methods known in the art, for example, by reacting with $BBr_3$ when PG is a methyl group The starting compound A can be prepared, for example, as described in Hupp C. D., et al., *Tetrahedron Letters* 51:2359-2361 (2010) and Ida Y., et al., *Bioorganic & Medical Chemistry* 20:949-961 (2012).

Compounds of Formula IV can be prepared analogously starting from the opposite isomer of compound A above with respect to $R^3$, which can be prepared, for example, as described in Polazzi J. O., et al., *J. Med. Chem.* 23:174-179 (1980).

Compounds of the Invention, where $R^4$ is alkyl can be prepared, for example, as described in Scheme 2.

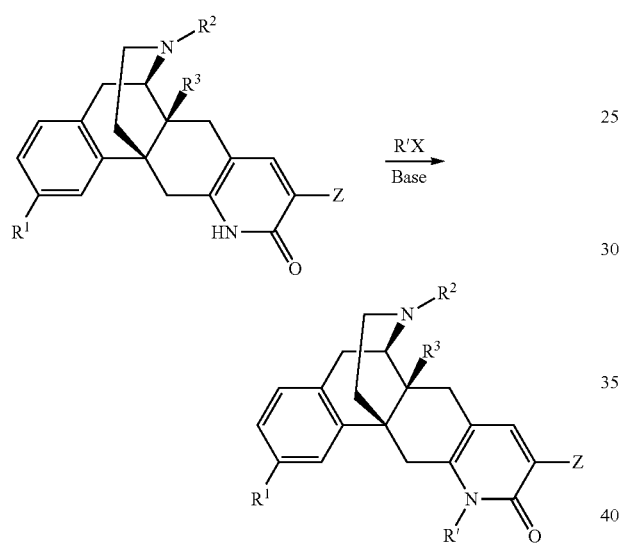

In Scheme 2, $R^1$—$R^3$ and Z are as described for Formula I and R' is alkyl. X is halogen, such as chlorine or bromine, and the base can be, for example, potassium carbonate ($K_2CO_3$).

The opposite isomers of the compounds described in Schemes 1 and 2 can be prepared starting from ketone A':

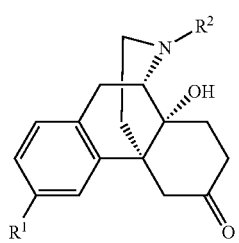

Ketone A' can be prepared according methods described in the art, such as, for example, in US 2009/0156818, US 2009/0156820, and Hupp C. D., et al. (supra). Accordingly, for example, ketone A', where $R^1$ is OMe and $R^2$ is cyclopropylmethyl, can be prepared as described in Scheme 3 starting from CAS#6080-33-7:

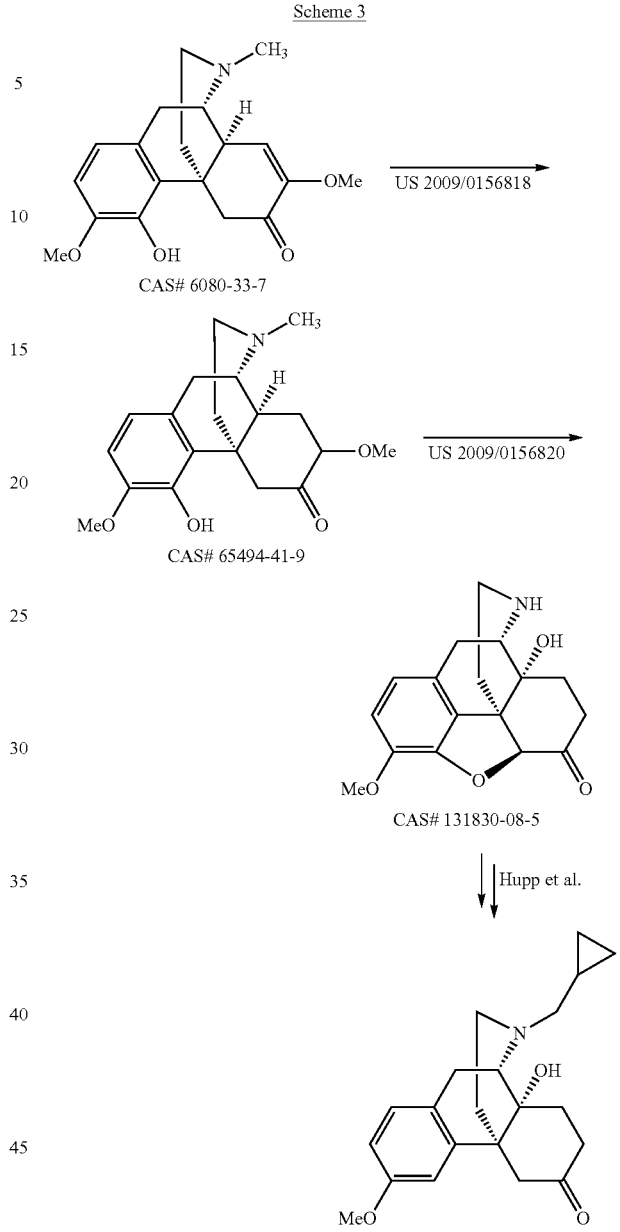

Compounds of Formulae I-A to X-A can be prepared according to the Schemes 1-3 and methods described above and Scheme 4 below;

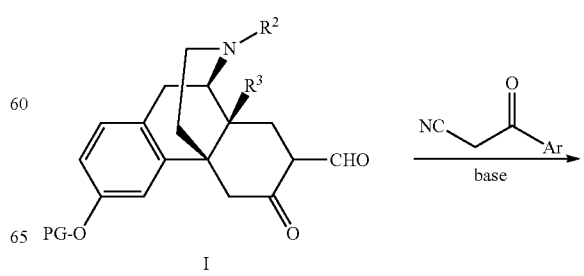

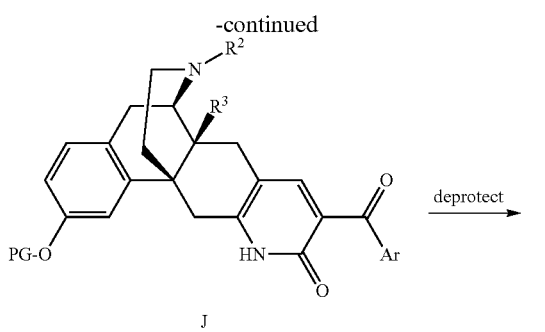

J

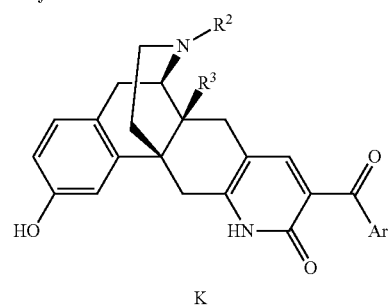

K

Compound I is converted to Compound J by treatment with a suitable aryl or hereroaryl ketonitrile in the presence of a suitable base, such as piperidine, in a suitable solvent, such as ACN. Compound J is deprotected to give Compound K by appropriate techniques (e.g. Wuts, P. G. M.; Greene, T. W., "Greene's Protective Groups in Organic Synthesis", 4th Ed., J. Wiley & Sons, NY, 2007) known to one skilled in the art.

Compounds of Formula VIII-A can be prepared as described in Scheme 5 below:

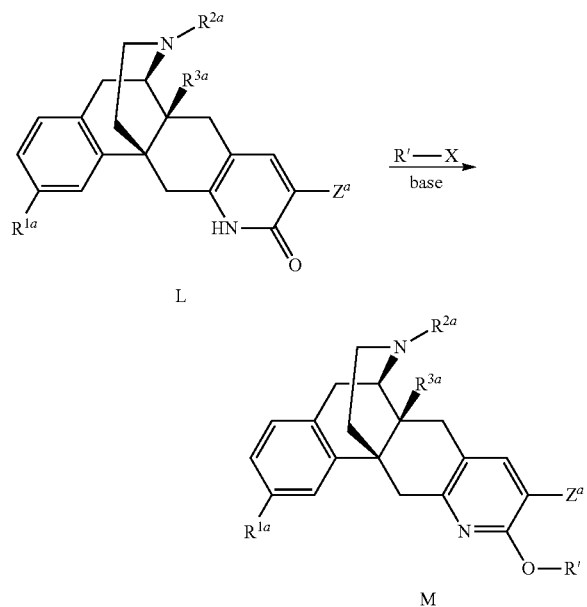

Compound L is converted to Compound M by treatment with a suitable base and an appropriate alkyl halide under conditions suitable for O- vs N-alkylation of pyridones (see e.g. Tieckelmann, H. J., et al., *J. Org. Chem.* 1967, 32, 4040).

In Vitro Assay Protocols

μ-Opioid Receptor Binding Assay Procedures: Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hours at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data: Generally, the lower the $K_i$ value, the more effective Compounds of the Invention will be at treating or preventing pain or another Condition. Typically, Compounds of the Invention exhibit a $K_i$ (nM) of about 1000 or less for binding to μ-opioid receptors. In one embodiment, Compounds of the Invention exhibit a $K_i$ (nM) of about 300 or less for binding to μ-opioid receptors. In another embodiment, Compounds of the Invention exhibit a $K_i$ (nM) of about 100 or less for binding to μ-opioid receptors. In another embodiment, Compounds of the Invention exhibit a $K_i$ (nM) of about 10 or less for binding to μ-opioid receptors. In still another embodiment, Compounds of the Invention exhibit a $K_i$ (nM) of about 1 or less for binding to μ-opioid receptors. In still another embodiment, Compounds of the Invention exhibit a $K_i$ (nM) of about 0.1 or less for binding to μ-opioid receptors.

μ-Opioid Receptor Functional Assay Procedures: [$^{35}$S]GTPγS functional assays were conducted using freshly thawed μ-receptor membranes prepared in-house from a cell line expressing recombinant μ opioid receptor in a HEK-293, CHO or U-2 OS cell background, or purchased from a commercial source (Perkin Elmer, Shelton, Conn.; or DiscovRx, Fremont, Calif.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hours. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP $EC_{50}$ is the concentration of a compound providing 50% of the maximal response for the compound at a μ-opioid receptor. Certain Compounds of the Invention can exhibit a μ GTP $EC_{50}$ (nM) of about 20,000 or less; or about 10,000 or less. In certain embodiments, Compounds of the Invention exhibit a μ GTP $EC_{50}$ (nM) of about 5000 or less. In certain embodiments, Compounds of the Invention exhibit a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention exhibit a μ GTP $E_{max}$ (%) of greater than about 10%; or greater than about 20%. In certain embodiments, Compounds of the Invention exhibit a μ GTP Emax (%) of greater than about 50%; or greater than about 65%; or greater than about 75%; or greater than about 85%; or greater than about 100%.

κ-Opioid Receptor Binding Assay Procedures: Membranes from HEK-293 cells, CHO or U-2 OS cells expressing the recombinant human kappa opioid receptor (κ) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard, Aliquots of κ receptor membranes were stored at 80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hour at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data: In certain embodiments, Compounds of the Invention exhibit a $K_i$ (nM) for κ receptors of about 10,000 or more (which, for purposes of this invention, is interpreted as having no binding to the κ receptors). Certain Compounds of the Invention exhibit a $K_i$ (nM) of about 20,000 or less for κ receptors. In certain embodiments, Compounds of the Invention exhibit a $K_i$ (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less for κ receptors.

κ-Opioid Receptor Functional Assay Procedures: Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data: κ GTP $EC_{50}$ is the concentration of a compound providing 50% of the maximal response for the compound at a κ receptor. Certain Compounds of the Invention exhibit a κ GTP $EC_{50}$ (nM) of about 20,000 or less to stimulate κ opioid receptor function. In certain embodiments, Compounds of the Invention exhibit a κ GTP $EC_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention exhibit a κ GTP $E_{max}$ (%) of greater than about 1%; or greater than about 5%; or greater than about 10%; or greater than about 20%. In certain embodiments, Compounds of the Invention exhibit a κ GTP $E_{max}$ (%) of greater than about 50%; or greater than about 75%; or greater than about 90%; or greater than about 100%.

δ-Opioid Receptor Binding Assay Procedures: δ-Opioid Receptor Binding Assay Procedures were conducted as follows. Radioligand dose-displacement assays used 0.2 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM $MgCl_2$, 5% DMSO, 50 mM Trizma base, pH 7.4). Non-specific binding was determined in the presence of 25 μM unlabeled naloxone. All reactions were performed in 96-deep well polypropylene plates for 1 hour at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 500 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

δ-Opioid Receptor Binding Data: In certain embodiments, Compounds of the Invention exhibit a $K_i$ (nM) for δ receptors of about 10,000 or more (which, for the purposes of this invention, is interpreted as having no binding to the δ receptors). Certain Compounds of the Invention exhibit a $K_i$ (nM) of about 20,000 or less for δ receptors. In one embodiment, Compounds of the Invention exhibit a $K_i$ (nM) of about 10,000 or less; or of about 9000 or less for δ receptors. In another embodiment, Compounds of the Invention exhibit a $K_i$ (nM) of about 7500 or less; or of about 6500 or less; or of about 5000 or less; or of about 3000 or less; or of about 2500 or less for δ receptors. In another embodiment, Compounds of the Invention exhibit a $K_i$ (nM) of about 1000 or less; or of about 500 or less; or of about 350 or less; or of about 250 or less; or of about 100 or less; or of about 10 or less for δ receptors.

δ-Opioid Receptor Functional Assay Procedures: Functional [$^{35}$S]GTPγS binding assays were conducted as follows. δ-Opioid receptor membrane solution was prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 1-2 hours. Fifty μl/well scintillation cocktail (Perkin Elmer, Shelton, Conn.) was added and plates were counted in a Packard Top-count for 1 min/well.

δ-Opioid Receptor Functional Data: δ GTP EC$_{50}$ is the concentration of a compound providing 50% of the maximal response for the compound at a δ receptor. Certain Compounds of the Invention exhibit a δ GTP EC$_{50}$ (nM) of about 20,000 or less; or about 10,000 or less. In certain embodiments, Compounds of the Invention exhibit a δ GTP EC$_{50}$ (nM) of about 3500 or less; or of about 1000 or less; or of about 500 or less; or of about 100 or less; or of about 90 or less; or of about 50 or less; or of about 25 or less; or of about 10 or less.

δ GTP E$_{max}$ (%) is the maximal effect elicited by a compound relative to the effect elicited by met-enkephalin. Certain Compounds of the Invention exhibit a δ GTP E$_{max}$ (%) of greater than about 1%; or of greater than about 5%; or of greater than about 10%. In one embodiment, Compounds of the Invention exhibit a δ GTP E$_{max}$ (%) of greater than about 30%. In another embodiment, Compounds of the Invention exhibit a δ GTP E$_{max}$ (%) of greater than about 50%; or of greater than about 75%; or of greater than about 90%. In another embodiment, Compounds of the Invention exhibit a δ GTP E$_{max}$ (%) of greater than about 100%.

ORL-1 Receptor Binding Assay Procedure: Membranes from recombinant HEK-293 cells expressing the human opioid receptor-like receptor (ORL-1) (Perkin Elmer, Shelton, Conn.) were prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes were collected by centrifugation at 30,000×g for 15 mM at 4° C. and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Radioligand binding assays (screening and dose-displacement) used 0.1 nM [$^3$H]-nociceptin (Perkin Elmer, Shelton, Conn.; 87.7 Ci/mmole) with 12 μg membrane protein in a final volume of 500 μl binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at room temperature. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by three filtration washes with 500 μl ice-cold binding buffer. Filter plates were subsequently dried at 50° C. for 2-3 hours. Fifty μl/well scintillation cocktail (Perkin Elmer, Shelton, Conn.) was added and plates were counted in a Packard Top-Count for 1 min/well. The data from screening and dose-displacement experiments were analyzed using Microsoft Excel and the curve fitting functions in GraphPad PRISM™, v. 3.0 or higher, respectively, or an in-house function for one-site competition curve-fitting.

ORL-1 Receptor Binding Data: Certain Compounds of the Invention have a $K_i$ (nM) of about 5000 or less. In one embodiment, certain Compounds of the Invention have a $K_i$ (nM) of about 1000 or less. In one embodiment, certain Compounds of the Invention have a $K_i$ (nM) of about 500 or less. In other embodiments, the Compounds of the Invention have a $K_i$ (nM) of about 300 or less; or of about 100 or less; or of about 50 or less; or of about 20 or less. In yet other embodiments, the Compounds of the Invention will have a $K_i$ (nM) of about 10 or less; or of about 1 or less; or of about 0.1 or less.

ORL-1 Receptor Functional Assay Procedure: Membranes from recombinant HEK-293 cells expressing the human opioid receptor-like (ORL-1) (Perkin Elmer, Shelton, Conn.) can be prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist/nociceptin prepared in DMSO. Plates are incubated for 30 mM at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 2-3 hours. Fifty μl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data: ORL-1 GTP EC$_{50}$ is the concentration of a compound providing 50% of the maximal response for the compound at an ORL-1 receptor. In certain embodiments, the Compounds of the Invention that have a high binding affinity (i.e. low $K_i$ value) can have an ORL-1 GTP EC$_{50}$ (nM) of greater than about 10,000 (i.e. will not stimulate at therapeutic concentrations) in certain embodiments Compounds of the Invention can have an ORL-1 GTP $EC_{50}$ (nM) of about 20,000 or less. In one embodiment, the Compounds of the Invention can have an ORL-1 GTP $EC_{50}$ (nM) of about 10,000 or less; or of about 5000 or less; or of about 1000 or less. In still other embodiments, the Compounds of the Invention can have an ORL-1 GTP $EC_{50}$ (nM) of about 100 or less; or of about 10 or less; or of about 1 or less; or of about 0.1 or less.

ORL-1 GTP $E_{max}$% is the maximal effect elicited by a compound relative to the effect elicited by nociceptin, a standard ORL-1 agonist. In certain embodiments, Compounds of the Invention can have an ORL-1 GTP $E_{max}$ of less than 10% (which, for the purposes of this invention, is interpreted as having antagonist activity at OR I, I receptors). Certain Compounds of the Invention can have an ORL-1 GTP $E_{max}$ (%) of greater than 1%; or of greater than 5%; or of greater than 10%. In other embodiments the Compounds of the Invention can have an ORL-1 GTP $E_{max}$ of greater than 20%; or of greater than 50%; or of greater than 75%; or of greater than 88%; or of greater than 100%.

In Vivo Assays for Pain

Test Animals: Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain: To assess the actions of a Compound of the Invention for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s} - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described in G. Woolfe and A. D. MacDonald, *J. Pharmacol. Exp. Ther.* 80:300-307 (1944).

Inflammatory Pain: To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat is gently restrained, its hindpaw is placed on a small round platform, and punctate pressure is applied to the dorsal surface of the hindpaw in a graded manner. The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus applied to the plantar surface of the hindpaw are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., *Intensive Care Med.* (26): 585-591 (2000).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in a patient in need thereof. The Compounds of the Invention can be administered to any patient requiring modulation of the opioid receptors. The term "patient" as used herein refers to any animal that may experience the beneficial effects of a Compound of the Invention. Foremost such animals are mammals, e.g., humans and companion animals, although the invention is not intended to be so limited.

When administered to a patient, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sublingual tablets or tabs, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16th ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage folds are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially immediately release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration of availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol. 2, Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each patient's circumstances. Variations in dosing may occur depending upon typical factors such as the weight, age, gender and physical condition (e.g., hepatic and renal function) of the patient being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the patient per day, although they are typically from about 0.01 mg/kg of body weight to about 2500 mg/kg of body weight of the patient per day or from about 0.01 mg/kg of body weight to about 1000 mg/kg of body weight of the patient per day. In one embodiment, the effective dosage amount is about 100 mg/kg of body weight of the patient per day or less. In another embodiment, the effective dosage amount ranges from about 0.01 mg/kg of body weight to about 100 mg/kg of body weight of the patient per day of a Compound of the Invention, in another embodiment, about 0.02 mg/kg of body weight to about 50 mg/kg of body weight of the patient per day, and in another embodiment, about 0.025 mg/kg of body weight to about 20 mg/kg of body weight of the patient per day.

Administration can be as a single dose or as a divided dose. In one embodiment, an effective dosage amount is administered about every 24 hours until the Condition is abated. In another embodiment, an effective dosage amount is administered about every 12 hours until the Condition is abated. In another embodiment, an effective dosage amount is administered about every 8 hours until the Condition is abated. In another embodiment, an effective dosage amount is administered about every 6 hours until the Condition is abated. In another embodiment, an effective dosage amount is administered about every 4 hours until the Condition is abated. The effective dosage amounts described herein refer to total amounts administered; that is, if more than one Compound of the Invention is administered, the effective dosage amounts correspond to the total amount administered.

Where a cell capable of expressing the μ-opioid receptors is contacted with a Compound of the Invention in vitro, the amount effective for inhibiting or activating the μ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the δ-opioid receptors is contacted with a Compound of the Invention in vitro, the amount effective for inhibiting or activating the δ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the κ-opioid receptors is contacted with a Compound of the Invention in vitro, the amount effective for inhibiting or activating the κ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the ORL-1 receptor is contacted with a Compound of the Invention in vitro, the amount effective for inhibiting or activating the ORL-1 receptor function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Compounds of the Invention can be assayed in vitro or in vivo for the desired therapeutic or prophylactic activity prior to use in humans. Animal model systems can be used to demonstrate safety and efficacy. Certain Compounds of the Invention are expected to have an $ED_{50}$ for treating inflammatory pain ranging from about 0.5 mg/kg to about 20 mg/kg. Certain Compounds of the Invention are expected to produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the present invention, methods for treating or preventing a Condition in a patient in need thereof can further comprise co-administering to the patient an effective amount of a second therapeutic agent in addition to a Compound of the Invention (i.e., a first therapeutic agent). An effective amount of the second therapeutic agent can be known or determinable by a medical practitioner in view of this disclosure and published clinical studies. In one embodiment of the invention, where a second therapeutic agent is administered to a patient for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

A composition of the invention is prepared by a method comprising admixing a Compound of the Invention with a pharmaceutically acceptable carrier or excipient. Admixing can be accomplished using methods known for admixing a compound (or derivative) and a pharmaceutically acceptable carrier or excipient. In one embodiment, the Compound of the Invention is present in the composition in an effective amount.

The present invention also relates to a kit, comprising a sterile container containing an effective amount of a Compound of the Invention and instructions for therapeutic use.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

(6R,6aS,12aR)-methyl 15-(cyclopropylmethyl)-6a-hydroxy-2-dimethoxy-10-oxo-6,6a,7,10,11,12-hexahydro-5H-6,12a-(epiminoethano)naphtho[2,1-g]quinoline-9-carboxylate (2)

A mixture of compound 1 (2.514 g, 7.36 mmol, 1 eq) in DMF-dimethylacetal (20 mL) was heated at reflux for 3 days. The reaction was then concentrated in vacuo, diluted with acetonitrile and concentrated in vacuo again to a foamy solid. This material was dissolved in MeOH (50 mL) and methyl cyanoacetate (1.95 mL, 22.1 mmol, 3 eq) was added. The mixture was heated at reflux overnight then concentrated in vacuo to an oil. The residue was chromatographed over silica gel with 0-15% (10% NH$_4$OH in MeOH) in DCM. The product fractions were evaporated in vacuo to a solid. The solid was triturated with 5 mL MeOH, filtered and rinsed twice with 5 mL MeOH. The solid was dried under vacuum to give the title compound 2 as a cream-colored powder (0.785 g, 1.74 mmol, 24% yield).

$^1$H NMR $\delta_H$ (400 MHz, DMSO-d$_6$): 11.94 (s, 1H), 7.64 (s, 1H), 7.05 (d, J=8.6 Hz, 1H), 6.70 (dd, J=8.3, 2.4 Hz, 1H), 6.64 (d, J=2.6 Hz, 1H), 4.69 (s, 1H), 3.66 (s, 3H), 3.65 (s, 3H), 3.16-3.10 (m, 2H), 3.06 (d, J=18.9 Hz, 1H), 2.90-2.81 (m, 2H), 2.61-2.55 (m, 1H), 2.49-2.42 (m, 1H), 2.38-2.31 (m, 3H), 2.10-1.94 (m, 2H), 1.19-1.12 (m, 1H), 0.92-0.80 (m, 1H), 0.54-0.43 (m, 2H), 0.17-0.07 (m, 2H).

LC/MS: m/z=451 [M+H]$^+$ (Calc: 450).

The starting compound 1 can be prepared as described in, for example, Hupp C. D., et al., *Tetrahedron Letters* 51:2359-2361 (2010).

Example 2

(6R,6aR,12aS)-methyl 15-(cyclopropylmethyl)-2-methoxy-10-oxo-6,6a,7,10,11,12-hexahydro-5H-6,12a-(epiminoethano)naphtho[2,1-g]quinoline-9-carboxylate (3)

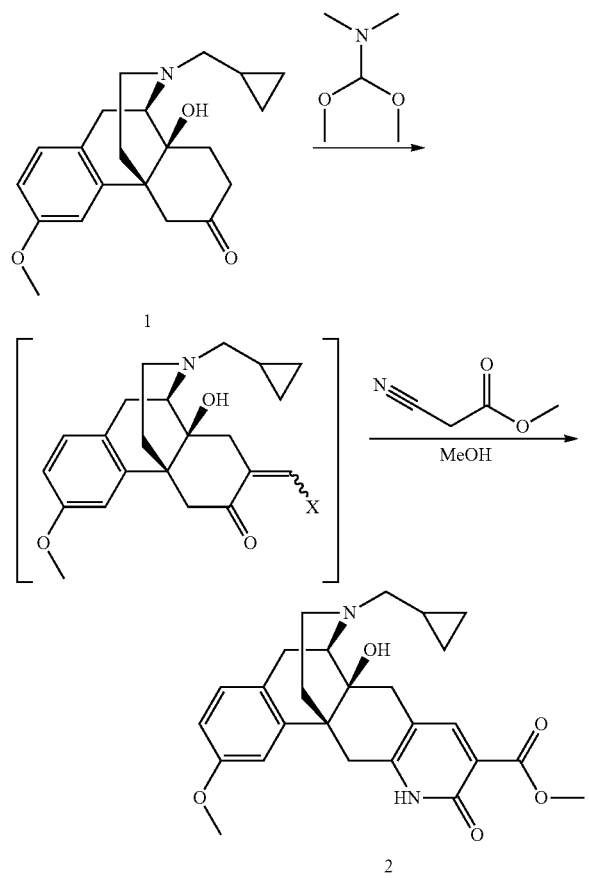

Compound 3 was prepared according to the procedure described in Example 1 from (4bS,8aR,9R)-11-(cyclopropylmethyl)-3-methoxy-8,8a,9,10-tetrahydro-5H-9,4-b-(epiminoethano)-phenanthren-6(7H)-one (CAS#71968-38-2) rather than (4bR,8aS,9R)-11-(cyclopropylmethyl)-8a-hydroxy-3-methoxy-8,8a,9,10-tetrahydro-5H-9,4-b-(epiminoethano)phenanthren-6(7H)-one (compound 1). Purification over silica gel with 0-25% (10% NH$_4$OH in MeOH) in DCM then trituration with acetonitrile gave the title compound 3 as a pink powder.

$^1$H NMR au (400 MHz, DMSO-d$_6$): 11.90 (s, 1H), 7.64 (s, 1H), 7.03 (d, J=8.3 Hz, 1H), 6.68 (dd, J=8.3, 2.4 Hz, 1H), 6.65 (d, J=2.2 Hz, 1H), 3.67-3.63 (m, 6H), 3.37-3.29 (m, 1H, overlap with water peak), 3.25-3.20 (m, 1H), 2.88 (d, J=18.6 Hz, 1H), 2.74-2.58 (m, 3H), 2.50-2.37 (m, 2H, overlap with DMSO peak), 2.32-2.24 (m, 1H), 2.24-2.17 (m, 1H), 2.10-2.00 (m, 1H), 1.99-1.90 (m, 1H), 1.80 (dt, J=12.3, 4.4 Hz, 1H), 1.39 (d, J=12.3 Hz, 1H), 0.86-0.75 (m, 1H), 0.50-0.40 (m, 2H), 0.14-0.03 (m, 2H).

LC/MS: m/z 435 [M+H]$^+$ (Calc: 434).

The starting compound, (4bS,8aR,9R)-11-(cyclopropylmethyl)-3-methoxy-8,8a,9,10-tetrahydro-5H-9,4-b-(epiminoethano)phenanthren-6(7H)-one, can be prepared as described in, for example, Ida Y., et al., *Bioorganic & Medical Chemistry* 20:949-961 (2012).

Example 3

(6R,6aS,12aR)-15-(cyclopropylmethyl)-6a-hydroxy-2-methoxy-10-oxo-6,6a,7,10,11,12-hexahydro-5H-6,12a-(epiminoethano)naphtho[2,1-g]quinoline-9-carboxamide (4)

(6R,6aS,12aR)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxamide (5)

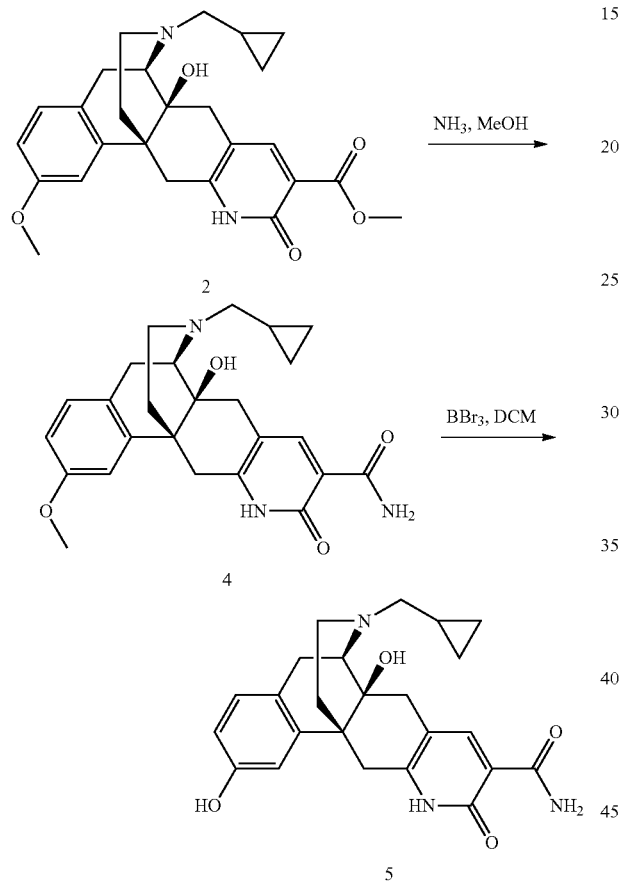

(a) A mixture of compound 2 (0.195 g, 0.433 mmol, 1 eq) and 7M $NH_3$ in MeOH (5 mL, 35 mmol, 81 eq) was heated at 50° C. in a sealed tube fir 8 days. After cooling to ambient temperature, the precipitated solid was filtered of and rinsed with mL MeOH. The solid was dried under vacuum to give the title compound 4 as a white powder (0.143 g, 0.328 mmol, 76% yield).

$^1$H NMR $\delta_H$ (400 MHz, DMSO-$d_6$): 12.23 (s, 1H), 9.03 (d, J=4.4 Hz, 1H), 7.86 (8, 1H), 7.39 (d, J=4.4 Hz, 1H), 7.05 (d, J=8.6 Hz, 1H), 6.70 (dd, J=8.6, 2.4 Hz, 1H), 6.65 (d, J=2.4 Hz, 1H), 4.69 (s, 1H), 3.65 (s, 3H), 3.23-3.13 (m, 2H), 3.06 (d, 18.6 Hz, 1H), 2.94-2.83 (m, 2H), 2.62-2.49 (m, 2H, overlap with DMSO peak), 2.44-2.33 (m, 3H), 2.12-1.94 (m, 2H), 1.20-1.13 (m, 1H), 0.93-0.81 (m, 1H), 0.54-0.43 (m, 2H), 0.18-0.07 (m, 2H).

LC/MS: m/z=436 [M+H]$^+$ (Calc: 435).

(b) A mixture of compound 4 (0.090 g, 0.207 mmol, 1 eq) in DCM (5 mL) was put into a sealed tube and cooled on an ice-salt bath. Neat $BBr_3$ (0.08 mL, 0.83 mmol, 4 eq) was added. The reaction was allowed to warm up to ambient temperature and stirred overnight. The reaction was quenched with ~4 mL saturated $NaHCO_3$ solution and the solid product was filtered off and rinsed with DCM and water. The solid was chromatographed reverse-phase with 0-60% acetonitrile in water (both +0.1% TFA). The product fractions were frozen and lyophilized to give the title compound 5 as a TFA-salt (a cream-colored powder) (0.078 g, 0.146 mmol, 71% yield).

$^1$H NMR $\delta_H$ (400 MHz, CD$_3$OD): 8.08 (s, 1H), 7.08 (d, J=8.3 Hz, 1H), 6.76-6.65 (m, 2H), 4.15-4.08 (m, 1H), 3.44-3.28 (m, 4H) 3.16-3.06 (m, 2H), 3.04-2.95 (m, 1H), 2.88-2.76 (m, 2H), 2.72-2.61 (m, 1H), 2.58-2.45 (m, 1H), 1.56 (d, J=13.8 Hz, 1H), 1.20-1.06 (m, 1H), 0.91-0.82 (m, 1H), 0.81-0.72 (m, 1H), 0.57-0.46 (m, 2H).

LC/MS: m/z=422 [M+H]$^+$ (Calc: 421).

Example 4

(6R,6aR,12aS)-15-(cyclopropylmethyl)-2-methoxy-10-oxo-6,6a,7,10,11,12-hexahydro-5H-6,12a-(epiminoethano)naphtho[2,1-g]quinoline-9-carboxamide (6)

(6R,6aR,12aS)-15-(cyclopropylmethyl)-2-hydroxy-10-oxo-6,6a,7,10,11,12-hexahydro-5H-6,12a-(epiminoethano)naphtho[2,1-g]quinoline-9-carboxamide (7)

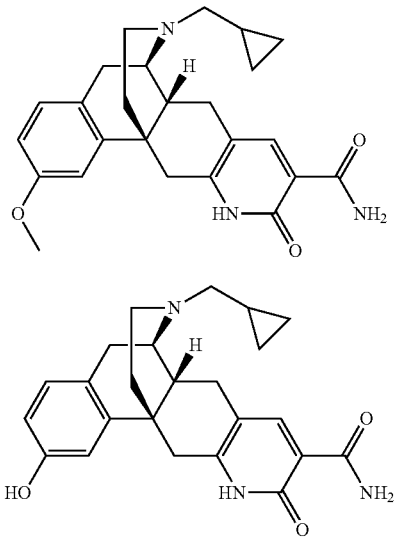

Compounds 6 and 7 were prepared as described in Example 3.

(a) Compound 6 was prepared from compound 3 (prepared in Example 2) rather compound 2. Trituration with methanol gave the title compound 6 as a white powder.

$^1$H NMR $\delta_H$ (400 MHz, DMSO-$d_6$): 12.21 (s, 1H), 9.03 (d, J=4.2 Hz, 1H), 7.87 (s, 1H), 7.40 (d, J=3.9 Hz, 1H), 7.03 (d, J=8.1 Hz, 1H), 6.71-6.64 (m, 2H), 3.65 (s, 3H), 3.39 (d, J=17.5 Hz, 1H), 3.27-3.22 (m, 1H), 2.89 (d, J=18.6 Hz, 1H), 2.77-2.66 (m, 2H), 2.66-2.59 (m, 1H), 2.59-2.51 (m, 1H), 2.45-2.37 (m, 1H), 2.33-2.18 (m, 2H), 2.16-2.04 (m, 1H), 2.01-1.90 (m, 1H), 1.82 (dt, J=12.3, 3.9 Hz, 1H), 1.41 (d, J=12.3 Hz, 1H), 0.87-0.75 (m, 1H), 0.51-0.40 (m, 2H), 0.15-0.03 (m, 2H).

LC/MS: m/z=420 [M+H]$^+$ (Calc: 419).

(b) Compound 7 was prepared from compound 6 using the procedure described in Example 3 for preparing compound 5. Purification over silica gel with 0-50% (10% NH₄OH in MeOH) in DCM then trituration with MeOH gave compound 7 as a white powder.

¹H NMR $\delta_H$ (400 MHz, DMSO-$d_6$): 12.28 (s, 1H), 9.08 (s, 1H), 9.04 (d, J=4.6 Hz, 1H), 7.88 (s, 1H), 7.40 (d, J=4.6 Hz, 1H), 6.89 (d, J=8.1 Hz, 1H), 6.55-6.47 (m, 2H), 3.33-3.27 (m, 1H, overlap with water peak), 3.25-3.19 (m, 1H), 2.84 (d, J=18.4 Hz, 1H), 2.73-2.57 (m, 3H), 2.55-2.49 (m, 1H, overlap with DMSO peak), 2.44-2.36 (m, 1H), 2.32-2.24 (m, 1H), 2.23-2.07 (m 2H), 2.02-1.91 (m, 1H), 1.80 (dt, J=12.3, 4.2 Hz, 1H), 1.38 (d, J=11.8 Hz, 1H), 0.87-0.75 (m, 1H), 0.51-0.40 (m, 2H), 0.15-0.03 (m, 2H).

LC/MS: m/z=406 [M+H]⁺ (Calc: 405).

Example 5

(6R,6aS,12aR)-15-(cyclopropylmethyl)-6a-hydroxy-2-methoxy-10-oxo-6,6a,7,10,11,12-hexahydro-5H-6,12a-(epiminoethano)naphtho[2,1-g]quinoline-9-carboxylic acid (8)

(6R,6aS,12aR)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxylic acid (9)

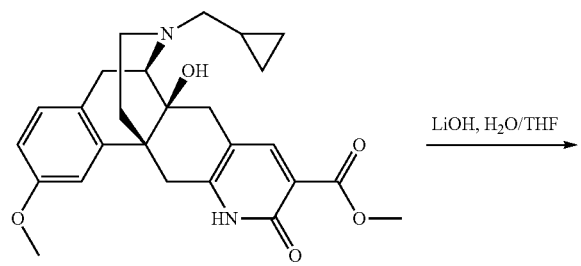

2

LiOH, H₂O/THF

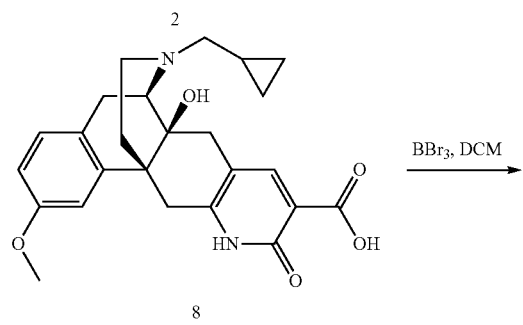

8

BBr₃, DCM

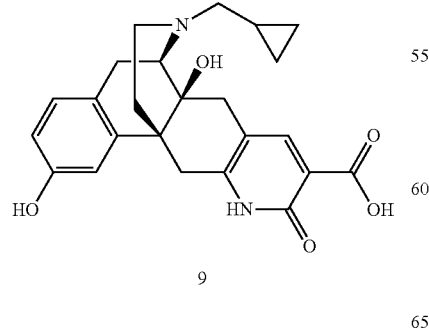

9

(a) To a mixture of compound 2 (0.779 g, 1.73 mmol, 1 eq) in THF (10 mL) and water (2 mL) was added LiOH.H₂O (0.084 g, 2.00 mmol, 1.16 eq). After 3 days, more LiOH.H₂O (0.042 g, 1.00 mmol, 0.58 eq) was added. After 5 more days, the reaction was concentrated to a paste in vacuo. The residue was diluted with 10 mL water to make a milky suspension. This was then acidified to a pH 5-6 with 3.0 mL 1N HCl. The solids were filtered off and rinsed three times with 2 mL water. The solid was dried under vacuum to give the title compound 8 as a cream-colored powder (0.646 g, 1.48 mmol, 86% yield).

¹H NMR $\delta_H$ (400 MHz, DMSO-$d_6$): 12.94 (br s, 1H), 7.91 (s, 1H), 7.08 (d, J=8.3 Hz, 1H), 6.74 (dd, J=8.3, 2.2 Hz, 1H), 6.68 (d, J=2.0 Hz, 1H), 5.17 (br s, 1H), 3.65 (s, 3H), 3.55-3.12 (m, 2H, overlap with water peak), 3.24-3.12 (m, 1H), 3.07-2.95 (m, 2H), 2.83-2.44 (m, 5H, overlap with DMSO peak), 2.25-2.08 (m, 2H), 1.36-1.22 (m, 1H), 1.01-0.88 (m, 1H), 0.63-0.46 (m, 2H), 0.30-0.14 (m, 2H).

LC/MS: m/z=437 [M+H]⁺ (Calc: 436).

(b) A mixture of compound 8 (0.101 g, 0.23 mmol, 1 eq) in DCM (5 mL) was put into a sealed tube and cooled on an ice-salt bath. Neat BBr₃ (0.09 mL, 0.93 mmol, 4 eq) was added. The reaction was allowed to warm up to ambient temperature and stirred overnight. An additional amount of neat BBr₃ (0.03 mL, 0.31 mmol, 1.3 eq) was added and the reaction stirred for an additional 3.5 hours. The reaction was quenched with 4 mL saturated NaHCO₃ solution and the solid product was filtered off and rinsed with DCM and water. The solid was chromatographed reverse-phase with 0-60% acetonitrile in water (both +0.1% TFA). The product fractions were frozen and lyophilized to give the title compound 9 as a TFA salt (as a cream-colored powder) (0.069 g, 0.13 mmol, 56% yield).

¹H NMR $\delta_H$ (400 MHz, CD₃OD): 8.11 (s, 1H), 7.09 (d, J=8.3 Hz, 1H), 6.75-6.70 (m, 2H), 4.17-4.10 (m, 1H), 3.44-3.33 (m, 4H), 3.22-3.07 (m, 2H), 3.05-2.96 (m, 1H), 2.92-2.77 (m, 2H), 2.76-2.67 (m, 1H), 2.53 (dt, J=13.8, 4.8 Hz, 1H), 1.63-1.54 (m, 1H), 1.21-1.07 (m, 1H), 0.92-0.82 (m, 1H), 0.82-0.73 (m, 1H), 0.58-0.47 (m, 2H).

LC/MS: m/z=423 [M+H]⁺ (Calc: 422).

Example 6

(6R,6aR,12aS)-15-(cyclopropylmethyl)-2-methoxy-10-oxo-6,6a,7,10,11,12-hexahydro-5H-6,12a-(epiminoethano)naphtho[2,1-g]quinoline-9-carboxylic acid (10)

(6R,6aR,12aS)-15-(cyclopropylmethyl)-2-hydroxy-10-oxo-6,6a,7,10,11,12-hexahydro-5H-6,12a-(epiminoethano)naphtho[2,1-g]quinoline-9-carboxylic acid (11)

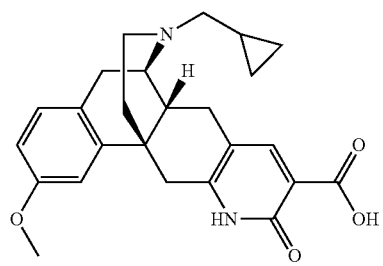

10

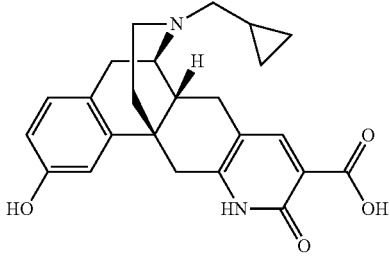

Compounds 10 and 11 were prepared as described in Example 5.

(a) Compound 10 was prepared from compound 3 (prepared in Example 2) rather than compound 2. Trituration with water gave the title compound 10 as a light tan powder.

$^1$H NMR $\delta_H$ (400 MHz, DMSO-d$_6$): 12.60 (br s, 1H), 7.88 (s, 1H), 7.05 (d, J=8.3 Hz, 1H), 6.74-6.66 (m, 2H), 3.65 (s, 3H), 3.53-3.42 (m, 2H, overlap with water peak), 2.98 (d, J=19.1 Hz, 1H), 2.90-2.75 (m, 3H), 2.70-2.58 (m, 2H), 2.53-2.47 (m, 1H, overlap with DMSO peak), 2.40-2.31 (m, 1H), 2.24-2.05 (m, 2H), 1.90 (dt, J=12.5, 3.7 Hz, 1H), 1.51 (d, J=12.7 Hz, 1H), 0.96-0.83 (m, 1.1), 0.56-0.45 (m, 2H), 0.22-0.12 (m, 2H).

LC/MS: m/z=421 [M+H]$^+$ (Calc: 420).

(b) Compound 11 was prepared from compound 10 according to the procedure described in Example 5. Purification over silica gel with 0-50% (10% NH$_4$OH in MeOH) in DCM then trituration with MeOH gave the title compound 11 as a light tan powder.

$^1$H NMR $\delta_H$ (400 MHz, DMSO-d$_6$): 12.66 (br s, 1H), 9.14 (s, 1H), 7.88 (s, 1H), 6.91 (d, J=8.1 Hz, 1H), 6.59-6.49 (m, 2H), 3.46-3.33 (m, 2H, overlap with water peak), 2.92 (d, J=18.6 Hz, 1H), 2.86-2.71 (m, 3H), 2.67-2.54 (m, 2H), 2.50-2.41 (m, 1H, overlap with DMSO peak), 2.35-2.05 (m, 3H), 1.92-1.81 (m, 1H), 1.47 (d, J=12.7 Hz, 1H), 0.93-0.81 (m, 1H), 0.55-0.44 (m, 2H), 0.22-0.09 (m, 2H).

LC/MS: m/z=407 [M+H]$^+$ (Calc: 406).

Example 7

(6R,6aS,12aR)—N-(2-amino-2-oxoethyl)-15-(cyclopropylmethyl)-6a-hydroxy-2-methoxy-10-oxo-6,6a,7,10,11,12-hexahydro-5H-6,12a-(epiminoethano)naphtho[2,1-g]quinoline-9-carboxamide (13)

(6R,6aS,12aR)—N-(2-amino-2-oxoethyl)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxamide (14)

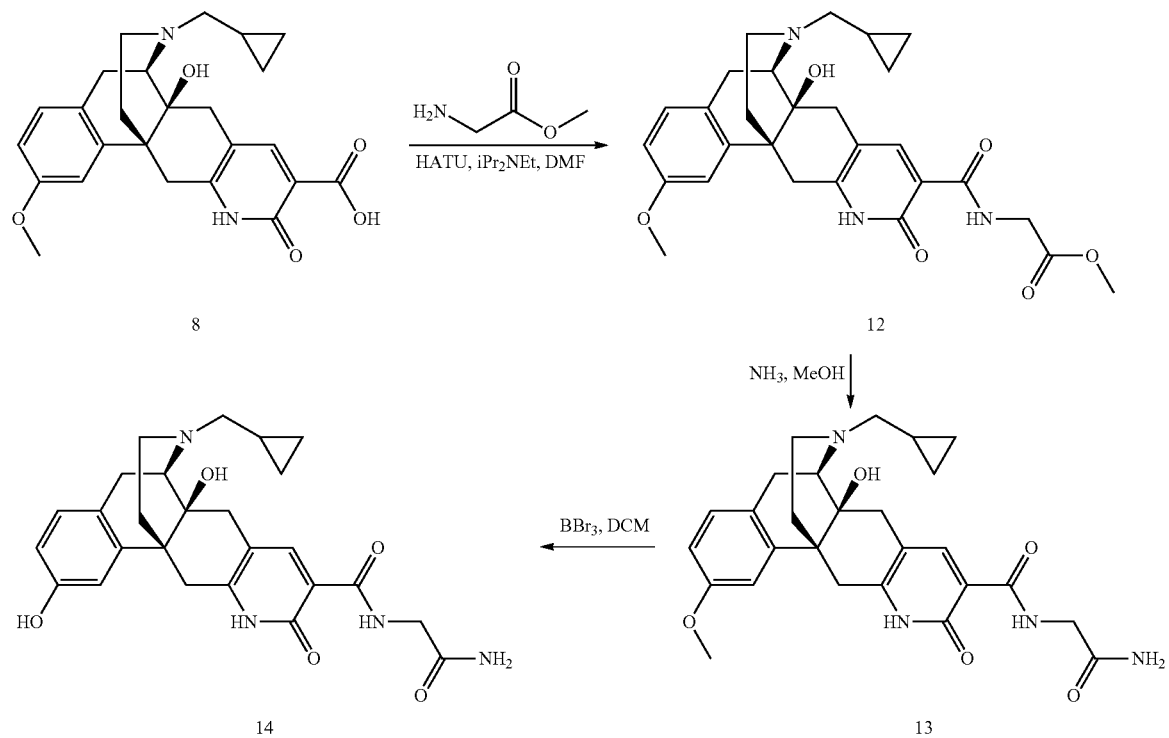

(a) To a mixture of compound 8 (0.250 g, 0.57 mmol, 1 eq) in DMF (5 mL) was added glycine methyl ester hydrochloride (0.077 g, 0.61 mmol, 1.1 eq), iPr$_2$NEt (0.22 mL, 1.26 mmol, 2.2 eq) and 1-[bis(dimethylamino)methylene]-1H-1,2,3-triazolo[4,5-b]pyridinium 3-oxid hexafluorophosphate (HATU; Sigma-Aldrich) (0.244 g, 0.64 mmol, 1.1 eq). After 5 hours, more glycine methyl ester hydrochloride (0.080 g, 0.64 mmol, 1.1 eq), iPr$_2$NEt (0.11 mL, 0.63 mmol, 1.1 eq) and HATU (0.250 g, 0.66 mmol, 1.2 eq) were added. After stirring overnight, more glycine methyl ester hydrochloride (0.079 g, 0.63 mmol, 1.1 eq), iPr$_2$NEt (0.11 mL, 0.63 mmol, 1.1 eq) and HATU (0.244 g, 0.64 mmol, 1.1 eq) were added. After 4 more hours, more glycine methyl ester hydrochloride (0.077 g, 0.61 mmol, 1.1 eq), iPr$_2$NEt (0.11 mL, 0.63 mmol, 1.1 eq) and HATU (0.249 g, 0.65 mmol, 1.1 eq) were added. After stirring overnight, the reaction was evaporated in vacuo. The residue was dissolved in 50 mL DCM and washed twice with 25 mL water and then once with 10 mL brine. The organics were dried over Na$_2$SO$_4$, filtered and evaporated in vacuo. The residue was chromatographed over silica gel with 0-100% acetone in hexanes then 0-25% (10% NH$_4$OH in MeOH) in DCM. The product fractions were evaporated in vacuo to give compound 12 as a tan solid (0.172 g, 0.34 mmol, 59% yield). LC/MS: m/z=508 [M+H]$^+$ (Calc: 507).

(b) A mixture of compound 12 (0.172 g, 0.34 mmol, 1 eq) in 7M NH$_3$ in MeOH (5 mL, 35 mmol, 103 eq) was heated at 50° C. in a sealed tube overnight. After cooling to ambient temperature, the precipitated solid was filtered off and rinsed once with ~1 mL MeOH. The filtrate was evaporated part way down and it formed another batch of solid. This was also filtered off and rinsed with MeOH. Lastly, the filtrate was evaporated to give a third batch of solid which was also filtered off and rinsed with MeOH. The three batches of solid were combined and dried under vacuum to give the title compound 13 as a light tan powder (0.116 g, 0.236 mmol, 70% yield).

$^1$H NMR $\delta_H$ (400 MHz, DMSO-d$_6$): 12.28 (s, 1H), 9.91 (t, J=5.3 Hz, 1H), 7.85 (s, 1H), 7.38 (s, 1H), 7.08-6.99 (m, 2H), 6.70 (d, J=8.3 Hz, 1H), 6.65 (s, 1H), 4.70 (s, 1H), 3.85 (d, J=5.3 Hz, 2H), 3.64 (s, 3H), 3.24-3.11 (m, 2H), 3.10-3.01 (m, 1H), 2.94-2.82 (m, 2H), 2.62-2.49 (m, 2H, overlap with DMSO peak), 2.45-2.31 (m, 3H), 2.12-1.93 (m, 2H), 1.25-1.13 (m, 1H), 0.93-0.80 (m, 1H), 0.54-0.42 (m, 2H), 0.17-0.06 (m, 2H).

LC/MS: m/z=493 [M+H]$^+$ (Calc: 492).

(c) A mixture of compound 13 (0.088 g, 0.18 mmol, 1 eq) in DCM (5 mL) was put into a sealed tube and cooled on an ice-salt bath. Neat BBr$_3$ (0.07 mL, 0.73 mmol, 4 eq) was added. After 1 hour, the ice bath was removed. Then the mixture was stirred at ambient temperature overnight. An additional amount of neat BBr$_3$ (0.05 mL, 0.52 mmol, 3 eq) was added and the reaction was stirred again overnight. The reaction was quenched into a mixture of ~1 mL concentrated NH$_4$OH in 15 mL MeOH then concentrated in vacuo. Fresh MeOH was added and the mixture was concentrated again in vacuo. The residue was chromatographed reverse-phase with 0-60% acetonitrile in water (both +0.1% TFA). The product fractions were frozen and lyophilized to give the title compound 14 as a TFA salt (a white powder) (0.037 g, 0.062 mmol, 35% yield).

$^1$H NMR $\delta_H$ (400 MHz, DMSO-d$_6$): 12.46 (s, 1H), 9.89 (t, J=5.5 Hz, 1H), 9.40 (s, 1H), 9.05-8.94 (m, 1H), 7.89 (s, 1H), 7.41 (s, 1H), 7.05 (s, 1H), 6.99 (d, J=8.3 Hz, 1H), 6.64 (dd, J=8.3, 2.2 Hz, 1H), 6.60 (d, J=2.4 Hz, 1H), 6.25 (s, 1H), 3.96 (d, J=6.1 Hz, 1H), 3.86 (d, J=5.3 Hz, 2H), 3.41-3.20 (m, 4H), 3.07-2.98 (m, 1H), 2.97-2.86 (m, 2H), 2.71-2.53 (m, 3H), 2.29 (dt, J=13.1, 4.4 Hz, 1H), 1.49-1.40 (m, 1H), 1.14-1.02 (m, 1H), 0.75-0.66 (m, 1H), 0.66-0.57 (m, 1H), 0.51-0.36 (m, 2H).

LC/MS: m/z=479 [M+H]$^+$ (Calc: 478).

Example 8

(6R,6aS,12aR)—N—OS)-1-amino-1-oxopropan-2-yl)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxamide (16)

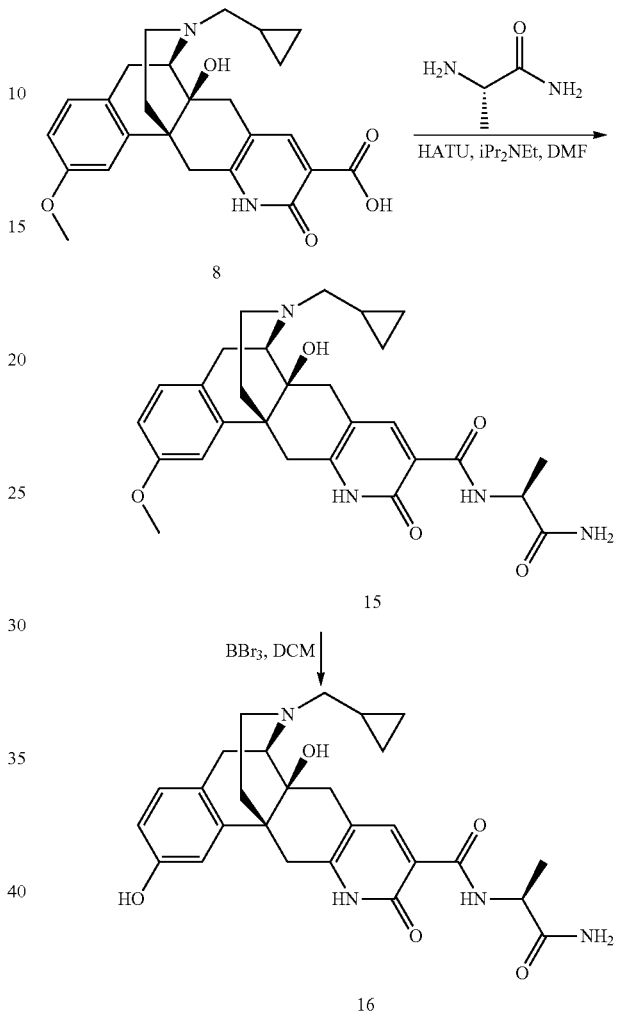

(a) To a mixture of compound 8 (0.119 g, 0.273 mmol, 1 eq) and L-alanamide hydrochloride (0.071 g, 0.570 mmol, 2 eq) in DMF (2 mL) was added iPr$_2$NEt (0.15 mL, 0.86 mmol, 3.2 eq) and HATU (0.215 g, 0.565 mmol, 2 eq). After stirring overnight, the reaction was evaporated in vacuo. The residue was chromatographed over silica gel with 0-50% (10% NH$_4$OH in MeOH) in DCM. The product fractions were evaporated in vacuo to give compound 15 as a tan-orange powder (0.099 g, 0.195 mmol, 72% yield). LC/MS: m/z=507 [M+H]$^+$ (Calc: 506).

(b) To a mixture of compound 15 (0.099 g, 0.195 mmol, 1 eq) in DCM (5 mL) was added 1M BBr$_3$ in DCM (0.60 mL, 0.60 mmol, 3 eq). After 6 hours, additional 1M BBr$_3$ in DCM (0.60 mL, 0.60 mmol, 3 eq) was added. After stirring at ambient temperature overnight, the reaction mixture was quenched with 3 mL 2.5M NH$_4$OH in MeOH. The solid salts were filtered off and the filtrate evaporated in vacuo to a residue. The residue was chromatographed reverse-phase with 0-40% acetonitrile in water (both +0.1% TFA). The product fractions were frozen and lyophilized to give the title compound as a TFA salt as a cream-colored powder (0.068 g, 0.11 mmol, 57% yield).

¹H NMR δ_H (400 MHz, DMSO-d_6): 12.43 (s, 1H), 9.97 (d, J=7.2 Hz, 1H), 9.39 (s, 1H), 9.04-8.94 (m, 1H), 7.88 (s, 1H), 7.46 (s, 1H), 7.03 (s, 1H), 6.99 (d, J=8.6 Hz, 1H), 6.64 (dd, J=8.3, 2.2 Hz, 1H), 6.60 (d, J=2.2 Hz, 1H), 6.24 (s, 1H), 4.39 (p, J=7.2 Hz, 1H), 3.96 (d, J=5.9 Hz, 1H), 3.41-3.20 (m, 4H, overlap with water peak), 3.07-2.98 (m, 1H), 2.96-2.86 (m, 2H), 2.71-2.53 (m, 3H), 2.28 (dt, J=13.4, 4.2 Hz, 1H), 1.44 (d, J=13.4 Hz, 1H), 1.26 (d, J=7.0 Hz, 3H), 1.14-1.02 (m, 1H), 0.75-0.66 (m, 1H), 0.66-0.57 (m, 1H), 0.51-0.36 (m, 2H).

LC/MS: m/z=493 [M+H]⁺ (Calc: 492).

Example 9

(6R,6aS,12aR)—N—((S)-1-amino-1-oxo-3-phenyl-propan-2-yl)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxamide (17)

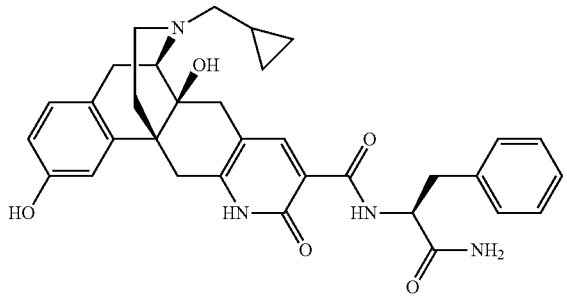 [SMILES: NC(=O)[C@H](Cc1ccccc1)NC(=O)c1cc2c([nH]c1=O)C[C@]13CCN(CC4CC4)[C@H](Cc4ccc(O)cc41)[C@]3(O)C2]

Compound 17 was prepared was prepared in a manner similar to that described in Example 8 for preparing compound 16 using L-phenylalanamide rather than L-alanamide hydrochloride. Purification by reverse-phase chromatography 0-40% acetonitrile in water (both +0.1% TFA) gave the title compound 17 as a TFA salt (a cream-colored powder).

¹H NMR δ_H (400 MHz, DMSO-d_6): 12.43 (s, 1H), 10.00 (d, J=8.1 Hz, 1H), 9.39 (s, 1H), 9.03-8.94 (m, 1H), 7.82 (s, 1H), 7.50 (s, 1H), 7.26-7.14 (m, 5H), 7.07 (s, 1H), 6.98 (d, J=8.6 Hz, 1H), 6.64 (dd, J=8.3, 2.4 Hz, 1H), 6.59 (d, J=2.4 Hz, 1H), 6.23 (s, 1H), 4.67-4.59 (m, 1H), 3.95 (d, J=6.1 Hz, 1H), 3.40-3.18 (m, 4H, overlap with water peak), 3.12-2.97 (m, 2H), 2.95-2.82 (m, 3H), 2.66-2.53 (m, 3H), 2.28 (dt, J=13.4, 4.6 Hz, 1H), 1.44 (d, J=12.7 Hz, 1H), 1.14-1.02 (m, 1H), 0.75-0.66 (m, 1H), 0.66-0.57 (m, 1H), 0.51-0.36 (m, 2H).

LC/MS: m/z=569 [M+H]⁺ (Calc: 568).

Example 10

(6R,6aS,12aR)—N—((S)-1-amino-4-methyl-1-oxo-pentan-2-yl)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxamide (18)

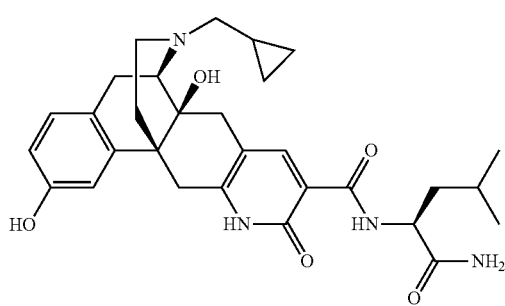 [SMILES: CC(C)C[C@H](NC(=O)c1cc2c([nH]c1=O)C[C@]13CCN(CC4CC4)[C@H](Cc4ccc(O)cc41)[C@]3(O)C2)C(N)=O]

Compound 18 was prepared in a manner similar to that described in Example 8 for preparing compound 16 using L-leucinamide hydrochloride rather than L-alanamide hydrochloride. Purification by reverse-phase chromatography 0-40% acetonitrile in water (both +0.1% TFA) gave the title compound 18 as a TFA salt (as a cream-colored powder).

¹H NMR δ_H (400 MHz, DMSO-d_6): 12.42 (s, 1H), 9.90 (d, J=78.3 Hz, 1H), 9.39 (s, 1H), 9.04-8.94 (m, 1H), 7.89 (s, 1H), 7.50 (s, 1H), 7.02-6.95 (m, 2H), 6.64 (dd, J=8.3, 2.4 Hz, 1H), 6.60 (d, J=2.2 Hz, 1H), 6.23 (s, 1H), 4.48-4.40 (m, 1H), 3.96 (d, J=5.9 Hz, 1H), 3.41-3.21 (m, 4H, overlap with water peak), 3.07-2.99 (m, 1H), 2.96-2.86 (m, 2H), 2.71-2.53 (m, 3H), 2.28 (dt, J=13.6, 4.6 Hz, 1H), 1.62-1.40 (m, 4H), 1.14-1.03 (m, 1H), 0.89 (d, 6.4 Hz, 3H), 0.86 (d, J=5.9 Hz, 3H), 0.75-0.66 (m, 1H), 0.66, 0.58 (m, 1H), 0.51-0.36 (m, 2H).

LC/MS: m/z=535 [M+H]⁺ (Calc: 534).

Example 11

(S)-1-((6R,6aS,12aR)-15-(cyclopropylmethyl)-2,6a-dihydroxy-10-oxo-6,6a,7,10,11,12-hexahydro-5H-6,12a-(epiminoethano)naphtho[2,1-g]quinoline-9-carbonyl)pyrrolidine-2-carboxamide (19)

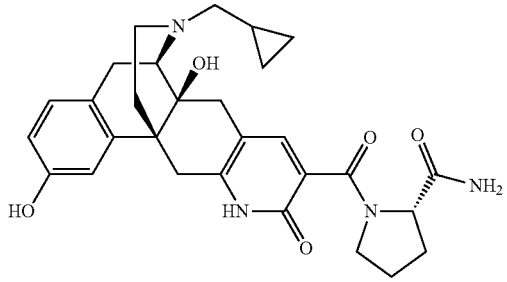 [SMILES: NC(=O)[C@@H]1CCCN1C(=O)c1cc2c([nH]c1=O)C[C@]13CCN(CC4CC4)[C@H](Cc4ccc(O)cc41)[C@]3(O)C2]

Compound 19 was prepared in a manner similar to that described in Example 8 for preparing compound 16 using L-prolinamide rather than L-alanamide hydrochloride. Purification by reverse-phase chromatography 0-40% acetonitrile in water (both +0.1% TFA) gave the title compound 19 as a TFA salt (a cream-colored powder).

¹H NMR δ_H (400 MHz, DMSO-d_6): Exists as a 4:1 ratio of conformers 12.09 (s, 0.8H), 11.91 (s, 0.2H), 9.40 (s, 1H), 9.04-8.92 (m, 1H), 7.42 (s, 0.8H), 7.33 (s, 0.2H), 7.19 (s, 0.8H), 7.10-6.94 (m, 2H), 6.76 (s, 0.2H), 6.68-6.56 (m, 2H), 6.22 (s, 1H), 4.43-4.37 (m, 0.2H), 4.32-4.24 (m, 0.8H), 3.99-3.90 (m, 1H), 3.47-3.09 (m, 6H, overlap with water peak), 3.07-2.96 (m, 1H), 2.96-2.80 (m, 2H), 2.69-2.48 (m, 3H, overlap with DMSO peak), 2.35-2.20 (m, 1H), 2.16-2.02 (m, 1H), 1.96-1.69 (m, 3H), 1.48-1.37 (m, 1H), 1.14-1.00 (m, 1H), 0.75-0.66 (m, 1H), 0.66-0.55 (m, 1H), 0.50-0.34 (m, 2H).

LC/MS: m/z=519 [M+H]⁺ (Calc: 518).

Example 12

(S)-2-((6R,6aS,12aR)-15-(cyclopropylmethyl)-2,6a-dihydroxy-10-oxo-6,6a,7,10,11,12-hexahydro-5H-6,12a-(epiminoethano)naphtho[2,1-g]quinoline-9-carboxamido)succinamide (20)

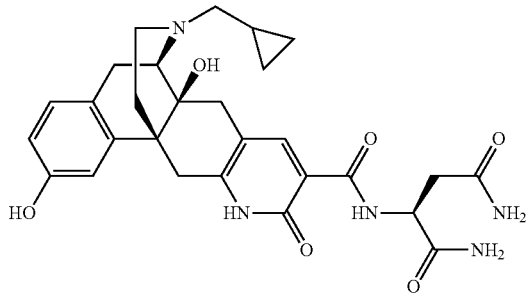 [SMILES: NC(=O)C[C@H](NC(=O)c1cc2c([nH]c1=O)C[C@]13CCN(CC4CC4)[C@H](Cc4ccc(O)cc41)[C@]3(O)C2)C(N)=O]

Compound 20 was prepared in a manner similar to that described in Example 8 for preparing compound 16 using L-asparaginamide hydrochloride rather than L-alanamide hydrochloride. Purification by reverse-phase chromatography 0-40% acetonitrile in water (both +0.1% TFA) gave the title compound 20 as a TFA salt (a cream-colored powder).

$^1$H NMR $\delta_H$ (400 MHz, DMSO-d$_6$): 12.40 (s, 1H), 9.98 (d, J=7.9 Hz, 1H), 9.39 (s, 1H), 9.04-8.93 (m, 1H), 7.87 (s, 1H), 7.36 (s, 1H), 7.28 (s, 1H), 7.03-6.96 (m, 2H), 6.86 (s 1H), 6.64 (dd, J=8.1, 2.2 Hz, 1H), 6.60 (d, J=2.2 Hz, 1H), 6.24 (s, 1H), 4.68-4.60 (m, 1H), 3.96 (d, J=5.7 Hz, 1H), 3.42-3.20 (m, 4H, overlap with water peak), 3.07-2.98 (m, 1H), 2.95-2.86 (m, 2H), 2.71-2.53 (m, 3H), 2.52-2.42 (m, 2H, overlap with DMSO peak), 2.28 (dt, J=13.4, 4.6 Hz, 1H), 1.44 (d, J=12.2 Hz, 1H), 1.14-1.02 (m, 1H), 0.75-0.66 (m, 1H), 0.66-0.57 (m, 1H), 0.51-0.36 (m, 2H).

LC/MS: m/z=536 [M+H]$^+$ (Calc: 535).

Example 13

(6R,6aR,12aS)—N-(2-amino-2-oxoethyl)-15-(cyclopropylmethyl)-2-hydroxy-10-oxo-6,6a,7,10,11,12-hexahydro-5H-6,12a-(epiminoethano)naphtho[2,1-g]quinoline-9-carboxamide (21)

(6R,6aR,12aS)—N—((S)-1-amino-1-oxopropan-2-yl)-15-(cyclopropylmethyl)-2-hydroxy-10-oxo-6,6a,7,10,11,12-hexahydro-5H-6,12a-(epiminoethano)naphtho[2,1-g]quinoline-9-carboxamide (22)

(6R,6aR,12aS)—N—((S)-1-amino-1-oxo-3-phenylpropan-2-yl)-15-(cyclopropylmethyl)-2-hydroxy-10-oxo-6,6a,7,10,11,12-hexahydro-5H-6,12a-(epiminoethano)naphtho[2,1-g]quinoline-9-carboxamide (23)

(6R,6aR,12aS)—N—((S)-1-amino-4-methyl-1-oxopentan-2-yl)-15-(cyclopropylmethyl)-2-hydroxy-10-oxo-6,6a,7,10,11,12-hexahydro-5H-6,12a-(epiminoethano)naphtho[2,1-g]quinoline-9-carboxamide (24)

(S)-1-((6R,6aR,12aS)-15-(cyclopropylmethyl)-2-hydroxy-10-oxo-6,6a,7,10,11,12-hexahydro-5H-6,12a-(epiminoethano)naphtho[2,1-g]quinoline-9-carbonyl)pyrrolidine-2-carboxamide (25)

(S)-2-(6R,6aR,12aS)-15-(cyclopropylmethyl)-2-hydroxy-10-oxo-6,6a,7,10,11,12-hexahydro-5H-6,12a-(epiminoethano)naphtho[2,1-g]quinoline-9-carboxamido)succinamide (26)

The title compounds were prepared following the procedure described in Example 8 for preparing compound 16 starting from compound 10 prepared in Example 6 rather than compound 8.

(a) Compound 21:

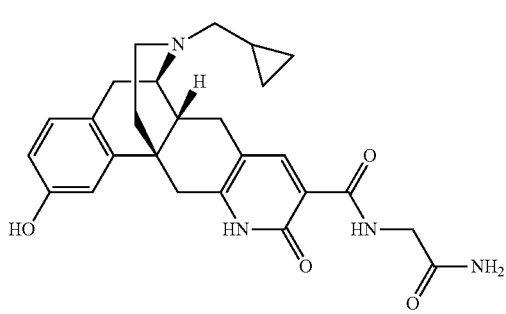

21

TFA salt: $^1$H NMR $\delta_H$ (400 MHz, DMSO-d$_6$): Exists as a 3:1 ratio of salt diastereomers 12.41 (s, 0.75H), 12.37 (s, 0.25H), 9.2-9.85 (m, 1H), 9.61 (s, 0.75H), 9.50 (s, 0.25H), 9.40-9.32 (m, 1H), 7.92-7.88 (m, 1H), 7.40 (s, 1H), 7.07-6.96 (m, 2H), 6.66-6.58 (m, 2H), 4.09-3.96 (m, 1H), 3.88-3.83 (m, 2H), 3.47-3.22 (m, 4H), 3.20-3.14 (m, 1H), 3.13-3.04 (m, 1H), 2.96-2.51 (m, 4H), 2.24-1.94 (m, 2H), 1.75 (d, J=13.8 Hz, 0.75H), 1.53 (d, J=13.8 Hz, 0.25H), 1.16-1.02 (m, 1H), 0.72-0.62 (m, 2H), 0.45-0.34 (m, 2H). LC/MS: m/z=463 [M+H]$^+$ (Calc: 462).

(b) Compound 22:

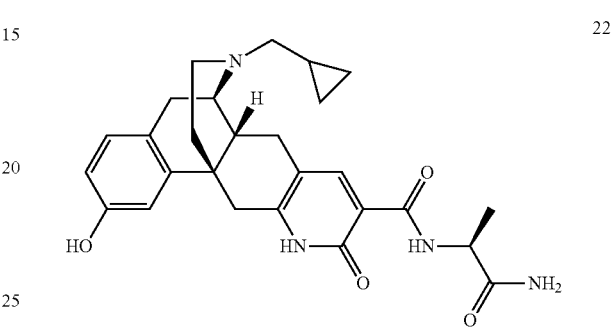

22

TFA salt: $^1$H NMR $\delta_H$ (400 MHz, DMSO-d$_6$) Exists as a—3:1 ratio of salt diastereomers 12.38 (s, 0.75H), 12.35 (s, 0.25H), 9.99-9.94 (m, 1H), 9.66 (s, 0.75H), 9.55 (s, 0.25H), 9.36 (s, 1H), 7.91-7.87 (m, 1H), 7.46 (s, 1H), 7.04-6.96 (m, 2H), 6.66-6.57 (m, 2H), 4.38 (p, J=7.0 Hz, 1H), 4.09-3.95 (m, 1H), 3.47-3.22 (m, 4H), 3.20-3.14 (m, 1H), 3.13-3.04 (m, 1H), 2.95-2.52 (m, 4H), 2.24-1.95 (m, 2H), 1.74 (d, J=13.4 Hz, 0.75H), 1.53 (d, J=14.3 Hz, 0.25H), 1.26 (d, =7.0 Hz, 3H), 1.16-1.02 (m, 1H), 0.72-0.61 (m, 2H), 0.44-0.34 (m, 24). LC/MS: m/z=477 [M+H]$^+$ (Calc: 476).

(c) Compound 23:

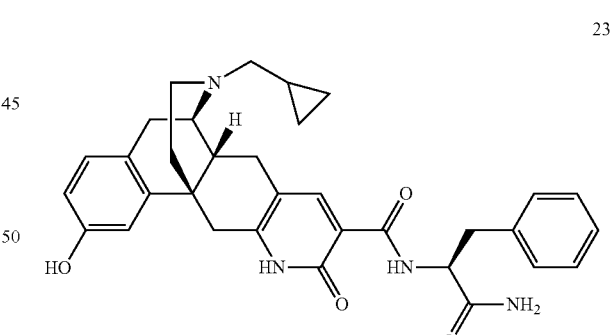

23

TFA salt: $^1$H NMR $\delta_H$ (400 MHz, DMSO-d$_6$): Exists as a 3:1 ratio of salt diastereomers 12.37 (s, 0.75H), 12.34 (s, 0.25H), 10.02-9.95 (m, 1H), 9.60 (s, 0.75H), 9.50 (s, 0.25H), 9.35 (s, 1H), 7.85-7.81 (m, 1H), 7.49 (s, 1H), 7.26-7.14 (m, 5H), 7.05 (s, 1H), 7.03-6.95 (m, 1H), 6.65-6.57 (m, 2H), 4.66-4.57 (m, 1H), 4.08-3.94 (m, 1H), 3.46-3.21 (m, 4H), 3.20-3.13 (m, 1H), 3.12-3.01 (m, 2H), 2.93-2.47 (m, 5H), 2.21-1.94 (m, 2H), 1.74 (d, J=14.3 Hz, 0.75H), 1.52 (d, J=14.0 Hz, 0.25H), 1.15-1.01 (m, 1H), 0.71-0.61 (m, 2H), 0.43-0.33 (m, 2H). LC/MS: m/z=553 [M+H]$^+$ (Calc: 552).

(d) Compound 24:

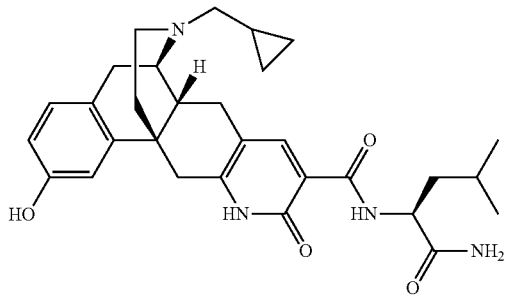

TFA salt: $^1$H NMR $\delta_H$ (400 MHz, DMSO-d$_6$): Exists as a 3:1 ratio of salt diastereomers 12.40-12.30 (m, 1H), 9.93-9.84 (m, 1H), 9.56 (s, 0.75H), 9.47 (s, 0.25H), 9.35 (s, 1H), 7.92-7.86 (m, 1H), 7.49 (s, 1H), 7.04-6.93 (m, 2H), 6.66-6.57 (m, 2H), 4.48-4.38 (m, 1H), 4.09-3.94 (m, 1H), 3.48-3.21 (m, 4H), 3.20-3.13 (m, 1H), 3.13-3.01 (m, 1H), 2.95-2.42 (m, 4H), 2.25-1.93 (m, 2H), 1.75 (d, J=12.7 Hz, 0.75H), 1.62-1.39 (m, 3.25H), 1.15-1.00 (m, 1H), 0.92-0.81 (m, 6H), 0.72-0.60 (m, 2H), 0.45-0.33 (m, 2H). LC/MS, m/z=519 [M+H]$^+$ (Calc: 518).

(e) Compound 25:

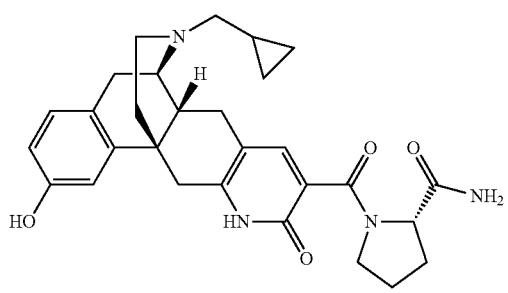

TFA salt: $^1$H NMR $\delta_H$ (400 MHz, DMSO-d$_6$): Exists as a 3:1 ratio of salt diastereomers combined with a 3:1 ratio of confirmational isomers 12.09-11.98 (m, 0.75H), 11.88-11.80 (m, 0.25H), 9.59 (s, 0.75H), 9.45 (s, 0.25H), 9.36 (s, 1H), 7.41 (s, 0.75H), 7.29 (s, 0.25H), 7.21-7.16 (m, 0.75H), 7.07 (s, 0.75H), 7.05-6.96 (m, 1.25H), 6.86 (s, 0.19H), 6.80 (s, 0.06H), 6.68-6.59 (m, 2H), 4.35-4.25 (m, 1H), 4.09-3.94 (m, 1H), 3.49-3.21 (m, 6H), 3.19-3.13 (m, 1H), 3.13-3.02 (m, 1H), 2.91-2.40 (m, 4H), 2.29-1.93 (m, 3H), 1.92-1.69 (m, 3.75H), 1.56-1.47 (m, 0.25H), 1.16-1.01 (m, 1H), 0.72-0.60 (m, 2H), 0.44-0.34 (m, 2H). LC/MS: m/z=503 [M+H]$^+$ (Calc: 502).

(f) Compound 26:

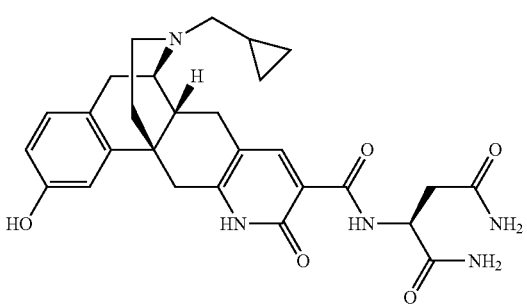

TFA salt: NMR $\delta_H$ (400 MHz, DMSO-d$_6$): Exists as a 3:1 ratio of salt diastereomers 12.35 (s, 0.75H), 12.32 (s, 0.25H), 9.98 (d, J=7.9 Hz, 1H), 9.59 (s, 0.75H), 9.48 (s, 0.25H), 9.36 (s, 1H), 7.90-7.86 (m, 1H), 7.36 (s, 1H), 7.27 (s, 1H), 7.04-6.95 (m, 2H), 6.85 (s, 1H), 6.66-6.57 (m, 2H), 4.67 (m, 1H), 4.10-3.95 (m, 1H), 3.47-3.22 (m, 4H), 3.20-3.14 (m, 1H), 3.13-3.03 (m, 1H), 2.95-2.43 (m, 6H), 2.24-1.94 (m, 2H), 1.75 (d, J=13.6 Hz, 0.75H), 1.52 (d, J=14.0 Hz, 0.25H), 1.16-1.02 (m, 1H), 0.72-0.61 (m, 2H), 0.44-0.33 (m, 2H). LC/MS: m/z 520 [M+H]$^+$ (Calc: 519).

Example 14

(6R,6aS,12aR)-methyl 15-(methyl)-6a-hydroxy-2-methoxy-10-oxo-6,6a,7,10,11,12-hexahydro-5H-6,12a-(epiminoethano)naphtho[2,1-g]quinoline-9-carboxylate (27)

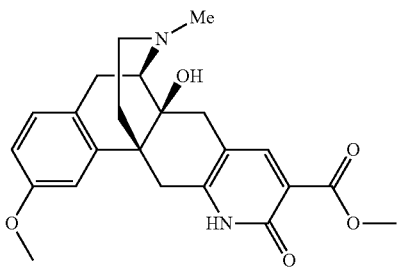

Compound 27 was prepared according to the procedure described in Example 1 from (4bR,8aS,9R)-11-methyl-8a-hydroxy-3-methoxy-8,8a,9,10-tetrahydro-5H-9,4-b-(epiminoethano)phenanthren-6(7H)-one (CAS#3442-60-2) rather than (4bR,849R)-11-(cyclopropylmethyl)-8a-hydroxy-3-methoxy-8,8a,9,10-tetrahydro-5H-9,4-b-(epiminoethano) phenanthren-6(7H)-one (compound 1). Purification over silica gel with 0-25% (10% NH$_4$OH in MeOH) in DCM then trituration with MeOH gave the title compound 27 as a pale pink powder.

$^1$H NMR $\delta_H$ (600 MHz, DMSO-d$_6$): 11.91 (s, 1H), 7.64 (s, 1H), 7.07 (d, J=8.4 Hz, 1H), 6.71 (d, J=8.4 Hz, 1H), 6.64 (s, 1H), 4.66 (s, 1H), 3.67-3.63 (m, 6H), 3.16-3.10 (m, 2H), 2.87-2.79 (m, 3H), 2.46 (d, J=16.9 Hz, 1H), 2.37-2.30 (m, 5H), 2.07 (dt, J=12.7, 4.6 Hz, 1H), 1.99 (t, 11.4 Hz, 1H), 1.13 (4, J=12.3 Hz, 1H). LC/MS: m/z=411.2 [M+H]$^+$ (Calc: 410.5).

The starting compound, (4bR,8aS,9R)-11-(methyl)-8a-hydroxy-3-methoxy-8,8a,9,10-tetrahydro-5H-9,4b)-(epiminoethano)phenanthren-6(7H)-one, can be prepared as described in, for example, Nagase, H et al., *Bioorganic & Medicinal Chemistry Letters* 20: 6302-6305 (2010).

Example 15

(6R,6aS,12aR)-15-(methyl)-6a-hydroxy-2-methoxy-10-oxo-6,6a,7,10,11,12-hexahydro-5H-6,12a-(epiminoethano)naphtho[2,1-g]quinoline-9-carboxamide (28)

(6R,6aS,12aR)-15-(methyl)-2,6a-dihydroxy-10-oxo-6,6a,7,10,11,12-hexahydro-5H-6,12a-(epiminoethano)naphtho[2,1-g]quinoline-9-carboxamide (29)

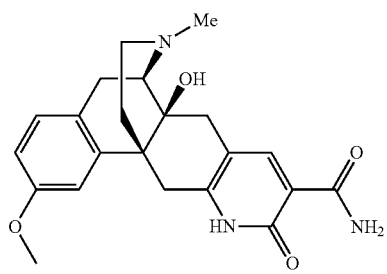

28

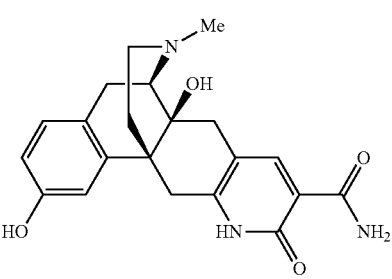

29

Compounds 28 and 29 were prepared as described in Example 3.

(a) Compound 28 was prepared from compound 27 (prepared in Example 14) rather than compound 2. Cooling the reaction mixture and filtration followed by rinsing with MeOH gave the title compound 28 as an off-white powder.

$^1$H NMR $\delta_H$ (400 MHz, DMSO-d$_6$): 12.22 (s, 1H), 9.03 (d, J=4.4 Hz, 1H), 7.86 (s, 1H), 7.39 (d, J=4.4 Hz, 1H), 7.07 (d, J=8.4 Hz, 1H), 6.71 (dd, J=8.4, 2.2 Hz, 1H), 6.64 (d, j=2.2 Hz, 1H), 4.67 (s, 1H), 3.65 (s, 3H), 3.22-3.10 (m, 2H), 2.90-2.82 (m, 3H), 2.54-2.48 (m, 1H, DMSO overlap), 2.42-2.33 (m, 2H), 2.32 (s, 3H), 2.08 (dt, J=12.7, 4.8 Hz, 1H), 1.99 (t, J=12.3 Hz, 1H), 1.14 (d, J=12.3 Hz, 1H). LC/MS: m/z=396.2 [M+H]$^+$ (Calc: 395.5).

(b) Compound 29 was prepared from compound 28 using the procedure described in Example 3 for preparing compound 5. Purification over silica gel with 0-50% (10% NH$_4$OH in MeOH) in DCM, then trituration with MeOH gave the title compound 29 as a white crystalline powder.

$^1$H NMR $\delta_H$ (400 MHz, DMSO-d$_6$): 12.30 (s, 1H), 9.13 (s, 1H), 9.04 (d, J=4.2 Hz, 1H), 7.87 (s, 1H), 7.39 (d, J=4.4 Hz, 1H), 6.93 (d, J=7.9 Hz, 1H), 6.54-6.50 (m, 2H), 4.63 (s, 1H), 3.13-3.06 (m, 2H), 2.87-2.77 (m, 3H), 2.55-2.50 (m, 1H, DMSO overlap), 2.38-2.32 (m, 2H), 2.31 (s, 3H), 2.10-1.98 (m, 2H), 1.11 (d, J=11.7 Hz, 1H). LC/MS: m/z=382.2 [M+H]$^+$ (Calc: 381.4).

Example 16

(6R,6aS,12aR)-methyl 15-benzyl-6a-hydroxy-2-methoxy-10-oxo-6,6a,7,10,11,12-hexahydro-5H-6,12a-(epiminoethano)naphtho[2,1-g]quinoline-9-carboxylate (30)

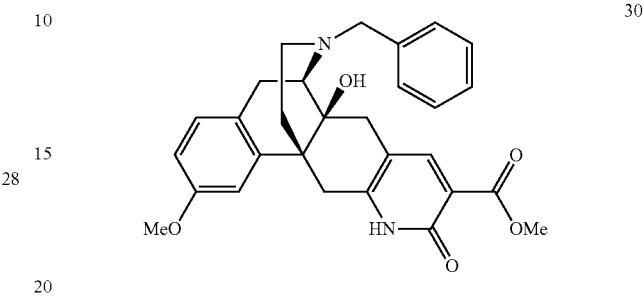

30

Compound 30 was prepared according to the procedure described in Example 1 from (4bR,8aS,9R)-11-benzyl-8a-hydroxy-3-methoxy-8,8a,9,10-tetrahydro-5H-9,4-b-(epiminoethano)phenanthren-6(7H)-one rather than (4bR,8aS,9R)-11-(cyclopropyl-methyl)-8a-hydroxy-3-methoxy-8,8a,9,10-tetrahydro-5H-9,4-b-(epiminoethano)-phenanthren-6(7H)-one (compound 1). Purification over silica gel with 0-11% (10% NH$_4$OH in MeOH) in DCM followed by trituration with MeOH gave the title compound 30 as peach-tan colored powder.

$^1$H NMR $\delta_H$ (600 MHz, DMSO-d$_6$): 11.92 (s, 1H), 7.61 (s, 1H), 7.45-7.39 (m, 2H), 7.37-7.30 (m, 2H), 7.29-7.23 (m, 1H), 7.09 (d, J=8.6 Hz, 1H), 6.73 (dd, J=8.4, 2.6 Hz, 1H), 6.65 (d, J=2.6 Hz, 1H), 4.66 (s, 1H), 3.72-3.59 (m, 8H), 3.24 (d, J=16.9 Hz, 1H), 3.14 (d, J=17.6 Hz, 1H), 2.93-2.82 (m, 3H), 2.48-2.37 (m, 2H), 2.28 (d, J=17.2 Hz, 1H), 2.12-2.00 (m, 2H), 1.21-1.10 (m, 1H)).

LC/MS: m/z=487 [M+H]$^+$ (Calc: 486).

The starting compound, (4bR,8aS,9R)-11-benzyl-8a-hydroxy-3-methoxy-8,8a,9,10-tetrahydro-5H-9,4-b-(epiminoethano)phenanthren-6(7H)-one, can be prepared as described in, for example, Nagase, H., et al., *Bioorganic & Medicinal Chemistry Letters* 20: 6302-6305 (2010).

Example 17

(6R,6aS,12aR)-15-benzyl-6a-hydroxy-2-methoxy-10-oxo-6,6a,7,10,11,12-hexahydro-5H-6,12a-(epiminoethano)naphtho[2,1-g]quinoline-9-carboxamide (31)

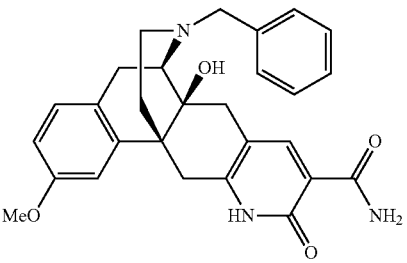

31

Compound 31 was prepared in a manner similar to that described for preparing compound 4 in Example 3 starting from compound 30 rather than compound 2. Trituration with MeOH gave the title compound 31 as a cream-colored powder.

$^1$H NMR $\delta_H$ (600 MHz, DMSO-d$_6$): 12.22 (s, 1H), 9.02 (d, J=4.4 Hz, 1H), 7.84 (s, 1H), 7.45-7.40 (m, 2H), 7.38 (d, J=4.4 Hz, 1H), 7.36-7.31 (m, 2H), 7.29-7.23 (m, 1H), 7.10 (d, J=8.4 Hz, 1H), 6.72 (dd, J=8.4, 2.4 Hz, 1H), 6.65 (d, J=2.4 Hz, 1H), 4.67 (s, J=1H), 3.72-3.60 (m, 5H), 3.29-3.15 (m, 2H), 2.95-2.85 (m, 3H), 2.51-2.45 (m, 1H, partial overlap with DMSO), 2.43-2.30 (m, 2H), 2.13-2.02 (m, 2H), 1.22-1.11 (m, 1H).

LC/MS, m/z=472 [M+H]$^+$ (Calc: 471).

Example 18

(6R,6aS,12aR)-6a-hydroxy-2-methoxy-10-oxo-6,6a,7,10,11,12-hexahydro-5H-6,12a-(epiminoethano)naphtho[2,1-g]quinoline-9-carboxamide (32)

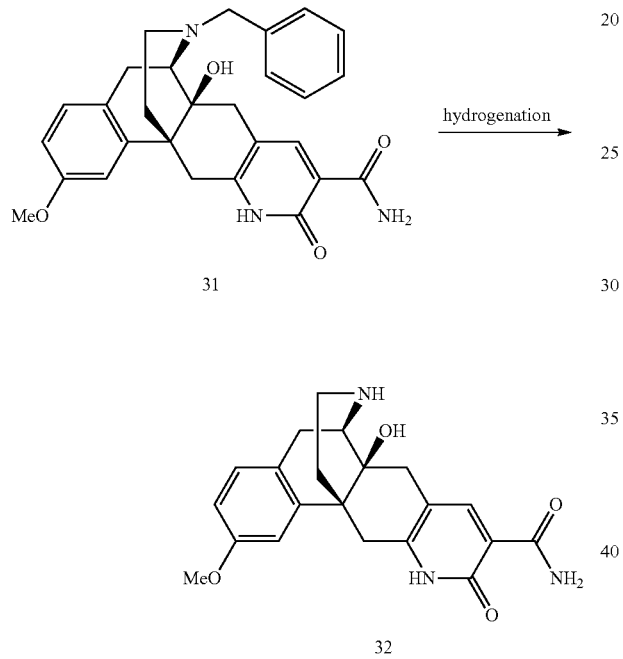

A mixture of compound 31 (4.553 g, 9.66 mmol, 1 eq) in AcOH (50 mL) was hydrogenated over Pearlman's catalyst (0.473 g) at 50 psi for 2 days. The reaction mixture was filtered through a pad of Celite and rinsed with MeOH. The filtrate was concentrated, treated with conc. NH$_4$OH (10 mL), MeOH (25 mL) and DCM (25 mL) and then concentrated. Purification over silica gel with 0-29% (10% NH$_4$OH in MeOH) in DCM followed by trituration with MeOH gave the title compound 32 as a white powder (3.061 g, 8.03 mmol, 83% yield).

$^1$H NMR $\delta_H$ (600 MHz, DMSO-d$_6$): 9.03 (d, J=4.4 Hz, 1H), 7.84 (s, 1H), 7.38 (d, J=4.4 Hz, 1H), 7.04 (d, J=8.4 Hz, 1H), 6.71 (dd, J=8.4, 2.6 Hz, 1H), 6.64 (d, J=12.4 Hz, 1H), 4.88 (s, 1H), 3.65 (s, 3H), 3.32-3.24 (m, 1H, partial overlap with water), 3.12 (d, J=17.4 Hz, 1H), 3.00-2.86 (m, 3H), 2.59-2.49 (m, 1H, partial overlap with DMSO), 2.47-2.32 (m, 3H), 1.99 (dt, J=12.5, 5.1 Hz, 1H), 1.00 (d, J=11.4 Hz, 1H).

LC/MS, m/z=382 [M+H]$^+$ (Calc: 381).

Example 19

(6R,6aS,12aR)-2,6a-dihydroxy-10-oxo-15-(2,2,2-trifluoroethyl)-6,6a,7,10,11,12-hexahydro-5H-6,12a-(epiminoethano)naphtho[2,1-g]quinoline-9-carboxamide (34)

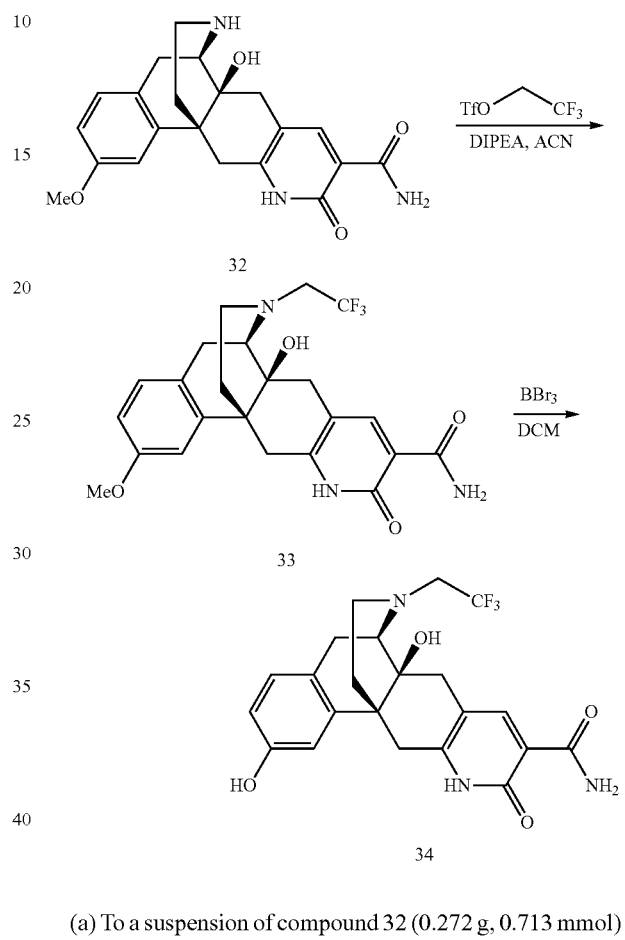

(a) To a suspension of compound 32 (0.272 g, 0.713 mmol) in ACN (10 mL) was added DIPEA (0.55 mL, 3.16 mmol) followed by 2,2,2-trifluoroethyl trifluoromethanesulfonate (0.51 mL, 3.54 mmol) (Sigma-Aldrich). The reaction mixture was heated at 80° C. for 20 h, cooled to RT and the solid filtered off to give compound 33 as a cream-colored powder. LC/MS, m/z=464 [M+H]$^+$ (Calc: 463).

(b) To a suspension of compound 33 (0.224 g, 0.483 mmol) in DCM (10 mL) was added 1 M BBr$_3$ in DCM (1.94 mL, 1.94 mmol). After stirring at RT for 5 h, the reaction was quenched by the addition of 5 M NH$_3$ in MeOH (1.75 mL). The reaction mixture was concentrated and purified over silica gel with 0-25% (10% NH$_4$OH in MeOH) in DCM followed by trituration with MeOH to give the title compound 34 as a white powder.

$^1$H NMR $\delta_H$ (400 MHz, DMSO-d$_6$): 12.30 (s, 1H), 9.16 (s, 1H), 9.03 (d, J=4.6 Hz, 1H), 7.87 (s, 1H), 7.38 (d, =4.4 Hz, 1H), 6.92 (d, J=8.1 Hz, 1H), 6.57-6.51 (m, 2H), 4.42 (s, 1H), 3.50-3.36 (m, 1H), 3.34-3.20 (m, 1H, overlap with water), 3.14-2.94 (m, 4H), 2.86 (d, J=17.8 Hz, 1H), 2.59-2.47 (m, 2H, overlap with DMSO), 2.46-2.34 (m, 2H), 2.13 (dt, J=12.8, 5.1 Hz, 1H), 1.08 (d, J=12.5 Hz, 1H).

LC/MS, m/z=450 [M+H]$^+$ (Calc: 449).

Example 20

(6R,6aS,12aR)-15-(2-fluoroethyl)-2,6a-dihydroxy-10-oxo-6,6a,7,10,11,12-hexahydro-5H-6,12a-(epiminoethano)naphtho[2,1-g]quinoline-9-carboxamide (35)

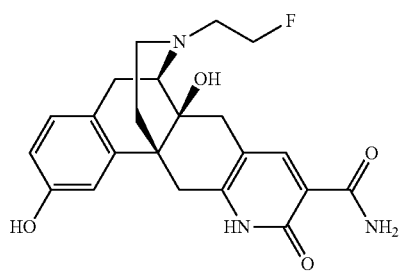

35

Compound 35 was prepared according to the procedure described in Example 19 from compound 32 using 1-bromo-2-fluoroethane rather than 2,2,2-trifluoroethyl trifluoromethanesulfonate. Purification over silica gel with 0-25% (10% NH$_4$OH in MeOH) in DCM followed by trituration with MeOH gave the title compound 35 as a cream-colored powder.

$^1$H NMR δ$_H$ (400 MHz, DMSO-d$_6$): 12.31 (s, 1H), 9.14 (s, 1H), 9.04 (d, J=4.4 Hz, 1H), 7.87 (s, 1H), 7.39 (d, J=4.4 Hz, 1H), 6.93 (d, J=8.1 Hz, 1H), 6.56-6.50 (m, 2H), 4.62 (t, J=5.1 Hz, 1H), 4.59 (s, 1H), 4.50 (t, J=5.1 Hz, 1H), 3.15-3.01 (m, 2H), 2.98 (d, J=6.4 Hz, 1H), 2.93-2.65 (m, 4H), 2.56-2.47 (m, 2H, overlap with DMSO), 2.37 (d, J=16.9 Hz, 1H), 2.19-2.10 (m, 1H), 2.05 (dt, J=12.5, 4.6 Hz, 1H), 1.13 (d, J=12.1 Hz, 1H).

LC/MS, m/z=414 [M+H]$^+$ (Calc: 413).

Example 21

(6R,6aS,12aR)-2,6a-dihydroxy-10-oxo-15-phenethyl-6,6a,7,10,11,12-hexahydro-5H-6,12a-(epiminoethano)naphtho[2,1-g]quinoline-9-carboxamide (37)

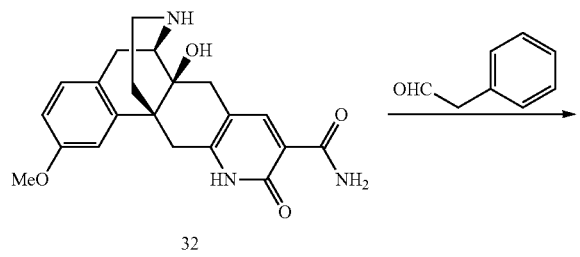

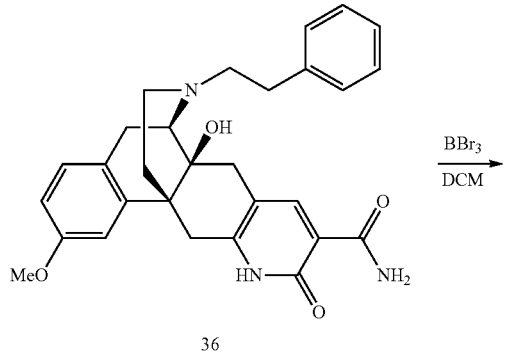

(a) To a suspension of compound 32 (0.272 g, 0.713 mmol) in DCM (10 mL) was added phenyl acetaldehyde (0.11 mL, 0.940 mmol) followed by NaBH(OAc)$_3$ (0.234 g, 1.104 mmol). After stirring at RT for 22 h, the reaction was quenched by the addition of 2 M aq. Na$_2$CO$_3$ (2 mL). The mixture was concentrated and suspended in water. The resulting solid was filtered to give compound 36 as a cream-colored powder. LC/MS, m/z=486 [M+H]$^+$ (Calc: 485).

(b) To a suspension of compound 36 (0.340 g, 0.700 mmol) in DCM (10 mL) was added 1 M BBr$_3$ in DCM (2.80 mL, 2.80 mmol). After stirring at RT for 5 h, the reaction was quenched by the addition of 5 M NH$_3$ in MeOH (2.50 mL). The reaction mixture was concentrated and purified over silica gel with 0-20% (10% NH$_4$OH in MeOH) in DCM followed by trituration with MeOH to give the title compound 37 as an off-white powder.

$^1$H NMR δ$_H$ (400 MHz, DMSO-d$_6$): 12.29 (s, 1H), 9.13 (s, 1H), 9.03 (d, J=4.4 Hz, 1H), 7.86 (s, 1H), 7.28 (d, J=4.4 Hz, 1H), 7.32-7.22 (m, 4H), 7.21-7.15 (m, 1H), 6.92 (d, J=8.1 Hz, 1H), 6.55-6.50 (m, 2H), 4.35 (s, 1H), 3.08 (t, J=17.8 Hz, 2H), 2.94 (d, J=6.4 Hz, 1H), 2.92-2.73 (m, 4H), 2.73-2.65 (m, 2H), 2.57 (dd, J=11.0, 4.0 Hz, 1H), 2.53-2.46 (m, 1H, overlap with DMSO), 2.33 (d, J=16.9 Hz, 1H), 2.13-2.04 (m, 1H), 1.96 (dt, J=12.5, 4.6 Hz, 1H), 1.14 (d, J=12.3 Hz, 1H).

LC/MS, m/z=472 [M+H]$^+$ (Calc: 471).

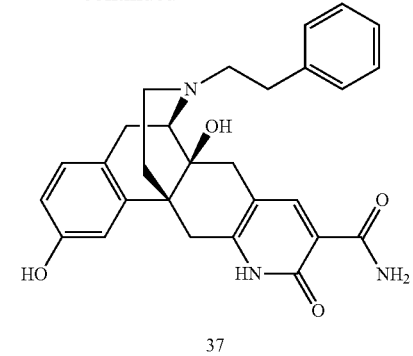

37

Example 22

(6R,6aS,12aR)-2,6a-dihydroxy-11,15-dimethyl-10-oxo-6,6a,7,10,11,12-hexahydro-5H-6,12a-(epiminoethano)naphtho[2,1-g]quinoline-9-carboxamide (39)

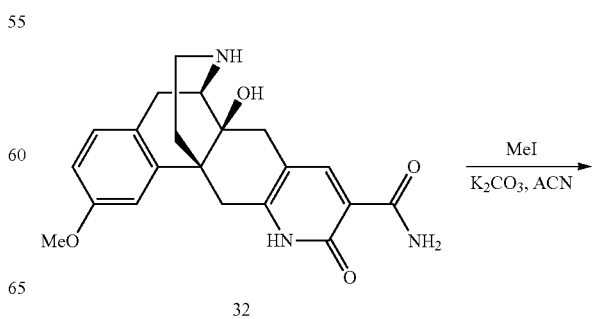

-continued

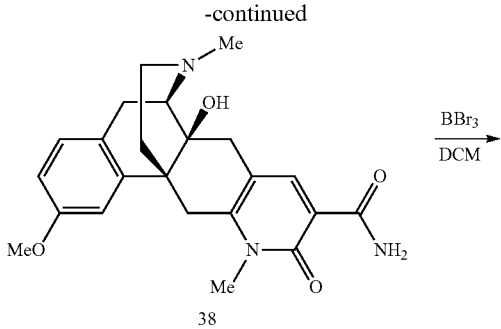

38

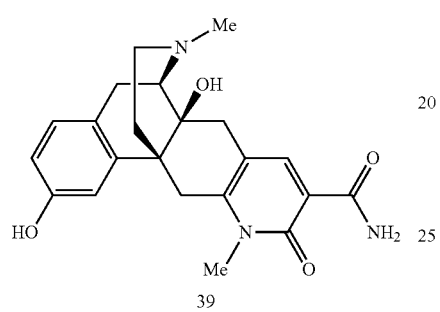

39

(a) To a suspension of compound 32 (0.763 g, 2.00 mmol) in ACN (20 mL) in a pressure tube was added $K_2CO_3$ (0.834 g, 6.03 mmol) and methyl iodide (0.25 mL, 4.02 mmol) dropwise in ACN (5 mL) over 3 min. The tube was sealed and heated at 65° C. for 24 h. The reaction mixture was cooled to RT, filtered and the filtrate concentrated. The residue was purified over silica gel with 0-25% (10% $NH_4OH$ in MeOH) in DCM followed by sonication with warm MeOH. The residue was purified by purified by reverse-phase prep HPLC (C18, 0-60% 0.1% TFA in water/0.1% TFA in ACN) to give compound 38 as the TFA salt as cream-colored powder. LC/MS, m/z=410 [M+H]+ (Calc: 409).

(b) To a solution of compound 38 (0.072 g, 0.138 mmol, TFA salt) in DCM (5 mL) was added 1 M $BBr_3$ in DCM (0.55 mL, 0.55 mmol). After stirring at RT for 20 h, additional 1 M $BBr_3$ in DCM (0.14 mL, 0.14 mmol) was added. After stirring at RT an additional 3 h, the reaction was quenched by the addition of 5 M $NH_3$ in MeOH (0.75 mL). The reaction mixture was concentrated and purified over silica gel with 0-20% (10% $NH_4OH$ in MeOH) in DCM followed by trituration with MeOH to give the title compound 39 as a cream-colored powder.

$^1H$ NMR $\delta_H$ (400 MHz, DMSO-$d_6$): 9.10 (d, J=4.4 Hz, 1H), 9.03 (s, 1H), 7.86 (s, 1H), 7.44 (d, J=4.4 Hz, 1H), 6.93 (d, J=8.4 Hz, 1H), 6.62 (d, J=2.2 Hz, 1H), 6.51 (dd, J=8.1, 2.2 Hz, 1H), 4.63 (s, 1H), 3.71 (s, 3H), 3.40 (d, J=18.0 Hz, 1H), 3.11 (d, J=17.8 Hz, 1H), 2.91 (d, J=18.0 Hz, 1H), 2.87-2.75 (m, 2H), 2.62 (d, J=16.9 Hz, 1H), 2.43-2.34 (m, 2H), 2.33 (s, 3H), 2.17-1.98 (m, 2H), 1.25-1.18 (m, 1H).

LC/MS, m/z=396 [M+H]+ (Calc: 395).

Example 23

(6R,6aS,12aR)-6a-hydroxy-2-methoxy-15-methyl-10-oxo-6,6a,7,10,11,12-hexahydro-5H-6,12a-(epiminoethano)naphtho[2,1-g]quinoline-9-carboxylic acid (40)

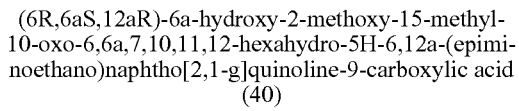

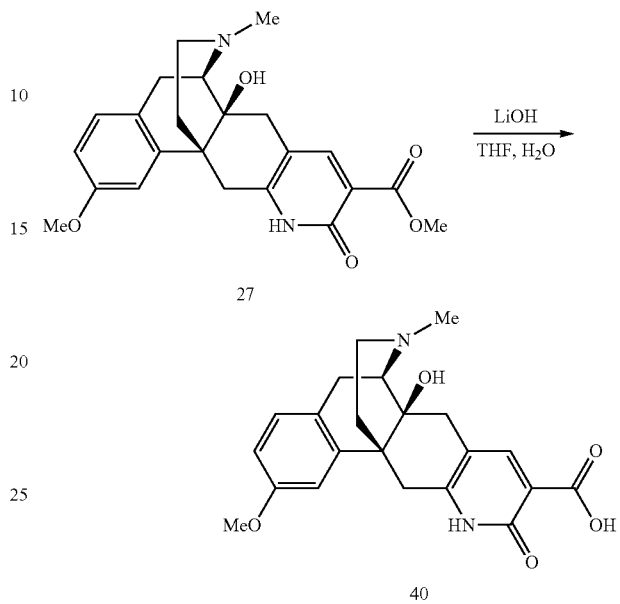

27

40

To a suspension of compound 27 (prepared in Example 14) (4.859 g, 11.84 mmol) in THF (50 mL) and water (10 mL) was added LiOH.H2O (0.839 g, 20.00 mmol). The vessel was sealed and the reaction heated at 50° C. for 2 days and then at 60° C. for an additional day. The reaction mixture was concentrated and to the residue was added water (50 mL) and 1N HCl (20 mL). The solution was filtered through a glass filter and the filtrate concentrated and purified over silica gel with 0-50% (10% $NH_4OH$ in MeOH) in DCM followed by trituration with ACN to give the title compound 40 as a light tan powder.

$^1H$ NMR $\delta_H$ (400 MHz, DMSO-$d_6$): 15.20 (br. s, 1H), 12.23 (very br. s, 1H), 7.86 (s, 1H), 7.09 (d, J=8.4 Hz, 1H), 6.73 (dd, J=8.4, 2.4 Hz, 1H), 6.68 (d, J=2.4 Hz, 1H), 5.13 (br. s, 1H), 3.65 (s, 3H), 3.32-3.16 (m, 2H, overlap with water), 3.09 (br. s, 1H), 3.03-2.90 (m, 2H), 2.65-2.50 (m, 3H, overlap with DMSO), 2.47 (s, 3H), 2.22-2.09 (m, 2H), 1.31-1.19 (m, 1H).

LC/MS: m/z 397 [M+H]+ (Calc: 396).

Example 24

(6R,6aS,12aR)-2,6a-dihydroxy-15-methyl-10-oxo-6,6a,7,10,11,12-hexahydro-5H-6,12a-(epiminoethano)naphtho[2,1-g]quinoline-9-carboxylic acid (41)

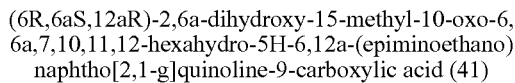

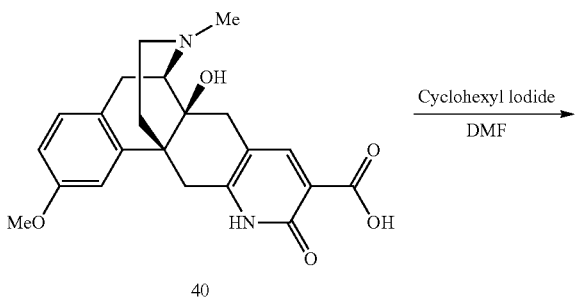

40

127

-continued

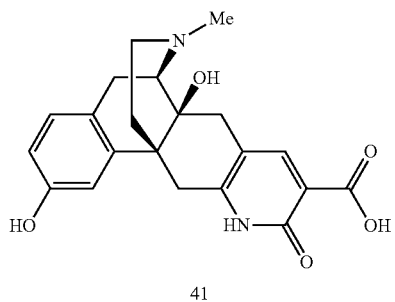

41

To a suspension of compound 40 (0.397 g, 1.00 mmol) in DMF (2.0 mL) was added cyclohexyl iodide (1.30 mL, 10.1 mmol). The mixture was heated at reflux for 8 h then quenched by the addition of water (10 mL) and aq. 2M Na$_2$CO$_3$ (2.5 mL). The reaction mixture was concentrated and purified over silica gel with 0-69% (10% NH$_4$OH in MeOH) in DCM followed by trituration with MeOH to give the title compound 41 as a cream-colored powder (0.208 g, 0.544 mmol, 54% yield).

$^1$H NMR δ$_H$ (400 MHz, DMSO-d$_6$): 15.38 (br s, 1H), 12.38 (very br. s, 1H), 9.18 (s, 1H), 7.85 (d, J=7.9 Hz, 1H), 6.58-6.51 (m, 2H), 5.02 (br. s, 1H), 3.23-3.12 (m, 2H), 3.03 (br. s, 1H), 2.99-2.84 (m, 2H), 2.63 (d, J=17.2 Hz, 1H), 2.56-2.46 (m, 2H, overlap with DMSO), 2.45 (s, 3H), 2.21-2.07 (m, 2H), 1.27-1.15 (m, 2H).

LC/MS: m/z=383.1 [M+H]$^+$ (Calc: 382.4).

Example 25

(6R,6aS,12aR)—N-(cyclohexylmethyl)-2,6a-dihydroxy-15-methyl-10-oxo-6,6a,7,10,11,12-hexahydro-5H-6,12a-(epiminoethano)naphtho[2,1-g]quinoline-9-carboxamide (44)

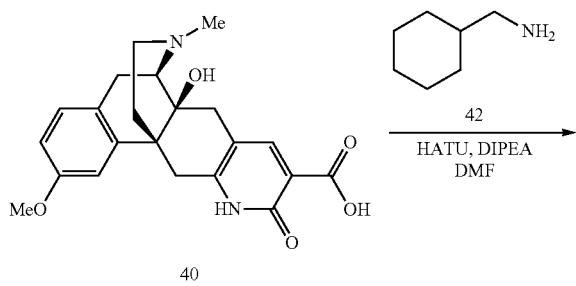

128

-continued

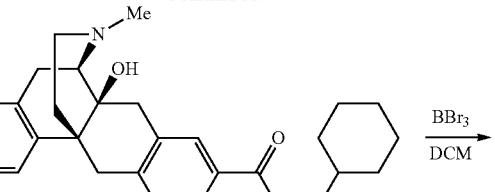

43

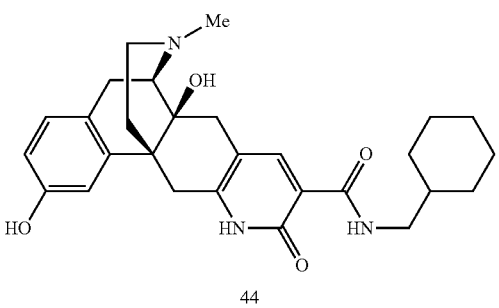

44

(a) To a suspension of compound 40 (0.252 g, 0.636 mmol) in DMF (5 mL) was added DIPEA (0.165 mL, 0.95 mmol) and compound 42 (0.099 mL, 0.76 mmol). HATU (0.293 g, 0.77 mmol) was added and the mixture stirred at RT for 19 h. Additional compound 42 (0.149 mL, 1.15 mmol), DIPEA (0.165 mL, 0.95 mmol) and HATU (0.435 g, 1.14 mmol) were added and the mixture was stirred an additional 3 days. The reaction mixture was concentrated, ACN (10 mL) was added and the mixture concentrated again. The residue was purified over silica gel with 0-25% (10% NH$_4$OH in MeOH) in DCM to give compound 43 as a tan solid (0.247 g, 0.503 mmol, 79% yield). LC/MS: m/z 492 [M+H]$^+$ (Calc: 491.3).

(b) To a solution of compound 43 (0.244 g, 0.497 mmol) in DCM (10 mL) at RT was added 1 M BBr$_3$ in DCM (2.00 mL, 2.00 mmol). After stirring at RT for 20 h, the reaction was quenched by the addition of 5 M NH$_3$ in MeOH (2.0 mL). The reaction mixture was concentrated and purified over silica gel with 0-25% (10% NH$_4$OH in MeOH) in DCM followed by trituration with MeOH and drying under vacuum to give to give the title compound 44 as a cream-colored powder (0.153 g, 0.320 mmol, 65% yield).

$^1$H NMR δ$_H$ (400 MHz, DMSO-d$_6$): 12.32 (br. s., 1H), 9.78 (t, J=5.9 Hz, 1H), 9.12 (s, 1H), 7.87 (s, 1H), 6.93 (d, J=8.1 Hz, 1H), 6.55-6.49 (m, 2H), 4.63 (br. s., 1H), 3.18-3.02 (m, 4H), 2.89-2.74 (m, 3H), 2.57-2.50 (m, 1H, overlap with DMSO), 2.41-2.28 (m, 5H), 2.12-1.96 (m, 2H), 1.71-1.54 (m, 5H), 1.48-1.35 (m, 1H), 1.24-1.03 (m, 4H), 0.97-0.83 (m, 2H).

LC/MS: m/z=478.2 [M+H]$^+$ (Calc: 477.6).

Example 26

(6R,6aS,12aR)—N-benzyl-2,6a-dihydroxy-15-methyl-10-oxo-6,6a,7,10,11,12-hexahydro-5H-6,12a-(epiminoethano)naphtho[2,1-g]quinoline-9-carboxamide (45)

(6R,6aS,12aR)-2,6a-dihydroxy-N,N,15-trimethyl-10-oxo-6,6a,7,10,11,12-hexahydro-5H-6,12a-(epiminoethano)naphtho[2,1-g]quinoline-9-carboxamide (46)

(6R,6aS,12aR)-2,6a-dihydroxy-15-methyl-9-(morpholine-4-carbonyl)-6a,7,11,12-tetrahydro-5H-6,12a-(epiminoethano)naphtho[2,1-g]quinolin-10(6H)-one (47)

(6R,6aS,12aR)-2,6a-dihydroxy-15-methyl-9-(pyrrolidine-1-carbonyl)-6a,7,11,12-tetrahydro-5H-6,12a-(epiminoethano)naphtho[2,1-g]quinolin-10(6H)-one (48)

(6R,6aS,12aR)-2,6a-dihydroxy-N-isopentyl-15-methyl-10-oxo-6,6a,7,10,11,12-hexahydro-5H-6,12a-(epiminoethano)naphtho[2,1-g]quinoline-9-carboxamide (49)

(6R,6aS,12R)—N—((S)-1-amino-1-oxopropan-2-yl)-26a-dihydroxy-15-methyl-10-oxo-6,6a,7,10,11,12-hexahydro-5H-6,12a-(epiminoethano)naphtho[2.1-g]quinoline-9-carboxamide (50)

(6R,6aS,12R)—N—((S)-1-amino-1-oxo-3-phenyl-propan-2-yl)-2,6a-dihydroxy-15-methyl-10-oxo-6,6a,7,10,11,12-hexahydro-5H-6,12a-(epiminoethano)naphtho[2.1-g]quinoline-9-carboxamide (51)

(6R,6aS,12R)—N—((S)-1-amino-4-methyl-1-oxopentan-2-yl)-2,6a-dihydroxy-15-methyl-10-oxo-6,6a,7,10,11,12-hexahydro-5H-6,12a-(epiminoethano)naphtho[2.1-g]quinoline-9-carboxamide (52)

(S)-1-((6R,6aS,12R)-2,6a-dihydroxy-15-methyl-10-oxo-6,6a,7,10,11,12-hexahydro-5H-6,12a-(epiminoethano)naphtho[2.1-g]quinoline-9-carbonyl)pyrrolidine-2-carboxamide (53)

(6R,6aS,12R)—N-benzyl-15-(cyclopropylmethyl)-10-oxo-6,6a,7,10,11,12-hexahydro-5H-6,12a-(epiminoethano)naphtho[2.1-g]quinoline-9-carboxamide (54)

(6R,6aS,12R)-15-(cyclopropylmethyl)-2-hydroxy-9-(pyrrolidine-1-carbonyl)-6,6a,7,12-tetrahydro-5H-6,12a-(epiminoethano)naphtho[2.1-g]quinolin-10(11H)-one (55)

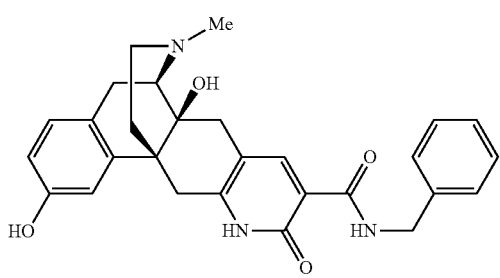

-continued

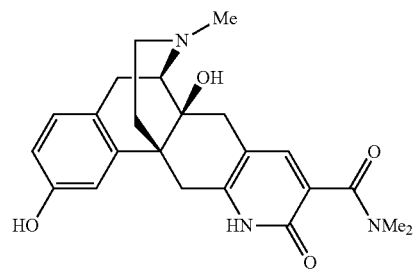

46

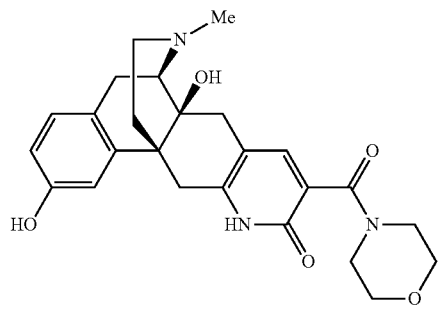

47

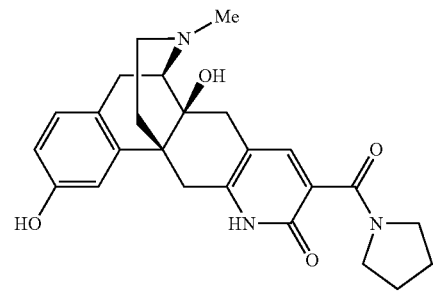

48

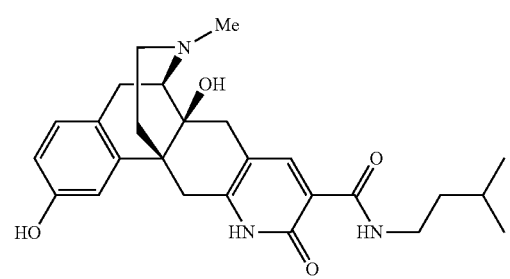

49

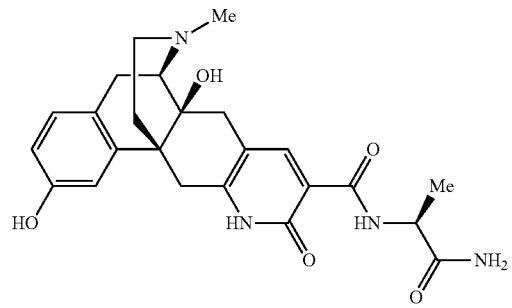

50

-continued

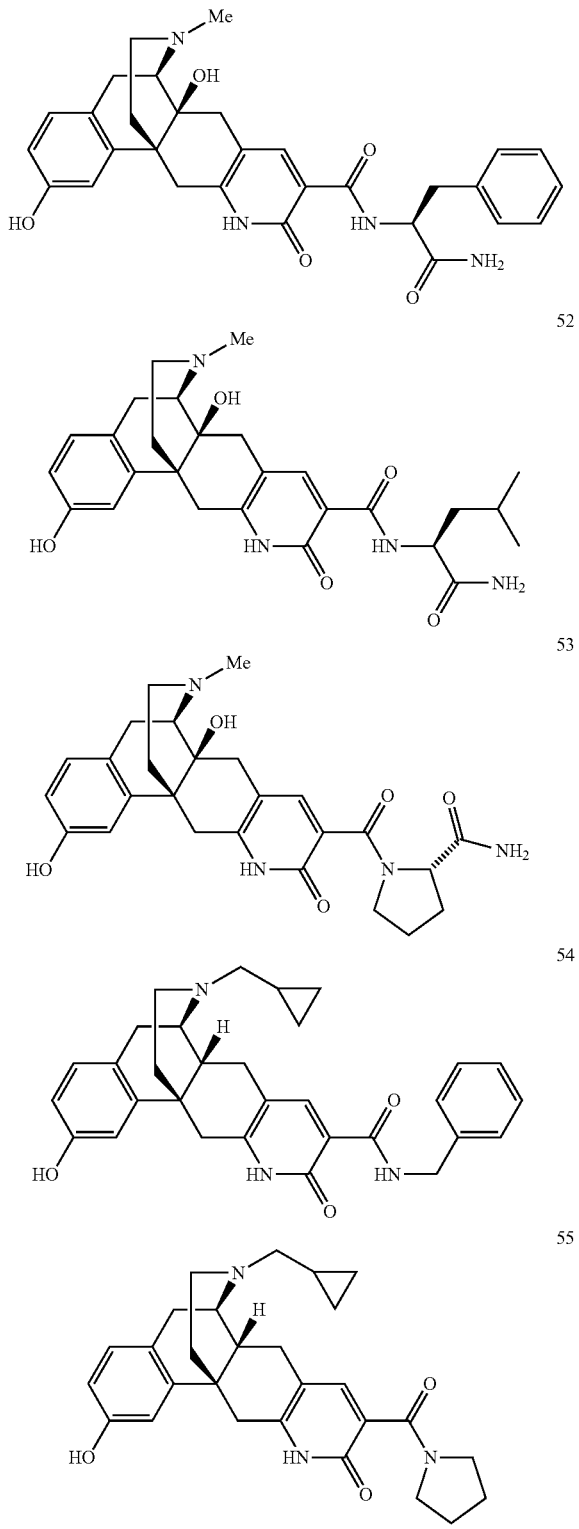

The title compounds were prepared in a manner similar to that described in Example 25:

(a) Compound 45 (TFA salt): $^1$H NMR $\delta_H$ (400 MHz DMSO-d$_6$): 12.49 (s, 1H), 10.08 (t, J=6.1 Hz, 1H), 9.39 (br, s., 1H), 9.23 (br. s., 1H), 7.96 (s, 1H), 7.35-7.19 (m, 5H), 7.01 (d, J=8.4 Hz, 1H), 6.65 (dd, J=8.3, 2.3 Hz, 1H), 6.60 (d, J=2.2 Hz, 1H), 6.18 (s, 1H), 4.57-4.41 (m, 2H), 3.67 (d, J=6.4 Hz, 1H, overlap with water), 3.43-3.33 (m, 1H), 3.30-3.18 (m, 2H), 3.09-2.98 (m, 1H), 2.95-2.87 (m, 1H), 2.85 (d, J=4.8 Hz, 3H), 2.72-2.52 (m, 3H), 2.25 (td, J=13.8, 4.6 Hz, 1H), 1.43 (d, J=12.8 Hz, 1H). LC/MS: m/z=472.2 [M+H]$^+$ (Calc: 471.6).

(b) Compound 46 (TFA salt): $^1$H NMR $\delta_H$ (400 MHz, DMSO-d$_6$): 11.87 (br. s., 1H), 9.39 (br. s., 1H), 9.21 (br. s., 1H), 7.11 (s, 1H), 7.01 (d, J=8.4 Hz, 1H), 6.69-6.59 (m, 2H), 6.13 (s, 1H), 3.64 (d, 6.4 Hz, 1H, overlap with water), 3.42-3.32 (m, 1H), 3.27-3.09 (m, 2l0), 3.07-2.98 (m, 1H), 2.91-2.76 (m, 10H), 2.64-2.42 (m, 3H, overlap With DMSO), 2.24 (td, J=13.7, 4.7 Hz, 1H), 1.41 (d, J=12.3 Hz, 1H). LC/MS: m/z=410.2 [M+H]$^+$ (Calc: 409.5).

(c) Compound 47 (TFA salt): $^1$H NMR $\delta_H$ (400 MHz, DMSO-d$_6$): 11.90 (br. s., 1H), 9.40 (br. s., 1H), 9.21 (br. s., 1H), 7.18 (s, 1H), 7.01 (d, J=8.4 Hz, 1H), 6.69-6.59 (m, 2H), 6.13 (s, 1H), 3.65 (d, J=6.4 Hz, 1H, overlap with water), 3.60-3.45 (m, 6H, overlap with water), 3.42-3.31 (m, 1H), 3.26-3.10 (m, 4H), 3.07-2.97 (m, 1H), 2.90-2.77 (m, 4H), 2.65-2.43 (m, 3H, overlap with DMSO), 2.24 (td, J=13.6, 4.6 Hz, 1H), 1.41 (d, J=12.8 Hz, 1H). LC/MS: m/z=452.2 [M+H]$^+$ (Calc: 451.5).

(d) Compound 48 (TFA salt): $^1$H NMR $\delta_H$ (400 MHz, DMSO-d$_6$): 11.89 (br. s., 1H), 9.39 (br. s., 1H), 9.20 (br. s., 1H), 7.14 (s, 1H), 7.01 (d, J=8.4 Hz, 1H), 6.68-6.60 (m, 2H), 6.12 (s, 1H), 3.64 (d, J=6.4 Hz, 1H), 3.42-3.29 (m, 3H), 3.29-3.09 (m, 4H), 3.07-2.97 (m, 1H), 2.89-2.77 (m, 4H), 2.64-2.42 (m, 3H), 2.24 (td, J=13.7, 4.7 Hz, 1H), 1.85-1.69 (m, 4H), 1.41 (d, J=12.3 Hz, 1H). LC/MS: m/z=436.2 [M+H]$^+$ (Calc: 435.5).

(e) Compound 49: $^1$H NMR $\delta_H$ (400 MHz, DMSO-d$_6$): 12.32 (br. s., 1H), 9.69 (t, J=5.7 Hz, 1H), 9.12 (s, 1H), 7.87 (s, 1H), 6.93 (d, J=8.1 Hz, 1H), 6.56-6.49 (m, 2H), 4.63 (br. s., 1H), 3.30-3.22 (m, 2H), 3.15-3.03 (m, 2H), 2.89-2.74 (m, 3H), 2.58-2.50 (m, 1H, overlap with DMSO), 2.41-2.27 (m, 5H), 2.12-1.95 (m, 2H), 1.64-1.50 (m, 1H), 1.35 (q, J=7.0 Hz, 2H), 1.11 (d, J=10.6 Hz, 1H), 0.87 (dd, J=6.6, 0.7 Hz, 6H). LC/MS: m/z=452.2 [M+H]$^+$ (Calc: 451.6).

(f) Compound 50 (TFA salt): $^1$H NMR $\delta_H$ (400 MHz, DMSO-d$_6$): 12.40 (s, 1H), 9.96 (d, J=7.3 Hz, 1H), 9.38 (s, 1H), 9.22 (br. s., 1H), 7.89 (s, 1H), 7.45 (s, 1H), 7.04-6.97 (m, 2H), 6.64 (dd, J=8.3, 2.3 Hz, 1H), 6.60 (d, J=2.2 Hz, 1H), 6.17 (s, 1H), 4.39 (quin, J=7.0 Hz, 1H), 3.66 (d, J=6.4 Hz, 1H, overlap with water), 3.42-3.33 (m, 1H, overlap with water), 3.30-3.18 (m, 2H), 3.09-2.99 (m, 1H), 2.94-2.81 (m, 4H), 2.70-2.53 (m, 3H), 2.25 (td, J=13.7, 4.7 Hz, 1H), 1.43 (d, J=12.5 Hz, 1H), 1.26 (d, J=6.8 Hz, 3H). LC/MS: m/z=453.1 [M+H]$^+$ (Calc: 452.5).

(g) Compound 51 (TFA salt): $^1$H NMR $\delta_H$ (400 MHz, DMSO-d$_6$): 12.39 (s, 1H), 9.98 (d, J=8.1 Hz, 1H), 9.37 (s, 1H), 9.21 (br. s., 1H), 7.83 (s, 1H), 7.49 (s, 1H), 7.27-7.12 (m, 5H), 7.05 (s, 1H), 7.00 (d, J=8.4 Hz, 1H), 6.63 (dd, J=8.4, 2.2 Hz, 1H), 6.59 (d, J=2.2 Hz, 1H), 6.14 (s, 1H), 4.63 (td, J=8.0, 5.4 Hz, 1H), 3.65 (d, J=6.6 Hz, 1H, overlap with water), 3.41-3.32 (m, 1H, overlap with water), 3.29-3.17 (m, 2H), 3.11-2.98 (m, 2H), 2.94-2.79 (m, 5H), 2.67-2.51 (m, 3H), 2.24 (td, J=13.6, 4.7 Hz, 1H), 1.43 (d, J=12.5 Hz, 1H). LC/MS: m/z=529.2 [M+H]$^+$ (Calc: 528.6).

(h) Compound 52 (TFA salt): $^1$H NMR $\delta_H$ (400 MHz, DMSO-d$_6$): 12.39 (s, 1H), 9.89 (d, J=8.4 Hz, 1H), 9.38 (s, 1H), 9.21 (br. s., 1H), 7.89 (s, 1H), 7.48 (s, 1H), 7.01 (d, J=8.4 Hz, 1H), 6.97 (s, 1H), 6.64 (dd, J=8.4, 2.4 Hz, 1H), 6.60 (d, J=2.2 Hz, 1H), 6.15 (s, 1H), 4.44 (td, J=8.6, 5.1 Hz, 1H), 3.67 (d, J=6.4 Hz, 1H, overlap with water), 3.42-3.33 (m, 1H, overlap with water), 3.31-3.18 (m, 2H), 3.09-2.98 (m, 1H), 2.94-2.80 (m, 4H), 2.70-2.53 (m, 3H), 2.25 (td, J=13.5, 4.5

Hz, 1H), 1.63-1.38 (m, 4H), 0.93-0.82 (m, 6H). LC/MS: m/z=495.3 [M+H]⁺ (Calc: 494.6).

(i) Compound 53 (TFA salt): ¹H NMR $\delta_H$ (400 MHz, DMSO-$d_6$) Material exists as an ~80/20 ratio of rotamers: 12.05 (s, 0.8H), 11.87 (s, 0.2H), 9.38 (br. s., 1H), 9.20 (br. s., 1H), 7.41 (br. s., 0.8H), 7.30 (s, 0.2H), 7.20 (s, 0.8H), 7.09-6.96 (m, 2H), 6.75 (s, 0.2H), 6.69-6.57 (m, 2H), 6.17-6.10 (m, 1H), 4.43-4.37 (m, 0.2H), 4.29 (dd, J=8.7, 3.4 Hz, 0.8H), 3.69-3.59 (m, 1H, overlap with water), 3.51-3.09 (m, 5H, overlap with water), 3.07-2.97 (m, 1H), 2.92-2.79 (m, 4H), 2.65-2.45 (m, 3H, overlap with DMSO), 2.21-2.18 (m, 1H), 2.16-2.03 (m, 1H), 1.96-1.68 (m, 3H), 1.47-1.35 (m, 1H). LC/MS: m/z=479.2 [M+H]⁺ (Calc: 478.5).

(j) Compound 54: ¹H NMR $\delta_H$ (400 MHz, DMSO-$d_6$): 12.36 (s, 1H), 10.11 (t, J=5.9 Hz, 1H), 9.06 (s, 1H), 7.93 (s, 1H), 7.35-7.18 (m, 5H), 6.89 (d, J=8.1 Hz, 1H), 6.57-6.47 (m, 2H), 4.55-4.41 (m, 2H), 3.39-3.27 (m, 1H, overlap with water), 3.26-3.18 (m, 1H), 2.90-2.79 (m, 1H), 2.76-2.58 (m, 3H), 2.58-2.51 (m, 1H, overlap with DMSO), 2.46-2.36 (m, 1H), 2.34-2.24 (m, 1H), 2.23-2.09 (m, 2H), 1.98 (t, J=11.2 Hz, 1H), 1.80 (td, J=12.4, 4.4 Hz, 1H), 1.38 (d, J=12.3 Hz, 1H), 0.88-0.75 (m, 1H), 0.51-0.40 (m, 2H), 0.16-0.03 (m, 2H). LC/MS: m/z®496.2 [M+H]⁺ (Calc: 495.6).

(k) Compound 55: ¹H NMR $\delta_H$ (400 MHz, DMSO-$d_6$): 11.76 (s, 1H), 9.06 (s, 1H), 7.10 (s, 1H), 6.89 (d, J=8.4 Hz, 1H), 6.56 (d, J=2.2 Hz, 1H), 6.51 (dd, J=8.3, 2.3 Hz, 1H), 3.37-3.16 (m, 6H), 2.84 (d, J=18.5 Hz, 1H), 2.70-2.55 (m, 3H), 2.45-2.35 (m, 2H), 2.32-2.23 (m, 1H), 2.19-2.11 (m, 1H), 2.11-1.91 (m, 2H), 1.85-1.69 (m, 5H), 1.36 (d, J=12.1 Hz, 1H), 0.86-0.74 (m, 1H), 0.50-0.39 (m, 2H), 0.15-0.02 (m, 2H). LC/MS: m/z=460.2 [M+H]⁺ (Calc: 459.6).

Example 27

(6R,6aS,12R)-9-benzoyl-15-(cyclopropylmethyl)-2, 6a-dihydroxy-6,6a,7,12-tetrahydro-5H-6,12a-(epiminoethano)naphtho[2.1-g]quinolin-10(11H)-one (59)

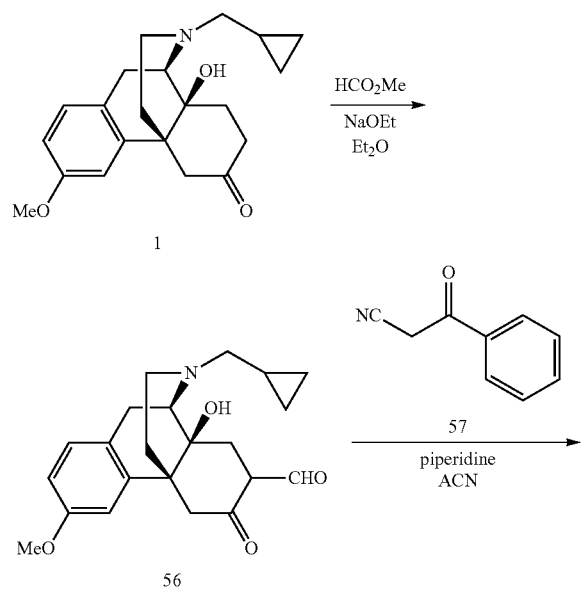

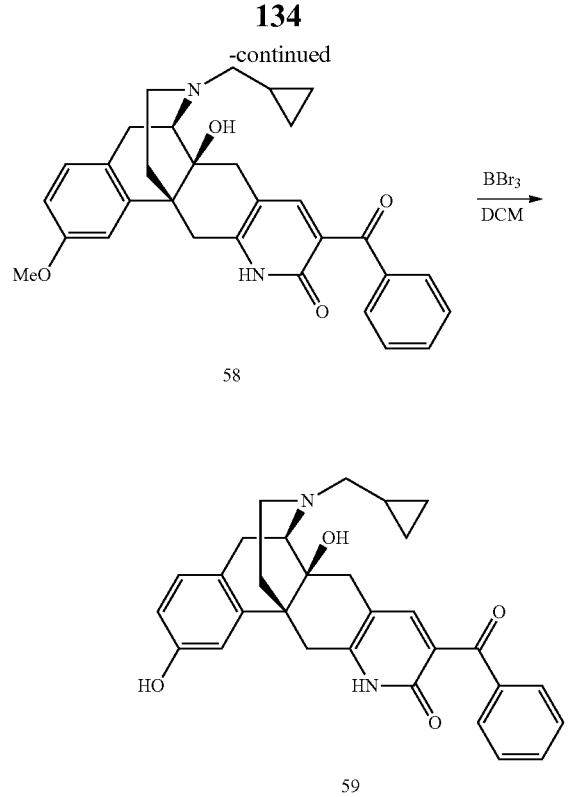

(a) To a suspension of compound 1 (10.021 g, 26.5 mmol) in Et₂O (100 mL) was added methyl formate (3.60 mL, 58.4 mmol) and NaOEt (7.946 g, 117 mmol). After stirring at RT for 1 h the reaction was quenched by the addition of conc. aq. NH₄OH (100 mL). The mixture was filtered to give compound 56 as a tan powder. LC/MS, m/z=370 [M+H]⁺ (Calc: 369).

(b) To a suspension of compound 56 (0.369 g, 1.00 mmol) in ACN (10 mL) in a pressure tube was added compound 57 (0.176 g, 1.212 mmol) and piperidine (0.099 mL, 1.002 mmol). The tube was sealed and heated at 65° C. for 4 days and at RT for 4 days. The reaction mixture was concentrated and purified over silica gel with 0-15% (10% NH₄OH in MeOH) in DCM to give compound 58 as an orange powder. LC/MS, m/z=497 [M+H]⁺ (Calc: 496).

(c) To a suspension of compound 58 (0.227 g, 0.457 mmol) in DCM (10 mL) was added 1 M BBr₃ in DCM (1.83 mL, 1.83 mmol). After stirring at RT for 2 h, the reaction was quenched by the addition of 5 M NH₃ in MeOH (1.5 mL). The reaction mixture was concentrated and purified over silica gel with 0-20% (10% NH₄OH in MeOH) in DCM followed by trituration with MeOH to give the title compound 59 as a cream-colored powder.

¹H NMR $\delta_H$ (400 MHz, DMSO-$d_6$): 11.99 (s, 1H), 9.17 (s, 1H), 7.69-7.65 (m, 2H), 7.60-7.54 (m, 1H), 7.48-7.41 (m, 2H), 7.35 (s, 1H), 6.93 (d, J=8.1 Hz, 1H), 6.58 (d, J=2.2 Hz, 1H), 6.55 (dd, J=8.1, 2.2 Hz, 1H), 4.67 (s, 1H), 3.15-3.07 (m, 2H), 3.03 (d, J=18.7 Hz, 1H), 2.90-2.77 (m, 2H), 2.62-2.56 (m, 1H), 2.56-2.49 (m, 1H, overlap with DMSO), 2.39-2.30 (m, 3H), 2.11-1.97 (m, 2H), 1.19-1.12 (m, 1H), 0.93-0.81 (m, 1H), 0.53-0.43 (m, 2H), 0.17-0.07 (m, 2H).

LC/MS, m/z=483 [M+H]⁺ (Calc: 482).

Example 28

(6R,6aR,12aS)-15-(cyclopropylmethyl)-9-(1,1-dioxidothiomorpholine-4-carbonyl)-2-hydroxy-6,6a,7,12-tetrahydro-5H-6,12a-(epiminoethano)naphtho[2,1-g]quinolin-10(11H)-one (60)

(6R,6aR,12aS)-15-(cyclopropylmethyl)-2-hydroxy-N-((1R,2S)-2-hydroxy-2,3-dihydro-1H-inden-1-yl)-10-oxo-6,6a,7,10,11,12-hexahydro-5H-6,12a-(epiminoethano)naphtho[2,1-g]quinoline-9-carboxamide (61)

(6R,6aR,12aS)-15-(cyclopropylmethyl)-2-hydroxy-N-((1S,2R)-2-hydroxy-2,3-dihydro-1H-inden-1-yl)-10-oxo-6,6a,7,10,11,12-hexahydro-5H-6,12a-(epiminoethano)naphtho[2,1-g]quinoline-9-carboxamide (62)

(6R,6aR,12aS)—N-cyclohexyl-15-(cyclopropylmethyl)-2-hydroxy-N-methyl-10-oxo-6,6a,7,10,11,12-hexahydro-5H-6,12a-(epiminoethano)naphtho[2,1-g]quinoline-9-carboxamide (63)

(6R,6aR,12aS)-15-(cyclopropylmethyl)-2-hydroxy-9-(isoindoline-2-carbonyl)-6,6a,7,12-tetrahydro-5H-6,12a-(epiminoethano)naphtho[2,1-g]quinolin-10(11H)-one (64)

(6R,6aR,12aS)-15-(cyclopropylmethyl)-2-hydroxy-9-((1R,R,5S)-3-hydroxy-8-azabicyclo[3.2.1]octane-8-carbonyl)-6,6a,7,12-tetrahydro-5H-6,12a-(epiminoethano)naphtho[2,1-g]quinolin-10(11H)-one (65)

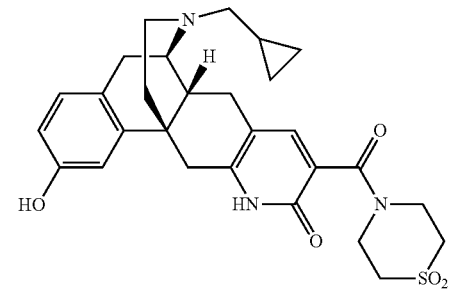

60

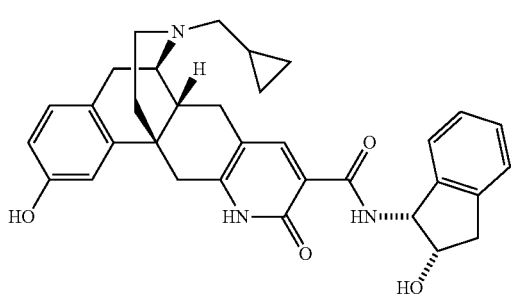

61

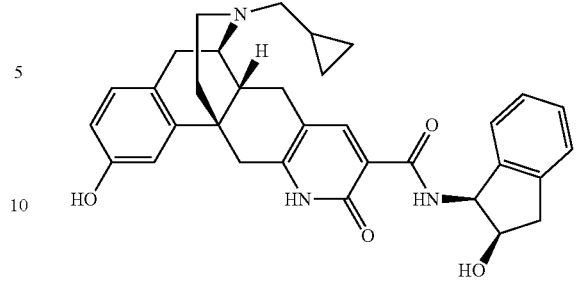

62

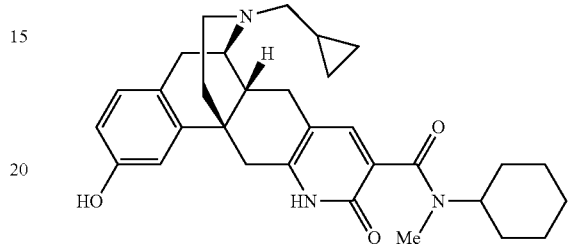

63

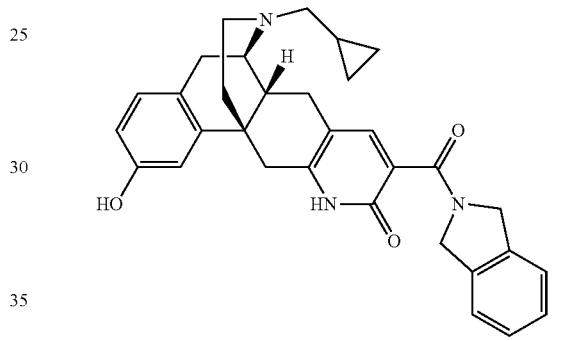

64

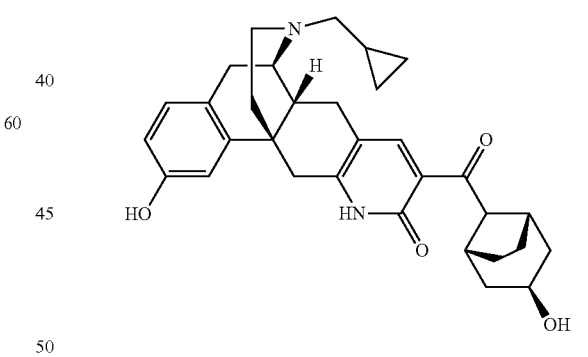

65

The title compounds were prepared in a manner similar to that described in Example 25:

(a) Compound 60: $^1$H NMR $\delta_H$ (400 MHz, DMSO-d$_6$): 11.93 (br. s., 1H), 9.09 (s, 1H), 7.23 (s, 1H), 6.90 (d, J=8.4 Hz, 1H), 6.56 (d, J=2.2 Hz, 1H), 6.51 (dd, J=8.4, 2.2 Hz, 1H), 4.03-3.83 (m, 2H), 3.61-3.50 (m, 2H), 3.29-3.17 (m, 4H), 3.17-3.07 (m, 2H), 2.85 (d, J=18.5 Hz, 1H), 2.72-2.56 (m, 3H), 2.46-2.36 (m, 2H), 2.32-2.22 (m, 1H), 2.21-2.02 (m, 2H), 2.02-1.90 (m, 1H), 1.85-1.73 (m, 1H), 1.37 (d, J=11.9 Hz, 1H), 0.87-0.75 (m, 1H), 0.50-0.40 (m, 2H), 0.15-0.03 (m, 2H). LC/MS, m/z=524.3 [M+H]$^+$ (Calc: 523.6).

Compound 61: $^1$H NMR $\delta_H$ (400 MHz, DMSO-d$_6$): 12.27 (br. s., 1H), 10.20 (d, J=8.4 Hz, 1H), 9.08 (s, 1H), 7.99 (s, 1H), 7.25-7.20 (m, 1H), 7.20-7.13 (m, 1H), 7.13-7.04 (m, 2H), 6.91 (d, J=8.1 Hz, 1H), 6.58-6.48 (m, 2H), 5.35 (dd, J=8.5, 5.0 Hz, 1H), 5.20 (d, J=4.4 Hz, 1H), 4.44 (q, J=4.5 Hz, 1H), 3.39-3.28 (m, 1H, overlap with water), 3.28-3.19 (m, 1H), 3.08 (dd, J=16.2, 4.5 Hz, 1H), 2.92-2.75 (m, 2H), 2.75-2.52 (m, 4H), 2.47-2.36 (m, 1H), 2.35-2.11 (m, 3H), 2.05-1.92 (m, 1H), 1.88-1.75 (m, 1H), 1.39 (d, J=11.7 Hz, 1H), 0.89-0.75 (m, 1H), 0.54-0.40 (m, 2H), 0.18-0.02 (m, 2H). LC/MS, m/z=538.2 [M+H]$^+$ (Calc: 537.7).

Compound 62: $^1$H NMR $\delta_H$ (400 MHz, DMSO-d$_6$): 12.27 (br. s., 1H), 10.18 (d, J=8.6 Hz, 1H), 9.07 (s, 1H), 7.98 (s, 1H), 7.27-7.07 (m, 4H), 6.90 (d, J=8.1 Hz, 1H), 6.57-6.47 (m, 2H), 5.33 (dd, J=8.4, 4.8 Hz, 1H), 5.12 (d, J=4.2 Hz, 1H), 4.40 (q, J=4.2 Hz, 1H), 3.38-3.28 (m, 1H, overlap with water), 3.27-3.20 (m, 1H), 3.07 (dd, J=16.2, 4.5 Hz, 1H), 2.91-2.53 (m, 6H), 2.46-2.36 (m, 1H), 2.35-2.25 (m, 1H), 2.25-2.09 (m, 2H), 2.04-1.93 (m, 1H), 1.82 (td, J=12.3, 4.2 Hz, 1H), 1.39 (d, J=12.1 Hz, 1H), 0.89-0.76 (m, 1H), 0.53-0.40 (m, 2H), 0.16-0.03 (m, 2H). LC/MS, m/z 538.2 [M+H]$^+$ (Calc: 537.7).

Compound 63: $^1$H NMR $\delta_H$ (400 MHz, DMSO-d$_6$): exists as a 1:1 ratio of conformers 11.78-11.62 (m, 1H), 9.09-9.02 (m, 1H), 7.00 (d, J=12.1 Hz, 1H), 6.92-6.85 (m, 1H), 6.60-6.54 (m, 1H), 6.54-6.46 (m, 1H), 4.25-4.14 (m, 0.5H), 3.28-3.09 (m, 2.5H), 2.89-2.77 (m, 1H), 2.77-2.54 (m, 6H), 2.46-2.34 (m, 2H), 2.32-2.22 (m, 1H), 2.20-2.10 (m, 1H), 2.10-1.89 (m, 2H), 1.85-1.70 (m, 2H), 1.70-1.19 (m, 8H), 1.17-0.87 (m, 2H), 0.87-0.73 (m, 1H), 0.50-0.39 (m, 2H), 0.15-0.01 (m, 2H). LC/MS, m/z 502.4 [M+H]$^+$ (Calc: 501.7).

Compound 64: $^1$H NMR $\delta_H$ (400 MHz, DMSO-d$_6$): 11.92 (s, 1H), 9.11 (s, 1H), 7.39-7.32 (m, 1H), 7.31-7.20 (m, 4H), 6.90 (d, J=8.1 Hz, 1H), 6.59 (d, J=2.2 Hz, 1H), 6.52 (dd, J=8.1, 2.2 Hz, 1H), 4.77-4.65 (m, 4H), 3.31-3.17 (m, 2H), 2.85 (d, J=18.3 Hz, 1H), 2.71-2.58 (m, 3H), 2.47-2.36 (m, 2H), 2.32-2.24 (m, 1H), 2.22-2.03 (m, 2H), 2.02-1.91 (m, 1H), 1.81 (td, J=12.3, 4.4 Hz, 1H), 1.38 (d, J=12.1 Hz, 1H), 0.87-0.75 (m, 1H), 0.51-0.40 (m, 2H), 0.14-0.03 (m, 2H). LC/MS, m/z=508.2 [M+H]$^+$ (Calc: 507.6).

Compound 65: $^1$H NMR $\delta_H$ (400 MHz, DMSO-d$_6$): 11.69 (br. s., 1H), 9.07 (br. s., 1H), 7.09 (d, J=4.6 Hz, 1H), 6.89 (d, J=8.1 Hz, 1H), 6.57 (s, 1H), 6.51 (d, J=7.9 Hz, 1H), 4.54 (dd, J=6.4, 2.2 Hz, 1H), 4.47-4.37 (m, 1H), 3.92-3.83 (m, 1H), 3.77-3.67 (m, 1H), 3.29-3.13 (m, 2H), 2.91-2.77 (m, 1H), 2.73-2.54 (m, 3H), 2.46-2.33 (m, 2H), 2.32-2.22 (m, 1H), 2.22-2.03 (m, 4H), 2.03-1.65 (m, 7H), 1.64-1.54 (m, 1H), 1.43-1.30 (m, 1H), 0.90-0.73 (m, 1H), 0.52-0.38 (m, 2H), 0.18-0.00 (m, 2). LC/MS, m/z=516.3 [M+H]$^+$ (Calc: 515.6).

Example 29

The following Tables provide results on the efficacy of binding and activity response of exemplified Compounds of the Invention at the ORL-1, μ-, δ- and κ-opioid receptors.

In TABLE 1, binding affinity of certain Compounds of the Invention to the ORL-1, μ, δ- and κ-opioid receptors was determined as described above.

In TABLE 2, activity response of certain Compounds of the Invention to the μ-, δ- and κ-opioid receptors was determined as described above for functional assays using HEK-293 or CHO cells.

TABLE 1

| Binding Affinity of Pyridonemorphinan Analogs | | | | | |
|---|---|---|---|---|---|
| | | $K_i$ (nM) | | | |
| Compd. | | | Opioid Receptor | | |
| No. | Structure | ORL-1 | μ | κ | δ |
| 2 | | | | 37.62 ± 4.75 | |
| 3 | | 448.70 ± 170.79 | 3.85 ± 1.09 | | 18.89 ± 7.84 |

TABLE 1-continued

Binding Affinity of Pyridonemorphinan Analogs

| Compd. No. | Structure | ORL-1 | μ | κ | δ |
|---|---|---|---|---|---|
| | | | $K_i$ (nM) Opioid Receptor | | |
| 4 | | | | 292.20 ± 17.01 | |
| 5 | | 1333.59 ± 309.92 | 6.55 ± 2.06 | 0.58 ± 0.15 | 26.43 ± 7.23 |
| 6 | | | | 35.68 ± 2.74 | |
| 7 | | | 4.55 ± 1.26 | 0.19 ± 0.04 | |
| 8 | | | | 728.34 ± 142.22 | |

TABLE 1-continued

Binding Affinity of Pyridonemorphinan Analogs

| Compd. No. | Structure | $K_i$ (nM) Opioid Receptor | | | |
|---|---|---|---|---|---|
| | | ORL-1 | μ | κ | δ |
| 9 | | 2323.91 ± 319.53 | 3.11 ± 0.90 | 1.52 ± 0.18 | 18.49 ± 2.14 |
| 10 | | | 182.83 ± 23.28 | | |
| 11 | | 4.91 ± 0.82 | 0.52 ± 0.12 | 18.53 ± 7.73 | |
| 13 | | | 467.11 ± 172.99 | | |
| 14 | | | 1.53 ± 0.26 | | |

TABLE 1-continued
Binding Affinity of Pyridonemorphinan Analogs
| Compd. No. | Structure | $K_i$ (nM) Opioid Receptor | | | |
|---|---|---|---|---|---|
| | | ORL-1 | μ | κ | δ |
| 16 | 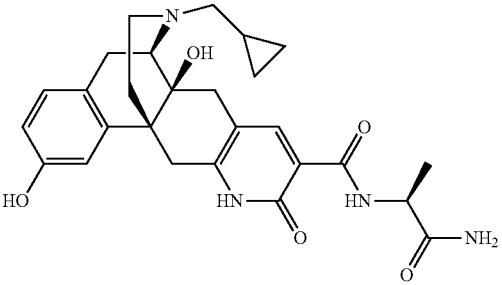 [SMILES: C[C@H](NC(=O)c1cc2c([nH]c1=O)C[C@]13CCN(CC4CC4)[C@H](Cc4ccc(O)cc41)[C@]3(O)C2)C(N)=O] | | | 1.05 ± 0.22 | |
| 17 | 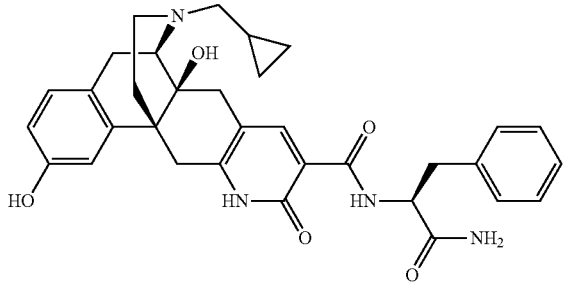 [SMILES: NC(=O)[C@H](Cc1ccccc1)NC(=O)c1cc2c([nH]c1=O)C[C@]13CCN(CC4CC4)[C@H](Cc4ccc(O)cc41)[C@]3(O)C2] | | | 0.85 ± 0.15 | |
| 18 | 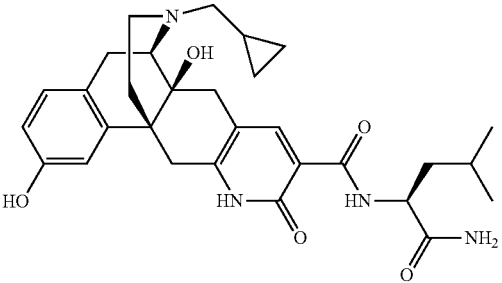 [SMILES: CC(C)C[C@H](NC(=O)c1cc2c([nH]c1=O)C[C@]13CCN(CC4CC4)[C@H](Cc4ccc(O)cc41)[C@]3(O)C2)C(N)=O] | | | 1.09 ± 0.05 | |
| 19 | 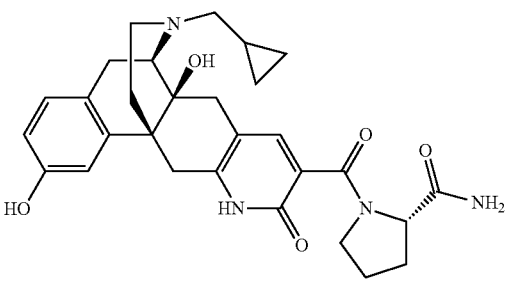 [SMILES: NC(=O)[C@@H]1CCCN1C(=O)c1cc2c([nH]c1=O)C[C@]13CCN(CC4CC4)[C@H](Cc4ccc(O)cc41)[C@]3(O)C2] | | | 0.97 ± 0.23 | |

TABLE 1-continued

Binding Affinity of Pyridonemorphinan Analogs

| Compd. No. | Structure | $K_i$ (nM) Opioid Receptor | | | |
|---|---|---|---|---|---|
| | | ORL-1 | μ | κ | δ |
| 20 | | | | 2.59 ± 0.99 | |
| 21 | | 2.04 ± 0.49 | 0.59 ± 0.15 | | |
| 22 | | 1.20 ± 0.21 | 0.56 ± 0.11 | | |
| 23 | | | | 1.86 ± 0.65 | 0.31 ± 0.05 |

TABLE 1-continued
Binding Affinity of Pyridonemorphinan Analogs
| Compd. No. | Structure | ORL-1 | K$_i$ (nM) Opioid Receptor μ | κ | δ |
|---|---|---|---|---|---|
| 24 | 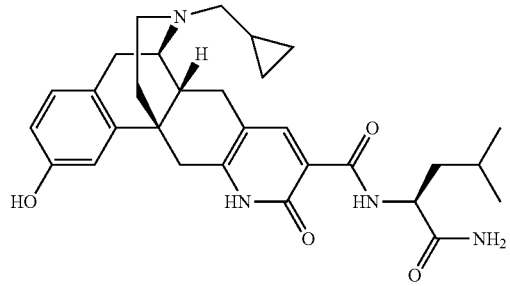 [SMILES: CC(C)C[C@H](NC(=O)c1cc2c([nH]c1=O)C[C@]13CCN(CC4CC4)[C@H](Cc4ccc(O)cc41)[C@@H]3C2)C(N)=O] | | 3.95 ± 1.84 | 0.96 ± 0.10 | |
| 25 | 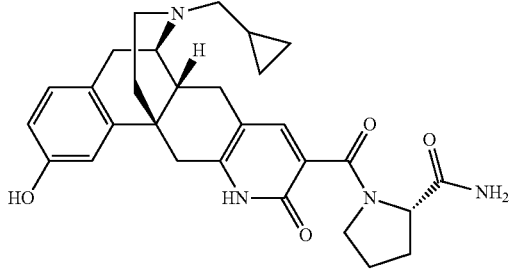 [SMILES: NC(=O)[C@@H]1CCCN1C(=O)c1cc2c([nH]c1=O)C[C@]13CCN(CC4CC4)[C@H](Cc4ccc(O)cc41)[C@@H]3C2] | | 0.41 ± 0.05 | 0.32 ± 0.06 | |
| 26 | 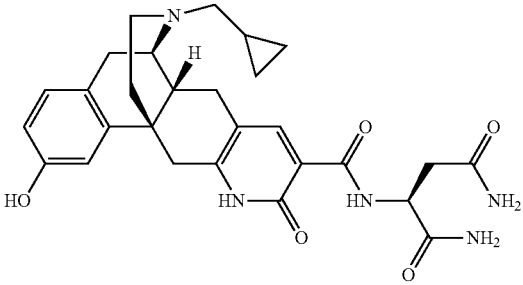 [SMILES: NC(=O)C[C@H](NC(=O)c1cc2c([nH]c1=O)C[C@]13CCN(CC4CC4)[C@H](Cc4ccc(O)cc41)[C@@H]3C2)C(N)=O] | | 0.71 ± 0.11 | 0.86 ± 0.23 | |
| 27 | 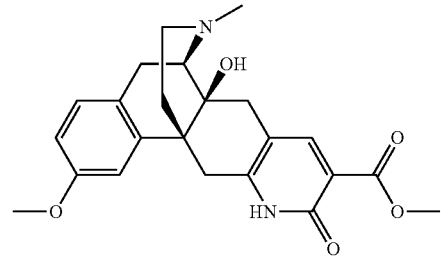 | | >20 μM | 3075.07 ± 127.51 | |
| 28 | 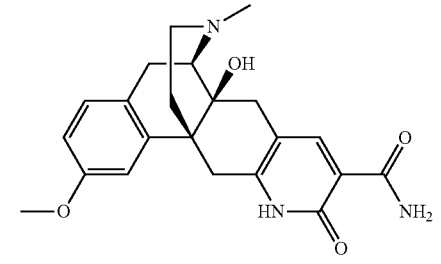 [SMILES: COc1ccc2c(c1)[C@]13CCN(C)[C@H](C2)[C@]1(O)Cc1cc(C(N)=O)c(=O)[nH]c1C3] | | 14367.18 ± 4137.46 | 12268.59 | |

TABLE 1-continued

Binding Affinity of Pyridonemorphinan Analogs

| Compd. No. | Structure | $K_i$ (nM) Opioid Receptor | | | |
|---|---|---|---|---|---|
| | | ORL-1 | μ | κ | δ |
| 29 | 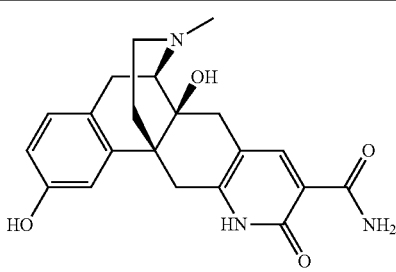 | | 651.45 ± 100.75 | 25.30 ± 4.86 | |
| 30 | 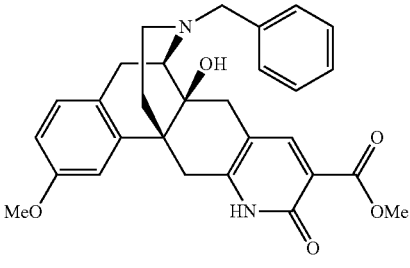 [SMILES: COC(=O)c1cc2c([nH]c1=O)C[C@]13CCN(Cc4ccccc4)[C@H](Cc4ccc(OC)cc41)[C@]3(O)C2] | | 3938 ± 860.2 | 599.3 ± 90.0 | |
| 31 | 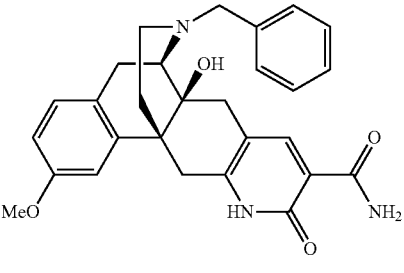 [SMILES: COc1ccc2c(c1)[C@]13CCN(Cc4ccccc4)[C@H](C2)[C@]1(O)Cc1cc(C(N)=O)c(=O)[nH]c1C3] | | 5593 ± 696.4 | 1582 ± 307.7 | |

TABLE 2

Activity Response of Pyridonemorphinan Analogs

| | Opioid Receptor | | | | | |
|---|---|---|---|---|---|---|
| Compd. | μ | | κ | | δ | |
| No. | $EC_{50}$ | $E_{max}$ (%) | $EC_{50}$ | $E_{max}$ (%) | $EC_{50}$ | $E_{max}$ (%) |
| 2 | >20 μM | | 593.86 ± 86.96 nM | 37.50 ± 2.25 | | |
| 3 | 34.85 ± 6.84 nM | 15.67 ± 3.48 | 39.09 ± 2.60 nM | 52.33 ± 1.76 | | |
| 4 | >20 μM | | 5378.42 ± 488.71 nM | 39.67 ± 5.78 | | |
| 5 | >20 μM | | 4.37 ± 1.11 nM | 10.25 ± 1.18 | >20 μM | |
| 6 | 527.95 ± 121.35 nM | 19.67 ± 2.02 | 2976.07 ± 586.72 nM | 59.33 ± 2.33 | | |
| 7 | >20 μM | | 33.95 ± 3.73 nM | 31.33 ± 3.18 | | |
| 9 | >20 μM | | >20 μM | 2.33 ± 1.33 | >20 μM | |
| 10 | 225.47 ± 89.57 nM | 25.67 ± 0.88 | 3493.15 ± 636.05 nM | 37.75 ± 1.70 | | |
| 11 | >20 μM | | 1.40 ± 0.56 nM | 19.00 ± 1.53 | 3.53 ± 1.50 nM | 36.00 ± 3.21 |
| 14 | >20 μM | | >20 μM | | | |
| 16 | 6.44 ± 0.41 nM | 14.67 ± 3.28 | >20 μM | | | |
| 17 | >20 μM | -0.33 ± 0.67 | >20 μM | | | |
| 18 | | | >20 μM | | | |
| 19 | >20 μM | | >20 μM | | | |
| 20 | >20 μM | | >20 μM | | | |
| 21 | 1.73 ± 0.41 nM | 23.67 ± 2.19 | 4.19 ± 0.79 nM | 41.00 ± 5.29 | | |
| 22 | 4.22 ± 1.00 nM | 30.00 ± 3.21 | 9.89 ± 2.40 nM | 36.67 ± 2.73 | | |
| 23 | 3.19 ± 0.46 nM | 41.33 ± 5.04 | 8.35 ± 2.25 nM | 25.67 ± 4.18 | | |
| 24 | 5.20 ± 1.35 nM | 37.00 ± 7.02 | 2.54 ± 0.55 nM | 23.00 ± 2.04 | | |

TABLE 2-continued

Activity Response of Pyridonemorphinan Analogs

| | Opioid Receptor | | | | | |
|---|---|---|---|---|---|---|
| Compd. | μ | | κ | | δ | |
| No. | $EC_{50}$ | $E_{max}$ (%) | $EC_{50}$ | $E_{max}$ (%) | $EC_{50}$ | $E_{max}$ (%) |
| 25 | 4.87 ± 0.52 nM | 29.33 ± 1.45 | 4.42 ± 0.85 nM | 44.67 ± 2.73 | | |
| 26 | 7.54 ± 1.97 nM | 38.00 ± 1.15 | 8.87 ± 1.35 nM | 39.00 ± 2.08 | | |
| 37 | 267.6 ± 53.1 nM | 98.0 ± 4.62 | >20 μM | 2.50 | | |
| 60 | >20 μM | −1.00 ± 1.00 | | | | |
| 61 | >20 μM | −1.00 | | | | |
| 62 | >20 μM | −1.00 ± 0.00 | | | | |
| 63 | >20 μM | −1.00 | | | | |
| 64 | >20 μM | 3.50 | | | | |
| 65 | >20 μM | 4.00 | | | | |

The in vitro test results of Tables 1 and 2 show that representative Compounds of the Invention generally have high binding affinity for opioid receptors, and that these compounds activate these receptors as partial to full agonists. Compounds of the Invention are therefore expected to be useful to treat Conditions, particularly pain, that are responsive to the activation of one or more opioid receptors.

Example 30

The following TABLE 3 provides results on the activity response of certain Compounds of the Invention at the μ- and κ-opioid receptors determined as described above using U-2 OS cells.

TABLE 3

Activity Response of Certain Compounds of the Invention

| Compound No. | Structure | Opioid Receptor | | | |
|---|---|---|---|---|---|
| | | μ | | κ | |
| | | $EC_{50}$ | $E_{max}$ (%) | $EC_{50}$ | $E_{max}$ (%) |
| 30 | [structure] | | | >20 μM | 1.00 |
| 31 | [structure] | | | >20 μM | 10.7 ± 5.21 |
| 32 | [structure] | >20 μM | 17.5 | >20 μM | 6.70 ± 6.56 |

TABLE 3-continued

Activity Response of Certain Compounds of the Invention

| Compound No. | Structure | Opioid Receptor | | | |
|---|---|---|---|---|---|
| | | μ | | κ | |
| | | $EC_{50}$ | $E_{max}$ (%) | $EC_{50}$ | $E_{max}$ (%) |
| 34 | 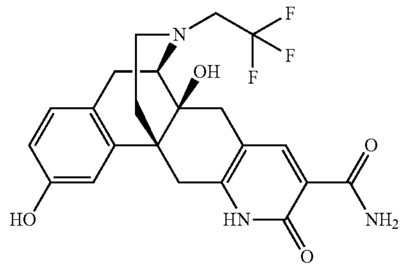 [SMILES: NC(=O)c1cc2c([nH]c1=O)C[C@]13CCN(CC(F)(F)F)[C@H](Cc4ccc(O)cc41)[C@]3(O)C2] | >20 μM | 8.50 | >20 μM | 0.00 |
| 35 | 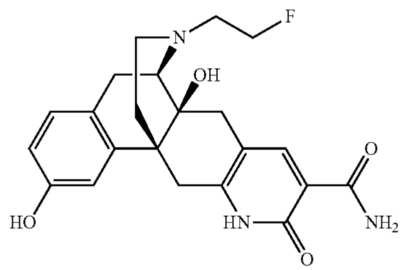 [SMILES: NC(=O)c1cc2c([nH]c1=O)C[C@]13CCN(CCF)[C@H](Cc4ccc(O)cc41)[C@]3(O)C2] | >20 μM | 2.50 | 93.7 ± 27.7 nM | 66.0 ± 1.53 |
| 37 | 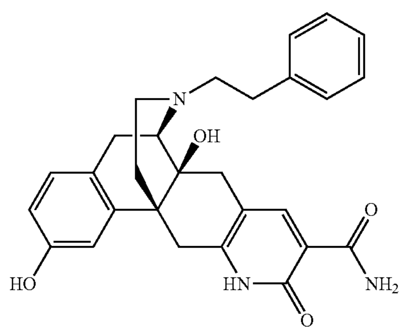 [SMILES: NC(=O)c1cc2c([nH]c1=O)C[C@]13CCN(CCc4ccccc4)[C@H](Cc4ccc(O)cc41)[C@]3(O)C2] | 72.7 ± 3.87 nM | 71.3 ± 0.33 | 373.9 ± 93.5 nM | 11.3 ± 1.45 |
| 39 | 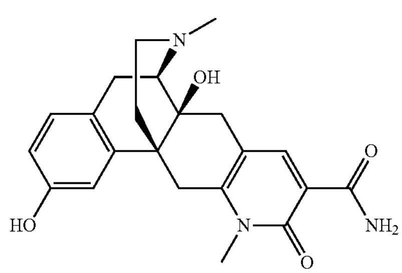 [SMILES: CN1CC[C@]23Cc4c(cc(C(N)=O)c(=O)n4C)C[C@@]2(O)[C@H]1Cc1ccc(O)cc13] | 164.3 ± 59.0 nM | 33.7 ± 8.01 | 641.6 ± 3.49 nM | 54.0 ± 3.61 |
| 40 | 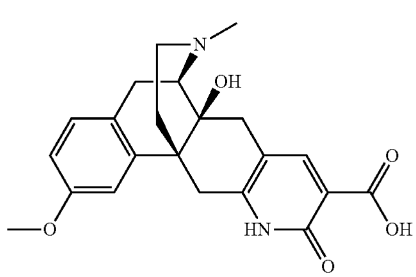 [SMILES: COc1ccc2c(c1)[C@]13CCN(C)[C@H](C2)[C@]1(O)Cc1cc(C(=O)O)c(=O)[nH]c1C3] | 13911 ± 1633 nM | 72.0 ± 4.16 | >20 μM | 96.0 ± 1.53 |

TABLE 3-continued

Activity Response of Certain Compounds of the Invention

| Compound No. | Structure | Opioid Receptor | | | |
|---|---|---|---|---|---|
| | | μ | | κ | |
| | | $EC_{50}$ | $E_{max}$ (%) | $EC_{50}$ | $E_{max}$ (%) |
| 41 | 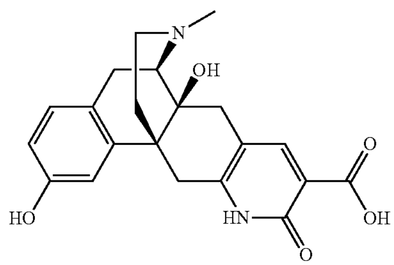 [SMILES: CN1CC[C@]23Cc4[nH]c(=O)c(C(=O)O)cc4C[C@@]2(O)[C@H]1Cc1ccc(O)cc13] | 110.6 ± 8.90 nM | 58.2 ± 2.32 | 568.2 ± 33.3 nM | 70.0 ± 4.58 |
| 44 | 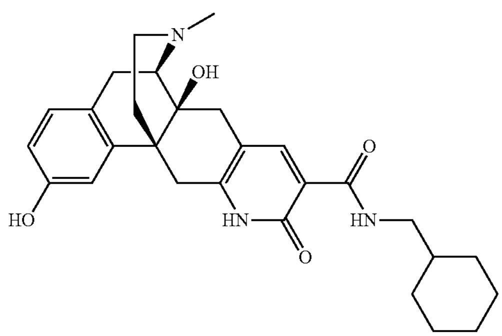 [SMILES: CN1CC[C@]23Cc4[nH]c(=O)c(C(=O)NCC5CCCCC5)cc4C[C@@]2(O)[C@H]1Cc1ccc(O)cc13] | 438.6 ± 27.4 nM | 88.3 ± 0.88 | 92.5 ± 24.2 nM | 67.0 ± 1.00 |
| 45 | 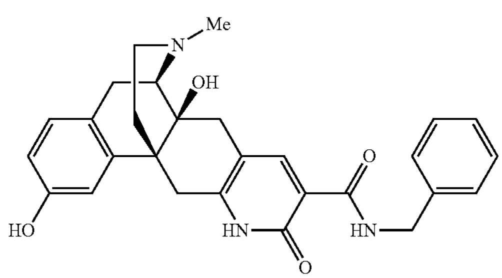 [SMILES: CN1CC[C@]23Cc4[nH]c(=O)c(C(=O)NCc5ccccc5)cc4C[C@@]2(O)[C@H]1Cc1ccc(O)cc13] | 305.8 ± 25.2 nM | 90.0 ± 1.53 | 127.5 ± 8.96 nM | 94.3 ± 5.61 |
| 46 | 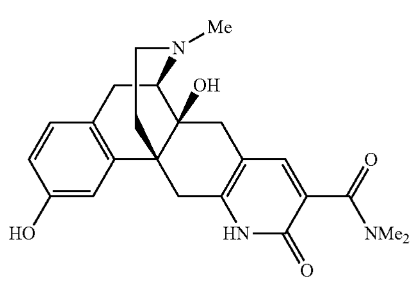 [SMILES: CN(C)C(=O)c1cc2c([nH]c1=O)C[C@]13CCN(C)[C@H](Cc4ccc(O)cc41)[C@]3(O)C2] | 157.1 ± 16.4 nM | 84.7 ± 2.19 | 624.0 ± 83.6 nM | 73.0 ± 6.99 |

TABLE 3-continued

Activity Response of Certain Compounds of the Invention

| Compound No. | Structure | Opioid Receptor | | | |
|---|---|---|---|---|---|
| | | μ | | κ | |
| | | $EC_{50}$ | $E_{max}$ (%) | $EC_{50}$ | $E_{max}$ (%) |
| 47 | | 155.8 ± 12.7 nM | 82.0 ± 1.73 | 511.3 ± 139.2 nM | 50.0 ± 2.74 |
| 48 | | 97.4 ± 4.35 nM | 82.7 ± 0.88 | 225.9 ± 4.41 nM | 90.3 ± 5.46 |
| 49 | | 444.7 ± 63.8 nM | 80.0 ± 3.61 | 203.7 ± 68.1 nM | 63.0 ± 1.73 |
| 50 | | 204.2 ± 11.3 nM | 95.0 ± 1.15 | 1068 ± 157.3 nM | 54.0 ± 2.74 |

TABLE 3-continued

Activity Response of Certain Compounds of the Invention

| Compound No. | Structure | Opioid Receptor | | | |
|---|---|---|---|---|---|
| | | μ | | κ | |
| | | $EC_{50}$ | $E_{max}$ (%) | $EC_{50}$ | $E_{max}$ (%) |
| 51 | 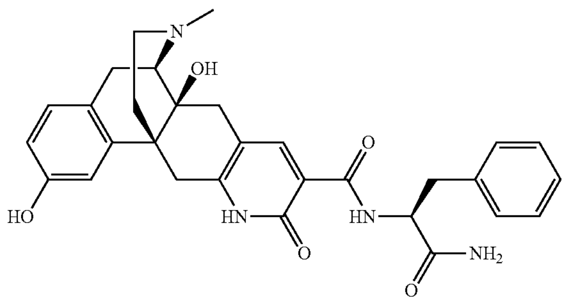 [SMILES: CN1CC[C@]23Cc4[nH]c(=O)c(C(=O)N[C@@H](Cc5ccccc5)C(N)=O)cc4C[C@@]2(O)[C@H]1Cc1ccc(O)cc13] | 126.0 ± 14.3 nM | 97.7 ± 1.45 | 488.4 ± 79.4 nM | 39.3 ± 3.84 |
| 52 | 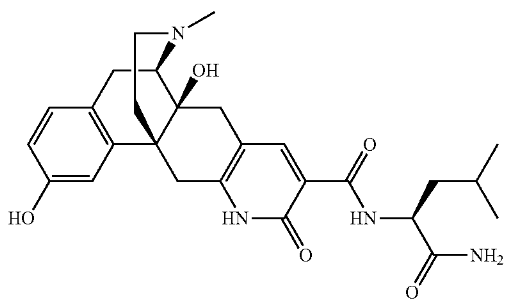 [SMILES: CC(C)C[C@H](NC(=O)c1cc2c([nH]c1=O)C[C@]13CCN(C)[C@H](Cc4ccc(O)cc41)[C@]3(O)C2)C(N)=O] | 244.2 ± 10.8 nM | 97.7 ± 1.45 | 3786 ± 1572 nM | 28.8 ± 2.17 |
| 53 | 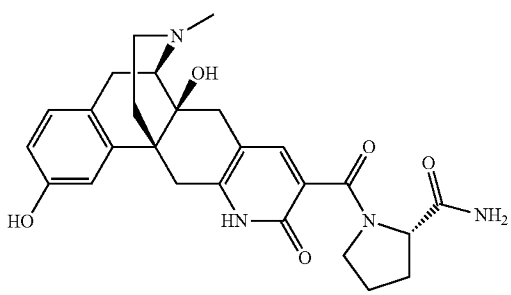 [SMILES: CN1CC[C@]23Cc4[nH]c(=O)c(C(=O)N5CCC[C@H]5C(N)=O)cc4C[C@@]2(O)[C@H]1Cc1ccc(O)cc13] | 123.2 ± 6.15 nM | 84.0 ± 2.08 | 601.8 ± 172.9 nM | 68.3 ± 3.38 |
| 54 | 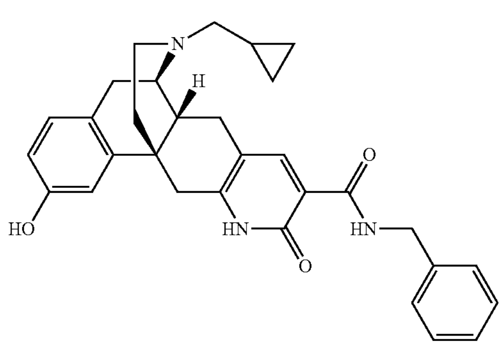 [SMILES: O=C(NCc1ccccc1)c1cc2c([nH]c1=O)C[C@]13CCN(CC4CC4)[C@H](Cc4ccc(O)cc41)[C@@H]3C2] | 0.60 ± 0.16 nM | 25.3 ± 2.67 | 0.27 ± 0.011 nM | 90.0 ± 1.68 |

TABLE 3-continued

Activity Response of Certain Compounds of the Invention

| Compound No. | Structure | Opioid Receptor | | | |
|---|---|---|---|---|---|
| | | μ | | κ | |
| | | $EC_{50}$ | $E_{max}$ (%) | $EC_{50}$ | $E_{max}$ (%) |
| 55 | 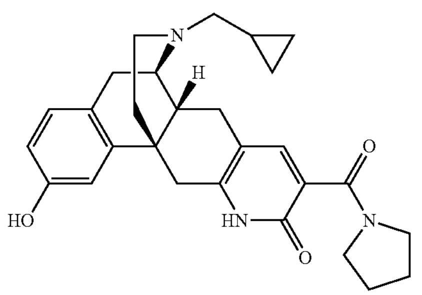 [SMILES: O=C(c1cc2c([nH]c1=O)C[C@]13CCN(CC4CC4)[C@H](Cc4ccc(O)cc41)[C@@H]3C2)N1CCCC1] | 0.79 ± 0.31 nM | 17.6 ± 0.68 | 0.33 ± 0.037 nM | 86.0 ± 2.68 |
| 59 | 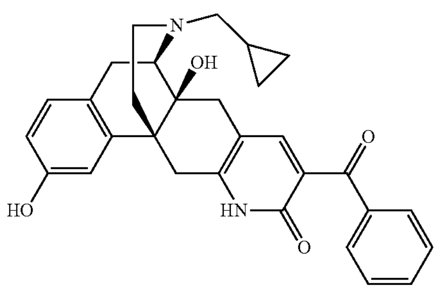 [SMILES: O=C(c1ccccc1)c1cc2c([nH]c1=O)C[C@]13CCN(CC4CC4)[C@H](Cc4ccc(O)cc41)[C@]3(O)C2] | >20 μM | 2.50 | 17907 ± 7548 nM | 16.8 ± 1.44 |

The in vitro test results of Table 3 show that representative Compounds of the Invention activate these receptors as partial to full agonists. Compounds of the Invention are therefore expected to be useful to treat Conditions, particularly pain, that are responsive to the activation of one or more opioid receptors.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and publications cited herein are fully incorporated by reference herein in their entirety.

What is claimed is:

1. A compound of Formula I:

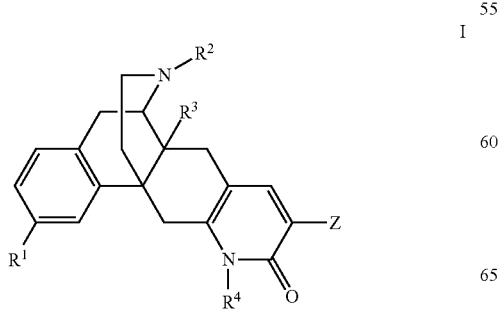

I or a pharmaceutically acceptable salt or solvate thereof, wherein:

$R^1$ is hydrogen, OH, halo, cyano, carboxy, or aminocarbonyl; or alkyl, alkenyl, alkynyl, alkoxy alkenyloxy or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^8$ groups; or —O-PG, wherein PG is a hydroxyl protecting group selected from the group consisting of alkyl, arylalkyl, heterocyclo, (heterocyclo)alkyl, acyl, silyl, and, carbonate, any of which is optionally substituted;

$R^2$ is (a) hydrogen or carboxamido; or (b) alkyl, alkenyl, alkynyl, cycloalkyl, cycloalkenyl, heterocyclo, aryl, heteroaryl, (cycloalky palkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected $R^8$ groups;

R³ is hydrogen, OH, or halo; or alkoxy, alkylamino, or dialkylamino, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected R⁸ groups;

R⁴ is hydrogen or alkyl;

Z is wherein

R⁵ is selected from the group consisting of a) OH;

b) optionally substituted alkoxy; and c) —NR⁶R⁷, wherein

R⁶ is hydrogen or alkyl;

R⁷ is hydrogen, optionally substituted carboxyalkyl, optionally substituted (alkoxycarbonyl)alkyi, optionally substituted (carboxamido)alkyl, or hydroxyalkyl; or R⁶ and R⁷ together with the nitrogen atom to which they are attached form an optionally substituted heterocyclic ring; and each R⁸ is independently selected from the group consisting of hydroxy, haloalkyl, amino, alkylamino, dialkylamino, carboxy, alkoxy, and alkoxycarbonyl.

2. The compound of claim 1, having the Formula II:

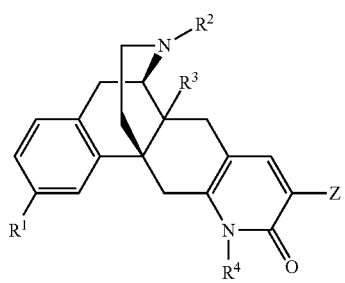

or a pharmaceutically acceptable salt or solvate thereof, wherein R¹—R⁴ and Z are as defined in claim 1.

3. The compound of claim 1, having the Formula III:

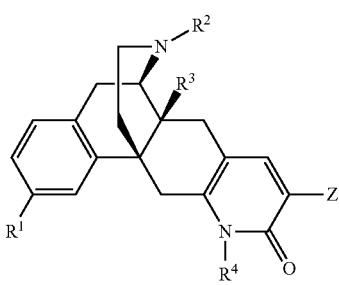

or a pharmaceutically acceptable salt or solvate thereof, wherein R¹—R⁴ and Z are as defined in claim 1.

4. The compound of claim 1, having the Formula V:

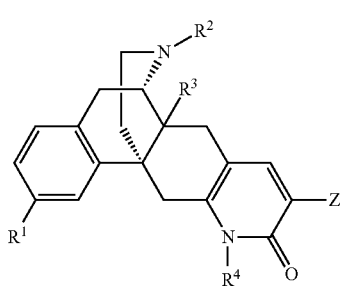

or a pharmaceutically acceptable salt or solvate thereof, wherein R¹—R⁴ and Z are as defined in claim 1.

5. The compound of claim 1, or a pharmaceutically acceptable salt or solvate thereof, wherein R¹ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamir m, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected R⁸ groups.

6. The compound of claim 5, or a pharmaceutically acceptable salt or solvate thereof, wherein R¹ is OH or unsubstituted $C_{1-6}$ alkoxy.

7. The compound of claim 1, or a pharmaceutically acceptable salt or solvate thereof, wherein R² is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein said aryl, heteroaryl, heterocyclo, cycloalkyl, and cycloalkenyl are optionally substituted with 1, 2, or 3 independently selected R⁸ groups.

8. The compound of claim 7, or a pharmaceutically acceptable salt or solvate thereof, wherein R² is $C_{3-7}$ (cycloalkyl)($C_{1-4}$)alkyl or $C_{3-7}$(cycloalkenyl)($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

9. The compound of claim 8, or a pharmaceutically acceptable salt or solvate thereof, wherein R² is unsubstituted $C_{1-4}$ alkyl, or cyclopropyl($C_{1-4}$) alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

10. The compound of claim 1, or a pharmaceutically acceptable salt or solvate thereof, wherein R³ is hydrogen.

11. The compound of claim 1a or a pharmaceutically acceptable salt or solvate. thereof, wherein R³ is OH.

12. The compound of claim 1, or a pharmaceutically acceptable salt or solvate thereof, wherein R⁴ is hydrogen.

13. The compound of claim 1, or a pharmaceutically acceptable salt or solvate thereof, wherein $R^5$ is OH.

14. The compound of claim 1, or a pharmaceutically acceptable salt or solvate thereof, wherein $R^5$ is optionally substituted alkoxy.

15. The compound of claim 1, or a pharmaceutically acceptable salt or solvate thereof, wherein $R^5$ is —$NR^6R^7$, wherein $R^6$ is hydrogen or alkyl; and $R^7$ is hydrogen, optionally substituted carboxyalkyl, optionally substituted (alkoxycarbonyl)alkyl, optionally substituted (carboxamido)alkyl, or hydroxyalkyl.

16. The compound of claim 15, or a pharmaceutically acceptable salt or solvate thereof, wherein $R^6$ is hydrogen or $C_{1-6}$ alkyl, and $R^7$ is hydrogen.

17. The compound of claim 15, or a pharmaceutically acceptable salt or solvate thereof, wherein $R^6$ is hydrogen or $C_{1-6}$ alkyl, and $R^7$ is optionally substituted carboxy($C_{1-6}$) alkyl, optionally substituted ($C_{1-6}$ alkoxycarbonyl) ($C_{1-6}$) alkyl, or optionally substituted (carboxamido)($C_{1-6}$)alkyl.

18. The compound of claim 17, or a pharmaceutically acceptable salt or solvate thereof, wherein $R^7$ is —$CHR^9$—$C(=O)$—$Z^1$, wherein $R^9$ is selected from the group consisting of hydrogen, alkyl, hydroxyalkyl, carboxyalkyl, aminoalkyl, (aminocarbonyl)alkyl, (alkylaminocarbonyl)alkyl, (dialkylaminocarbonyl)alkyl, mercaptoalkyl, (alkylthio)alkyl, guanidinoalkyl, arylalkyl, (cycloalkyl)alkyl, (cycloalkenyl)alkyl, (heterocyclo)alkyl, and (heteroaryl)alkyl, wherein the aryl, cycloalkyl, cycloalkenyl, heterocyclo, and heteroaryl portions are optionally substituted with 1, 2, or 3 substituents, each independently selected from the group consisting of hydroxy, halo, haloalkyl, amino, alkylamino, dialkylamino, carboxy, alkoxy, and alkoxycarbonyl; and $Z^1$ is $OR^{10}$ or $NR^{11}R^{12}$, wherein $R^{10}$ is hydrogen or alkyl; and $R^{11}$ and $R^{12}$ are each independently selected from the group consisting of hydrogen and alkyl.

19. The compound of claim 1, or a pharmaceutically acceptable salt or solvate thereof, wherein $R^5$ is —$NR^6R^7$ and $R^6$ and $R^7$ together with the nitrogen atom to which they are attached form an optionally substituted heterocyclic ring.

20. The compound of claim 1, or a pharmaceutically acceptable salt or solvate thereof, wherein Z is selected from the group consisting

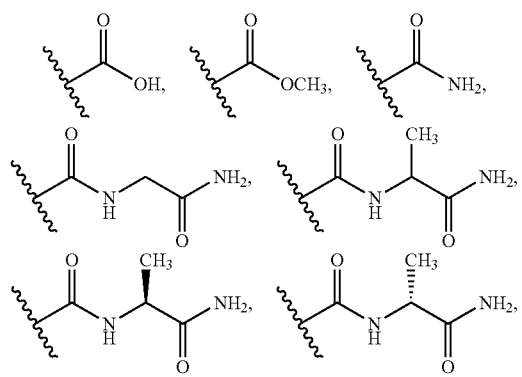

-continued

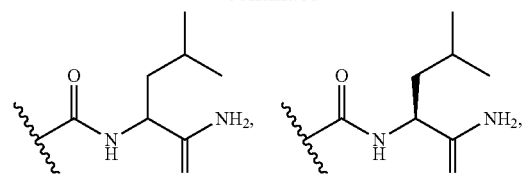

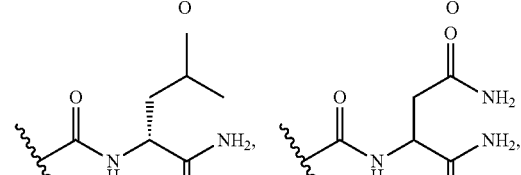

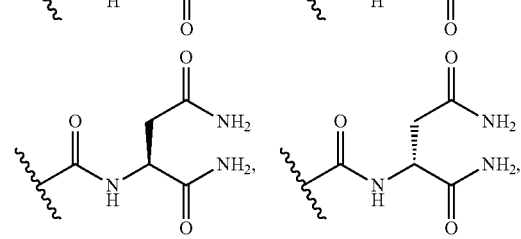

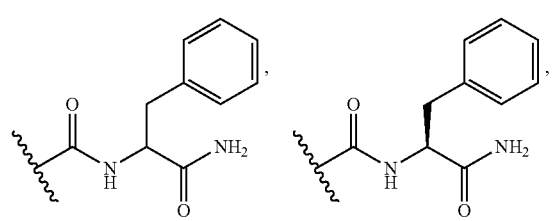

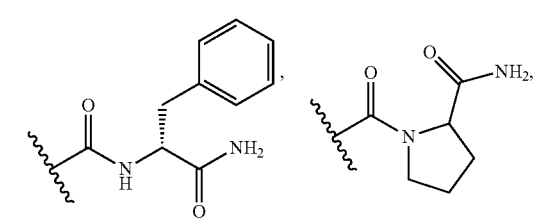

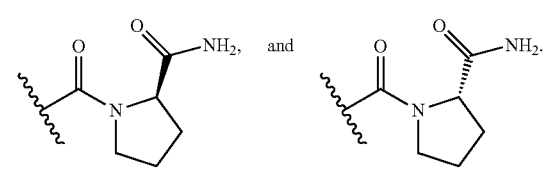

21. The compound of claim 20, or a pharmaceutically acceptable salt or solvate thereof, wherein $R^1$ is OH or unsubstituted $C_{1-6}$ alkoxy;

$R^2$ is unsubstituted $C_{1-4}$ alkyl, or cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;

$R^3$ is hydrogen; and $R^4$ is hydrogen.

22. The compound of claim 1, having the Formula VIII:

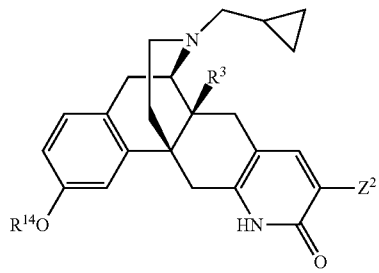

VIII or a pharmaceutically acceptable salt or solvate thereof, wherein $R^{14}$ is H or $C_{1-6}$ alkyl optionally substituted with 1 or 2 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;

$R^3$ is hydrogen or OH; and $Z^2$ is selected from the group consisting of

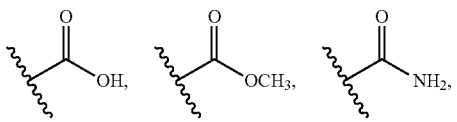

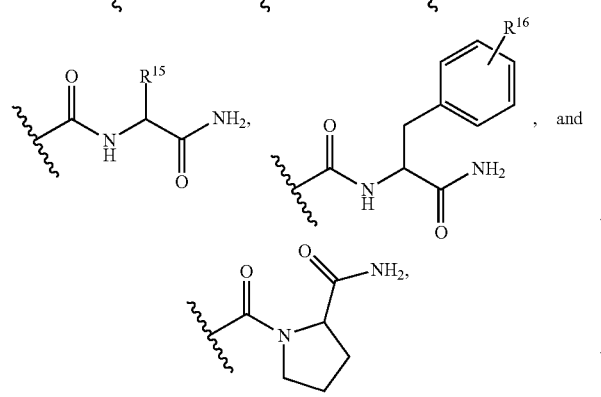

, and

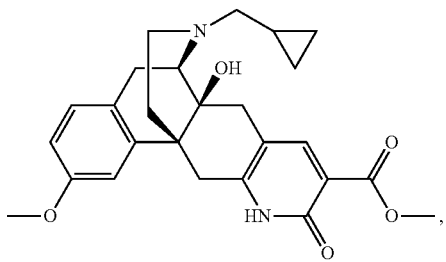

wherein $R^{15}$ is $C_{1-4}$ alkyl or -($C_{1-4}$)alkyl-C(=O)NH$_2$, and $R^{16}$ is selected from the group consisting of $C_{1-4}$ alkyl, hydroxy, halo, halo($C_{1-2}$)alkyl, $C_{1-2}$ alkoxy, $C_{1-2}$ alkoxycarbonyl, and aminocarbonyl.

23. The compound of claim 1, selected from the group consisting of

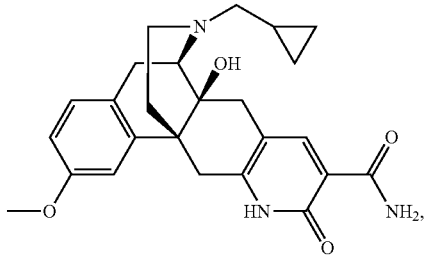

-continued

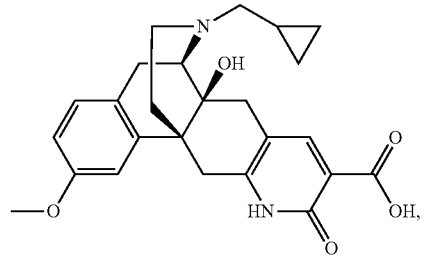

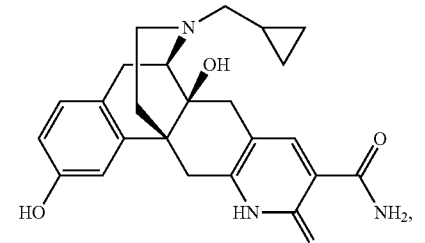

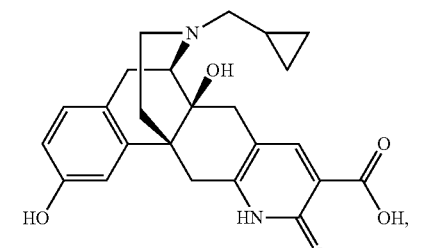

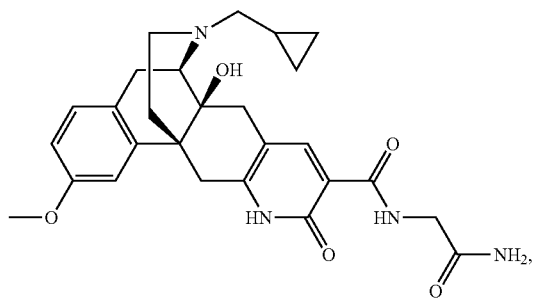

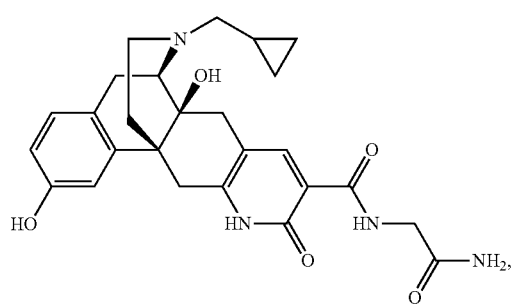

169
-continued
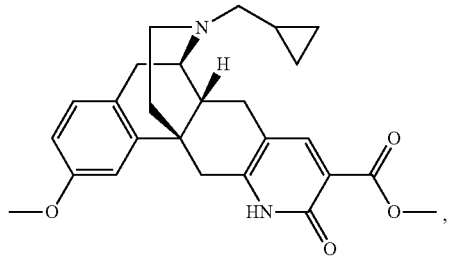
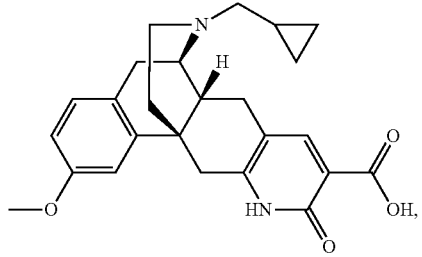
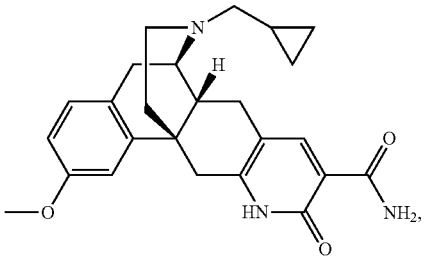
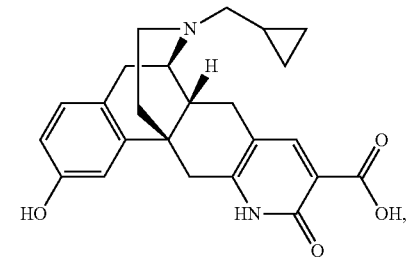
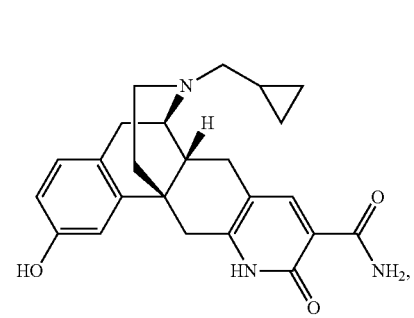
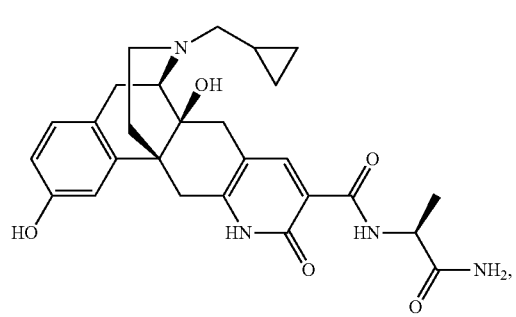
170
-continued
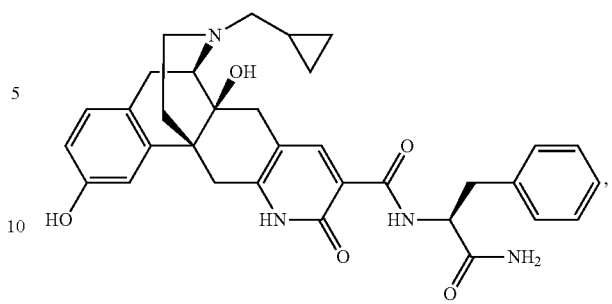
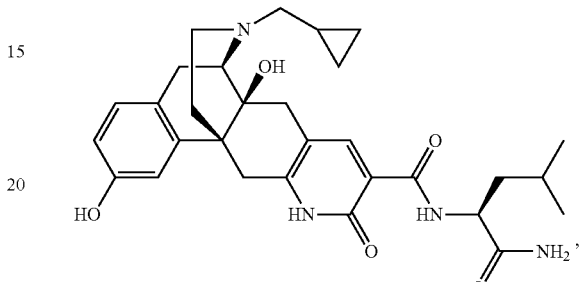
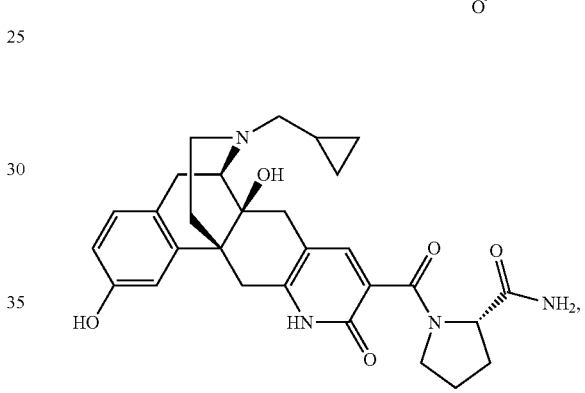
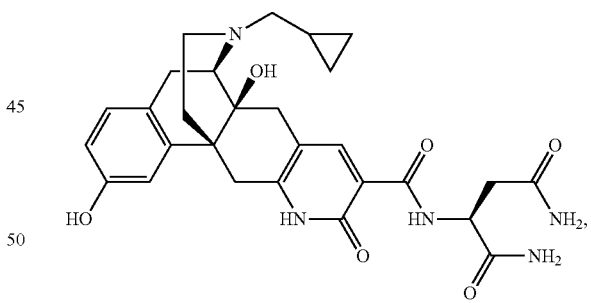
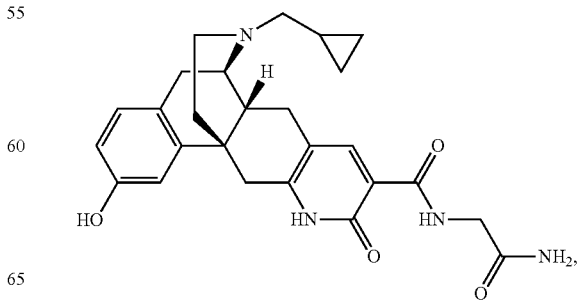

-continued

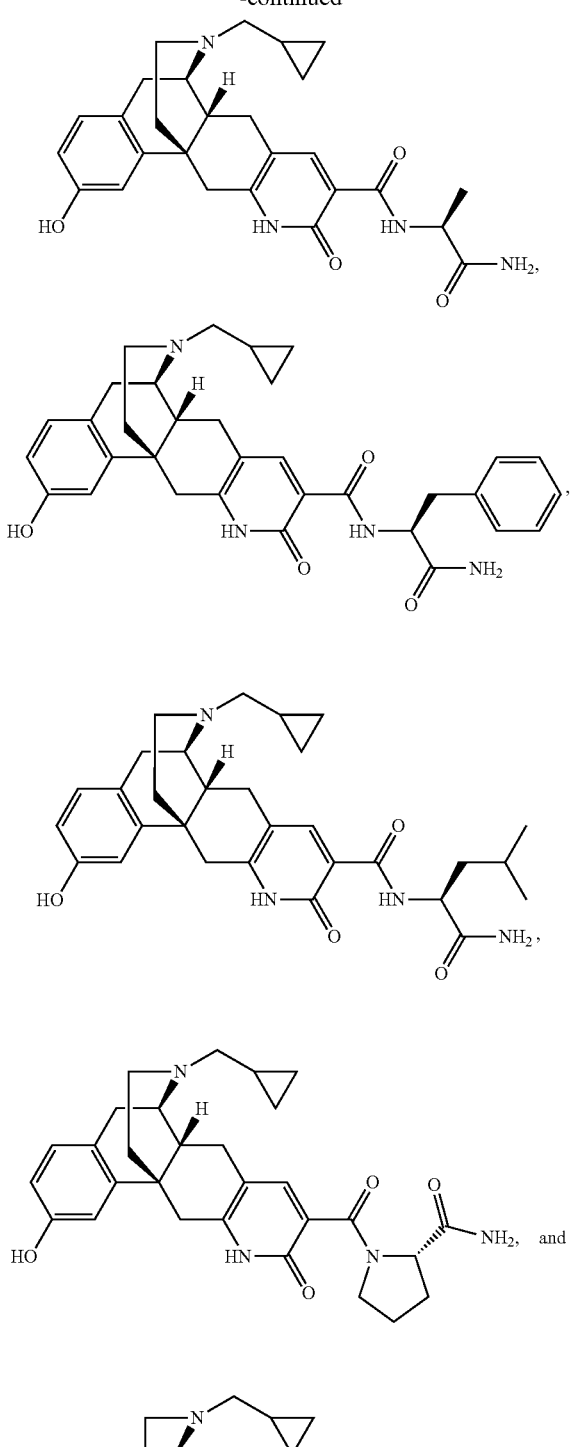

or a pharmaceutically acceptable salt or solvate thereof.

24. The compound of claim 1 selected from the group consisting of

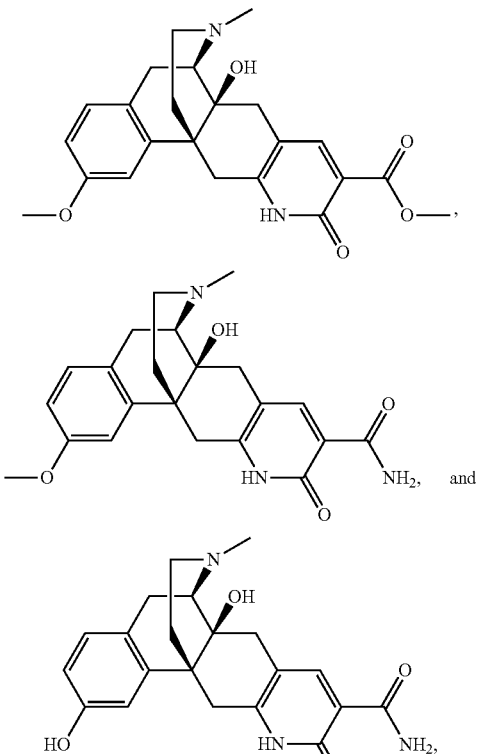

or a pharmaceutically acceptable salt or solvate thereof.

25. A pharmaceutical composition, comprising a therapeutically effective amount of a compound of claim 1, or a pharmaceutically acceptable salt or solvate thereof, and one or more pharmaceutically acceptable carriers.

26. A method of treating pain in a patient, comprising administering an effective amount of a compound of claim 1, or a pharmaceutically acceptable salt or solvate thereof, to the patient in need of such treatment.

27. The method of claim 26, wherein said pain is acute pain, chronic pain or surgical pain.

28. A process for preparing a compound of claim 1 having Formula I

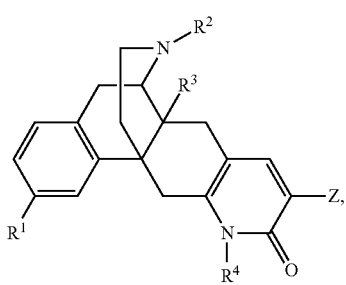

comprising:
reacting a compound of Formula X
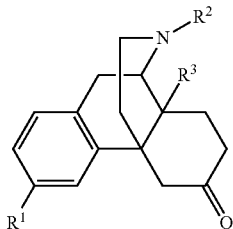
wherein $R^1$—$R^3$ are as defined in claim 1,
with N,N-dimethylformarnideacetal to form an intermediate, and
reacting the intermediate with
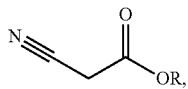
wherein R is an optionally substituted alkyl, to obtain a compound of Formula I, wherein $R^4$ is hydrogen and Z is
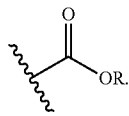
* * * * *